US011959087B2

(12) United States Patent
Thelen et al.

(10) Patent No.: US 11,959,087 B2
(45) Date of Patent: *Apr. 16, 2024

(54) INCREASING PLANT OIL CONTENT BY ALTERING A NEGATIVE REGULATOR OF ACETYL-COA CARBOXYLASE

(71) Applicant: The Curators of The University of Missouri, Columbia, MO (US)

(72) Inventors: Jay Thelen, Columbia, MO (US); Matthew Salie, Columbia, MO (US)

(73) Assignee: THE CURATORS OF THE UNIVERSITY OF MISSOURI, Columbia, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/089,241

(22) Filed: Nov. 4, 2020

(65) Prior Publication Data

US 2021/0171970 A1    Jun. 10, 2021

Related U.S. Application Data

(63) Continuation of application No. 15/756,468, filed as application No. PCT/US2016/041386 on Jul. 7, 2016, now Pat. No. 10,883,113.

(60) Provisional application No. 62/211,371, filed on Aug. 28, 2015.

(51) Int. Cl.
*C12N 15/82* (2006.01)
*C07K 14/415* (2006.01)
*C12N 9/00* (2006.01)
*C12N 15/113* (2010.01)
*C12N 15/87* (2006.01)

(52) U.S. Cl.
CPC ........ *C12N 15/8247* (2013.01); *C07K 14/415* (2013.01); *C12N 9/93* (2013.01); *C12N 15/113* (2013.01); *C12N 15/87* (2013.01); *C12Y 604/01* (2013.01); *C12Y 604/01002* (2013.01); *C12N 2310/14* (2013.01)

(58) Field of Classification Search
None
See application file for complete search history.

(56) References Cited

U.S. PATENT DOCUMENTS

| | | | |
|---|---|---|---|
| 2003/0110533 A1* | 6/2003 | Cahoon | C12N 9/93 435/320.1 |
| 2004/0093638 A1 | 5/2004 | Sasaki et al. | |
| 2012/0102600 A1 | 4/2012 | Nadolska-Orczyk et al. | |
| 2013/0096032 A1 | 4/2013 | Bush et al. | |
| 2014/0230091 A1* | 8/2014 | Shanklin | A61P 3/02 530/370 |

FOREIGN PATENT DOCUMENTS

| | | |
|---|---|---|
| WO | WO 1994/023027 A2 | 10/1994 |
| WO | WO 1998/05758 A1 | 2/1998 |
| WO | 02/10210 A2 | 2/2002 |
| WO | 2008/122980 A2 | 10/2008 |
| WO | 2013/003608 A1 | 1/2013 |
| WO | WO 2017/039834 A1 | 3/2017 |

OTHER PUBLICATIONS

Gutterson (HortScience 30:964-966, 1995).*
Bruening (Proc. Natl. Acad. Sci., 95:13349-13351, 1998).*
Elomaa et al. (Molecular Breeding, 2:41-50, 1996).*
Colliver et al. (Plant molecular Biology, 35:509-522, 1997).*
Emery et al. (Current Biology 13:1768-1774, 2003).*
Arziman et al. (Nucleic Acids Research, 33:582-588, 2005).*
Wesley et al. (The Plant Journal, 27:581-590, 2001).*
Bourrellier et al. (PNAS, 107:502-507, 2010).*
Salanoubat et al. (GenBank Sequence Accession No. NM_115471; Published Jan. 22, 2014).*
Dougherty and Parks, Transgenes and gene suppression: telling US something new?, Current Opinion in Cell Biology 7:399-405, 1995.
Andre, C., et al., "Feedback Regulation of Plastidic Acetyl-CoA Carboxylase by 18:1-acyl Carrier Protein in *Brassica napus*," Proceedings of the National Academy of Sciences of the United States of America 109(25):10107-10112 (2012).
Baud, S., et al., "Wrinkled1 Specifies the Regulatory Action of Leafy Cotyledon2 Towards Fatty Acid Metabolism During Seed Maturation in Arabidopsis," The Plant Journal 50(5):825-838 (2007).
Chen, M., et al., "System Analysis of an Arabidopsis Mutant Altered in de Novo Fatty Acid Synthesis Reveals Diverse Changes in Seed Composition and Metabolism," Plant Physiology 150(1):27-41 (2009).
Feria Bourrelier, A.B., et al., "Chloroplast Acetyl-CoA Carboxylase Activity is 2-oxoglutarate-Regulated by Interaction of PII With the Biotin Carboxyl Carrier Subunit," Proceedings of the National Academy of Sciences of the United States of America 107(1):502-507 (2010).
Fukuda, N., et al., "Expression of the Genes Coding for Plastidic Acetyl-CoA Carboxylase Subunits Is Regulated by a Location-Sensitive Transcription Factor Binding Site," Plant Molecular Biology 82(4-5):473-483 (2013).
Hunter, S.C., and Ohlrogge, J.B., "Regulation of Spinach Chloroplast Acetyl-CoA Carboxylase," Archives of Biochemistry and Biophysics 359(2):170-178, 1998.
International Search Report and Opinion regarding International Application No. PCT/US16/41386, dated Dec. 1, 2016.

(Continued)

*Primary Examiner* — Vinod Kumar
(74) *Attorney, Agent, or Firm* — Dentons US LLP

(57) ABSTRACT

The present invention provides a method and means to change fatty acid and ultimately triacylglycerol production in plants and algae. Methods of the invention comprise the step of altering the activity levels of the committed step for de novo fatty acid biosynthesis, acetyl-CoA carboxylases (ACCase). More specifically, methods of the invention directly enhance the activity of ACCase by down-regulating the biotin/lipoyl attachment domain containing (BADC) genes through biotechnology or selective breeding approaches.

11 Claims, 18 Drawing Sheets

Specification includes a Sequence Listing.

(56) References Cited

OTHER PUBLICATIONS

International Preliminary Report on Patentability regarding International Application No. PCT/US2017/040851, dated Jul. 30, 2018.
International Search Report and Written Opinion regarding International Application No. PCT/US2017/040851, dated Dec. 29, 2017.
Kozaki, A., et al., "Thiol-Disulfide Exchange Between Nuclear-Encoded and Chloroplast-Encoded Subunits of Pea Acetyl-CoA Carboxylase," The Journal of Biological Chemistry 276(43):39919-39925, 2001.
Li, L., et al., "PlantOrDB: a Genome-Wide Ortholog Database for Land Plants and Green Algae," BMC Plant Biology, vol. 15:161, 2015.
Lu and Kang, "Generation of Transgenic Plants of a Potential Oilseed Crop Camelina sativa by Agrobacterium-Mediated Transformation," Plant Cell Reports 27(2):273-278 (2008).
Sasaki, Y., and Nagano, Y., "Plant Acetyl-CoA Carboxylase: Structure, Biosynthesis, Regulation, and Gene Manipulation for Plant Breeding," Bioscience, Biotechnology and Biochemistry 68(6):1175-1184 (2004).
Sasaki, Y., et al., "Link Between Light and Fatty Acid Synthesis: Thioredoxin-Linked Reductive Activation of Plastidic Acetyl-CoA Carboxylase," Proceedings of the National Academy of Sciences of the United States of America 94(20):11096-11101, (1997).
Thelen, J.J., and Ohlrogge, J.B., "Both Antisense and Sense Expression of Biotin Carboxyl Carrier Protein Isoform 2 Inactivates the Plastid Acetyl-Coenzyme A Carboxylase in *Arabidopsis thaliana*," The Plant Journal 32(4):419-431, Nov. 2002.
GenBank Accession No. AF164510, dated Jul. 1, 2000.
GenBank Accession No. AF164511, dated Jul. 1, 2000.
GenBank Accession No. AF165158, dated Aug. 1, 2000.
GenBank Accession No. AF165159, dated Aug. 1, 2000.
GenBank Accession No. NM_001248305, dated Oct. 18, 2018.
GenBank Accession No. NM_001249264, dated Mar. 2, 2017.
GenBank Accession No. NP_001319767, dated Feb. 14, 2019.
GenBank Accession No. NM_001339770, dated Feb. 14, 2019.
GenBank Accession No. U34392, dated Jul. 16, 1996.
GenBank Accession No. U40979, dated Jul. 16, 1996.
GenBank Accession No. AF092443, dated Jul. 26, 2016.
GenBank Accession No. NM_115471, dated Feb. 14, 2019.
GenBank Accession No. NP_567035, dated Feb. 14, 2019.
Extended European Search Report regarding Europe Application No. 16842484.4 dated Apr. 12, 2019.
Salie, "Discovery and Characterization of Regulatory Mechanisms Affecting the Heteromeric Acetyl-Coenzyme a Carboxylase in *Arabidopsis*," Retrieved from the Internet: URL:https://mospace.umsystem.edu/xmlui/bitstream/handle/10355/60417/research.pdf?sequence=2&isAllowed=y [retrieved on Mar. 26, 2019] *Chapter II* May 1, 2016.
Salie, M., et al., "A Family of Negaticve Regulators Targets the Committed Step of de Novo Fatty Acid Biosysthesis," The Plant Cell 28(9):2312-2325 (Aug. 24, 2016).
EBI Accession No. EMBL:BT001187, dated Nov. 13, 2002.

\* cited by examiner

| Name | Accession | Sequence |
|---|---|---|
| BCCP1 sense | AT5G16390 | 5'-CATATGTCAGCTGAAGGAAAGGAGAAAACTCATTG-3' |
| BCCP1 anti-sense | | 5'-GGATCCCTACGGTTGAACCACAAACAGAGGAG-3' |
| BCCP2 sense | AT5G15530 | 5'-CATATGGAATTATGGCTAAAGTCTCTGGTCTT-3' |
| BCCP2 anti-sense | | 5'-GGATCCTCAAGGTGCGATGACAAAAGAG-3' |
| BADC1 sense | AT3G56130 | 5'-GAATTCGCTAAGGCCGCTAAATCTTCGAC-3' |
| BADC1 anti-sense | | 5'-CTCGAGTCACTGGATGTTGATGTCGTG-3' |
| BADC2 sense | AT1G52670 | 5'-CATATGACGACTCTGCGATCTGTGAAAGCT-3' |
| BADC2 anti-sense | | 5'-GGATCCTTACTGAAGCTTCTTGATGCCAGGA-3' |
| BADC3 sense | AT3G15690 | 5'-CATATGGCTGTCCAAGTGTCTACTGTCCC-3' |
| BADC3 anti-sense | | 5'-GGATCCTTACTGAAGCTTCTTGATCCCAGGG-3' |
| apo-BCCP1 mutant sense | AT5G16390 | 5'-GCATTGTTGAAGCCATGAGGTTAATGAATGAAATA-3' |
| apo-BCCP1 mutant antisense | | 5'-TATTTCATTCATTAACCTCATGGCTTCAACAATGC-3' |

B

| Name | Predicted target peptide length |
|---|---|
| BCCP1 | 82 |
| BCCP2 | 87 |
| BADC1 | 56 |
| BADC2 | 47 |
| BADC3 | 54 |

FIG. 4

| Protein Name | BCCP2 | BADC1 | BADC2 | BADC3 |
|---|---|---|---|---|
| BCCP1 | 51.0% | 24.4 | 27.3 | 29.3 |
| BCCP2 |  | 25.2 | 26.0 | 28.1 |
| BADC1 |  |  | 34.2 | 41.7 |
| BADC2 |  |  |  | 61.6 |

FIG. 6A

```
BCCP1  QKGQVLCIVF AMKI MNEIESDHTGTVVDIVAEDGKPVSLDTPLFVVQP----------
BCCP2  QKGQIVCIIE AMKI MNEIEAEKSGTIMELLAEDGKPVSVDTPLFVIAP----------
BADC1  KEGQVIGYLH QLGT ELPVTSDVAGEVLKLLSDDGDSVGYGDPLVAVLPSFHDINIQ-
BADC2  KEGQVLCYIE QLGG QIPVESDVSGEIVKILREDGEPVGYNDALITVLPSFPGIKKLQ
BADC3  KEGQILCYIF QLGG QFPIESDVTGEVVKILREDGEPVGYNDALISILPSFPGIKKLQ
```

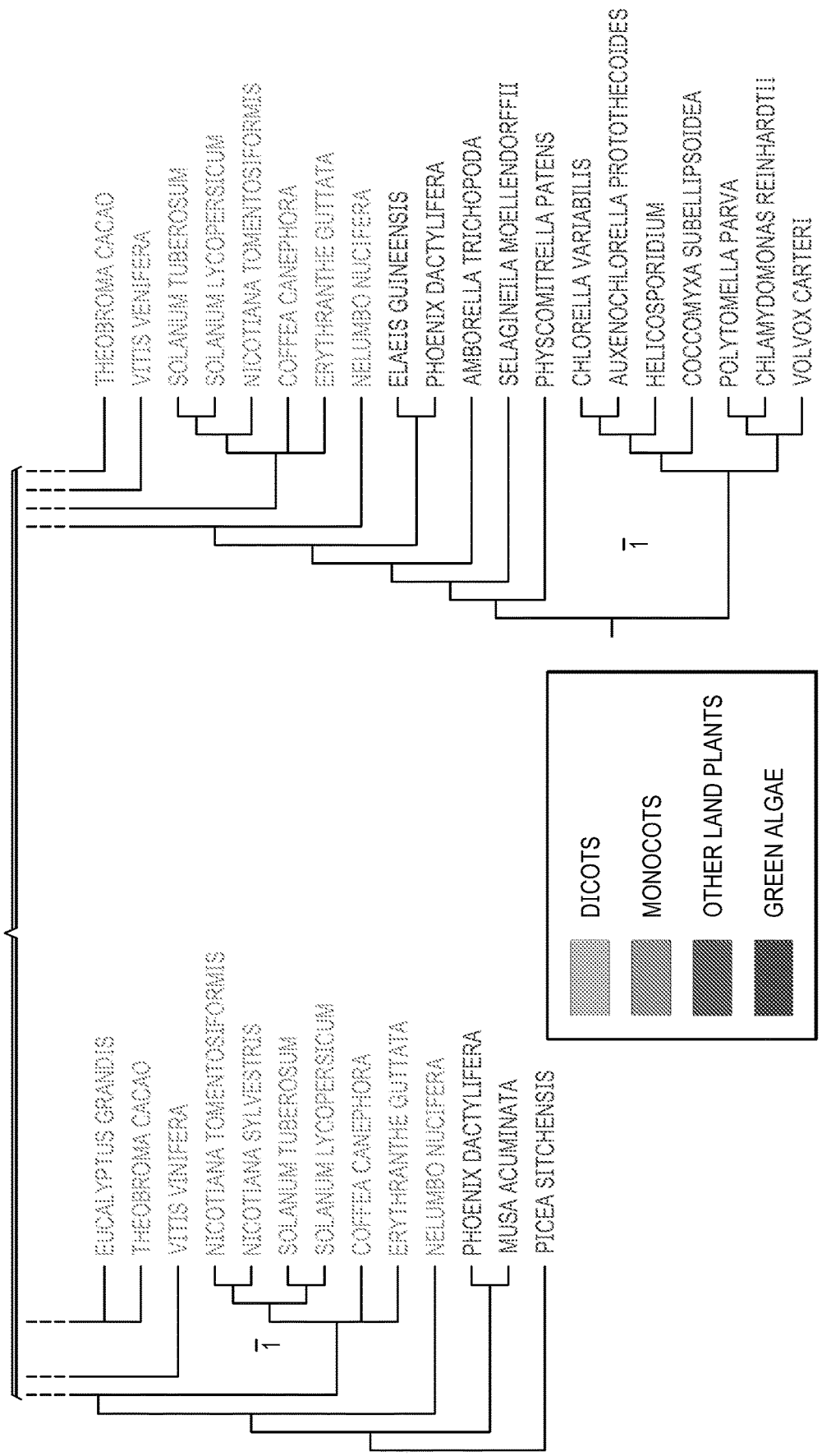

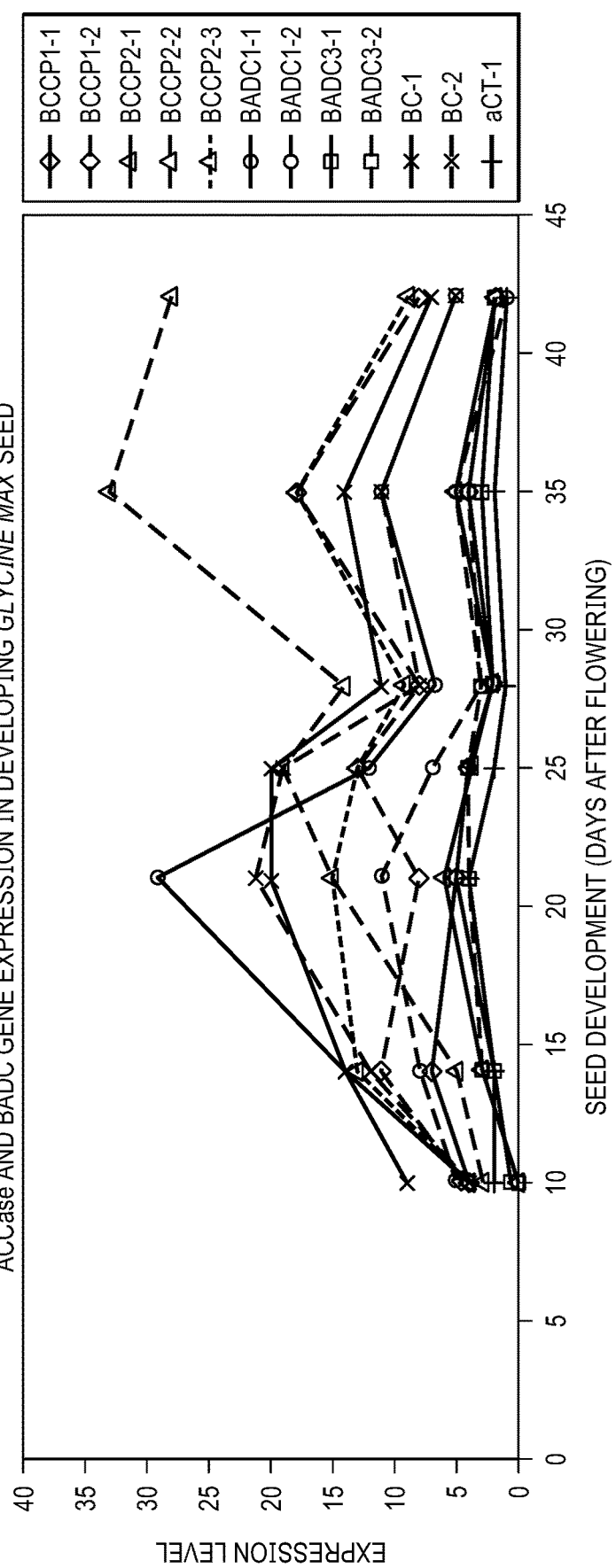

ID NOs: 7 or 138. In some embodi-
INCREASING PLANT OIL CONTENT BY ALTERING A NEGATIVE REGULATOR OF ACETYL-COA CARBOXYLASE

CROSS REFERENCE TO RELATED APPLICATIONS

This application is a continuation of U.S. application Ser. No. 15/756,468, filed Feb. 28, 2018, which application is a 371 National Stage application of International Application No. PCT/US2016/041386, filed Jul. 7, 2016, which application claims the benefit of U.S. Provisional Application No. 62/211,371, filed Aug. 28, 2015, each of which are herein incorporated by reference in its entirety.

STATEMENT REGARDING FEDERALLY SPONSORED RESEARCH

This invention was made with Government support under Grant No. PGRP 10S-1339385 awarded by National Science Foundation and Grant No. T32 GM008396 by the National Institutes of Health. The Government has certain rights in the invention.

INCORPORATION OF SEQUENCE LISTING

The sequence listing that is contained in the file named "UVMO115_ST25.txt," which is 331 kilobytes as measured in Microsoft Windows operating system and was created on Jul. 6, 2016, is filed electronically herewith and incorporated herein by reference.

FIELD OF THE INVENTION

The present invention relates to methods and systems for increasing plant oil content, and more particularly to constructs and methods to down-regulate expression of a negative regulator of de novo fatty acid synthesis in order to increase fatty acid and ultimately triacylglycerol production in plants and algae that harbor this family of negative regulators.

BACKGROUND OF THE INVENTION

Vegetable oils are an important renewable source of hydrocarbons for food, energy, and industrial feedstocks. As demand for this commodity increases, discovering ways to enhance oil production in crops will be an agronomic priority. Oil production begins with the de novo fatty acid synthesis (FAS) pathway to generate the acyl chains that are eventually esterified to glycerol to produce triacylglycerol, the major storage lipid in the seed. The committed step of de novo FAS is catalyzed by acetyl-coenzyme A carboxylase (ACCase) which carboxylates acetyl-CoA to form malonyl-CoA in a two-step reaction requiring ATP, bicarbonate, and biotin cofactor. In prokaryotes, and in plastids of most plants, ACCase is a heteromeric complex requiring four distinct subunits: biotin carboxylase (BC), biotin carboxyl carrier protein (BCCP), and α- and β-carboxyltransferases (CT). Gramineous monocots possess a homomeric form of plastid ACCase where the catalytic components are adjoined in tandem as a single polypeptide. Structural models for the heteromeric ACCase are primarily based on studies in *Escherichia coli*. The *E. coli* ACCase is composed of two subcomplexes: an α/β-CT heterotetramer and a BC/BCCP heterotetramer. The components of the two subcomplexes form stable associations, while the subcomplexes themselves show a relatively weak interaction with one another. This property has contributed to the difficulties in biochemical and structural characterization of heteromeric ACCase from plants. Plastidial ACCase is regulated by light, feedback inhibition, and a 2-oxoglutarate-binding protein PII. It remains unknown if such regulation is mediated by additional proteins, or if other factors are involved, as the plant heteromeric ACCase has never been fully characterized. A comprehensive study of ACCase protein interactions is needed.

Therefore, there is a need to provide a better understanding of protein structure and regulation of ACCase to leverage the potential for manipulating flux through this committed and irreversible step for de novo FAS. There is also a need to develop a novel method to efficiently increase ACCase activity to consequently increase fatty acid and, ultimately, triacylglycerol production in plants and algae.

SUMMARY OF THE INVENTION

In one aspect, the present invention provides methods/systems to modulate or alter fatty acid and protein production in plants and algae. Such methods comprise the step of altering the activity level of ACCase, the committed step for de novo fatty acid biosynthesis. The invention may comprise the step of altering the expression of a gene family of negative regulators, biotin/lipoyl attachment domain containing (BADC or BLADC) proteins, which bind to the multi-subunit ACCase found in the plastids of dicotyledon and non-gramineous monocot plants, as well as algae. Decreasing BADC levels may enable higher oil content in algae and/or land plants, in either vegetative or reproductive tissues including, but not limited to, leaves and seeds. In addition, increasing or overexpressing expression of one or more BADC genes in a plant or alga may enable higher protein content by reducing ACCase activity and flux through de novo FAS.

According to one embodiment of the invention, the method may comprise the step of enhancing plastid ACCase activities in the plant or algal cell by down-regulating BADC genes through biotechnology or selective breeding approaches. In some embodiments, total or partial silencing may comprises antisense, RNAi, CRISPR, TALON, nanobodies, EMS, T-DNA or transposon-mediated gene knockout, or conventional mutagenesis/targeted breeding. In one embodiment, such a method may further comprise an RNAi cassette comprising SEQ ID NOs:7 or 138. In some embodiments, such approaches may comprise total or partial silencing of one or more BADC genes, such as genes and gene orthologs of BADC1, BADC2, and/or BADC3 or artificial genes containing essential BADC motifs. In one embodiment, the one or more BADC genes may comprise from about 70% to about 100% sequence identity to a nucleotide sequence selected from the group consisting of SEQ ID NOs: 2, 4, 6, 7, and 138, or a complement thereof. In another embodiment, the one or more BADC genes may encode a polypeptide comprising from about 70% to about 100% sequence identity to a polypeptide sequence selected from the group consisting of SEQ ID NOs: 1, 3, 5, 8-137, and 139-143. In another embodiment, the invention provides a plant or part thereof produced by a method described herein, wherein the plant comprises increased seed oil content, or a seed that produces the plant or part thereof, wherein the seed comprises increased seed oil content. In some embodiments, such methods may be carried out in organisms that contain orthologs to the *Arabidopsis thaliana* BADC genes, such as *Amborella trichopoda, Arabidopsis lyrata, Arabidopsis* alpine, *Arachis hypogaea, Auxenochlorella prototheocoides, Brassica napus, Brassica rapa, Camelina sativa, Capsella rubella, Cathamus tinctorius, Chlamydomonas reinhardtii, Chlorella variabilis, Cicer arietinum, Citrus clementina, Citrus sinensis, Coccomyxa subellipsoideas* C-169, *Coffea canephora, Cucumis melo, Cucumis sativus, Elaeis guineensis, Erythranthe guttata, Eucalyptus grandis, Eutrema salsugineum, Fragaria vesca, Genlisea aurea, Glycine max, Helianthus annuus, Helicosporidium* ATCC 50920, *Jatropha curcas, Lotus japonicas, Medicago truncatula, Morus notabilis, Musa acuminate, Nelumbo nucifera, Nicotiana sylvestris, Nicotiana tomentosiformis, Phaseolus vulgaris, Pheonix dactylifera, Physcomitrella patens, Picea sitchensis, Polytomella parva, Populus trichocarpa, Prunus mume, Prunes persica, Pyrus x bretschneideri, Ricinus communis, Selaginella moellendoiffii, Sesamum indicum, Solanum lycopersicum, Solanum tuberosum, Theobroma cacao, Thlaspi arvense, Vitis vinifera,* or *Volvox carteri.*

In another embodiment of the invention, the method may comprises the step of reducing plastid ACCase activity by up-regulating BADC genes through biotechnology or selective breeding approaches in an organism that contains an ortholog to the *Arabidopsis thaliana* BADC genes. In one embodiment, such up-regulation of one or more BADC genes may comprise altering expression of one or more BADC genes in either seed or vegetative tissue of a plant or alga, such as genes and gene orthologs of BADC1, BADC2, and/or BADC3 or artificial genes containing essential BADC motifs. In one embodiment, the one or more BADC genes may comprise from about 70% to about 100% sequence identity to a nucleotide sequence selected from the group consisting of SEQ ID NOs: 2, 4, 6, 7, and 138, or a complement thereof. In another embodiment, the one or more BADC genes may encode a polypeptide comprising from about 70% to about 100% sequence identity to a polypeptide sequence selected from the group consisting of SEQ ID NOs: 1, 3, 5, 8-137, and 139-143. In another embodiment, the invention provides a plant or part thereof produced by a method described herein, wherein the plant comprises increased seed oil content, or a seed that produces the plant or part thereof, wherein the seed comprises increased seed oil content, such as *Amborella trichopoda, Arabidopsis lyrata, Arabidopsis alpine, Arachis hypogaea, Auxenochlorella prototheocoides, Brassica napus, Brassica rapa, Camelina sativa, Capsella rubella, Cathamus tinctorius, Chlamydomonas reinhardtii, Chlorella variabilis, Cicer arietinum, Citrus clementina, Citrus sinensis, Coccomyxa subellipsoideas* C-169, *Coffea canephora, Cucumis melo, Cucumis sativus, Elaeis guineensis, Erythranthe guttata, Eucalyptus grandis, Eutrema salsugineum, Fragaria vesca, Genlisea aurea, Glycine max, Helianthus annuus, Helicosporidium* ATCC 50920, *Jatropha curcas, Lotus japonicas, Medicago truncatula, Morus notabilis, Musa acuminate, Nelumbo nucifera, Nicotiana sylvestris, Nicotiana tomentosiformis, Phaseolus vulgaris, Pheonix dactylifera, Physcomitrella patens, Picea sitchensis, Polytomella parva, Populus trichocarpa, Prunus mume, Prunes persica, Pyrus x bretschneideri, Ricinus communis, Selaginella moellendorffii, Sesamum indicum, Solanum lycopersicum, Solanum tuberosum, Theobroma cacao, Thlaspi arvense, Vitis vinifera,* or *Volvox carteri.*

Further areas of applicability of the present disclosure will become apparent from the description provided herein. It should be understood that the description and specific examples are intended for purposes of illustration only and are not intended to limit the scope of the present teachings.

BRIEF DESCRIPTION OF THE DRAWINGS

For a more complete understanding of the features and advantages of the present invention, reference is now made to the detailed description of the invention along with the accompanying figures. The drawings described herein are for illustration purposes only and are not intended to limit the scope of the present teachings in any way.

FIG. 2—Shows primer design for yeast two-hybrid and recombinant expression cloning studies. (A) Primers used to amplify the genes shown were ordered from Sigma-Aldrich and include: BCCP1 (accession no. AT5G16390) sense and antisense primers (SEQ ID NOs:144 and 145, respectively); BCCP2 (accession no. AT5G15530) sense and antisense primers (SEQ ID NOs:146 and 147, respectively); BADC1 (accession no. AT3G56130) sense and antisense primers (SEQ ID NOs:148 and 149, respectively); BADC2 (accession no. AT1G52670) sense and antisense primers (SEQ ID NOs:150 and 151, respectively); BADC3 (accession no. AT3G15690) sense and antisense primers (SEQ ID NOs:152 and 153, respectively), and apo-BCCP1 (accession no. AT5G16390) mutant sense and antisense primers (SEQ ID NOs:160 and 161, respectively). Underlined segments indicate a restriction endonuclease site. (B) Transit peptide lengths were predicted using TargetP. Primers were designed to omit the bases coding for these peptides from the gene of interest to allow for proper protein folding.

FIG. 4—Shows that BADC proteins share substantial sequence identity with BCCP subunits of ACCase in *Arabidopsis thaliana*. Protein sequences from *Arabidopsis thaliana* were aligned and percent amino acid identity was calculated using Clustal-W.

FIG. 6A—Shows an alignment of the C-termini of the *Arabidopsis thaliana* BCCP and BADC proteins demonstrating that the BADC proteins resemble BCCP isoforms but lack the conserved biotinylation motif and biotinyl lysine residue. BCCP1 (SEQ ID NO:139), BCCP2 (SEQ ID NO:140), BADC1 (SEQ ID NO:1), BADC2 (SEQ ID NO:3), and BADC3 (SEQ ID NO:5).

FIG. 13B—Shows a scatter plot demonstrating the expression profiles of ACCase and BADC genes in developing seed of *Glycine max*.

BRIEF DESCRIPTION OF THE SEQUENCES

Figure 1:
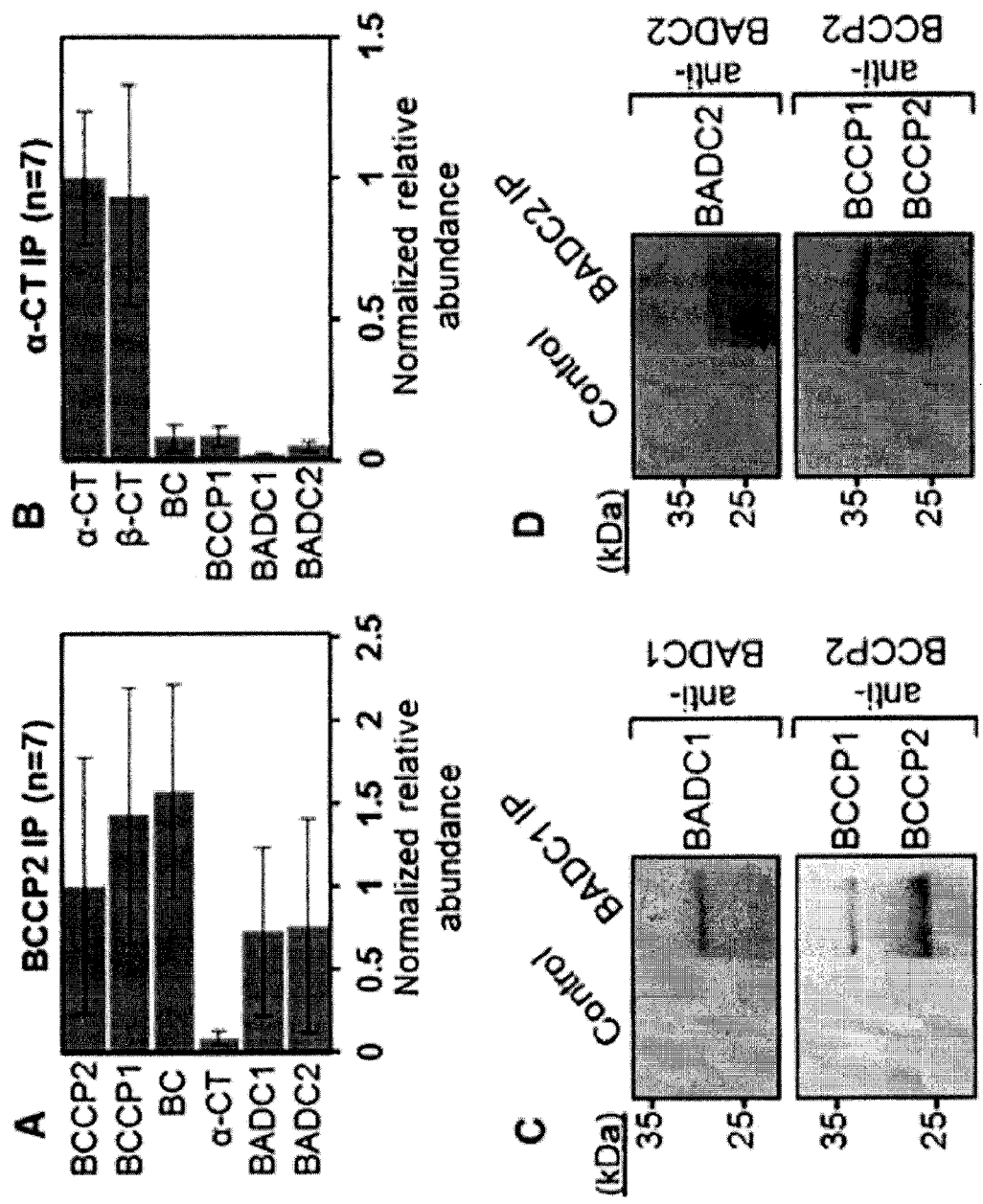
FIG. 1—Shows co-immunoprecipitation of ACCase and BADC proteins from *Arabidopsis thaliana* seedlings. (A and B) Proteins were precipitated from *Arabidopsis thaliana* crude chloroplast lysate using antibodies specific for ACCase subunits BCCP2 (A) or α-CT (B) and identified by LC-MS/MS. Control precipitations were performed with uncoated Protein A Sepharose beads. For both sets of studies, n=7. Error bars represent standard deviation. Semi-quantitative normalized relative abundance values were determined by dividing total spectral matches for each protein by protein size and normalizing to the antibody-specific protein. (C and D) Protein blot analysis of reciprocal co-IPs from the same *Arabidopsis* lysate showed that the BCCP subunits of ACCase co-precipitated with BADC1 (C) and BADC2 (D). Blots are representative of three biological replicates.

SEQ ID NO:1—BADC1 polypeptide sequence, AT3G56130, biotin/lipoyl attachment domain-containing protein.

SEQ ID NO:2—BADC1 full genomic nucleic acid sequence, AT3G56130, biotin/lipoyl attachment domain-containing protein.

SEQ ID NO:3—BADC2 polypeptide, AT1G52670, Single hybrid motif protein.

SEQ ID NO:4—BADC2 full genomic nucleic acid, AT1G52670, Single hybrid motif protein.

SEQ ID NO:5—BADC3 polypeptide, AT3G15690, Single hybrid motif protein.

SEQ ID NO:6—BADC3 full genomic nucleic acid, AT3G15690, Single hybrid motif protein.

SEQ ID NO:7—Nucleic acid, RNAi cassette for BADC1 silencing in *Arabidopsis thaliana*.

SEQ ID NOs:8-134—Polypeptide sequences of each BADC ortholog across various organisms. Orthologous proteins were identified by performing a PSI-BLAST search using the protein sequence of each BADC from *Arabidopsis thaliana* as the query against known plant and algae proteomes. Orthologs were confirmed by reciprocal BLAST search against the *Arabidopsis thaliana* proteome. Sequences show GenBank ID, reference number, protein annotation, and name of the genus and species.

SEQ ID NOs:135-137—Show the consensus sequence identified by multiple sequence alignment of all identified BADC orthologs and the three BADC isoforms in *Arabidopsis thaliana*. This consensus sequence identifies a protein as a BADC ortholog.

SEQ ID NO:135—Polypeptide sequence of internal 44 amino acids of *Arabidopsis thaliana* BADC1 protein, accession AT3G56130. The 44 amino acids are conserved among the BADC protein family.

SEQ ID:136—Internal 44 amino acids of BADC consensus motif 1, with identical amino acid residues at positions 1, 2, 11, 12, 28, 29, 36, 38, and 42.

SEQ ID NO:137—Internal 44 amino acids of BADC consensus motif 1, with variable amino acid residues at positions 1, 2, 11, 12, 28, 29, 36, 38, and 42, and providing variable residues.

SEQ ID NO:138—Nucleic acid, RNAi cassette to target BADC1 and BADC3 genes in *Glycine max*.

SEQ ID NO:139—BCCP1 protein sequence.
SEQ ID NO:140—BCCP2 protein sequence.
SEQ ID NO:141—BADC1 protein sequence.
SEQ ID NO:142—BADC2 protein sequence.
SEQ ID NO:143—BADC3 protein sequence.

SEQ ID NOs:144 and 145—Sequences of BCCP1 (accession no. AT5G16390) sense and antisense primers, respectively.

SEQ ID NOs: 146 and 147—Sequences of BCCP2 (accession no. AT5G15530) sense and antisense primers, respectively.

SEQ ID NOs:148 and 149—Sequences of BADC1 (accession no. AT3G56130) sense and antisense primers, respectively.

SEQ ID NOs:150 and 151—Sequences of BADC2 (accession no. AT1G52670) sense and antisense primers, respectively.

SEQ ID NOs:152 and 153—Sequences of BADC3 (accession no. AT3G15690) sense and antisense primers, respectively.

SEQ ID NO:154 and 155—Primer Sequences used to amplify AtBADC1.

SEQ ID NOs:156—Sequence of sense primer used to amplify BADC1.

SEQ ID NOs:157—Sequence of antisense primer used to amplify BADC1.

SEQ ID NOs:158—Sequence of sense primer used to amplify Actin 8.

SEQ ID NOs:159—Sequence of antisense primer used to amplify Actin 8.

SEQ ID NOs:160 and 161—Sequences of apo-BCCP1 (accession no. AT5G16390) mutant sense and antisense primers, respectively.

DETAILED DESCRIPTION OF THE INVENTION

The present invention provides methods and means to modulate fatty acid, and ultimately triacylglycerol, production, as well as protein production, in plants and algae. Such methods comprise altering the activity levels of the committed step for de novo fatty acid biosynthesis, catalyzed by acetyl-CoA carboxylases (ACCase). In accordance with the invention, a method described herein may increase or decrease ACCase activity levels by down- or up-regulating the biotin/lipoyl attachment domain containing (BADC) genes, respectively.

The BADC proteins are a family of three proteins in *Arabidopsis thaliana* and resemble the biotin carboxyl carrier protein (BCCP) subunit to ACCase. BADC protein expression has a negative effect on ACCase activity, which in turn affects oil production in plants and algae. The activity of ACCase in catalyzing the committed step of de novo fatty acid synthesis and regulation of flux through this central metabolic pathway is known in the art. In dicot and non-gramineous monocot plants and algae, plastid ACCase is a heteromeric complex comprised of four catalytic subunits: biotin carboxylase (BC), biotin carboxyl carrier protein (BCCP), and α- and β-carboxyltransferase (α-CT, β-CT). The plant complex is recalcitrant to conventional purification schemes and hence the structure and composition of the full assembly is unknown.

As described in detail below, in vivo co-immunoprecipitation with subunit-specific antibodies was used to identify a novel family of BADC proteins, provided herein as SEQ ID NOs:1-6, in *Arabidopsis thaliana*. It was determined that BADC proteins resemble BCCP (subunits of ACCase complex) but cannot be biotinylated, and based on the results from orthogonal techniques, all three BADC proteins interact with the two *A. thaliana* BCCP isoforms and the biotin carboxylase subunit of ACCase, based on yeast two-hybrid and heterologous co-expression analyses. None of the BADC proteins were biotinylated in planta or when expressed in *Escherichia coli*, unlike BCCP controls. Gene orthologs to BADC were found only in plant and green algae species that contain a heteromeric ACCase suggesting BADC genes co-evolved with this form of ACCase. It was further discovered that expression of BADC proteins inhibited ACCase activity when co-expressed with a functional BCCP in a temperature-sensitive *Escherichia coli* BCCP mutant. Thus, BADC proteins regulate ACCase by competing with BCCP to form less active complexes. Down-regulating BADC genes (i.e., silencing the expression of BADC protein) promotes the formation of active ACCase complexes, which in turn increases ACCase activity levels and thus oil production in plants and/or algae. Down-regulating one or more BADC genes may be achieved via various biotechnology or selective breeding approaches as described herein and/or known in the art.

The invention also provides methods of reducing fatty acid synthesis in plants and/or algae by overexpression of BADC genes. Such methods would reduce the amount of triacylglycerol stored in the seed and concomitantly increase the amount of protein stored in the seed. Overexpression of BADC genes may therefore reduce ACCase activity and in turn reduce fatty acid biosynthesis.

The present disclosure provides a method of marker-assisted selection as a screening tool for plant and/or algae species that contain higher oil content. The BADC genes are traits that can be monitored to select for specific organisms that may have the potential to produce more triacylglycerol. The expression level of BADC genes may be the marker used to assist in such selection, wherein organisms with naturally reduced expression of BADC genes may be selected.

Plant oils are an important renewable source of hydrocarbons for food, energy, and industrial feedstocks. Acyl chains stored as triacylglycerol are produced by the de novo fatty acid synthesis (FAS) pathway. The committed step of de novo FAS is catalyzed by the heteromeric acetyl-coenzyme A carboxylase (hetACCase) which carboxylates acetyl-CoA to form malonyl-CoA in a two-step reaction requiring ATP, bicarbonate, and biotin cofactor. In prokaryotes, and in plastids of dicots and non-gramineous monocots, hetACCase is a heteromeric complex requiring four distinct subunits: biotin carboxylase (BC), biotin carboxyl carrier protein (BCCP), and α- and β-carboxyltransferase (CT). Gramineous monocots possess a homomeric form of plastid ACCase wherein the catalytic components are fused in tandem as a single polypeptide. Structural models for hetACCase are based on studies of the *Escherichia coli* homolog. The *E. coli* hetACCase is composed of two enzymatic subcomplexes: an α/β-CT heterotetramer and a BC/BCCP heterooctamer. The components of each subcomplex form stable associations while the two subcomplexes themselves show a relatively weak interaction with one another. This property has contributed to the difficulties in biochemical and structural characterization of hetACCase from plants.

Without being limited to a particular theory, a plant useful for the present invention may be include, but is not limited to, plant or algal apecies, such as *Amborella trichopoda, Arabidopsis lyrata, Arabidopsis alpine, Auxenochlorella protothecoides, Brassica napus, Brassica rapa, Capsella rubella, Chlamydomonas reinhardtii, Chlorella variabilis, Cicer arietinum, Citrus clementina, Citrus sinensis, Coccomyxa subellipsoideas* C-169, *Coffea canephora, Cucumis melo, Cucurnis sativus, Elaeis guineensis, Erythranthe guttata, Eucalyptus grandis, Eutrema salsugineum, Fragaria vesca, Genlisea aurea, Glycine max, Helianthus annuus, Helicosporidium* ATCC 50920, *Jatropha curcas, Lotus japonicas, Medicago truncatula, Morus notabilis, Musa acuminate, Nelumbo nucifera, Nicotiana sylvestris, Nicotiana tomentosiformis, Phaseolus vulgaris, Pheonix dactylifera, Physcomitrella patens, Picea sitchensis, Polytomella parva, Populus trichocarpa, Prunus mume, Prunes persica, Pyrus x bretschneideri, Ricinus communis, Selaginella moellendorffii, Solanum lycopersicum, Solanum tuberosum, Theobroma cacao, Vitis vinifera,* or *Volvox carteri.*

I. Nucleic Acids, Polypeptides and Plant Transformation Constructs

Certain embodiments of the current invention concern isolated nucleic acid sequences and the corresponding polypeptide sequences for a novel family of BADC proteins, provided herein as SEQ ID NOs:1-6, in *Arabidopsis thaliana*. Complements to any nucleic acid or protein sequences described herein are also provided.

"Identity," as is well understood in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences. Methods to determine "identity" are designed to give the largest match between the sequences tested. Moreover, methods to determine identity are codified in publicly available programs. "Identity" can be readily calculated by known methods including, but not limited to, those described in Lesk, ed., (1988); Smith, ed., (1993); Griffin, and Griffin, eds., (1994); von Heinje, (1987); Gribskov and Devereux, eds., (1991); and Carillo and Lipman, (1988). Computer programs can be used to determine "identity" between two sequences these programs include but are not limited to, GCG (Devereux, 1984); suite of five BLAST programs, three designed for nucleotide sequences queries (BLASTN, BLASTX, and TBLASTX) and two designed for protein sequence queries (BLASTP and TBLASTN) (Coulson, 1994; Birren, et al., 1997). The BLASTX program is publicly available from NCBI and other sources (BLAST Manual, Altschul, S., et al., NCBI NLM NIH, Bethesda, Md. 20894; Altschul, S., et al., 1990). The well known Smith Waterman algorithm can also be used to determine identity.

In accordance with the invention, a polynucleotide or polypeptide sequence as described herein may exhibit at least from about 70% to about 100% sequence identity to at least one of the sequences set forth herein. For example, in one embodiment, a BADC gene as described herein may comprise, for example, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a sequence selected from SEQ ID NO:2, 4, 6, 7, or 138, or a complement thereof. In other embodiments, a BADC protein as described herein may comprise for example, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to a sequence selected from SEQ ID NO:1, 3, or 5, or a complement thereof.

Parameters for polypeptide sequence comparison include the following: Algorithm: Needleman and Wunsch (1970); Comparison matrix: BLOSUM62 from Hentikoff and Hentikoff, (1992); Gap Penalty: 12; and Gap Length Penalty: 4. A program which can be used with these parameters is publicly available as the "gap" program from Genetics Computer Group, Madison WI The above parameters along with no penalty for end gap may serve as default parameters for peptide comparisons.

Parameters for nucleic acid sequence comparison include the following: Algorithm: Needleman and Wunsch (1970); Comparison matrix: matches=+10; mismatches=0; Gap Penalty: 50; and Gap Length Penalty: 3. A program which can be used with these parameters is publicly available as the "gap" program from Genetics Computer Group, Madison Wis. The above parameters may serve as the default parameters for nucleic acid comparisons.

As used herein, "hybridization," "hybridizes," or "capable of hybridizing" is understood to mean the forming of a double- or triple-stranded molecule or a molecule with partial double- or triple-stranded nature. Such hybridization may take place under relatively high-stringency conditions, including low salt and/or high temperature conditions, such as provided by a wash in about 0.02 M to about 0.15 M NaCl at temperatures of about 50° C. to about 70° C. for 10 min. In one embodiment of the invention, the conditions are 0.15 M NaCl and 70° C. Stringent conditions tolerate little mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like. Also included may be a protein or polypeptide, or fragment thereof, such as any of those set forth herein.

The nucleic acids provided herein as SEQ ID NOs:1-6 may be from any source, e.g., identified as naturally occurring in a plant, or synthesized, e.g., by mutagenesis of SEQ ID NOs:1-6. In an embodiment, the naturally occurring sequence may be from any plant or algal species, such as *Amborella trichopoda, Arabidopsis lyrata, Arabidopsis alpine, Auxenochlorella prototheocoides, Brassica napus, Brassica rapa, Capsella rubella, Chlamydomonas reinhardtii, Chlorella variabilis, Cicer arietinum, Citrus clementina, Citrus sinensis, Coccomyxa subellipsoideas* C-169, *Coffea canephora, Cucumis meld, Cucumis sativus, Elaeis guineensis, Erythranthe guttata, Eucalyptus grandis, Eutrema salsugineum, Fragaria vesca, Genlisea aurea, Glycine max, Helianthus annuus, Helicosporidium* ATCC 50920, *Jatropha curcas, Lotus japonicas, Medicago truncatula, Morus notabilis, Musa acuminate, Nelumbo nucifera, Nicotiana sylvestris, Nicotiana tomentosiformis, Phaseolus vulgaris, Pheonix dactylifera, Physcomitrella patens, Picea sitchensis, Polytomella parva, Populus trichocarpa, Prunus mume, Prunes persica, Pyrus x bretschneideri, Ricinus communis, Selaginella moellendorffii, Solanum lycopersicum, Solanum tuberosum, Theobroma cacao, Vitis vinifera,* or *Volvox carteri.*

Coding sequences may be provided in a recombinant vector operably linked to a heterologous promoter functional in plants, in either sense or antisense orientation. Expression constructs may also be provided comprising these sequences, including antisense oligonucleotides thereof. In other embodiments, plants and plant cells transformed with the sequences may be provided. The construction of vectors which may be employed in conjunction with plant transformation techniques using these or other sequences according to the invention will be known to those of skill of the art in light of the present disclosure (see, for example, Sambrook et al., 1989; Gelvin et al., 1990). The techniques of the current invention are thus not limited to any particular nucleic acid sequences.

The choice of any additional elements used in conjunction with a coding sequences or corresponding encoded product may depend on the purpose of the transformation. One of the major purposes of transformation of crop plants is to add commercially desirable, agronomically important traits to the plant, as described herein.

Vectors used for plant transformation may include, for example, plasmids, cosmids, YACs (yeast artificial chromosomes), BACs (bacterial artificial chromosomes) or any other suitable cloning system, as well as fragments of DNA therefrom. Thus when the term "vector" or "expression vector" is used, all of the foregoing types of vectors, as well as nucleic acid sequences isolated therefrom, are included. It is contemplated that utilization of cloning systems with large insert capacities will allow introduction of large DNA sequences comprising more than one selected gene. In accordance with the invention, this could be used to introduce genes corresponding to, e.g., an entire biosynthetic pathway, into a plant.

Particularly useful for transformation are expression cassettes which have been isolated from such vectors. DNA segments used for transforming plant cells will generally comprise the cDNA, gene, or genes which one desires to introduce into and have expressed in the host cells. These DNA segments can further include structures such as promoters, enhancers, polylinkers, or even regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant. Preferred components likely to be included with vectors used in the current invention are as follows.

A. Regulatory Elements

Exemplary promoters for expression of a nucleic acid sequence include plant promoters such as the CaMV 35S promoter (Odell et al., 1985), or others such as CaMV 19S (Lawton et al., 1987), nos (Ebert et al., 1987), Adh (Walker et al., 1987), sucrose synthase (Yang and Russell, 1990), α-tubulin, actin (Wang et al., 1992), cab (Sullivan et al., 1989), PEPCase (Hudspeth and Grula, 1989) or those promoters associated with the R gene complex (Chandler et al., 1989). Tissue-specific promoters such as leaf specific promoters, or tissue selective promoters (e.g., promoters that direct greater expression in leaf primordia than in other tissues), and tissue-specific enhancers (Fromm et al., 1986) are also contemplated to be useful, as are inducible promoters such as ABA- and turgor-inducible promoters. Any suitable promoters known in the art may be used to express coding sequences in a plant.

The DNA sequence between the transcription initiation site and the start of the coding sequence, i.e., the untranslated leader sequence, can also influence gene expression. One may thus wish to employ a particular leader sequence with a transformation construct of the invention. In an embodiment, leader sequences are contemplated to include those which comprise sequences predicted to direct optimum expression of the attached gene, i.e., to include a consensus leader sequence which may increase or maintain mRNA stability and prevent inappropriate initiation of translation. The choice of such sequences will be known to those of skill in the art in light of the present disclosure.

It is envisioned that a sequence useful for altering activity levels of ACCase as described herein may comprise any sequence set forth herein, for example SEQ ID NOs:1-6. In certain embodiments, a gene useful for altering ACCase levels may comprise altering expression of a BADC gene, such as BADC1, BADC2, BADC3, set forth herein as SEQ ID NOs:2, 4, and 6, respectively, or orthologs or homologs thereof. Such an ortholog or homolog may be from any species useful in accordance with the invention. Such a sequence may be introduced into a plant under the control of novel promoters, enhancers, etc., or homologous or tissue-specific or tissue-selective promoters or control elements. Vectors for use in tissue-specific targeting of genes in transgenic plants will typically include tissue-specific or tissue-selective promoters and may also include other tissue-specific or tissue-selective control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters, which have higher activity in roots; or napin and glycinin promoters, which have higher activity in developing seed.

B. Terminators

Transformation constructs prepared in accordance with the invention may include a 3' end DNA sequence that acts as a signal to terminate transcription and allow for the polyadenylation of the mRNA produced by coding sequences operably linked to a promoter. In one embodiment of the invention, the native terminator of a BADC coding sequence may be used. Alternatively, a heterologous 3' end may enhance the expression of sense or antisense BADC coding sequences. Examples of terminators that may be used in this context include those from the nopaline synthase gene of *Agrobacterium tumefaciens* (nos 3' end) (Bevan et al., 1983), the terminator for the T7 transcript from the octopine synthase gene of *Agrobacterium tumefaciens*, and the 3' end of the protease inhibitor I or II gene from potato or tomato. Regulatory elements such as an Adh intron (Callis et al., 1987), sucrose synthase intron (Vasil et al., 1989) or TMV omega element (Gallie et al., 1989), may further be included where desired.

C. Transit or Signal Peptides

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids and other intracellular organelles) and signal sequences (usually to the endoplasmic reticulum, Golgi apparatus, and outside of the cellular membrane). By facilitating the transport of the protein into compartments inside and outside the cell, these sequences may increase the accumulation of gene products by protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit or signal peptide will transport the protein to a particular intracellular or extracellular destination, respectively, and will then be post-translationally removed.

D. Marker Genes

By employing a selectable or screenable marker, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the invention.

Many selectable marker coding regions are known and could be used with the present invention including, but not limited to, neo (Potrykus et al., 1985), which provides kanamycin resistance and can be selected for using kanamycin, G418, paromomycin, etc.; bar, which confers bialaphos or phosphinothricin resistance; a mutant EPSP synthase protein (Hinchee et al., 1988) conferring glyphosate resistance; a nitrilase such as bxn from *Klebsiella ozaenae* which confers resistance to bromoxynil (Stalker et al., 1988); a mutant acetolactate synthase (ALS) which confers resistance to imidazolinone, sulfonylurea or other ALS inhibiting chemicals (European Patent Application 154, 204, 1985); a methotrexate resistant DHFR (Thillet et al., 1988), a dalapon dehalogenase that confers resistance to the herbicide dalapon; or a mutated anthranilate synthase that confers resistance to 5-methyl tryptophan.

An illustrative embodiment of selectable marker capable of being used in systems to select transformants are those that encode the enzyme phosphinothricin acetyltransferase, such as the bar gene from *Streptomyces hygroscopicus* or the pat gene from *Streptomyces viridochromogenes*. The enzyme phosphinothricin acetyl transferase (PAT) inactivates the active ingredient in the herbicide bialaphos, phosphinothricin (PPT). PPT inhibits glutamine synthetase, (Murakami et al., 1986; Twell et al., 1989) causing rapid accumulation of ammonia and cell death.

One beneficial use of the sequences provided by the invention may be in the alteration of plant phenotypes such as fatty acid or triacylglycerol production, as well as protein production, in plants and/or algae by genetic transformation with a coding sequence set forth herein, such as a BADC coding sequence. A BADC coding sequence such as described herein may be provided with other sequences. Where an expressible coding region that is not necessarily a marker coding region is employed in combination with a marker coding region, one may employ the separate coding regions on either the same or different DNA segments for transformation. In the latter case, the different vectors are delivered concurrently to recipient cells to maximize cotransformation.

II. Genetic Transformation

Additionally provided herein are transgenic plants transformed with the above-identified recombinant vector encoding a BADC, or a sequence modulating expression thereof.

Suitable methods for transformation of plant or other cells for use with the current invention are believed to include virtually any method by which DNA can be introduced into a cell, such as by direct delivery of DNA such as by PEG-mediated transformation of protoplasts (Omirulleh et al., 1993), by desiccation/inhibition-mediated DNA uptake (Potrykus et al., 1985), by electroporation (U.S. Pat. No. 5,384,253, specifically incorporated herein by reference in its entirety), by agitation with silicon carbide fibers (Kaeppler et al., 1990; U.S. Pat. No. 5,302,523, specifically incorporated herein by reference in its entirety; and U.S. Pat. No. 5,464,765, specifically incorporated herein by reference in its entirety), by *Agrobacterium*-mediated transformation (U.S. Pat. Nos. 5,591,616 and 5,563,055; both specifically incorporated herein by reference) and by acceleration of DNA coated particles (U.S. Pat. Nos. 5,550,318; 5,538,877; and 5,538,880; each specifically incorporated herein by reference in its entirety), etc. Through the application of techniques such as these, the cells of virtually any plant species may be stably transformed, and these cells developed into transgenic plants.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described by Fraley et al., (1985), Rogers et al., (1987) and U.S. Pat. No. 5,563,055, specifically incorporated herein by reference in its entirety.

*Agrobacterium*-mediated transformation is most efficient in dicotyledonous plants and is the preferable method for transformation of dicots, including *Arabidopsis*, tobacco, tomato, alfalfa and potato. Indeed, while *Agrobacterium*-mediated transformation has been routinely used with dicotyledonous plants for a number of years, including alfalfa (Thomas et al., 1990), it has only recently become applicable to monocotyledonous plants. Advances in *Agrobacterium*-mediated transformation techniques have now made the technique applicable to nearly all monocotyledonous plants. For example, *Agrobacterium*-mediated transformation techniques have now been applied to rice (Hiei et al., 1997; U.S. Pat. No. 5,591,616, specifically incorporated herein by reference in its entirety), wheat (McCormac et al., 1998), barley (Tingay et al., 1997; McCormac et al., 1998) and maize (Ishidia et al., 1996).

Modern *Agrobacterium* transformation vectors are capable of replication in *E. coli* as well as *Agrobacterium*, allowing for convenient manipulations as described (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described (Rogers et al., 1987) have convenient multi-linker regions flanked by a promoter and a polyadenylation site for direct expression of inserted polypeptide coding genes and are suitable for present purposes. Gateway™ and other recombination-based cloning technology is also available in vectors useful for plant transformation. In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

One also may employ protoplasts for electroporation transformation of plants (Bates, 1994; Lazzeri, 1995). For example, the generation of transgenic soybean plants by electroporation of cotyledon-derived protoplasts is described by Dhir and Widholm in Intl. Patent Appl. Publ. No. WO 9217598 (specifically incorporated herein by reference). Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

Another method for delivering transforming DNA segments to plant cells in accordance with the invention is microprojectile bombardment (U.S. Pat. Nos. 5,550,318; 5,538,880; 5,610,042; and PCT Application WO 94/09699; each of which is specifically incorporated herein by reference in its entirety). In this method, particles may be coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

An illustrative embodiment of a method for delivering DNA into plant cells by acceleration is the Biolistics Particle Delivery System, which can be used to propel particles coated with DNA or cells through a screen, such as a stainless steel or Nytex screen, onto a filter surface covered with monocot plant cells cultured in suspension. The screen disperses the particles so that they are not delivered to the recipient cells in large aggregates. Microprojectile bombardment techniques are widely applicable, and may be used to transform virtually any plant species. Examples of species for which have been transformed by microprojectile bombardment include monocot species such as maize (PCT Application WO 95/06128), barley (Ritala et al., 1994; Hensgens et al., 1993), wheat (U.S. Pat. No. 5,563,055, specifically incorporated herein by reference in its entirety), rice (Hensgens et al., 1993), oat (Torbet et al., 1995; Torbet et al., 1998), rye (Hensgens et al., 1993), sugarcane (Bower et al., 1992), and sorghum (Casa et al., 1993; Hagio et al., 1991); as well as a number of dicots including tobacco (Tomes et al., 1990; Buising and Benbow, 1994), soybean (U.S. Pat. No. 5,322,783, specifically incorporated herein by reference in its entirety), sunflower (Knittel et al. 1994), peanut (Singsit et al., 1997), cotton (McCabe and Martinell, 1993), tomato (VanEck et al. 1995), and legumes in general (U.S. Pat. No. 5,563,055, specifically incorporated herein by reference in its entirety).

The transgenic plants of the present invention expressing heterologous BADC can be of any plant or algal apecies, such as *Amborella trichopoda, Arabidopsis lyrata, Arabidopsis alpine, Auxenochlorella protothecoides, Brassica napus, Brassica rapa, Capsella rubella, Chlamydomonas reinhardtii, Chlorella variabilis, Cicer arietinum, Citrus clementina, Citrus sinensis, Coccomyxa subellipsoideas C-169, Coffea canephora, Cucumis melo, Cucumis sativus, Elaeis guineensis, Erythranthe guttata, Eucalyptus grandis, Eutrema salsugineum, Fragaria vesca, Genlisea aurea, Glycine max, Helianthus annuus, Helicosporidium* ATCC 50920, *Jatropha curcas, Lotus japonicas, Medicago truncatula, Morus notabilis, Musa acuminate, Nelumbo nucifora, Nicotiana sylvestris, Nicotiana tomentosiformis, Phaseolus vulgaris, Pheonix dactylifera, Physcomitrella patens, Picea sitchensis, Polytomella parva, Populus trichocarpa, Prunus mume, Prunes persica, Pyrus x bretschneideri, Ricinus communis, Selaginella moellendorffii, Solanum lycopersicum, Solanum tuberosum, Theobroma cacao, Vitis vinifera*, or *Volvox carteri*. The plant can be an $R_0$ transgenic plant (i.e., a plant derived from the original transformed tissue). The plant can also be a progeny plant of any generation of an $R_0$ transgenic plant, wherein the transgenic plant has the nucleic acid sequence from the $R_0$ transgenic plant.

Seeds of the any above-described transgenic plants may also be provided, particularly where the seed comprises the nucleic acid sequence. Additionally contemplated are host cells transformed with the above-identified recombinant vector. In some embodiments, the host cell is a plant cell.

Also contemplated herein is a plant genetically engineered to increase expression of a BADC, where the BADC comprises a protein product of SEQ ID NOs: 2, 4, 6, 7, or 138, where the protein product (e.g. a polypeptide) alters plant morphology as described herein. Such a protein product may comprise SEQ ID NOs:1, 3, or 5, or any other sequence described herein that is appropriate for use with the present invention. In an embodiment, the altered plant morphology may be increased or decreased fatty acid content. Such altered morphology may be accomplished by increasing or decreasing ACCase activity levels by down- or up-regulating a BADC gene described herein. Such plants are described in the Examples, and may be useful, e.g., as commercial plants.

The plants of these embodiments having altered expression of ACCase or one or more BADC genes may be of any species. The species may be any monocotyledonous or dicotyledonous plant, such as those described herein. One of skill in the art will recognize that the present invention may be applied to plants of other species by employing methods described herein and others known in the art.

Application of these systems to different plant strains depends upon the ability to regenerate that particular plant strain from protoplasts. Illustrative methods for the regeneration of cereals from protoplasts have been described (Toriyama et al., 1986; Yamada et al., 1986; Abdullah et al., 1986; Omirulleh et al., 1993 and U.S. Pat. No. 5,508,184; each specifically incorporated herein by reference in its entirety). Examples of the use of direct uptake transformation of cereal protoplasts include transformation of rice (Ghosh-Biswas et al., 1994), sorghum (Battraw and Hall, 1991), barley (Lazerri, 1995), oat (Zheng and Edwards, 1990) and maize (Omirulleh et al., 1993).

Tissue cultures may be used in certain transformation techniques for the preparation of cells for transformation and for the regeneration of plants therefrom. Maintenance of tissue cultures requires use of media and controlled environments. "Media" refers to the numerous nutrient mixtures that are used to grow cells in vitro, that is, outside of the intact living organism. A medium usually is a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. The rate of cell growth also will vary among cultures initiated with the array of media that permit growth of that cell type.

Tissue that can be grown in a culture includes meristem cells, Type I, Type II, and Type III callus, immature embryos and gametic cells such as microspores, pollen, sperm, and egg cells. Type I, Type II, and Type III callus may be initiated from tissue sources including, but not limited to, immature embryos, seedling apical meristems, root, leaf, microspores and the like. Those cells which are capable of proliferating as callus also are recipient cells for genetic transformation.

Somatic cells are of various types. Embryogenic cells are one example of somatic cells which may be induced to regenerate a plant through embryo formation. Non-embryogenic cells are those which typically will not respond in such a fashion. Certain techniques may be used that enrich recipient cells within a cell population. For example, Type II callus development, followed by manual selection and culture of friable, embryogenic tissue, generally results in an enrichment of cells. Manual selection techniques which can be employed to select target cells may include, e.g., assessing cell morphology and differentiation, or may use various physical or biological means. Cryopreservation also is a possible method of selecting for recipient cells.

A. Altering Gene Expression in a Plant

In accordance with the invention, alteration of expression of a gene as described herein may comprise increasing expression of a gene, or decreasing expression of a gene. As described herein, the present invention may comprise altering expression of a BADC gene. In some embodiments, methods are provided comprising completely silencing or down-regulating expression of a gene. In other embodiments, partial or incomplete silencing or down-regulation of a gene may be sufficient to achieve the desired effect.

Alteration of gene expression in a plant may be accomplished by a variety of methods known in the art. In accordance with the invention, any method useful for altering expression of a gene or gene product may be used, including, but not limited to, antisense, RNAi, CRISPR, TALON, nanobodies, EMS, T-DNA or transposon-mediated gene knockout, or conventional mutagenesis/targeted breeding. Such methods are known in the art. As used herein the words "gene suppression" are intended to refer to any of the well-known methods for reducing the levels of protein produced as a result of gene transcription to mRNA and subsequent translation of the mRNA.

Gene suppression is also intended to mean the reduction of protein expression from a gene or a coding sequence including post-transcriptional gene suppression and transcriptional suppression. Post-transcriptional gene suppression is mediated by the homology between of all or a part of a mRNA transcribed from a gene or coding sequence targeted for suppression and the corresponding double stranded RNA used for suppression, and refers to the substantial and measurable reduction of the amount of available mRNA available in the cell for binding by ribosomes. The transcribed RNA may be in the sense orientation to effect what is called co-suppression, in the anti-sense orientation to effect what is called anti-sense suppression, or in both orientations, in which case a dsRNA may be produced to achieve RNA interference (RNAi). Such methods may be useful in accordance with the invention for down-regulating or silencing a BADC gene as described herein. Transcriptional suppression is mediated by the presence in the cell of a dsRNA, a gene suppression agent, exhibiting substantial sequence identity to a DNA sequence or the complement thereof to result in promoter trans-suppression. Gene suppression may be effective against a native gene associated with a trait, e.g., to produce a plant with reduced levels of a protein encoded by the native gene or with enhanced or reduced levels of an affected gene product. A gene product may include an RNA molecule, including, but not limited to, mRNA, rRNA, tRNA, siRNA, shRNA, or the like. A gene product may also include a protein or polypeptide, or a fragment thereof.

Post-transcriptional gene suppression by anti-sense or sense-oriented RNA to regulate gene expression in plant cells is known in the art, as is the use of dsRNA to suppress genes in plants. Post-transcriptional gene suppression in plants may employ both sense-oriented and anti-sense-oriented, transcribed RNA that is stabilized, e.g., as a hairpin or stem-and-loop structure.

As used herein, the term "expression" refers to the transcription and stable accumulation of sense or anti-sense RNA derived from a nucleic acid. "Expression" may also refer to translation of mRNA into a polypeptide or protein. As used herein, the term "antisense RNA" refers to an RNA transcript that is complementary to all or a part of a mRNA that is normally produced in a cell. The complementarity of an antisense RNA may be with any part of the specific gene transcript, i.e., at the 5' non-coding sequence, 3' non-translated sequence, introns, or the coding sequence. As used herein, the term "RNA transcript" refers to the product resulting from RNA polymerase-catalyzed transcription of a DNA sequence. When the RNA transcript is a perfect complementary copy of the DNA sequence, it is referred to as the primary transcript or it may be an RNA sequence derived from post-transcriptional processing of the primary transcript and is referred to as the mature RNA.

As used herein, the phrase "inhibition of gene expression" or "inhibiting expression of a target gene" refers to the absence (or observable decrease) in the level of protein and/or mRNA product from the target gene. Specificity refers to the ability to inhibit the target gene without manifest effects on other genes of the cell and without any effects on any gene within the cell that is producing the dsRNA molecule. The inhibition of gene expression of a target gene as described herein may result in novel phenotypic traits in the plant.

III. Production and Characterization of Stably Transformed Plants

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

It is believed that DNA is introduced into only a small percentage of target cells in any one study. In order to provide an efficient system for identification of those cells receiving DNA and integrating it into their genomes one may employ a means for selecting those cells that are stably transformed. One exemplary embodiment of such a method is to introduce, into the host cell, a marker gene which confers resistance to some normally inhibitory agent, such as an antibiotic or herbicide. Examples of antibiotics which may be used include the aminoglycoside antibiotics neomycin, kanamycin and paromomycin, or the antibiotic hygromycin. Resistance to the aminoglycoside antibiotics is conferred by aminoglycoside phosphotransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

One herbicide which constitutes a desirable selection agent is the broad-spectrum herbicide bialaphos. Another example of a herbicide which is useful for selection of transformed cell lines in the practice of the invention is the broad-spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived therefrom. U.S. Pat. No. 4,535,060 describes the isolation of EPSPS mutations which confer glyphosate resistance on the EPSPS of *Salmonella typhimurium*, encoded by the gene aroA. The EPSPS gene from *Zea mays* was cloned and mutations similar to those found in a glyphosate resistant aroA gene were introduced in vitro. Mutant genes encoding glyphosate resistant EPSPS enzymes are described in, for example, International Patent WO 97/4103.

To use the bar-bialaphos or the EPSPS-glyphosate selective system, transformed tissue is cultured for 0-28 days on nonselective medium and subsequently transferred to medium containing from 1-3 mg/l bialaphos or 1-3 mM glyphosate as appropriate. While ranges of 1-3 mg/l bialaphos or 1-3 mM glyphosate will typically be preferred, it is proposed that ranges of 0.1-50 mg/l bialaphos or 0.1-50 mM glyphosate will find utility.

Cells that survive the exposure to the selective agent, or cells that have been scored positive in a screening assay, may be cultured in media that supports regeneration of plants. In an exemplary embodiment, MS and N6 media may be modified by including further substances such as growth regulators. One such growth regulator is dicamba or 2,4-D. However, other growth regulators may be employed, including NAA, NAA+2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 weeks, then transferred to media conducive to maturation of embryoids. Cultures are transferred every 2 weeks on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soilless plant growth mix, and hardened, e.g., in an environmentally controlled chamber, for example, at about 85% relative humidity, 600 ppm $CO_2$, and 25-250 microeinsteins $m^{-2} s^{-1}$ of light. Plants may be matured in a growth chamber or greenhouse. Plants can be regenerated in from about 6 weeks to 10 months after a transformant is identified, depending on the initial tissue. During regeneration, cells are grown on solid media in tissue culture vessels. Illustrative embodiments of such vessels are Petri dishes and Plant Cons. Regenerating plants can be grown at about 19 to 28° C. After the regenerating plants have reached the stage of shoot and root development, they may be transferred to a greenhouse for further growth and testing.

To confirm the presence of the exogenous DNA or "transgene(s)" in the regenerating plants, a variety of assays may be performed. Such assays include, for example, "molecular to biological" assays, such as Southern and northern blotting and PCR™; "biochemical" assays, such as detecting the presence of a protein product, e.g., by immunological means (ELISAs and western blots) or by enzymatic function; plant part assays, such as leaf or root assays; and also, by analyzing the phenotype of the whole regenerated plant.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR™, e.g., the presence of a gene, but also demonstrates integration into the genome and characterizes each individual transformant.

Both PCR™ and Southern hybridization techniques can be used to demonstrate transmission of a transgene to progeny. In most instances the characteristic Southern hybridization pattern for a given transformant will segregate in progeny as one or more Mendelian genes (Spencer et al., 1992) indicating stable inheritance of the transgene.

Whereas DNA analysis techniques may be conducted using DNA isolated from any part of a plant, RNA will only be expressed in particular cells or tissue types and hence it will be necessary to prepare RNA for analysis from these tissues. PCR™ techniques also may be used for detection and quantitation of RNA produced from introduced genes. In this application of PCR™ it is first necessary to reverse transcribe RNA into DNA, using enzymes such as reverse transcriptase, and then through the use of conventional PCR™ techniques amplify the DNA. In most instances PCR™ techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species also can be determined using dot or slot blot northern hybridizations. These techniques are modifications of northern blotting and will only demonstrate the presence or absence of an RNA species.

The expression of a gene product is often determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes that change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

IV. Breeding Plants of the Invention

In addition to direct transformation of a particular plant genotype with a construct prepared according to the current invention, transgenic plants may be made by crossing a plant having a selected DNA of the invention to a second plant lacking the construct. For example, a selected BADC coding sequence can be introduced into a particular plant variety by crossing, without the need for ever directly transforming a plant of that given variety. Therefore, the current invention not only encompasses a plant directly transformed or regenerated from cells which have been transformed in accordance with the current invention, but also the progeny of such plants. As used herein, the term "progeny" denotes the offspring of any generation of a parent plant prepared in accordance with the instant invention, wherein the progeny comprises a selected DNA construct prepared in accordance with the invention. "Crossing" a plant to provide a plant line having one or more added transgenes relative to a starting plant line, as disclosed herein, is defined as the techniques that result in a transgene of the invention being introduced into a plant line by crossing a plant of a starting line with a plant of a donor plant line that comprises a transgene of the invention. To achieve this one could, for example, perform the following steps:
  (a) plant seeds of the first (starting line) and second (donor plant line that comprises a transgene of the invention) parent plants;
  (b) grow the seeds of the first and second parent plants into plants that bear flowers;
  (c) pollinate a flower from the first parent plant with pollen from the second parent plant; and
  (d) harvest seeds produced on the parent plant bearing the fertilized flower.

Backcrossing is herein defined as the process including the steps of:
  (a) crossing a plant of a first genotype containing a desired gene, DNA sequence or element to a plant of a second genotype lacking the desired gene, DNA sequence or element;
  (b) selecting one or more progeny plant containing the desired gene, DNA sequence or element;
  (c) crossing the progeny plant to a plant of the second genotype; and
  (d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

V. Definitions

As used herein, accessions AT3G56130, AT1G52670, and AT3G15690 are intended to refer to BADC1, BADC2, and BADC3, respectively.

As used herein, $\alpha$-CT refers to AT2G38040; $\beta$-CT refers to ATCG00500; BC refers to AT5G35360; BCCP1 refers to AT5G16390; BCCP2 refers to AT5G15530; BADC1 refers to AT3G56130; BADC2 refers to AT1G52670; and BADC3 refers to AT3G15690.

Endogenous: A sequence natively found in a host cell or a cell of the same species. In one embodiment, an endogenous sequence may be overexpressed or expressed at a higher level compared to wildtype and still be considered endogenous.

Expression: The combination of intracellular processes, including transcription and translation, undergone by a coding DNA molecule such as a structural gene to produce a polypeptide.

Genetic Transformation: A process of introducing a DNA sequence or construct (e.g., a vector or expression cassette) into a cell or protoplast in which that exogenous DNA is incorporated into a chromosome or is capable of autonomous replication.

Heterologous: A sequence which is not normally present in a given host genome in the genetic context in which the sequence is currently found. In this respect, the sequence may be native to the host genome, but be rearranged with respect to other genetic sequences within the host sequence. For example, a regulatory sequence may be heterologous in that it is linked to a different coding sequence relative to the native regulatory sequence. In addition, a particular sequence can be "heterologous" with respect to a cell or organism into which it is introduced (for example, a sequence that does not naturally occur in that particular cell or organism).

Obtaining: When used in conjunction with a transgenic plant cell or transgenic plant, obtaining means either transforming a non-transgenic plant cell or plant to create the transgenic plant cell or plant, or planting transgenic plant seed to produce the transgenic plant cell or plant. Such a transgenic plant seed may be from an $R_0$ transgenic plant or may be from a progeny of any generation thereof that inherits a given transgenic sequence from a starting transgenic parent plant.

Promoter: A recognition site on a DNA sequence or group of DNA sequences that provides an expression control element for a structural gene and to which RNA polymerase specifically binds and initiates RNA synthesis (transcription) of that gene.

$R_0$ transgenic plant: A plant that has been genetically transformed or has been regenerated from a plant cell or cells that have been genetically transformed.

Regeneration: The process of growing a plant from a plant cell (e.g., plant protoplast, callus, or explant).

Selected DNA: A DNA segment which one desires to introduce or has introduced into a plant genome by genetic transformation.

Transformation construct: A chimeric DNA molecule designed for introduction into a host genome by genetic transformation. Preferred transformation constructs will comprise all of the genetic elements necessary to direct the expression of one or more exogenous genes. In particular embodiments of the instant invention, it may be desirable to introduce a transformation construct into a host cell in the form of an expression cassette.

Transformed cell: A cell in which the DNA complement has been altered by the introduction of an exogenous DNA molecule into that cell.

Transgene: A segment of DNA which has been incorporated into a host genome or is capable of autonomous replication in a host cell and is capable of causing the expression of one or more coding sequences. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

Transgenic plant: A plant or progeny plant of any subsequent generation derived therefrom, wherein the DNA of the plant or progeny thereof contains an introduced exogenous DNA segment not naturally present in a non-transgenic plant of the same strain. The transgenic plant may additionally contain sequences which are native to the plant being transformed, but wherein the "exogenous" gene has been altered in order to alter the level or pattern of expression of the gene, for example, by use of one or more heterologous regulatory or other elements.

Vector: A DNA molecule designed for transformation into a host cell. Some vectors may be capable of replication in a host cell. A plasmid is an exemplary vector, as are expression cassettes isolated therefrom.

The description herein is merely exemplary in nature and, thus, variations that do not depart from the gist of that which is described are intended to be within the scope of the teachings. Such variations are not to be regarded as a departure from the spirit and scope of the teachings.

EXAMPLES

The following examples are included to demonstrate preferred embodiments of the invention. It should be appreciated by those of skill in the art that the techniques disclosed in the examples, which follow represent techniques discovered by the inventor to function well in the practice of the invention, and thus can be considered to constitute preferred modes for its practice. However, those of skill in the art should, in light of the present disclosure, appreciate that many changes can be made in the specific embodiments, which are disclosed and still obtain a like or similar result without departing from the spirit and scope of the invention.

Example 1

Two Novel Proteins, BADC1 and BADC2, Co-Immunoprecipitate with hetACCase

To discover unknown protein interactors with the hetACCase, quantitative co-immunoprecipitation (co-IP) analyses were performed. Wild type *A. thaliana* (ecotype-Columbia-0) were grown in a growth chamber with long-day (16 h, 23° C., 50% humidity, 50 pmol m$^{-2}$ s$^{-1}$) and short-night (8 h, 20° C., 50% humidity) conditions. For co-immunoprecipitation studies, 8.5 cm×8.5 cm pots were filled with moist soil (Sunshine Mix #6, Sun Gro Horticulture), covered with screen (1 mm$^2$ pore size), and coated with seeds.

For co-immunoprecipitation of hetACCase from *Arabidopsis* seedlings, crude chloroplasts were isolated from approximately 10 g 14-d-old *A. thaliana* seedlings after 1 h light exposure. Fresh leaves were homogenized in ice-cold grinding buffer (50 mM HEPES-KOH pH 8.0, 330 mM sorbitol, 1.5 mM MnCl$_2$, 2 mM MgCl$_2$, 2 mM EDTA, 0.1% (w/v) BSA) using a Waring blender. Homogenate was filtered through two layers of Miracloth and centrifuged at 2,600 g at 4° C. for 20 min. Chloroplasts were lysed for 30 min in ice-cold lysis buffer (50 mM HEPES-KOH pH 8.0, 10% (v/v) glycerol, 0.5% (v/v) Triton X-100). Lysates were homogenized ten times in a Dounce homogenizer on ice and then centrifuged at 30 k g for 20 min at 4° C. Then, 1 mL of the 30 k g supernatant was added to 25 µL Protein A-Sepharose beads (Sigma Aldrich) either uncoated (control) or coated with antibody specific for α-CT, BCCP, BADC1, or BADC2. Co-immunoprecipitations (co-IP) were carried out at 4° C. for 3 h with gentle mixing. The heads were washed twice with 1 mL ice-cold lysis buffer and precipitated protein was eluted by adding 30 µL 6×SDS sample buffer (350 mM Tris-HCl, pH 6.8, 350 mM SDS, 30% (v/v) glycerol, 100 mM dithiothreitol, 2.5 mM bromophenol blue) and heating at 65° C. for 10 min. Eluted proteins were resolved on 10% SDS-PAGE gels for western and mass spectrometry analysis.

As described in detail above, clarified chloroplast lysates from 14-d-old *A. thaliana* seedlings were incubated with Protein A-Sepharose beads coated with polyclonal antibodies to either BCCP2 or α-CT. Control precipitations were performed using uncoated beads. Precipitated proteins were identified by LC-MS/MS analysis of trypsin-digested peptides.

For mass spectrometry, sample preparation and analysis was as follows. Precipitated proteins from co-IPs were resolved by 10% SDS-PAGE and stained with colloidal Coomassie Brilliant Blue (CBB) G-250. Each lane was separated into 0.5 cm segments and subsequently diced into approximately 1 mm$^3$ gel pieces. Gel pieces were digested with sequencing-grade trypsin and peptides were extracted according to methods known in the art. Tryptic peptides were lyophilized and stored at −20° C. until analysis by liquid chromatography-tandem mass spectrometry (LC-MS/MS). Lyophilized peptides were prepared for mass spectrometry analysis as described previously. Samples were analyzed on a LTQ Orbitrap XL ETD (Thermo Fisher Scientific) according to Swatek et al., (*Biochem J* 459(1): 15-25, 2014), with the exception that peptides were eluted using a 30 min acetonitrile gradient (5-43% acetonitrile), the top 8 masses from the precursor scan were selected for data-dependent acquisition, and precursor ions were fragmented using CID (collision-induced dissociation). Dynamic exclusion was enabled with the following settings: repeat count, 3; repeat duration, 30 s; exclusion list, 50; and exclusion list duration, 30 s.

Acquired spectra were searched against the TAIR10 protein database (70,773 entries, downloaded on Jun. 11, 2012), concatenated to a randomized TAIR10 database as a decoy. Search parameter settings of SEQUEST were static modification of cysteine-carboxyamidomethylation and variable modification of methionine-oxidation. Other search parameter settings of SEQUEST included two missed tryptic cleavage sites, absolute threshold: 1000, minimum ion count: 10, mass range: 650-3500, and a parent and fragment ion tolerance of 1 Da and 1000 ppm, respectively. Search result files were loaded into Proteome Discoverer 1.3 (Thermo Fisher Scientific). Identified peptides were filtered to <1% false discovery rate using the following criteria: 10 ppm peptide mass deviation, 'Xcorr versus charge state', and 2 and 1 peptide minimum for co-IPs and 2D BN-SDS PAGE, respectively. Protein grouping was also enabled. False discovery rate was calculated manually using spectral counting. Files generated for each biological replicate by Proteome Discoverer 1.3 were exported into Microsoft Excel for further analysis.

Proteins identified from SEQUEST searches were compared against uncoated Sepharose bead controls that had been treated in an identical manner to the hetACCase subunit co-IPs. Proteins that were only identified in the hetACCase subunit co-IPs were considered as putative interacting clients. All other proteins were disregarded. The hetACCase subunits were never identified in controls.

Quantitative mass spectrometry of these co-IPs revealed all four known subunits to ACCase and two unknown proteins annotated as 'biotin/lipoyl attachment domain containing' (BADC) proteins. From seven biological replicates of the α-CT co-IPs, the entire hetACCase complex was identified. Likewise, all subunits, except β-CT, were identified from co-IPs with antibodies to BCCP2 (FIGS. 1A and 1B). As expected, the BC/BCCP and α/β-CT subcomplexes were relatively higher in abundance in the BCCP2 and α-CT co-IPs, respectively. Additionally, two unknown proteins with a "biotin attachment domain-containing" region, hereafter termed BADC1 (AT3G56130) and BADC2 (AT1G52670), were identified from both co-IPs. The BADC1 protein was present in seven and one replicate of the BCCP2 and α-CT co-IPs, respectively, while BADC2 was present in six and two replicates of the BCCP2 and α-CT co-IPs, respectively. The normalized, relative abundance of these proteins was more commensurate with BC and BCCP abundance than α- and β-CT from both co-IP analyses. Reciprocal co-IPs using antibodies specific to BADC1 and BADC2 precipitated both BCCP isoforms (FIGS. 1C and 1D). Thus, BADC1 and BADC2 appear to interact with the BC/BCCP components of hetACCase.

Example 2

Recombinant Protein Expression and Purification and Immunoblotting

The ORFs of BCCP1, BCCP2, BADC1, BADC2, and BADC3 were amplified via PCR from a cDNA clone (ABRC). The primer pairs for these amplifications were the same as those used in the yeast two-hybrid construct formation (FIG. 2). These primers were designed to remove the transit peptide, as predicted by TargetP. The amplified ORF of all five genes were cloned into either the expression vector pET28a or pET11a producing an N-terminal His-tagged fusion protein or an untagged recombinant protein, respectively. All constructs were sequence confirmed via DNA sequencing. Constructs were then transformed into *E. coli* strain BL21 (B2685: Sigma). Recombinant protein was expressed and purified from transformed BL21 cells as described in Swatek et al., *J Proteome Res* 10(9):4076-4087, 2011). For co-expression studies, ~200 ng of each plasmid was used to transform BL21 cells.

Proteins resolved by SDS-PAGE were transferred to PVDF membrane and stained with the appropriate primary antibody overnight at 4° C. for western blot analysis. All antibodies were used at 1:5000 dilution in PBS-T (10 mM $NaH_2PO_4$—NaOH pH 7.2, 150 mM NaCl, 0.3% (v/v) Tween 20). hetACCase antibodies used in this study were derived from rabbits immunized with recombinant *P. sativum* α-CT, recombinant *A. thaliana* BCCP2, or recombinant *A. thaliana* BADC1. Blots were rinsed twice in PBS-T and probed in secondary antibody for 1 h at room temperature and developed. Goat anti-rabbit IgG secondary antibody conjugated to alkaline phosphatase was obtained from Sigma-Aldrich (St. Louis, MO).

Example 3

Orthogonal Approaches Confirm a Direct Interaction Between Three BADC and Two BCCP Isoforms from *Arabidopsis*

Yeast two-hybrid construct design. The ORF of genes of interest were inserted into bait and prey vectors PGBKT7 and pGADT7. Primers were designed to exclude the transit peptide from the coding region, as predicted by TargetP (FIG. 2). Genes were amplified from cDNA clones obtained from the *Arabidopsis* Biological Resource Center Amplicons were first inserted into Zero Blunt TOPO vector (Life Technologies) and checked for errors by DNA sequencing. Error-free amplicons were then subcloned into either pGBKT7 or pGADT7 vector. Completed constructs were transformed into competent DH5α cells. Cells transformed with pGBKT7 and pGADT7 were grown on LB media agar plates containing 50 pg/mL kanamycin (Kan) and 100 pg/mL ampicillin (Amp), respectively. Plasmids were purified from 5 mL culture of positive colonies using QIAprep Spin Miniprep kit (Qiagen).

To confirm the co-IP results and determine which hetACCase subunit directly interacts with BADC1 and BADC2, targeted yeast two-hybrid analysis was employed using an adaptation of the lithium acetate method. Strain AH109 yeast were transformed with 100 ng of bait and prey vector. Pelleted transformed cells were resuspended in 300 μL sterile water. Aliquots of 100 μL cell suspension were plated on synthetic dropout (SD) media lacking leucine, tryptophan, and histidine. Plates were incubated at 30° C. for 4 d and then imaged. Images shown are representative of at least three replicate studies.

Figure 3:
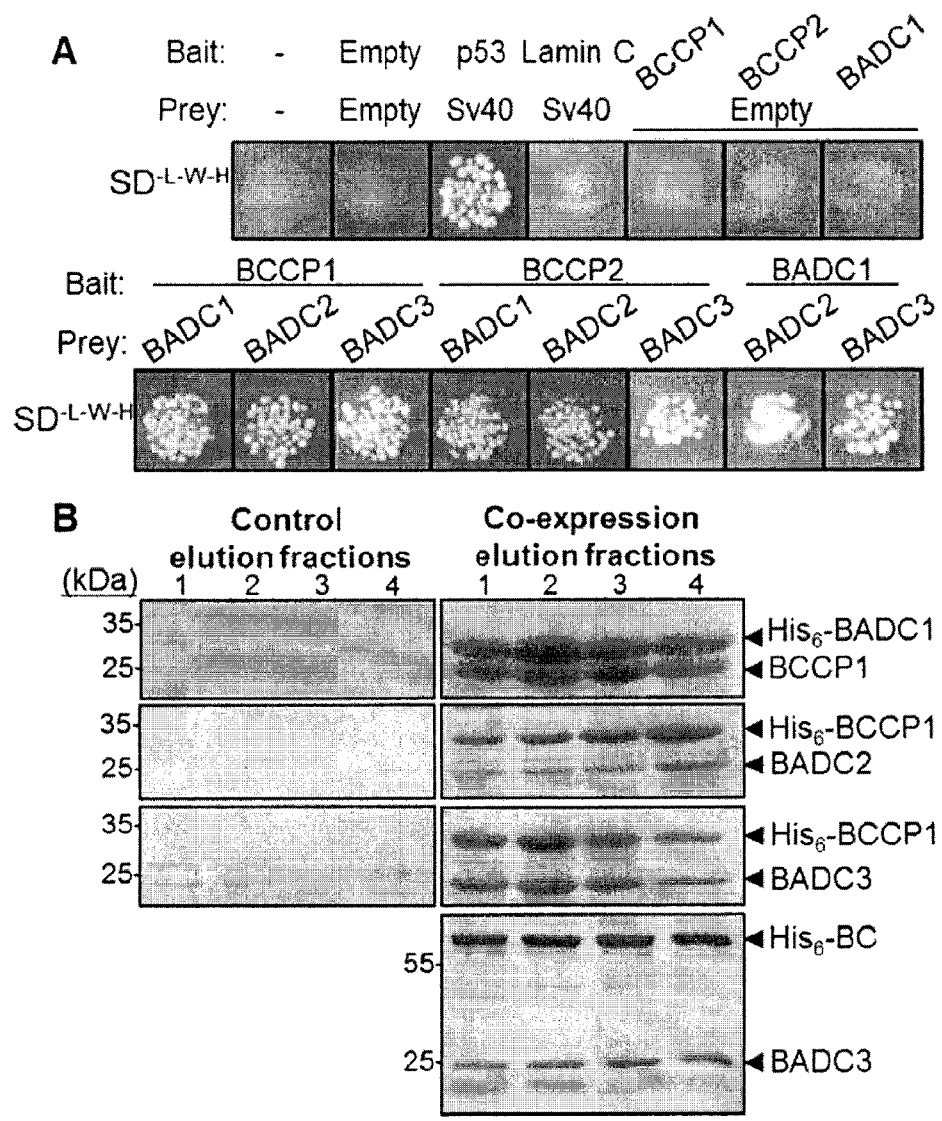
FIG. 3—Shows the direct interaction of BADC proteins with BCCP subunits of ACCase. (A) Strain AH109 yeast was transformed with bait and prey constructs containing the genes shown. Negative controls showed minimal or no growth. Sv40 and p53 were used as positive controls. Lamin C was used as a negative control. Transformed yeast were plated on media lacking Trp, Leu, and His. Results shown are representative of three biological replicates. (B) Coomassie-stained gels showing the elution fractions of $Ni^{2+}$-NTA-purified protein from *E. coli*. At right, a native protein was co-expressed with a $His_6$-tagged protein. At left, the native protein was expressed alone. The native proteins were present strongly in the elution fractions only when co-expressed with the $His_6$-tagged protein. Protein identities were confirmed by LC-MS/MS.

In addition to the two experimentally-identified BADCs a third, putative BADC isoform was also tested, termed BADC3 (AT3G15690), identified by BLAST interrogation of the *A. thaliana* genome. This protein shares 61% amino acid identity with BADC2, suggesting it might have similar function. Based upon yeast two hybrid analyses, each of the three BADC proteins interacted with each BCCP isoform. As shown in FIG. 3A, strain AH109 yeast was transformed with bait and prey constructs containing the genes shown.

Negative controls showed minimal or no growth. Sv40 and p53 were used as positive controls. Transformed yeast were plated on media lacking Trp, Leu, and His. Results shown are representative of three biological replicates. Additionally, each of the BADC isoforms interacts with one another.

To further evaluate the interaction between BADC and BCCP, *A. thaliana* BCCP1 was co-expressed with each of the three *A. thaliana* BADC proteins in *E. coli*. In these studies, either the BADC or BCCP1 protein was expressed with a $His_6$-tag, while the other contained no affinity tag. When the Hiss-tagged protein was purified by $Ni^{2+}$-NTA affinity chromatography, the respective "untagged" protein was present in the same elution fractions. In FIG. 3B, the Coomassie-stained gels show the elution fractions of $Ni^{2+}$-NTA-purified protein from *E. coli*. At right, a native protein was co-expressed with a $His_6$-tagged protein. At left, the native protein was expressed alone. The native proteins were present strongly in the elution fractions only when co-expressed with the $His_6$-tagged protein. Protein identities were confirmed by LC-MS/MS. These studies were performed to test if the BADC proteins can interact directly with ACCase. The results confirm the BADC proteins associate with ACCase via a direct interaction with the BCCP and BC subunits. As a control, it was verified that untagged proteins were unable to bind to the affinity column. Using this system, it was observed that *A. thaliana* BC and BADC3 also co-purified, suggesting that BADC3, and likely BADC1 and 2, may also interact with BC. These studies confirm BADC isoforms directly interact with the BCCP and BC subunits of hetACCase.

Example 4

Biotin is not Required for BADC-BCCP Interaction

To determine if the BCCP-BADC interaction involves the biotin cofactor, as previously reported for PII interaction with hetACCase, the biotinyl Lys245 residue on BCCP1 was mutated to Arg by site-directed mutagenesis. This mutation prevents biotinylation of BCCP1. Using this 'apo-BCCP1', the yeast two-hybrid and co-expression analysis was repeated with BADCs. All BADC isoforms were shown to interact with apo-BCCP1.

Example 5

Recombinant AtBADC1 and AtBADC3 Form Homodimers Through a Disulfide Bond

Previous analysis of *E. coli* BCCP suggested that this subunit forms functional homodimers in vivo. Through intact mass analysis of purified recombinant BCCP2, it was observed that plant BCCP can also form homodimers. In addition, analysis of recombinant BADCs showed that BADC1 and BADC3, but not BADC2, can form homodimers. The observed monomer size for each BADC was in agreement with the predicted mass, suggesting these proteins are unmodified. In the absence of DTT, purified recombinant BCCP2, BADC1, and BADC3 show a monomer and dimer band when denatured and resolved by SDS-PAGE. Recombinant BADC2 shows only a monomer band. Increasing DTT concentration led to the disappearance of the dimer band, suggesting a disulfide bond is involved in dimer formation of BADCs and plant BCCPs.

Example 6

BADCs Resemble BCCPs but are not Biotinylated

Figure 5:
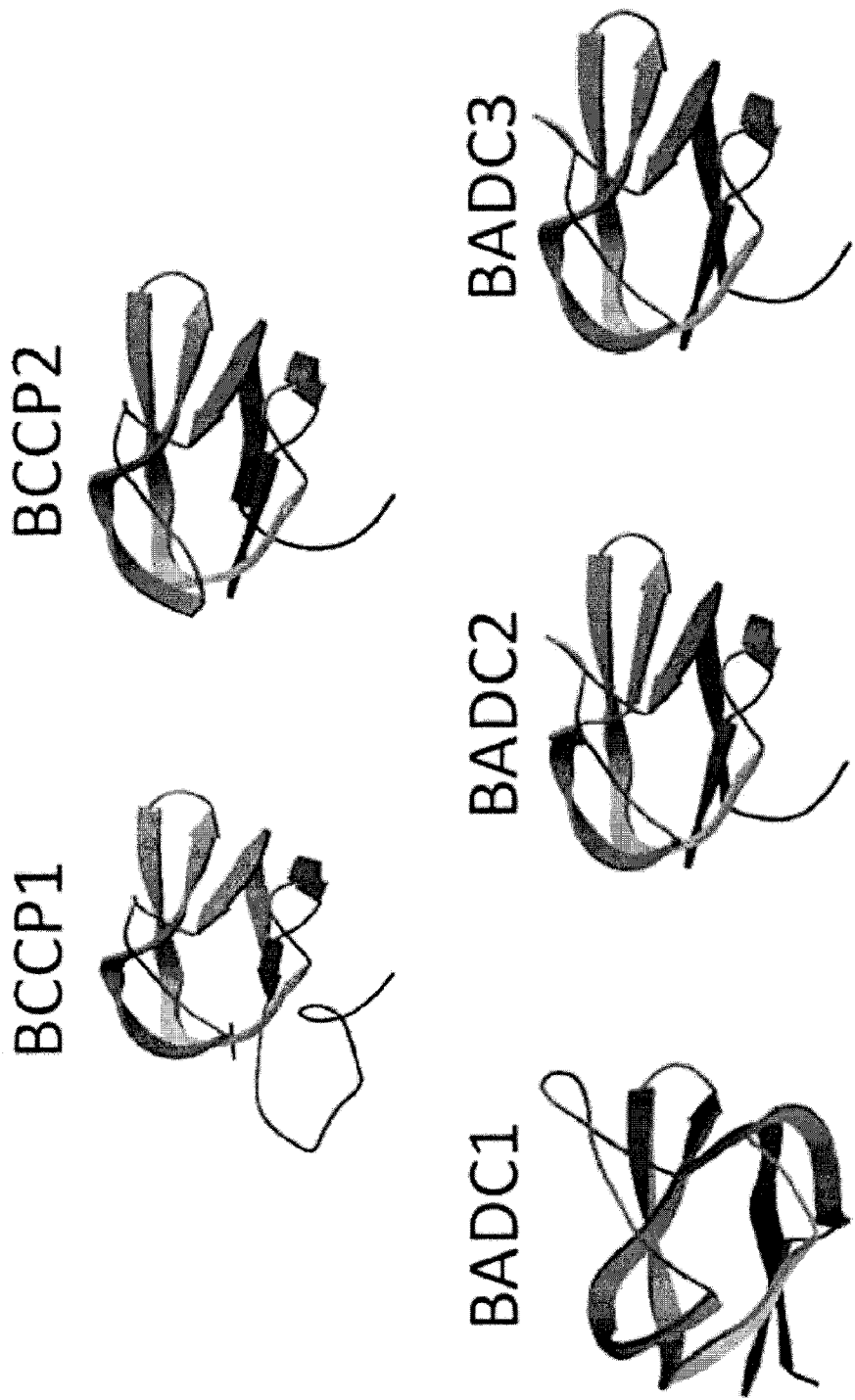
FIG. 5—Shows predicted structures of BADC proteins resemble BCCP subunits of ACCase in *Arabidopsis thaliana*. Structures of each protein were generated using SWISS-MODEL. Protein sequences lacking the predicted transit peptide residues were used as the input.

The three BADC isoforms share many characteristics with the two BCCP isoforms from *A. thaliana*. First, these proteins contain a canonical plastid target peptide and are plastid localized based upon bioinformatic predictions, co-IP, and western blot studies. Secondly, the BADC isoforms share 24 to 29% amino acid identity with the BCCP isoforms (FIG. 4). Last, structural predictions of the BADC and BCCP proteins (FIG. 5) show similar β-sheet secondary structure with a characteristic "thumb motif" as previously observed for the *E. coli* BCCP. Intact mass analysis showed that BADC proteins are able to form homodimers.

Despite these similarities, the BADC proteins lack the canonical biotinylation motif. As shown in FIG. 6A, the alignment of the C-termini of the *Arabidopsis thaliana* BCCP1 and BCCP2 and BADC proteins (BADC1, BADC2, and BADC3) shows multiple conserved residues (shown in bold). The canonical biotinylation motif containing the biotinyl Lys in BCCP1/2 is shown boxed in on lines 1 and 2 of the sequence alignment. The alignment comparison indicates the BADC proteins resemble BCCP isoforms but lack a canonical biotinylation motif. The tetrapeptide (Ala-Nal)-Met-Lys-(Met/Leu) is the known biotinylation motif and is usually located 34 or 35 residues from the C-terminus. The BADC proteins do, however, possess a conserved Lys residue in a similar (Val/Ile)-(LeuNal)-Lys-(Leu/Ile) motif located near the C-terminus suggesting the possibility of a non-canonical biotinylation motif.

Figures 6B, 6C:
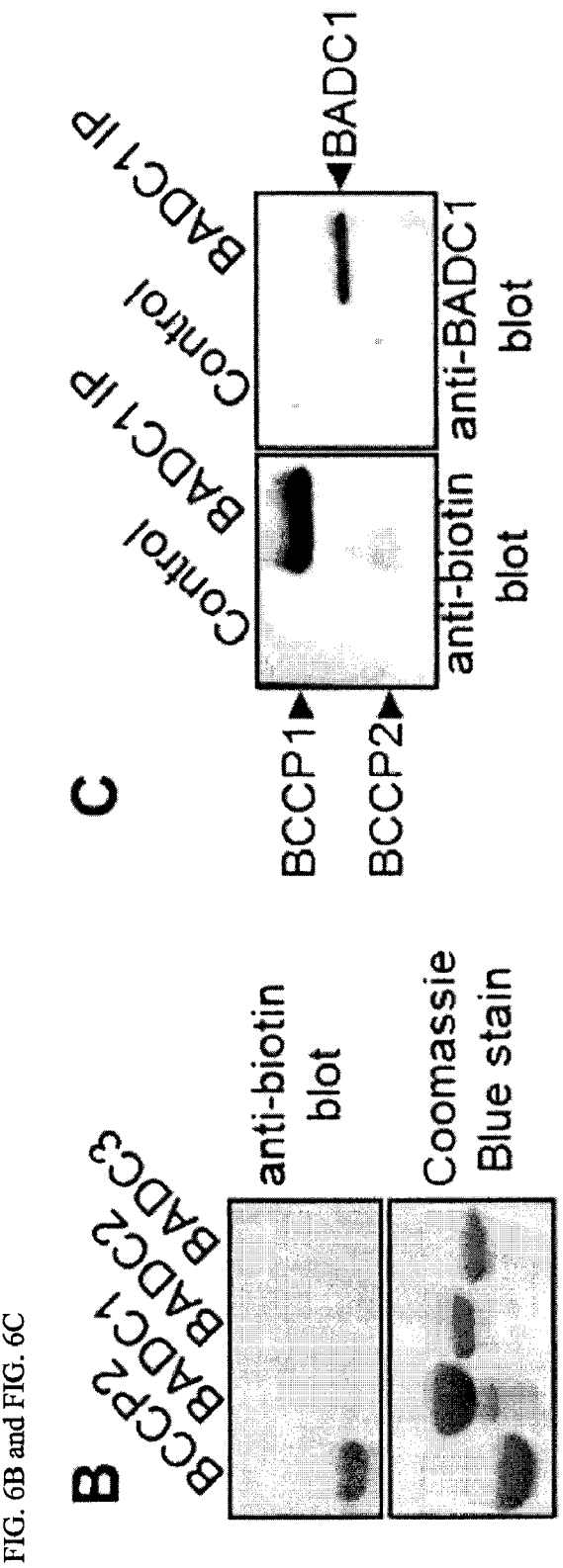
FIG. 6B and FIG. 6C—Show differences in biotinylation between the BCCP and BADC proteins, illustrating that the BADC proteins resemble BCCP isoforms but are not biotinylated. (B) Western blotting analysis of recombinant *Arabidopsis* proteins using a biotin-specific antibody. BCCP2 was observed to be biotinylated while the BADCs were not. (C) Protein blot analysis of immunoprecipitated in vivo BADC1 from *Arabidopsis* seedlings. Blotting precipitate with BADC1-specific antibody showed the presence BADC1 in the sample, while blotting with biotin-specific antibody showed no recognition of BADC1.

To test this possibility, recombinant BADC proteins expressed in *E. coli* and the native BADC1 protein from *A. thaliana* seedlings were purified and probed for biotinylation using a biotin-specific antibody. As shown in FIG. 6B, based on the western blotting analysis of recombinant *Arabidopsis* proteins using a biotin-specific antibody, BCCP2 is observed to be biotinylated, while the BADCs are not. As shown in FIG. 6C, which is the protein blot analysis of immunoprecipitated in vivo BADC1 from *Arabidopsis* seedlings, blotting precipitate with BADC1-specific antibody shows the presence BADC1 in the sample, while blotting with biotin-specific antibody shows no recognition of BADC1. Results of these studies confirmed that the BADC proteins are not biotinylated in vivo, although BCCP controls clearly were.

Example 7

BADC Orthologs are Present in Green Algae and Land Plants but not Bacteria

Identification of BADC orthologs and co-occurrence analysis suggests BADCs first appeared in red algae. The evidence of a direct BADC-BCCP interaction suggests that BADC function is linked to hetACCase. If true, orthologs to *A. thaliana* BADCs (AtBADC) would be expected to reside only in organisms that contain hetACCase, not the homomeric form that predominates in eukaryotes. To search for the presence of AtBADC orthologous proteins, the primary sequence of each AtBADC was used to search against the KEGG Sequence Similarity database. Putative orthologs were confirmed by reciprocal BLAST searches against the *A. thaliana* proteome. All AtBADC orthologs lacked the conserved biotinyl Lys found in BCCPs. Orthologous proteins were identified for AtBADCs across 78 different species of land plants and algae (Table 1). The full-length protein sequences of identified AtBADC orthologs were used to generate a maximum-likelihood phylogenetic tree. All of the species that harbor a putative AtBADC ortholog also contain the heteromeric form of ACCase. No orthologs were detected in organisms that contain only the homomeric ACCase. Additionally, no AtBADC orthologs were detected in prokaryotes, which also contain a hetACCase. The presence of orthologs in algae but not prokaryotes suggests that BADCs first appeared in algae.

TABLE 1

Orthologous proteins identified for AtBADC1, AtBADC2, and AtBADC3.

| Species | Category | BCCP1 | BCCP2 | BADC1 | BADC2 | BADC3 |
|---|---|---|---|---|---|---|
| Amborella trichopoda | Flowering Plants | XP_011621081.1 | N/A | XP_011627066.1 | N/A | XP_011622803.1 |
| Arabidopsis lyrata subsp. lyrata | Eudicots | XP_002873773.1 | XP_002871669.1 | XP_002876350.1 | XP_002894393.1 | XP_002882958.1 |
| Arabidopsis thaliana | Eudicots | NP_197143.1 | NP_568316.1 | NP_567035.1 | NP_564612.1 | NP_188190.1 |
| Arabis alpina | Eudicots | KFK25879.1 | KFK25777.1 | KFK34856.1 | N/A | KFK38917.1 |
| Arachis duranensis | Eudicots | XP_015962701.1 | XP_015946097.1 | XP_015944188.1 | N/A | XP_015933506.1 |
| Arachis ipaensis | Eudicots | XP_016194346.1 | XP_016181644.1 | XP_016181047.1 | N/A | XP_016170604.1 |
| Auxenochlorella protothecoides | Green Algae | XP_011398894.1 | N/A | N/A | N/A | XP_011395766.1 |
| Beta vulgaris subsp. vulgaris | Eudicots | XP_010679318.1 | N/A | XP_010692910.1 | N/A | XP_010691182.1 |
| Brachypodium distachyon | Monocots | N/A | N/A | N/A | N/A | N/A |
| Brassica napus | Eudicots | XP_013663621.1 | XP_013728269.1 | XP_013663447.1 | N/A | XP_013645085.1 |
| Brassica oleracea var. oleracea | Eudicots | XP_013625183.1 | XP_013621850.1 | XP_013605292.1 | N/A | XP_013585896.1 |
| Brassica rapa | Eudicots | XP_009131537.1 | XP_009131471.1 | XP_009116310.1 | N/A | XP_009115305.1 |
| Cajanus cajan | Eudicots | KYP60383.1 | N/A | KYP44948.1 | N/A | KYP59593.1 |
| Camelina sativa | Eudicots | XP_010453799.1 | XP_010453692.1 | XP_010504497.1 | XP_010479781.1 | XP_010465548.1 |
| Capsella rubella | Eudicots | XP_006286538.1 | XP_006288243.1 | N/A | XP_006305526.1 | XP_006298142.1 |
| Capsicum annuum | Eudicots | XP_016573862.1 | N/A | XP_016575440.1 | N/A | XP_016578500.1 |
| Chlamydomonas reinhardtii | Green Algae | N/A | XP_001700442.1 | N/A | N/A | XP_001690119.1 |
| Chlorella variabilis | Green Algae | N/A | XP_005850451.1 | N/A | N/A | XP_005845403.1 |
| Cicer arietinum | Eudicots | XP_012569122.1 | N/A | XP_004500525.1 | N/A | XP_004486692.1 |
| Citrus clementina | Eudicots | N/A | XP_006431277.1 | XP_006435833.1 | N/A | XP_006427204.1 |
| Citrus sinensis | Eudicots | N/A | XP_006482733.1 | XP_006486239.1 | N/A | XP_006465373.1 |
| Coccomyxa subellipsoidea C-169 | Green Algae | N/A | XP_005649768.1 | N/A | N/A | XP_005646014.1 |
| Cucumis melo | Eudicots | N/A | XP_008456473.1 | XP_008441486.1 | N/A | XP_008461084.2 |
| Cucumis sativus | Eudicots | N/A | XP_004137199.1 | XP_011656420.1 | N/A | XP_004135840.1 |
| Daucus carota subsp. sativus | Eudicots | KZM82431.1 | N/A | KZM80059.1 | N/A | KZM88409.1 |
| Dorcoceras hygrometricum | Eudicots | KZV23283.1 | N/A | KZV16809.1 | N/A | N/A |
| Elaeis guineensis | Monocots | XP_010936329.1 | N/A | XP_010938420.1 | N/A | XP_010921048.1 |
| Elythranthe guttata | Eudicots | XP_012834625.1 | XP_012844390.1 | XP_012858601.1 | N/A | XP_012856758.1 |
| Eucalyptus grandis | Eudicots | XP_010038361.1 | XP_010032526.1 | XP_010067567.1 | N/A | XP_010033940.1 |
| Eutrema salsugineum | Eudicots | XP_006400177.1 | XP_006400073.1 | XP_006403020.1 | XP_006392894.1 | XP_006406933.1 |
| Fragaria vesca subsp. vesca | Eudicots | N/A | XP_004304236.1 | XP_004307696.1 | N/A | XP_004302964.1 |
| Genlisea aurea | Eudicots | EPS63946.1 | N/A | N/A | EPS63437.1 | N/A |
| Glycine max | Eudicots | N/A | XP_003543944.1 | XP_006590336.1 | N/A | XP_003543673.1 |
| Glycine soja | Eudicots | KHN13569.1 | N/A | KHN04794.1 | N/A | KHN44161.1 |
| Gonium pectorale | Green Algae | N/A | KXZ51015.1 | N/A | N/A | KXZ55249.1 |
| Gossypium arboreum | Eudicots | KHG03380.1 | KHG02691.1 | N/A | KHG02291.1 | N/A |
| Gossypium hirsutum | Eudicots | XP_016683408.1 | XP_016752201.1 | XP_016724217.1 | N/A | N/A |
| Gossypium raimondii | Eudicots | XP_012451021.1 | N/A | XP_012462883.1 | N/A | XP_012454990.1 |
| Helicosporidium sp. ATCC 50920 | Green Algae | KDD76354.1 | N/A | N/A | N/A | KDD73528.1 |
| Jatropha curcas | Eudicots | XP_012085783.1 | XP_012084810.1 | XP_012086589.1 | N/A | XP_012073227.1 |
| Klebsormidium flaccidum | Green Plants | N/A | GAQ84037.1 | N/A | N/A | GAQ80014.1 |
| Malus domestica | Eudicots | N/A | XP_008379410.1 | XP_008374383.1 | N/A | N/A |
| Marchantia polymorpha subsp. polymorpha | Liverworts | OAE20385.1 | N/A | N/A | N/A | OAE28621.1 |
| Medicago truncatula | Eudicots | XP_003624197.1 | N/A | XP_003616717.1 | N/A | XP_003597852.2 |
| Morus notabilis | Eudicots | N/A | XP_010089617.1 | XP_010087032.1 | XP_010097264.1 | N/A |
| Musa acuminata subsp. malaccensis | Monocots | XP_009394324.1 | N/A | XP_009418932.1 | N/A | N/A |
| Nelumbo nucifera | Eudicots | XP_010259375.1 | N/A | XP_010250846.1 | N/A | XP_010254348.1 |
| Nicotiana sylvestris | Eudicots | XP_009759359.1 | N/A | XP_009785832.1 | XP_009787427.1 | N/A |
| Nicotiana tabacum | Eudicots | XP_016465895.1 | XP_016481002.1 | XP_016473105.1 | N/A | XP_016514334.1 |
| Nicotiana tomentosiformis | Eudicots | XP_009588294.1 | XP_009616596.1 | XP_009618778.1 | N/A | XP_009628995.1 |
| Phaseolus vulgaris | Eudicots | XP_007139713.1 | N/A | XP_007163588.1 | N/A | XP_007150717.1 |
| Phoenix dactylifera | Monocots | XP_008805110.1 | N/A | XP_008789922.1 | N/A | XP_008809725.1 |
| Physcomitrella patens | Mosses | N/A | XP_001754932.1 | N/A | N/A | XP_001775667.1 |
| Populus euphratica | Eudicots | XP_011013398.1 | XP_011013434.1 | XP_011004753.1 | N/A | XP_011040023.1 |
| Populus trichocarpa | Eudicots | N/A | XP_002305399.1 | XP_002311250.1 | N/A | XP_002299605.2 |
| Prunus mume | Eudicots | XP_008240458.1 | N/A | XP_008233825.1 | XP_008228653.1 | N/A |
| Prunus persica | Eudicots | XP_007204703.1 | XP_007215770.1 | XP_007218764.1 | XP_007215787.1 | N/A |
| Pyrus x bretschneideri | Eudicots | N/A | XP_009360536.1 | XP_009369234.1 | XP_009349124.1 | XP_009348645.1 |
| Ricinus communis | Eudicots | XP_015572257.1 | XP_002526099.1 | XP_002520803.1 | N/A | XP_015573743.1 |
| Selaginella moellendoiffii | Club-Mosses | XP_002963883.1 | N/A | N/A | N/A | XP_002963889.1 |
| Sesamum indicum | Eudicots | N/A | XP_011072842.1 | XP_011084859.1 | N/A | XP_011072247.1 |
| Setaria italica | Monocots | N/A | N/A | N/A | N/A | N/A |
| Solanum lycopersicum | Eudicots | NP_001234322.1 | N/A | XP_004240889.1 | N/A | XP_004241703.1 |
| Solanum pennellii | Eudicots | XP_015076155.1 | N/A | XP_015080112.1 | N/A | XP_015079819.1 |
| Solanum tuberosum | Eudicots | XP_006345777.1 | N/A | XP_006353414.1 | N/A | XP_006356200.1 |
| Sorghum bicolor | Monocots | N/A | N/A | N/A | N/A | N/A |
| Spinacia oleracea | Eudicots | KNA11791.1 | N/A | KNA11168.1 | N/A | KNA24821.1 |
| Tarenaya hassleriana | Eudicots | XP_010558581.1 | XP_010551815.1 | XP_010534633.1 | XP_010535127.1 | N/A |

TABLE 1-continued

Orthologous proteins identified for AtBADC1, AtBADC2, and AtBADC3.

| Species | Category | BCCP1 | BCCP2 | BADC1 | BADC2 | BADC3 |
|---|---|---|---|---|---|---|
| *Theobroma cacao* | Eudicots | N/A | XP_007029252.1 | XP_007008844.1 | N/A | XP_007023903.1 |
| *Triticum urartu* | Monocots | N/A | N/A | N/A | N/A | N/A |
| *Vigna angularis* | Eudicots | N/A | KOM56589.1 | KOM39631.1 | N/A | KOM44575.1 |
| *Vigna radiata* var. *radiata* | Eudicots | N/A | XP_014523207.1 | XP_014494474.1 | N/A | XP_014498647.1 |
| *Vitis vinifera* | Eudicots | XP_010649227.1 | XP_002284374.1 | XP_002278151.2 | N/A | XP_002285378.1 |
| *Volvox carteri* f. *nagariensis* | Green Algae | N/A | XP_002952670.1 | N/A | N/A | XP_002954026.1 |
| *Zea mays* | Monocots | N/A | N/A | N/A | N/A | N/A |
| *Ziziphus jujuba* | Eudicots | XP_015875754.1 | XP_015879793.1 | XP_015877502.1 | N/A | XP_015868335.1 |
| *Zostera marina* | Monocots | N/A | KMZ60645.1 | KMZ56653.1 | KMZ55983.1 | N/A |
| *Gaidieria sulphuraria* | Red Algae | N/A | YP_009051081.1 | XP_005708748.1 | N/A | N/A |

To determine if BADCs arose from a previously functional BCCP in algae, co-occurrence analysis was performed. With the exception of two red algae and *Cyanophora paradoxa* all species contained AtBCCP and AtBADC orthologs. In red algae, only one putative AtBADC1 ortholog (GenBank ID: XP_005708748.1) was identified in the species *Galdieria sulphuraria*. This protein shares the same number of identical (31) and similar (46) amino acid residues with both AtBADC1 and AtBADC2, as well as 30 identical and 44 similar amino acid residues with AtBADC3. However, the BLAST search attributed the highest score to AtBADC1. In addition, two putative BCCP proteins were identified in the red algae species *Chondrus crispus* and *Cyanidioschyzon merolae* to lack the biotin motif residue but shared higher sequence similarity to AtBCCP2 than AtBADCs (GenBank ID XP_005715802.1 and XP_005535248.1, respectively), suggesting that BADCs originated from a BCCP gene duplication and loss-of-function mutation in red algae. From this observation, it appears not only that BADCs and BCCPs are related, but that the branch point between these proteins occurred in red algae, particularly since the more primitive glaucophytes contain no AtBADC orthologs.

Figure 7:
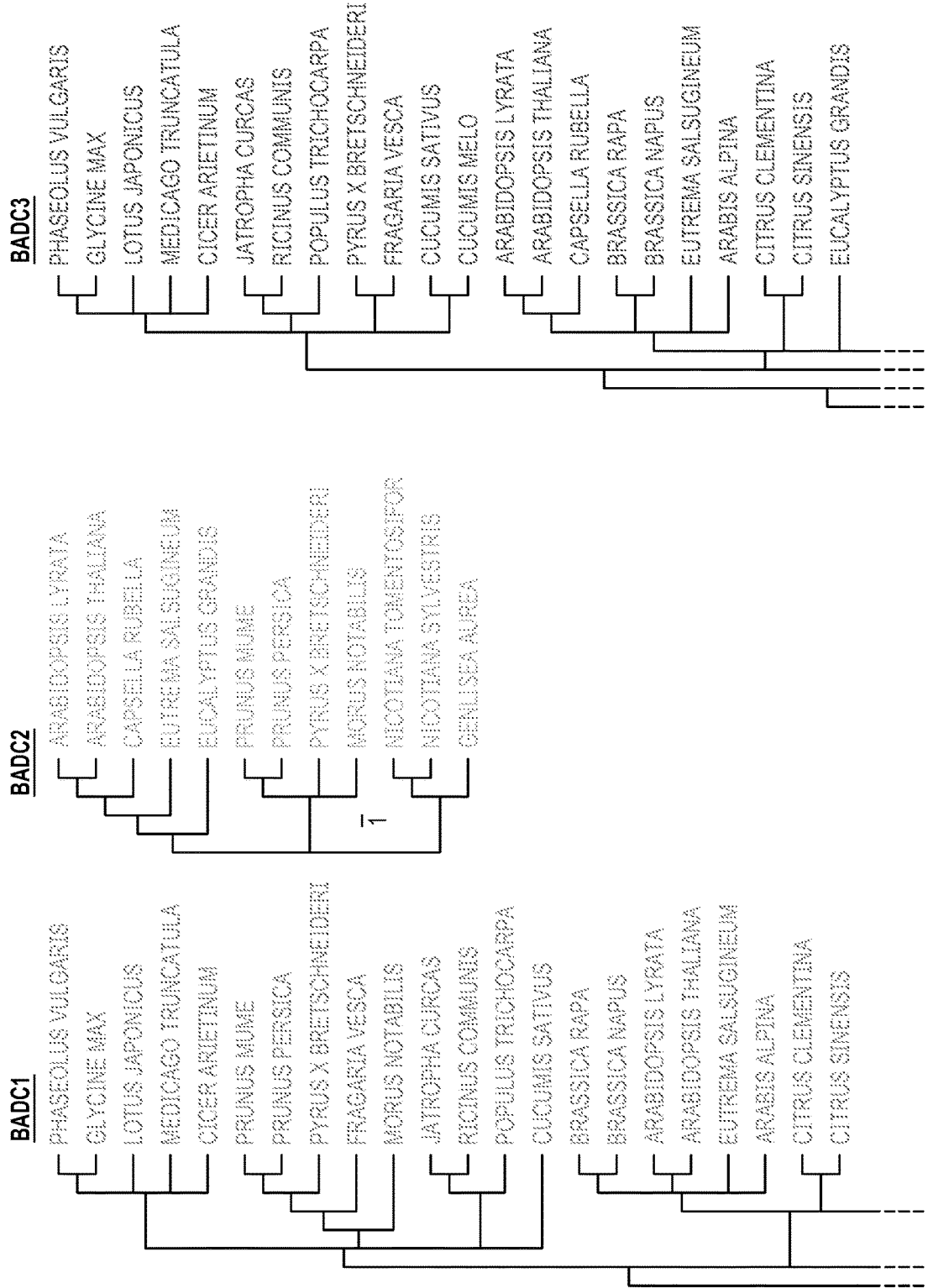
FIG. 7—Shows species containing orthologs of the *Arabidopsis thaliana* BADC proteins. Phylogenetic trees showing all species that were identified to contain an ortholog to one or more of the BADC proteins in *A. thaliana*. Ortholog candidates were identified by performing PSI-BLAST on the primary sequence of each BADC protein. Results were filtered by performing a reciprocal BLAST against the *A. thaliana* proteome. Species classification is indicated by color. All species identified contain heteromeric ACCase.

If BADC proteins are exclusive to acetyl-CoA carboxylases and not other acyl-CoA carboxylases, BADC protein orthologs would be found only in plant clades that contain hetACCase. To search for BADC ortholog-containing species, PSI-BLAST was performed using the primary sequence of each BADC from *A. thaliana*. Putative orthologs were confirmed by reciprocal BLAST searches against the *A. thaliana* proteome and all putative BADCs were manually confirmed to lack a conserved biotinyl Lys. FIG. 7 shows the phylogenetic tree of species containing an ortholog to all three BADCs. Orthologs to the *A. thaliana* BADCs were only observed in dicots, non-gramineous monocots, and green algae. The founding member of the family, BADC3, dates back to green algae. All of these plant clades contain a hetACCase. No BADC ortholog was detected in prokaryotes or gramineous monocots, the latter containing only the homomeric form of ACCase.

Example 8

BADC3 Expression Reduces hetACCase Activity in a Temperature-Sensitive *E. coli* Mutant Due to their similarity with BCCPs but lack of a conserved biotinylation motif, BADCs may be negative regulators of hetACCase activity. As *E. coli* contain hetACCase but lack BADC orthologs, this system was appropriate to test this theory. In vivo growth assays in *E. coli* accb strain L8 were performed to evaluate the potential the effect of the BADC proteins on hetACCase activity. This strain contains temperature-sensitive (Ts) mutations in the BCCP gene (accB) that prevent de novo FAS. Thus, cell growth at 37° C. is directly correlated to hetACCase activity when lacking an exogenous source of fatty acids. Experiments were performed in minimal media containing only glucose and glycerol as carbon sources. In brief, the temperature-sensitive (Ts) L8 strain *E. coli* was obtained from the *Coli* Genetic Stock Center (Yale, New Haven, CT) and transformed with the vectors in the text using the heat shock method. Transformants were selected by antibiotic resistance and confirmed by PCR. Prior to the growth experiment, cultures were grown overnight in LB media at 30° C. Overnight cultures were centrifuged at 3,000 g and resuspended in 5 mL sterile deionized water. Cultures were centrifuged again and resuspended in M63 minimal media to make OD600=3.75. Then 200 µL cell suspension was added to 7 mL M63 media plus antibiotics in 15 mL sterile culture tubes. Cultures contained Kan, and Amp if necessary, at 50 µg/mL each as well as 1 µM isopropyl β-D-1-thiogalactopyranoside at T=0.

Figure 8:
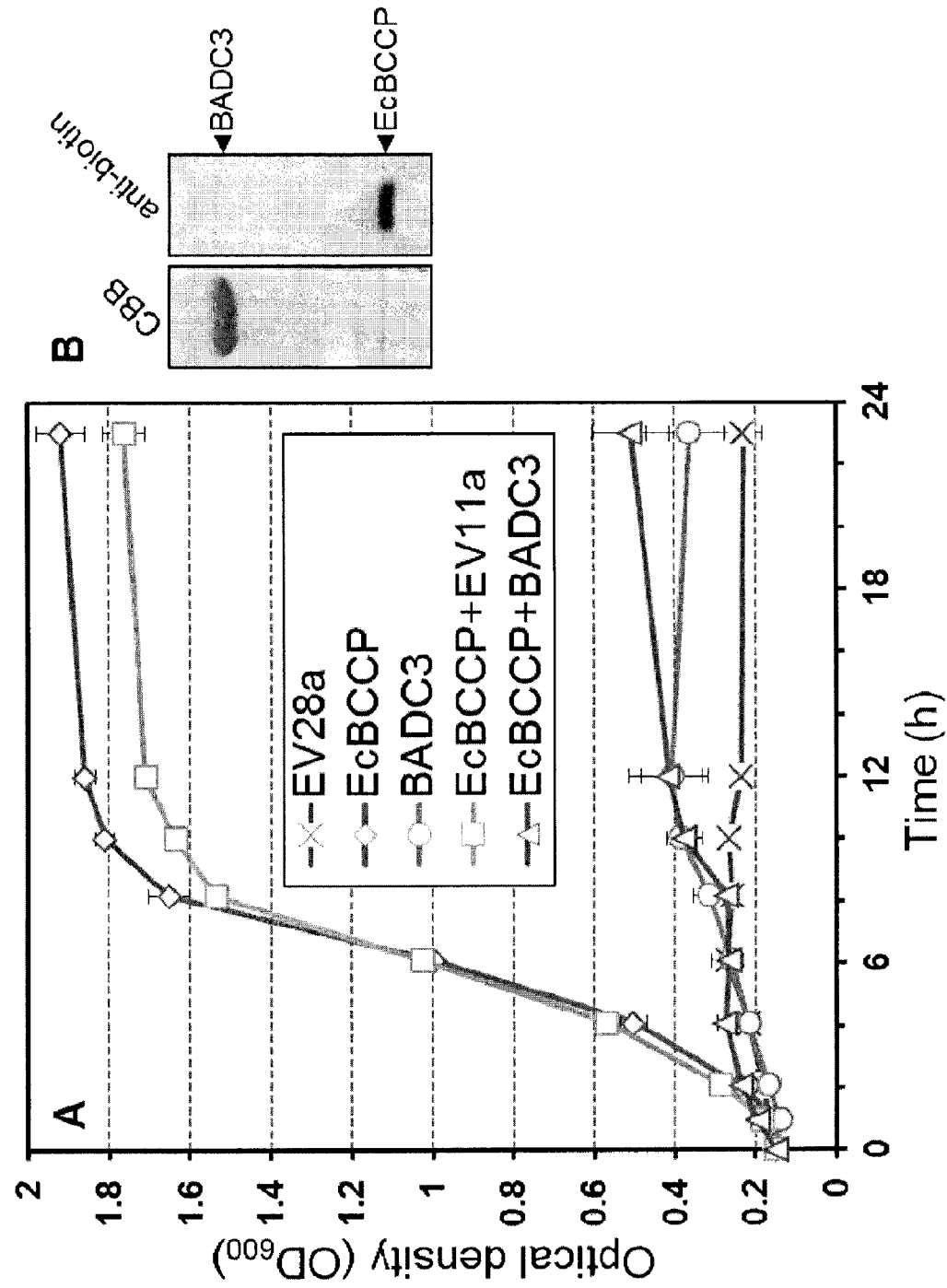
FIG. 8—Shows BADC3 reduces ACCase activity in *E. coli*. (A) Growth curves showing the optical density of L8 *E. coli* cells over time. Cultures were grown in M63 liquid culture at 37° C. in the absence of fatty acids. Transformed cells contained the following vectors: empty pET28a (EV28a), pET28a containing the *E. coli* BCCP gene (EcBCCP), empty pET11a (EV11a), and/or pET11a containing the *A. thaliana* BADC3 gene (BADC3). The EV control cells show minimal growth at 37° C., while re-introduction of native EcBCCP complemented the temperature-sensitive phenotype. BADC3 expression alone showed no statistical difference from EV control except at T=10 h, while co-expression of BADC3 with EcBCCP showed an approximate 75% reduction in growth compared to EcBCCP alone across multiple studies. Results shown are representative of three separate studies. Error bars represent standard deviation. (B) Coomassie blue stain and anti-biotin protein blot of $Ni^{2+}$-NTA purified $His_6$-BADC3.

To complement the Ts phenotype, the native *E. coli* BCCP (EcBCCP) gene was cloned into L8 cells in the inducible pET28a vector. Induced expression of EcBCCP rescued cell growth at 37° C. in media lacking fatty acids, while empty vector controls showed minimal growth. In FIG. 8A, the growth curves show the optical density of L8 *E. coli* cells over time. Cultures of transformed L8 cells were grown in M63 liquid culture at 37° C. in the absence of fatty acids. Transformed cells contained the following vectors: empty pET28a (EV28a), pET28a containing the *E. coli* BCCP gene (EcBCCP), empty pET11a (EV11a), and/or pET11a containing the AtBADC3 gene (BADC3). At T=0 h, the optical density was 0.15 and protein expression was induced with 1 µM IPTG. The EV control cells show minimal growth at 37° C., while re-introduction of native EcBCCP complemented the temperature-sensitive phenotype. BADC3 expression alone showed no statistical difference from EV control except at T=10 h, while co-expression of BADC3 with EcBCCP showed an approximate 75% reduction in growth compared to EcBCCP alone across multiple studies. Results shown are representative of three separate studies. Error bars represent standard deviation.

In the same way, the *A. thaliana* BADC3 gene was cloned into L8 cells and was unable to complement the Ts phenotype. Co-expression of BADC3 with EcBCCP reduced the complementing effect of EcBCCP expression by 71 to 74% over multiple replicates. Affinity pull-down assays with tagged BADC3 confirmed the inhibition was mediated by interaction with EcBCCP. FIG. 8B shows the Coomassie blue stain and anti-biotin protein blot of $Ni^{2+}$-NTA purified $His_6$-BADC3. Protein blot shows that EcBCCP protein co-purifies with $His_6$-BADC3, indicating its direct effect on ACCase activity. The experiment demonstrated that BADC protein expression has a negative effect on *E. coli* growth. Co-association of BADC3 with EcBCCP in vivo verified that this growth phenotype is due to a direct inhibition of hetACCase activity by BADC3.

Example 9

Recombinant BADC Inhibits Plant hetACCase Activity

To test if the BADCs can also inhibit plant hetACCase, enzyme activity assays were performed on ten-day-old *A. thaliana* silique extracts. The activity of hetACCase was monitored in vitro in ten-d-old siliques by measuring the incorporation of $H^{14}CO_3$ into acid-stable products. *A. thaliana* WT Col-0 10-d-old siliques were harvested after six hours of light exposure. In each trial, four biological replicates of three siliques were assayed. Siliques were pulverized in homogenization buffer (20 mM TES, pH 7.5, 10% glycerol, 5 mM EDTA, 2 mM DTT, 2 mM benzamidine, 2 mM PMSF, 1% Triton X-100), centrifuged at 10 k g for 15 s, and assayed within 5 minutes of harvest to minimize loss of hetACCase activity. Assays were performed in the presence of 10 µM haloxyfop to inhibit homomeric ACCase activity. Enzyme activity values for (−)acetyl-CoA controls were subtracted from (+)acetyl-CoA trials to determine the true hetACCase activity levels. Purified recombinant protein was added to assay tubes prior to addition of silique lysate.

Figure 9:
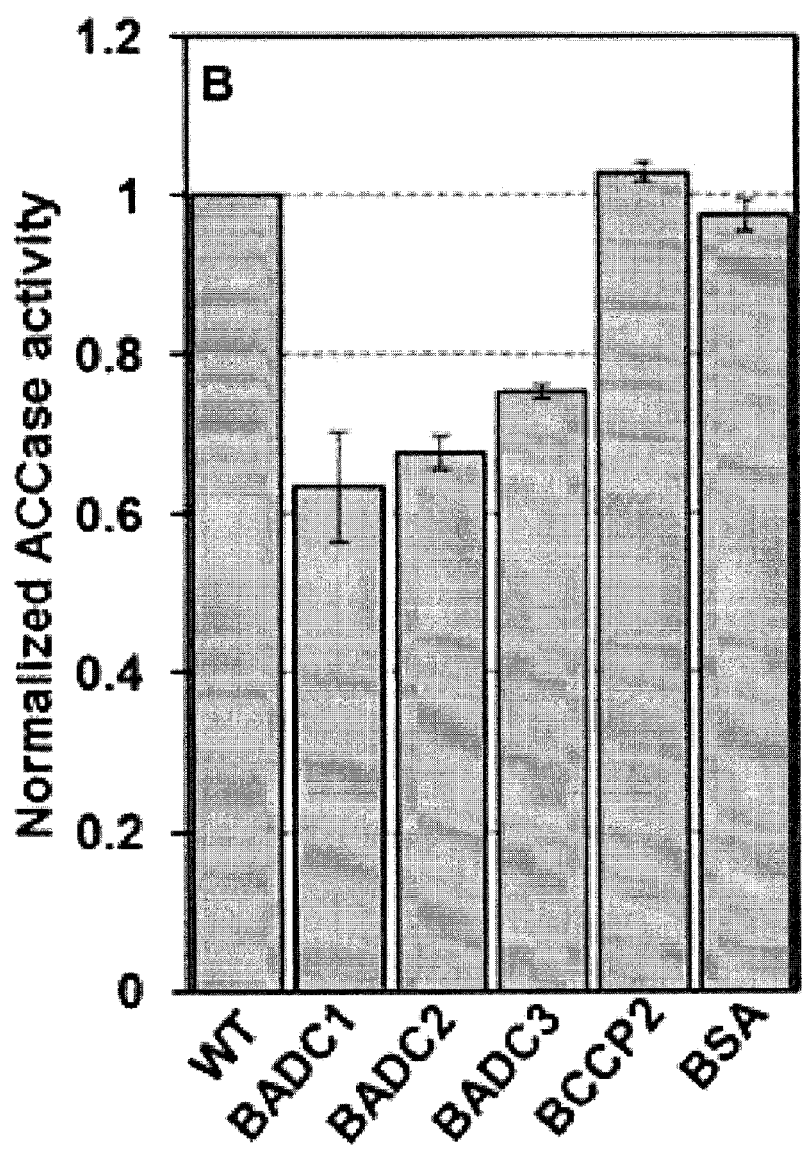
FIG. 9—BADCs reduce ACCase activity in *A. thaliana*. Protein extracted from 10-d-old *A. thaliana* siliques was assayed for ACCase activity by incorporation of radiolabelled sodium bicarbonate into acid-stable products. Assays were performed in the absence (WT) or presence of 10 μM recombinant BADC1, BADC2, BADC3, BCCP2, or BSA. Specific activities were calculated for each assay and then normalized to WT control. Four biological replicates were performed for each trial. Error bars denote SEM.

Assays were performed in the presence of 10 µM purified recombinant BADC1, BADC2, BADC3, BCCP2, or BSA and compared to buffer control (WT). The average of four biological replicates showed that all three BADCs inhibited hetACCase activity by 25 to 37%, while BCCP2 and BSA showed no effect (FIG. 9). These results, in addition to the *E. coli* expression results (FIG. 8A), confirm the BADCs can negatively affect hetACCase activity.

Example 10

Expression Profiles of BADC and hetACCase Subunits Respond Differently to Light

Figure 10:
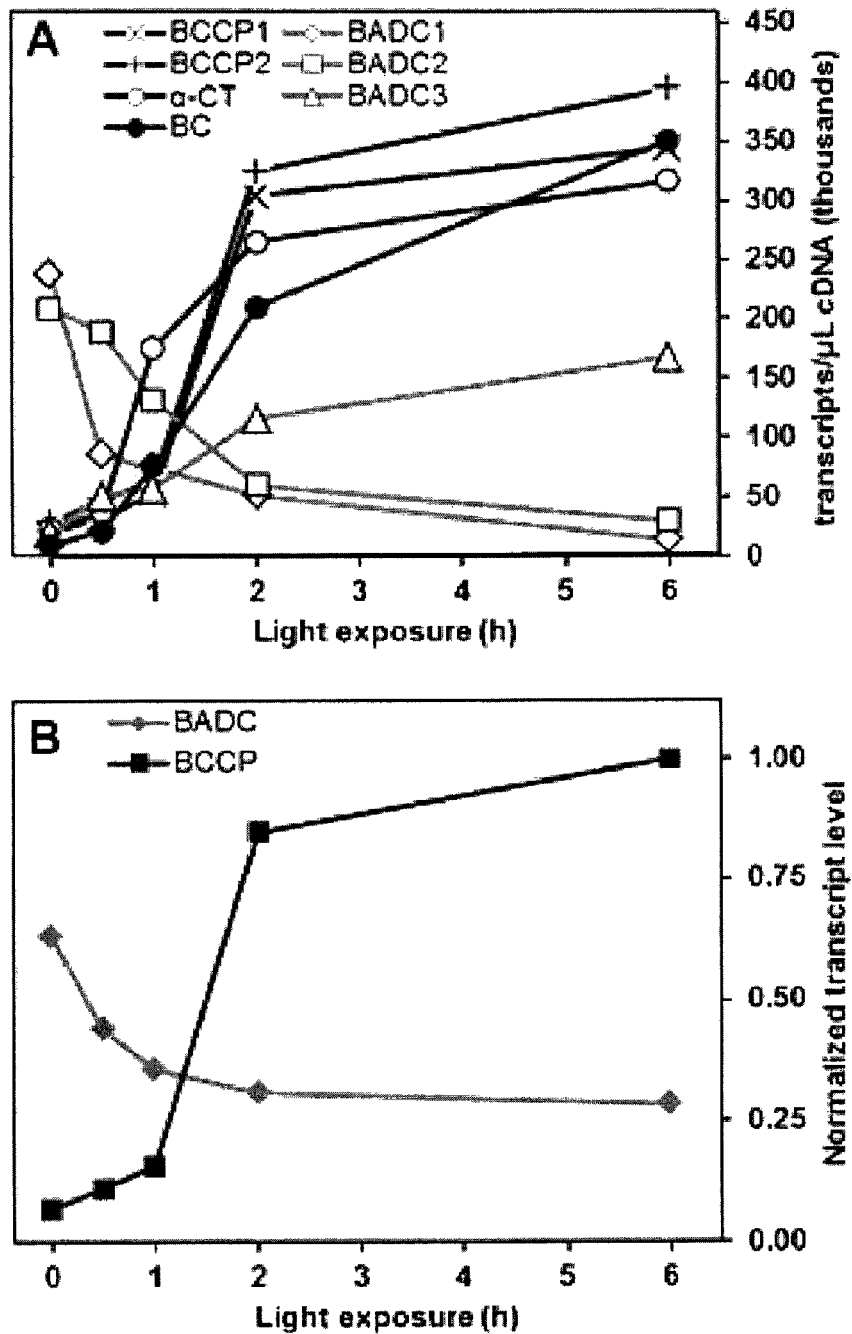
FIG. 10—Shows light-dependent changes in gene expression of BADC and hetACCase in *A. thaliana* siliques. (A) Graph shows the absolute expression level of the given genes obtained by qPCR. Ten d old *A. thaliana* siliques were collected after various amounts of light exposure. RNA extracted from these tissues was used to create cDNA for this analysis. Average values of four biological replicates are shown. Standard error was approximately 5 to 10 percent for all data points. (B) Graph depicts the shift in BADC and BCCP total transcript level in response to light. The sum of transcript levels from BCCPs and BADCs in (A) for each time point were normalized to the sum of BCCP transcripts at six hours light exposure. At T=0, the ratio of BADC: BCCP transcript is 9:1. At T=6, the ratio shifts to 1:4.

HetACCase activity is enhanced upon light exposure in photosynthetic cells. Absolute transcript levels of the BADCs and nuclear-encoded hetACCase subunits were monitored in ten-d-old *A. thaliana* siliques to determine the effect of light on gene expression. Siliques were harvested after dark-adaption or exposure to various lengths of light. Quantitative PCR analysis of RNA extracts from these samples showed that gene expression for each nuclear-encoded catalytic subunit to hetACCase increases significantly in response to light. After six hours, expression of BCCP1, BCCP2, and α-CT increased approximately 15-fold, while BC expression increased 35-fold (FIG. 10A). In contrast, BADC1 and BADC2 expression was reduced approximately ten-fold, while BADC3 expression increased eight-fold. Despite the conflicting changes in BADC isoforms, total BADC transcript level was reduced by half after six hours light exposure (FIG. 10B). The total BADC:BCCP transcript ratio is approximately 9:1 prior to light exposure, and then shifts to almost 1:4 after six hours light exposure (FIG. 10B), suggesting that BADC protein levels are relatively greater than BCCP protein levels in the dark, and vice versa in the light. These data further support the premise that BADC genes are negative regulators of ACCase.

Example 11

Oil Production in *Arabidopsis thaliana* Seed Increases in Response to Silencing the BADC1 Gene The inventors further designed an in planta experiment to confirm that silencing BADC protein expression has a positive effect on ACCase activity in *Arabidopsis thaliana*, and results in increased fatty acid production. An RNAi cassette (SEQ ID NO:7) was produced and transformed into wild type plants in order to silence BADC1 expression in *A. thaliana*. Inverted repeats targeting AtBADC1 were inserted into the pMU103 vector. The repeats coded for bases 774 to 1034 of the cDNA sequence (accession AT3G56130.1). Primers used to amplify the sequence were 5'-GTGTTAGT-CACATCTCCCGCAGT-3' (SEQ ID NO:154) and 5'-GATGTTGATGTCGTGGAAAGATGGC-3' (SEQ ID NO:155). A sequence confirmed construct was transformed into *A. thaliana* ecotype Col-0 using the floral dip method. Basta herbicide screening was used to identify independent lines. Expression of the RNAi cassette was driven by the glycinin promoter. For monitoring seed oil content, T2 plants from each independent line were grown to maturity alongside wild type plants. Dry seed was harvested for analysis.

Figure 11:
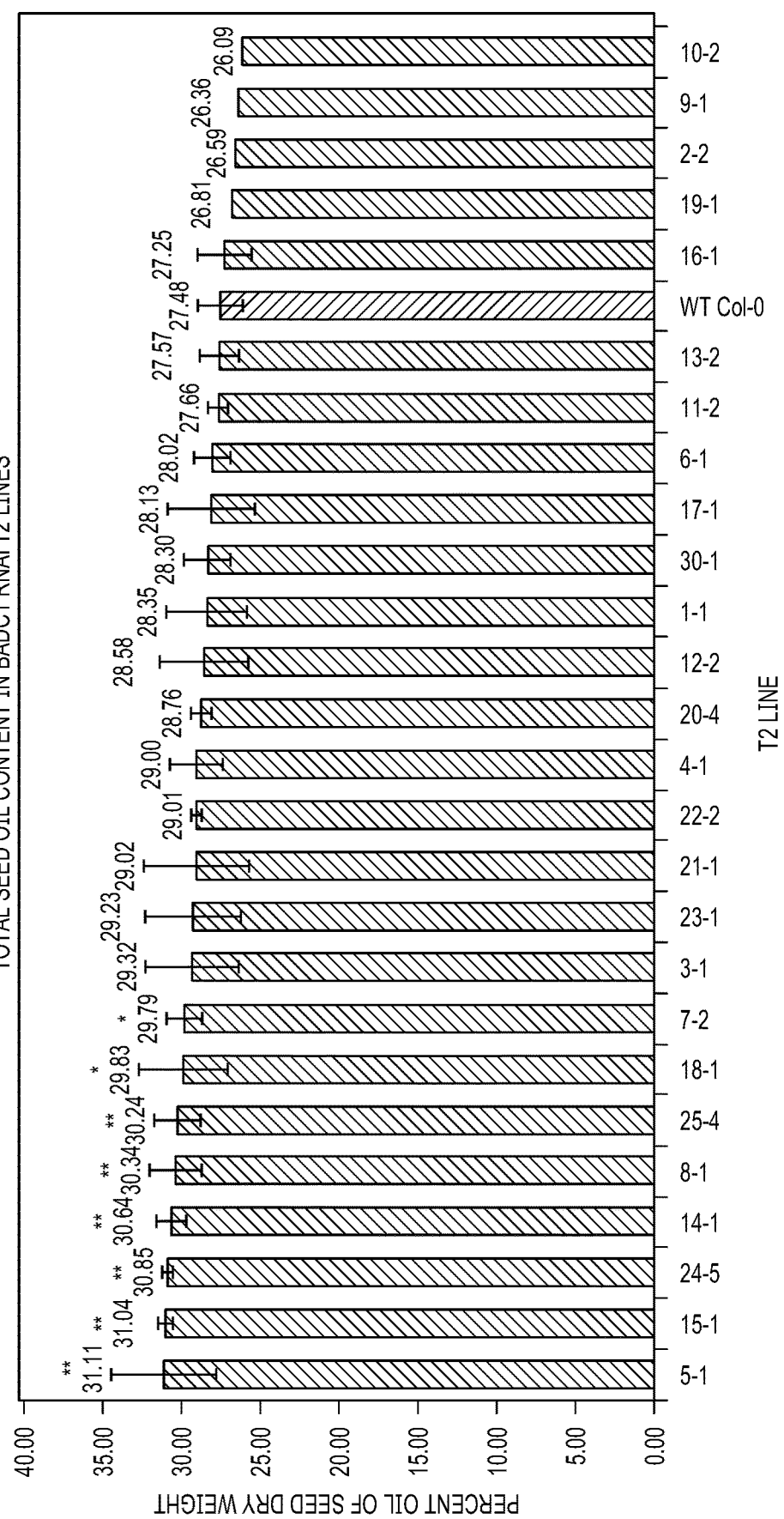
FIG. 11—Shows a bar graph illustrating seed oil content of 26 mutant BADC1 RNAi lines and one wild type. Statistical significance was determined by Student's t-test (*, P<0.05).

The fatty acid content in the T3 generation were collected and analyzed to show increased oil production. Seed oil was derivatized as described by Li et al., *Phytochemistry* 67, 904-915, 2006). Heptadecanoic acid was used as an internal standard. FAMEs were analyzed by a Hewlett Packard 6890 gas chromatography system. For WT and each independent line, 5 mg seed from thirteen and four plants, respectively, were analyzed. Seeds were dried over desiccant for one week prior to analysis FIG. 11 illustrates that the oil production (in *Arabidopsis thaliana* seed) increases in response to silencing of the BADC1 gene. Total seed oil content of 26 independent *A. thaliana* lines containing the BADC1 RNAi cassette has been analyzed along with wild type. The bar graph shows 22 of the 27 lines higher contained higher seed oil content on average. Asterisks signify statistical significance (*, $P<0.05$, **, $P<0.01$). Among the 26 lines, eight lines showed statistically higher seed oil content with increases of 7.7 to 11.7%, which is listed in Table 2.

TABLE 2

| T3 lines with statistically higher seed oil content | | |
|---|---|---|
| Plant line | P value | Percent change from wild type |
| 5-1 | 0.006 | 11.7 |
| 15-1 | 0.000 | 11.5 |
| 24-5 | 0.008 | 10.9 |
| 14-1 | 0.001 | 10.3 |
| 8-1 | 0.005 | 9.4 |
| 25-4 | 0.005 | 9.1 |
| 18-1 | 0.040 | 7.9 |
| 7-2 | 0.023 | 7.7 |

Figure 12:
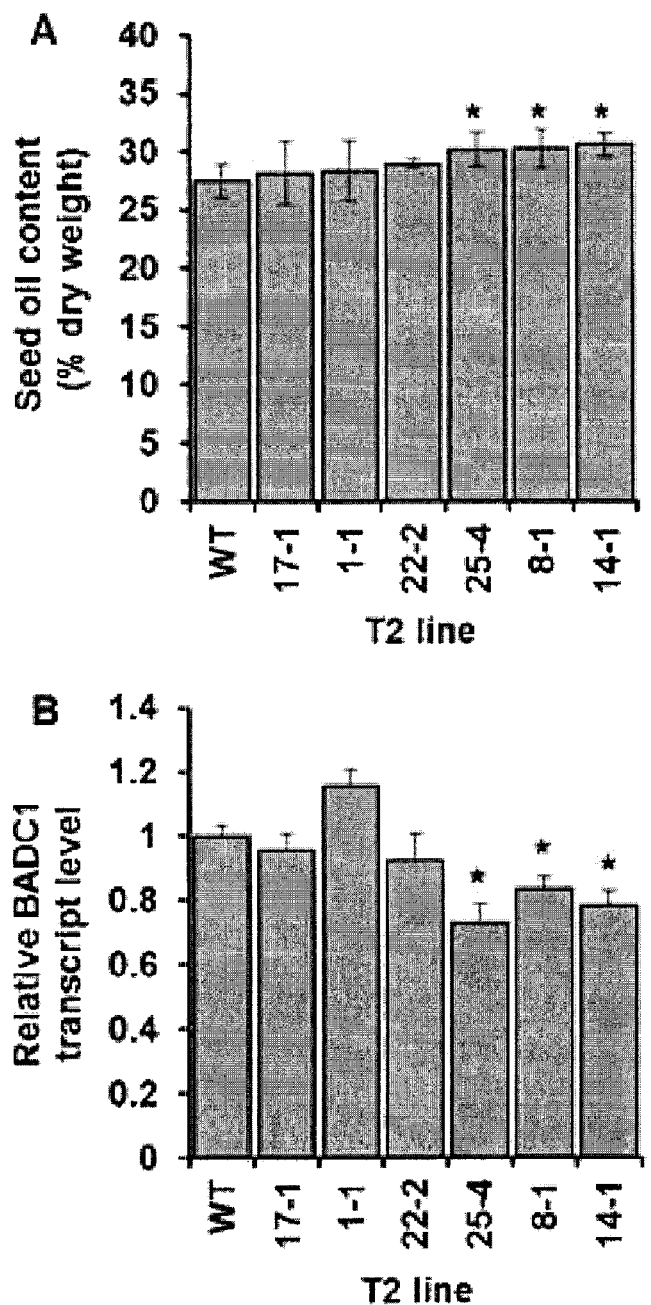
FIG. 12—Seed specific RNAi silencing of BADC1 increases seed oil content in *A. thaliana*. (A) Bar graph shows total seed oil content in WT and basta-resistant T2 *A. thaliana* lines containing a construct that silences BADC1 expression in the seed. Each bar represents the average of four plants. Error bars denote SD. (B) RT-PCR analysis of BADC1 RNAi silencing lines. BADC1 transcript level was quantified relative to Actin transcript level and normalized to WT. RNA used for analysis was extracted from four biological replicates of ten d old siliques. Error bars denote SEM. In both graphs, statistical significance was determined by Student's t-test (*, P<0.05).

Seed oil content analysis showed a significant increase in oil in three of six independent T2 lines (FIG. 12A). Additionally, RT-PCR analysis of whole silique tissue showed a significant reduction in BADC1 transcript level of approximately 22% on average in the three lines containing significantly higher seed oil (FIG. 12B). RNA for RT-PCR and qPCR analysis was extracted from 10-d-old siliques using the RNeasy Plant Mini Kit (Qiagen). cDNA was synthesized from 500 ng RNA of four biological replicates. Primers used in analysis were: BADC1 sense, 5'-GCTCCTAGCCCATCT-CAAGC-3' (SEQ ID NO:156); BADC1 antisense, 5'-TCCAGATGCCTCCAAAGCAG-3' (SEQ ID NO:157); Actin 8 sense, 5'-CCAGATCTTCATCGTCGTGGT-3' (SEQ ID NO:158); Actin 8 antisense, 5'-ATCCAGCCTTAAC-CATTCCAGT-3' (SEQ ID NO:159). qPCR assays were performed on an ABI 7500 system (Applied Biosystems). Reaction volumes were 20 μL and contained SYBR Green PCR Master Mix (Applied Biosystems). Control reactions contained no template and were performed in triplicate. Amplicon identity was confirmed through melting curve analysis. For qPCR analysis, absolute transcript quantities were calculated using a standard curve of serially diluted amplicons of known concentrations. The fractional silencing is partly due to the use of whole silique tissue instead of isolated seed for RT-PCR analysis. These results demonstrate that BADC proteins are negative regulators of het-ACCase.

Example 12

Gene Expression Levels of BADC and ACCase Genes During Seed Development in *Arabidopsis thaliana*

Figure 13A:
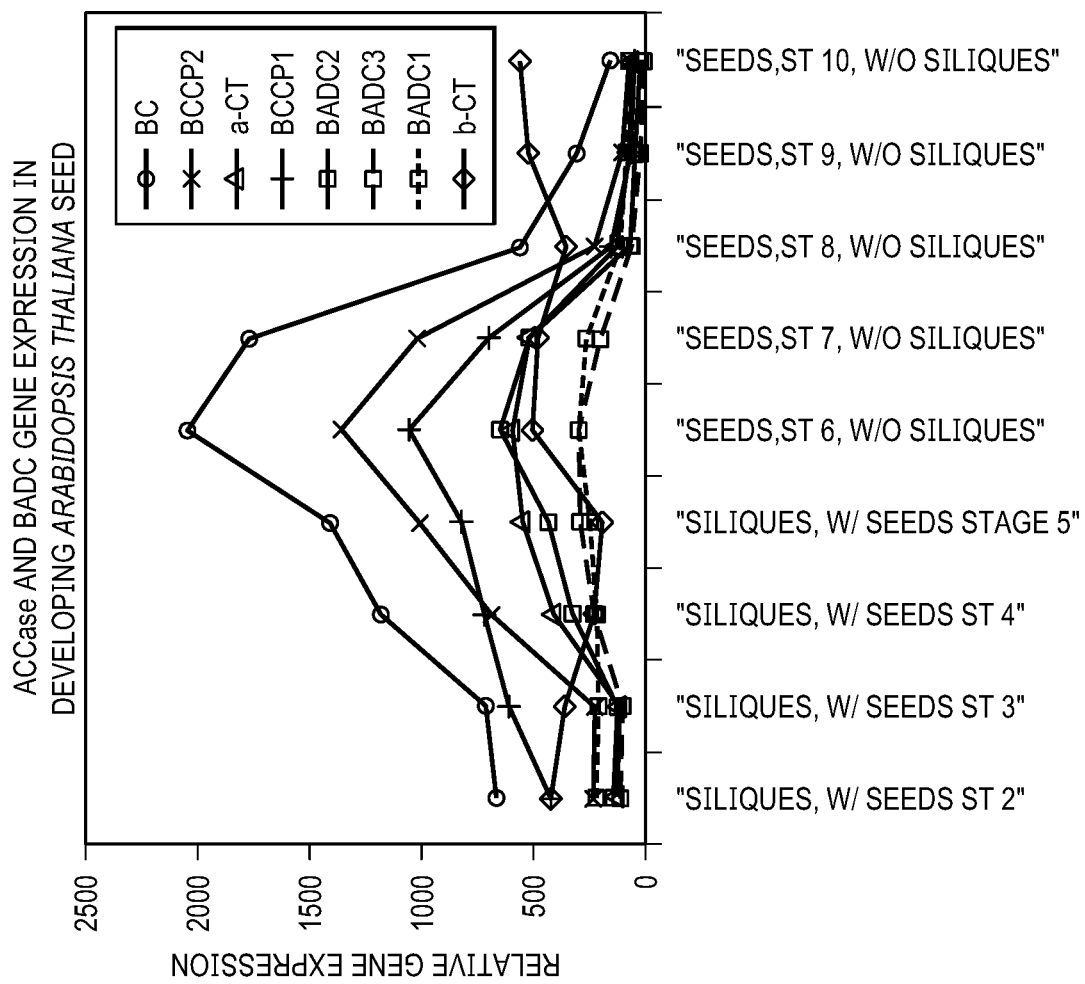
FIG. 13A—Shows a scatter plot demonstrating the expression profiles of ACCase and BADC genes in developing seed of *Arabidopsis thaliana* using publicly available transcriptomics data.

FIG. 13A shows the gene expression levels of BADC and ACCase genes during seed development in *Arabidopsis thaliana* (Comprehensive Systems Biology project, csbdb.mpimp-golm.mpg.de). Although all three BADC proteins are expressed during seed filling, BADC2 showed the highest expression over these time points. FIG. 13B shows the gene expression levels of BADC and ACCase genes in *Glycine max* during seed development (Soybase Database, soybase.org). In this species, the BADC1 ortholog is the most highly expressed in the seed, while BADC3 is relatively lower in expression and BADC2 is not present. Therefore RNAi silencing of BADC1 is the most likely to increase ACCase activity in the seed of *Glycine max*. Nevertheless, the presence of multiple BADC genes in most plants suggests targeted gene silencing (i.e. specific promoter) of multiple copies may be necessary to obtain maximal increases in ACCase activity and thus oil yield, due to the potential for gene compensation.

Example 13

Dose-Dependent Inhibition of ACCase Activity by BADC1

Figure 14:
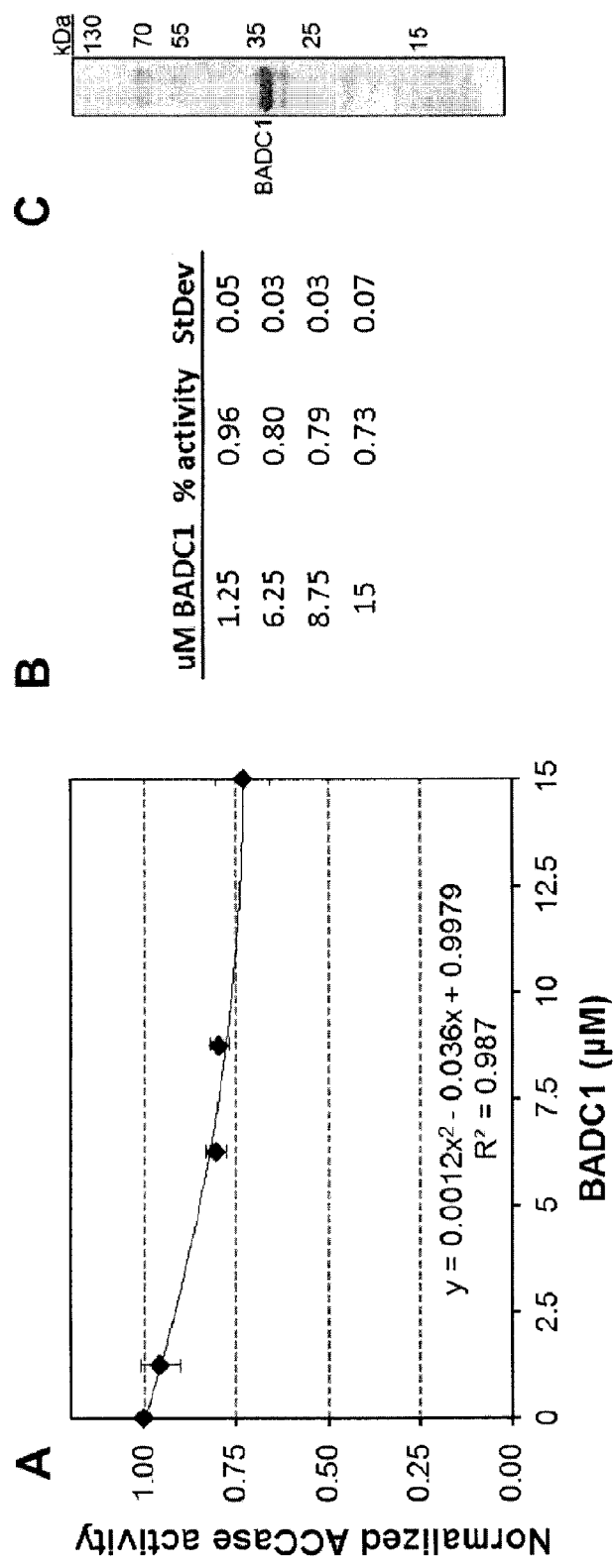
FIG. 14—Shows dose-dependent inhibition of ACCase activity by BADC1. (A) Shows ACCase activity from 20-day-old *A. thaliana* leaf extracts, average of four biological replicates. Error bars denote standard deviation. (B) Shows a table of the values from (A). (C) shows SDS-PAGE analysis of purified recombinant BADC1 protein used in assays for panel (A).
Figure 15:
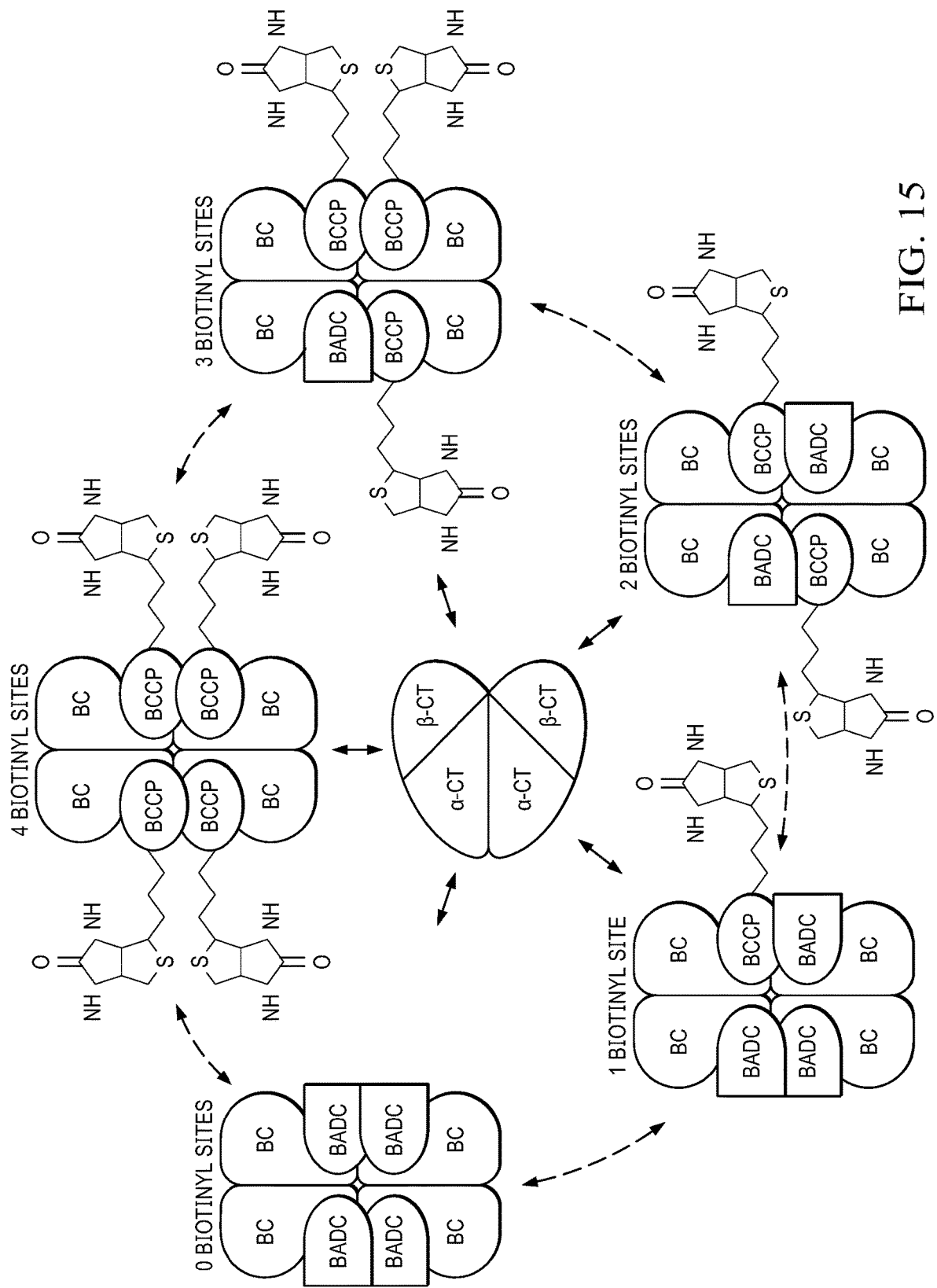
FIG. 15—Shows a model of negative regulation of ACCase by BADC. The BC-BCCP subcomplex of ACCase consists of two dimers of BC and four BCCP proteins. A model was proposed in which BADC proteins compete with BCCP for binding to BC. Binding of BADC prevents binding of the essential BCCP subunit. The pool of BC/BCCP and BC/BCCP/BADC subcomplexes then compete for interaction with the CT subcomplex, leading to variable reductions in ACCase activity. While a transient association of the two ACCase half reactions is known, it is unclear whether BADC can displace BCCP from an assembled BC/BCCP subcomplex (dashed arrows). Abbreviations: BC, biotin carboxylase; BCCP, biotin carboxyl carrier protein; BADC, biotin/lipoyl attachment domain protein; CT, carboxyltransferase.

As shown in FIG. 14, ACCase activity was monitored in vitro in 20-day-old *A. thaliana* leaf extracts with increasing concentrations of recombinant BADC1. Specific activity was determined for each experiment and 0 μM controls were normalized to 1. Specific activity values for controls ranged from 0.84-2.00 nmol/min/mg. Each data point represents the average of four biological replicates, with each biological replicate comprised of four light-adapted leaves. The data fit to a polynomial curve where $R^2=0.987$. The Ki for BADC1 was determined to be approximately 4.3 μM under these conditions. SDS-PAGE analysis was also performed to demonstrate purity of recombinant BADC1 protein used in the assays.

The invention claimed is:

1. A transgenic plant transformed with a recombinant nucleic acid molecule comprising an expression cassette which comprises a heterologous promoter operably linked to an inhibitory polynucleotide that targets an endogenous BADC1 gene in the transgenic plant to reduce or eliminate expression of a BADC1 protein encoded by the endogenous BADC1 gene, wherein the inhibitory polynucleotide encodes an antisense RNA or an RNAi directed towards said endogenous BADC1 gene, wherein said BADC1 protein has at least 95% amino acid sequence identity to SEQ ID NO: 1, wherein said BADC1 protein lacks the conserved biotinylation motif and biotinyl lysine residue of a BCCP1 protein, and wherein said transgenic plant expresses said inhibitory polynucleotide and exhibits (i) increase in the activity levels of the committed step for de novo fatty acid biosynthesis, acetyl-CoA carboxylase (ACCase) and (ii) increase in fatty acid and/or triacylglycerol production in said transgenic plant as compared to a control plant of the same species lacking said recombinant nucleic acid molecule and grown under identical growth conditions.

2. A transgenic seed obtained from the transgenic plant of claim 1, wherein said transgenic seed has increased seed oil content as compared to a control seed of the same plant species, and wherein said transgenic seed comprises said recombinant nucleic acid molecule.

3. The transgenic plant of claim 1, wherein said transgenic plant is a *Glycine max*, *Brassica* sp., *Thlaspi arvense*, *Helianthus annuus*, *Carthamus tinctorius*, *Jatropha curcas*, *Chlamydomonas reinhardtii*, *Chlorella variabilis*, or *Camelina sativa* plant.

4. The transgenic plant of claim 3, wherein said transgenic plant is a *Brassica napus* plant.

5. The transgenic plant of claim 3, wherein said transgenic plant is a *Glycine max* plant.

6. The transgenic plant of claim 1, wherein said inhibitory polynucleotide is said RNAi.

7. The transgenic plant of claim 6, wherein said RNAi is encoded by an RNAi cassette comprising SEQ ID NO:138.

8. The transgenic plant of claim 1, wherein said inhibitory polynucleotide is said antisense RNA.

9. A method of obtaining a transgenic plant comprising:
(i) transforming plants with a recombinant nucleic acid molecule comprising an expression cassette which comprises a heterologous promoter operably linked to an inhibitory polynucleotide that targets an endogenous BADC1 gene in the transgenic plant to reduce or eliminate expression of a BADC1 protein encoded by the endogenous BADC1 gene, wherein the inhibitory polynucleotide encodes an anti-sense RNA or an RNAi directed towards said endogenous BADC1 gene, wherein said BADC1 protein has at least 95% amino acid sequence identity to SEQ ID NO: 1, wherein said BADC1 protein lacks the conserved biotinylation motif and biotinyl lysine residue of a BCCP1 protein; and (ii) selecting a transgenic plant from the transgenic plants of step (i) that exhibits increase in the activity levels of the committed step for de novo fatty acid biosynthesis, acetyl-CoA carboxylase (ACCase) and increase in fatty acid and/or triacylglycerol production in said transgenic plant as compared to a control plant of the same species lacking said recombinant nucleic acid molecule and grown under identical growth conditions.

10. The method of claim 9, further comprising obtaining transgenic seeds from the selected transgenic plant of step (ii), and wherein said transgenic seeds have increase in seed oil content as compared to oil content in control seeds of the same plant species lacking said recombinant nucleic acid molecule.

11. A plant part of the transgenic plant of claim 1, wherein said plant part comprises said recombinant nucleic acid molecule.

* * * * *

SEQUENCE LISTING

```
<160> NUMBER OF SEQ ID NOS: 161

<210> SEQ ID NO 1
<211> LENGTH: 281
<212> TYPE: PRT
<213> ORGANISM: Arabidopsis thaliana

<400> SEQUENCE: 1

Met Ala Ser Ser Ala Ala Leu Gly Ser Leu His Gln Thr Leu Gly Ser
1               5                   10                  15

Ala Ile Asn Ser Gln Ser Glu Val His Ser Leu Ser Gly Asn Trp Ser
            20                  25                  30

Ala Ser Gly Asn Ser Cys Val Pro Arg Trp Arg Leu Ser Asn Arg Asn
        35                  40                  45

Ser Asn Tyr Arg Leu Val Leu Arg Ala Lys Ala Ala Lys Ser Ser Thr
    50                  55                  60

Thr Thr Ile Ser Asp Gly Ser Ser Asp Ala Ser Val Ser Asp Gly Lys
65                  70                  75                  80

Lys Thr Val Arg Arg Ile Thr Phe Pro Lys Glu Val Glu Ala Leu Val
                85                  90                  95

His Glu Met Cys Asp Glu Thr Glu Val Ala Val Leu Gln Leu Lys Val
            100                 105                 110

Gly Asp Phe Glu Met Asn Leu Lys Arg Lys Ile Gly Ala Ala Thr Asn
        115                 120                 125

Pro Ile Pro Val Ala Asp Ile Ser Pro Thr Val Ala Pro Pro Ile Pro
    130                 135                 140
```

Ser Glu Pro Met Asn Lys Ser Ala Ser Ala Pro Ser Pro Ser Gln
145                 150                 155                 160

Ala Lys Pro Ser Ser Glu Lys Val Ser Pro Phe Lys Asn Thr Ser Tyr
            165                 170                 175

Gly Lys Pro Ala Lys Leu Ala Ala Leu Glu Ala Ser Gly Ser Thr Asn
            180                 185                 190

Tyr Val Leu Val Thr Ser Pro Ala Val Gly Lys Phe Gln Arg Ser Arg
            195                 200                 205

Thr Val Lys Gly Lys Lys Gln Ser Pro Ser Cys Lys Glu Gly Asp Ala
210                 215                 220

Ile Lys Glu Gly Gln Val Ile Gly Tyr Leu His Gln Leu Gly Thr Glu
225                 230                 235                 240

Leu Pro Val Thr Ser Asp Val Ala Gly Glu Val Leu Lys Leu Leu Ser
            245                 250                 255

Asp Asp Gly Asp Ser Val Gly Tyr Gly Asp Pro Leu Val Ala Val Leu
            260                 265                 270

Pro Ser Phe His Asp Ile Asn Ile Gln
            275                 280

<210> SEQ ID NO 2
<211> LENGTH: 2613
<212> TYPE: DNA
<213> ORGANISM: Arabidopsis thaliana

<400> SEQUENCE: 2

| | | | | | |
|---|---|---|---|---|---|
| acggaccgta | gtgtagtagt | agatgcggcg | gacggagtta | ccaaagaaga | aggccgctca | 60 |
| aaataattaa | atttgttcaa | ccgtcatctt | cttcaactga | tcttagctca | actaacacac | 120 |
| tctttcttct | tggcgtcaat | tcaatcaacc | aaaacctttt | tctcctatct | agctcacgct | 180 |
| ttcttcttct | tccaatggcg | tcttctgcag | ctctcggatc | tctccatcgt | gagtctcttg | 240 |
| ctctctcact | ctctgcgttt | tacttattct | gttgatttca | tgaggatagg | aaaactagaa | 300 |
| atggaggacc | atgagtaaaa | tttcggaaat | gaaaggcata | gattggagct | atccgttagt | 360 |
| gacgttgttg | cttcttagag | tgtaatttag | cgacttaatt | aagtttcaat | ctcggatctt | 420 |
| gtgtgtctaa | tttgtatcaa | gagatgtttc | agctagaaaa | agtgaatttt | atttgttcca | 480 |
| ttttacagag | actttagggt | cagccattaa | ttcacagagt | gaggttcact | cgctttctgg | 540 |
| aaactggtct | gcctctggta | attcatgtgt | gccacggtgg | agattatcca | acaggaacag | 600 |
| caactacagg | ctcgtgttac | gtgctaaggc | cgctaaatct | tcgacaacaa | ccataagtga | 660 |
| tggtgagttt | atcttccaca | attcttcttc | atgttcattt | tgctggttaa | tgccttttt | 720 |
| tactatcagg | cttgtctcat | cactttgcta | atacgatcca | ttggccaaag | atggtattaa | 780 |
| tctgttttgc | tcttaaagga | actggaactg | aaattcttag | tctcgtttgc | tcttaaagga | 840 |
| actagaaatg | taactgtaag | cctcggtctt | ttaccagctg | tcttggaacc | aggagataca | 900 |
| gtgatgtgat | attggaacat | ttttctttta | tttcctatga | cttttgctta | tttttggctt | 960 |
| tgcaggttca | tctgatgcta | gtgtgtcaga | cgggaagaaa | acagttcgac | ggataacttt | 1020 |
| cccgaaagaa | gtggaggttt | cttccttgcc | tttcatgggt | cttagatatt | aggttcttta | 1080 |
| atttataagt | ttggtaggtg | atgatatgac | gatttcctca | aatatgcact | ttctagatcg | 1140 |
| tcaggatttt | ggatgcataa | cttcaggcaa | tctactctta | taatttttaa | tcatgacgta | 1200 |
| tggatgtacc | tttctttata | tgttgttaga | tgaaatgttg | caggcactgg | ttcacgagat | 1260 |
| gtgtgatgaa | actgaggttg | ctgtgctgca | acttaaggca | agtctctctg | ccattagttt | 1320 |

```
taacttcatt attattatta tttgtaaact ttctttgagg ctactacaaa gacgagtgca    1380
ttttactcaa ccaacaatat ggggctaaat atcactgatt tgagataata gaatgtaggt    1440
tccaacaatt agactcttct gaagctttct tttgctacag gttggagatt tcgagatgaa    1500
cctaaaacgg aagattggag cagccacaaa ccccattccc gtggcggata tatctccaac    1560
tgtagcgcct cctattcctt ctgaacctat gaataaatct gcttcttcgg ctcctagccc    1620
atctcaagca aagccttcct ctgagaaagt gtctccattt aagaatacat catatgggaa    1680
accagcaaag ttggctgctt tggaggcatc tggatccacc aactatgtgt tagtcacatc    1740
tcccgcagta tgagatccat ttcctaatta gtggttgctt tcatatccct taatttctct    1800
gcagttttct tgtttgattt gatcttgttt cttctcttac caaaaggtgg gcaagtttca    1860
gaggagcaga actgtaaaag gaaagaaaca atctcctagc tgcaaagagg taaacgactc    1920
taaattcttt tgcatctctt agaacaaaag aacagaaata agatcaaaga gctaagtgaa    1980
aaaaactcct tagggtgatg caataaagga aggccaagtt attggatact tacatcagtt    2040
gggaacagaa cttccagtga cggtaatatc ttaactaata tatccatctc ttctttgaaa    2100
ctatctaatc agactcatcg atcttgctat tgtcgagca gtcagatgta gctggagaag     2160
tccttaagct tctttcagat gacggaggta acatttgag tattcaaacc gtttcattta     2220
gtatgaacat tcagaaatta tataagtgaa ttgatatgaa ctcatgcttc gtgtgcaaac    2280
agactccgta ggttatggag atcctctggt tgcagtcttg ccatctttcc acgacatcaa    2340
catccagtga tgatggtttc ttcagcccaa ttccatagca aatgaatagt ctttcatccg    2400
gagactgtac tattcatctt ctcctgtgtt tgttcaatga agatttgtaa tctgtttagt    2460
tgcaaagagt ctactttgat cttgctctca tcatttgtca cgtaatgtgg attttctgca    2520
ccagagaaaa aaacaattg tggaatttt atagaaatga cgtggctatc ttatcttctc      2580
cgatcatcaa ataaaatcaa ggctcaaaaa ttc                                  2613
```

<210> SEQ ID NO 3
<211> LENGTH: 274
<212> TYPE: PRT
<213> ORGANISM: Arabidopsis thaliana

<400> SEQUENCE: 3

```
Met Asn Ser Cys Ser Leu Gly Ala Pro Lys Val Arg Ile Phe Ala Thr
1               5                   10                  15

Asn Phe Ser Arg Leu Arg Cys Gly Asn Leu Leu Ile Pro Asn Asn Gln
            20                  25                  30

Arg Leu Phe Val Asp Gln Ser Pro Met Lys Tyr Leu Ser Leu Arg Thr
        35                  40                  45

Thr Leu Arg Ser Val Lys Ala Ile Gln Leu Ser Thr Val Pro Pro Ala
    50                  55                  60

Glu Thr Glu Ala Ile Ala Asp Val Lys Asp Ser Asp Glu Thr Lys Ser
65                  70                  75                  80

Thr Val Val Asn Thr His Leu Met Pro Lys Ser Glu Val Glu Ala
            85                  90                  95

Leu Ile Ser Glu Ile Thr Asp Ser Ser Ser Ile Ala Glu Phe Glu Leu
            100                 105                 110

Lys Leu Gly Gly Phe Arg Leu Tyr Val Ala Arg Lys Leu Thr Asp Glu
        115                 120                 125

Ser Ser Pro Pro Gln Gln Ile Gln Pro Val Val Ala Ala Ser Ala
    130                 135                 140
```

```
Thr Pro Glu Gly Val His Thr Asn Gly Ser Ala Thr Ser Ser Ser Leu
145                 150                 155                 160

Ala Ile Thr Lys Thr Ser Ser Ser Ala Asp Arg Pro Gln Thr Leu
            165                 170                 175

Ala Asn Lys Ala Ala Asp Gln Gly Leu Val Ile Leu Gln Ser Pro Thr
        180                 185                 190

Val Gly Tyr Phe Arg Arg Ser Lys Thr Ile Lys Gly Lys Arg Thr Pro
        195                 200                 205

Thr Ile Cys Lys Glu Lys Asp Ile Val Lys Glu Gln Val Leu Cys
    210                 215                 220

Tyr Ile Glu Gln Leu Gly Gly Gln Ile Pro Val Glu Ser Asp Val Ser
225                 230                 235                 240

Gly Glu Ile Val Lys Ile Leu Arg Glu Asp Gly Glu Pro Val Gly Tyr
                245                 250                 255

Asn Asp Ala Leu Ile Thr Val Leu Pro Ser Phe Pro Gly Ile Lys Lys
            260                 265                 270

Leu Gln

<210> SEQ ID NO 4
<211> LENGTH: 2631
<212> TYPE: DNA
<213> ORGANISM: Arabidopsis thaliana

<400> SEQUENCE: 4
atcaaattcg atttcatcgt cgtcactcgt caatcgccaa atcaacaaaa tcgtcttcct      60
cgttcgtatc gttcactcag ctttttttccc atcttcttct tcgcatcaca tattcttcat    120
tactaatata tctcctactc cagtcttcct ccatgaattc ctgtaagttt ctctatcttg    180
ttgcctcatg aatgattttg ttgttctcgt gaatccttgt tttaatctgt tcttcgttga    240
tactcaaatg ggtttgaaca agaagagtta ttttgcaat gtgattagtg ttgatgcatc     300
ttcgtttcaa gataatgcgt ttaaagcttg tactttataa tgctattgtt tctctacttg    360
tttcaagact atgacttgca atgataaatt atacattgaa acatgtatag gtcaaggtaa    420
aagggatcta tggaggagtg ttgataactt tttgattctg tttcaggtag cttaggagct    480
cctaaagtta gaattttgc aacaaattc agtagattaa gatgtggaaa cttgctgata     540
ccgaacaatc aaagactatt tgttgaccaa agccctatga agtatctgag tctgagaacg    600
actctgcgat ctgtgaaagc tatccaattg tctactgtcc cacctgcaga aacagaaggt    660
atatagtaat ctgtctgtgt atttctgttt cacttgattg tgttttactg tttgtcataa    720
aatcctttag acaatgttca gatttgtggc ttatgaagtg gtatcgtttg cttgtttcct   780
tctttaacat tcttcactac agctattgca gacgtaaaag attctgacga gaccaaatca    840
actgttgtga atactcacct catgcccaag tcctccgagg taggtgttac tttcctgttt    900
aacctctcat attcaagacc aagtatgatg cacaactgtt ataaccctt aggggtttca    960
atttgggatt gttttgagaa atcacaaaag ttagaaagtt gcatttcagt gcaatagcac   1020
gatactgtgg ttctttgtta ttatgatgct agagaaggaa gaatgtgtga cctcgttgag   1080
ctagcttaga catgagctat gtcaaatcta atcattatgt tacattttca tcttctaggt   1140
ggaagcactc atcagcgaaa tcaccgattc ctcatccatt gcagagtttg aactcaaagt   1200
aagcccccact tctgatttct gaactcataa ctatgttatt tattgttgct cagatcattt   1260
acttgtctct gctaagtttt tcataaaat cgtgtctatg atagaagtag ttttactatt    1320
gacttaagtt tcatcttaac catggtttat tgtgaaagta aaccatggtt ggtttagctt   1380
```

```
ttctggtttg gtcaatgtcc ttatatagcg tctgagagat atgtgagagt tttatcgagt   1440
atttggtgag taatctaggg gagtgggagg agctccatta atcaaattcc tcaaggtctt   1500
gtaattctcg attgataagc tatgaaatat cagtttctat aagcaaatcg tatcagtcta   1560
ataattctgg tttctcccat ttgcatattt ctaatagctg ggaggtttcc gcctgtatgt   1620
agcaaggaaa ttaactgacg aaagtagtcc accacctcag caaattcagc ctgtggttgc   1680
tgcaagcgca actcctgagg gggttcacac taatggctca gctacttctt cgtcattggc   1740
tatcacaaaa acatcatctt cttcggcaga cagaccacaa acactcgcta acaaagctgc   1800
tgatcagggt ttagtgattc tccaatctcc aacggttaga gactagatca tttcttttgaa   1860
actgacatga aatgattaaa attcatgatc tctcaactgg atggataatt atttgttgca   1920
ggtcggttat ttcaggagat ccaagaccat aaaagggaaa cgcactccta caatctgtaa   1980
agaggtactt cttctcctat gttttgaaca agtctttcaa aatatccatc ttcaaggagc   2040
atttggaatc tctcaattga ttatatattt gcttttggtt attctacaga aagacatagt   2100
gaaagaaggt caagttctat gctacattga acagctcggt ggccaaatcc cagttgaggt   2160
aacaatcgta atccctttcg gtttctttac ttttttttgc tttctcagtc ttcttattgt   2220
gttctttctt tcagtctgat gtttccggag agattgtcaa aatactccgc gaagatggcg   2280
gtaagaccct atttgctata tgtctttgaa tcggtactca tatagctatc aattctctct   2340
actgactttt gtttttttct tcttctgttt tgtgattcgg cagagcctgt aggatacaac   2400
gatgctctca tcacagtact tccctcattt cctggcatca agaagcttca gtaagaactg   2460
attttggctt aattgtgttt gtgctttgtg tattttgctt cttagttttt ctccacatag   2520
acaaaaataa gctctactcc aaaaaatctt tgtccgtacc attacctttg ttttaccaaa   2580
atttaattga aactttttg tttaccactg atattagaac atttcattct t             2631
```

<210> SEQ ID NO 5
<211> LENGTH: 263
<212> TYPE: PRT
<213> ORGANISM: Arabidopsis thaliana

<400> SEQUENCE: 5

```
Met Ala Ser Cys Ser Leu Gly Val Pro Lys Ile Lys Ile Ser Ala Val
1               5                   10                  15

Asp Leu Ser Arg Val Arg Ser Gly Ser Leu Leu Ile Pro Tyr Asn Gln
                20                  25                  30

Arg Ser Leu Leu Arg Gln Arg Pro Val Lys Tyr Leu Ser Leu Lys Thr
            35                  40                  45

Thr Phe Gly Ser Val Lys Ala Val Gln Val Ser Thr Val Pro Thr Ala
        50                  55                  60

Glu Thr Ser Ala Thr Ile Glu Val Lys Asp Ser Lys Glu Ile Lys Ser
65                  70                  75                  80

Ser Arg Leu Asn Ala Gln Leu Val Pro Lys Pro Ser Glu Val Glu Ala
                85                  90                  95

Leu Val Thr Glu Ile Cys Asp Ser Ser Ser Ile Ala Glu Phe Glu Leu
                100                 105                 110

Lys Leu Gly Gly Phe Arg Leu Tyr Val Ala Arg Asn Ile Ala Asp Asn
            115                 120                 125

Ser Ser Leu Gln Pro Pro Thr Pro Ala Val Thr Ala Ser Asn Ala
        130                 135                 140

Thr Thr Glu Ser Pro Glu Ser Asn Gly Ser Ala Ser Ser Thr Ser Leu
```

|     |     |     |     | 145 |     |     |     |     | 150 |     |     |     |     | 155 |     |     |     |     | 160 |
| --- | --- | --- | --- | --- | --- | --- | --- | --- | --- | --- | --- | --- | --- | --- | --- | --- | --- | --- | --- |

Ala Ile Ser Lys Pro Ala Ser Ala Ala Asp Gln Gly Leu Met Ile
                165                 170                 175

Leu Gln Ser Pro Lys Val Gly Phe Phe Arg Arg Ser Lys Thr Ile Lys
                180                 185                 190

Gly Lys Arg Leu Pro Ser Ser Cys Lys Glu Lys Asp Gln Val Lys Glu
                195                 200                 205

Gly Gln Ile Leu Cys Tyr Ile Glu Gln Leu Gly Gly Gln Phe Pro Ile
        210                 215                 220

Glu Ser Asp Val Thr Gly Glu Val Val Lys Ile Leu Arg Glu Asp Gly
225                 230                 235                 240

Glu Pro Val Gly Tyr Asn Asp Ala Leu Ile Ser Ile Leu Pro Ser Phe
                245                 250                 255

Pro Gly Ile Lys Lys Leu Gln
                260

<210> SEQ ID NO 6
<211> LENGTH: 2698
<212> TYPE: DNA
<213> ORGANISM: Arabidopsis thaliana

<400> SEQUENCE: 6

```
accactctgg ttgtatcgaa cgagcgaaac ccaaccaacg acgagcgttc acctcaaata      60
ttttgatttg atcaaatcat ctccacactc gccaaatcgt tgtgtcctcg ttcatatcgt     120
tatcgtatca gctcaaaaat ctcaatctct cttccttaca ttcttctgtt tctcgaatcc     180
ttgtctccct ccatggcttc ctgtaagttt ctctacctgt ctcttgttgt cttgcttgtt     240
ccagttttct tgggatcgta cactaaattg ggtttgtgtt tcctcattca aatttgaatg     300
ctttcgtagt tttctgctct catagaatca tattcatcga aaggttgtaa ctttggggat     360
tctgtttatt gagtgatagg aaaactcaga aagggactta actttgaaca attaggttga     420
ttttggtata aattagagat ctaaagttga agaatttgtc ttcagtatct gtttcaatgg     480
agatgagatt caagttactt catttgatat tgaattgcca agctaatcta attgatgagt     540
ttggcagtga taagttaatt tcataatttg tatctcttaa tatgaattac tcgacaacat     600
tacttaatct ttcactgttg agtatacgtg gagatcggtt aacgtgagtt tattctaaga     660
cattatattt tgaattactt aaaactttct ggagctatct tggattgagt gtataagatt     720
tgcttatgct caattttaaa aagtgaggga tcatattgaa gataagtgct tatttagtct     780
ttcttttttga ctctgtcttg ttttggctga tttcccatat tgagaccttg gcgtatgacg     840
tatgttacag gtagcctagg agttcctaaa attaaaatct cggcagtaga ccttagtaga     900
gtaagatctg gaagcttact gataccatac aatcaaagat cattgcttcg acaaaggcca     960
gtgaagtact tgagtctgaa gacaacattt ggatctgtga agctgtccaa gtgtctact     1020
gtcccaactg cagaaacatc aggtacactt atctctatat gttttcttaa cttgaatatg     1080
ctcatttta ccgattttac tatcgatatg ttttgcacat cgagtgtgtt cacatgtggg     1140
ctgatgtgtt cctagaaagt ctcttttagt tttcctttaa tgctttctga tttattcttg     1200
ttatcaacag ctactataga agtaaaagat tctaaagaga tcaagtcatc tcgattaaac     1260
gctcagcttg ttcccaagcc ttctgaggtg ggttttgatt ttccatttaa tgttagaatg     1320
tcaatttaag aactctggtt cttctcccctt attgtcaaat ggaagagaag aaatgtgttg     1380
tcttgaggat taagtggaga attcacttgt tgcctgcaca ataaaaccat ttgagtctgt     1440
```

-continued

| | | | | |
|---|---|---|---|---|
| tttttttaatt | ggatgcattc | aatatgattt | cttttcgat | cttttaggtg gaagcccttg | 1500 |
| taactgaaat | atgcgattct | tcatcaattg | cagagtttga | actgaaagta aggctctact | 1560 |
| caattgaatt | gttgtcatgt | tattgctctt | ttgcagagtc | atctcagcta agttttgaa | 1620 |
| taggattctt | atctaataat | ttcggcctct | ttcatttgca | cattctaata gctgggggt | 1680 |
| ttccgactat | atgtagcaag | gaacatagct | gacaatagta | gtctacaacc tccgccaact | 1740 |
| cctgctgtga | ctgcttcaaa | tgcaactacc | gagagtcctg | agtcgaatgg atcagcttcc | 1800 |
| tctacttcac | tggctatctc | aaaaccagca | tcgtcagccg | ctgatcaggg tttgatgatt | 1860 |
| ctccaatctc | caaaagtaag | agaccacaca | actcaaaggc | aaaatgtcat atactctgtt | 1920 |
| ggaaaatgct | atatttata | gtttcaatca | gaaagttgat | cccaatctaa atggtgtgta | 1980 |
| atatgtgcag | gtagggttct | tcaggagatc | caaaaccata | aagggtaaac gcctgccttc | 2040 |
| gtcttgtaaa | gaggtataac | caatcttctt | gaacagaaga | gagtgtttga tttcatgggg | 2100 |
| gaaaccactg | actaatctct | tatttgctct | tgtttaatct | gacagaaaga ccaagtgaaa | 2160 |
| gaaggtcaaa | ttctgtgcta | cattgaacaa | ctcggtggcc | aatttccaat cgaggttaga | 2220 |
| taatattcca | ttttaattcc | tgatttagta | attactatca | cttgcttcaa ccaactcagt | 2280 |
| taaattgctt | ctctgtttat | cgatcaatct | tctagtctga | tgttaccggc gaggtagtca | 2340 |
| agatactccg | agaagatgga | ggcaagtctc | tcgtcttctt | taacctttct tcgttttct | 2400 |
| taaaacctcg | gtgtaatgat | ttttcttatc | gttttctcat | tcggaacaga gcctgtagga | 2460 |
| tacaatgatg | ctctcatctc | catccttcca | tccttccctg | ggatcaagaa gcttcagtaa | 2520 |
| aaccaaattc | gagctggttt | tgagttatga | cactgtgcct | tgtgtatgct tttagataaa | 2580 |
| gaaacttcat | tcatatttgt | atttgtcttt | tgcttgtatg | aaagttcttc tttaagactc | 2640 |
| ttttattctg | tatgcttttt | cttatatata | aaaacattat | ggtatttttt tttaatcg | 2698 |

<210> SEQ ID NO 7
<211> LENGTH: 1676
<212> TYPE: DNA
<213> ORGANISM: Artificial sequence
<220> FEATURE:
<223> OTHER INFORMATION: RNAi cassette

<400> SEQUENCE: 7

| | | | | |
|---|---|---|---|---|
| cccggggtgt | tagtcacatc | tcccgcagtg | ggcaagtttc | agaggagcag aactgtaaaa | 60 |
| ggaaagaaac | aatctcctag | ctgcaaagag | ggtgatgcaa | taaggaagg ccaagttatt | 120 |
| ggatacttac | atcagttggg | aacagaactt | ccagtgacgt | cagatgtagc tggagaagtc | 180 |
| cttaagcttc | tttcagatga | cggagactcc | gtaggttatg | gagatcctct ggttgcagtc | 240 |
| ttgccatctt | tccacgacat | caacatcgag | ctccactgaa | ttgaattgtt taaggtttgg | 300 |
| tgagcctaaa | agaatttgaa | ctggttttca | aataaatgaa | ttaagatgtt aattaggaga | 360 |
| attgaagttt | attacaattt | ggattgggga | ttagaatttg | aagctacatt taaaattcga | 420 |
| aaaaaaaga | cagtgaaact | taaaacgttc | ataaaaagga | ccaaagtttt ttaaaaaat | 480 |
| tgtcgctaaa | actcaaacat | atatattaca | atgccatatg | tgcttataag gacttaagga | 540 |
| gcagttctt | gggtggctag | gggatatgac | atttttttac | tgcacaataa atatcctggc | 600 |
| cgttgcaccc | ggagatgcac | agagctttga | gcagatcaga | tgaatgatta aattgttttg | 660 |
| aagagaatct | attccttcac | actgaattct | tgcacaaaac | cttgacactg aatttaattg | 720 |
| tgccaaatca | acaattcttt | tagcccagga | aatataatcc | attttttaat ttctgctac | 780 |
| ttattttcat | cttcttaata | caaagatata | caagtatttt | gcatattcag attttttttt | 840 |

```
gccaaaacaa taaatctagc tatatacatt ttcctttgac caactcggct actaaaattg    900
gttggattct gattttacta tttgtgaatt tcaatcttag ctttgaccta tacccaaaat    960
aaaccctcct gatctgtttc tccagtggcg agagacatga tttaacgaga gttgaacaca   1020
agatctagac tctagaataa aaaagacac gaatattaga aaatgatcta atataaaata    1080
attataagga gtgagacttc aaatctaggt cagctagccc accatcttgt ggagctagtt   1140 ggaaacccc tgggtgtgtt tctctagact ctagaataac attgatcagc ctaaccaaac    1200
ataacgaacg aagatttaat atcaggacat atatatggat cttggcaagt caattaatta   1260
attaattaat ttccagccca acaccttaca gaaattagca tgtatgagac tacttgtaag   1320
gaaaaacgag caatgaaaga tgcatgtgat cgatctgaat aagagggaa acaagaatt    1380 ataaacatat atgtatacct tcctagggat gttgatgtcg tggaaagatg caagactgc    1440 aaccagagga tctccataac ctacggagtc tccgtcatct gaaagaagct taaggacttc   1500
tccagctaca tctgacgtca ctggaagttc tgttcccaac tgatgtaagt atccaataac   1560
ttggccttcc tttattgcat caccctcttt gcagctagga gattgtttct ttccttttac   1620
agttctgctc ctctgaaact tgcccactgc gggagatgtg actaacacgg cgcgcc      1676
```

<210> SEQ ID NO 8
<211> LENGTH: 234
<212> TYPE: PRT
<213> ORGANISM: Arabidopsis thaliana

<400> SEQUENCE: 8

```
Met Lys Tyr Leu Ser Leu Arg Thr Thr Leu Arg Ser Val Lys Ala Ile
1               5                   10                  15

Gln Leu Ser Thr Val Pro Pro Ala Glu Thr Glu Ala Ile Ala Asp Val
            20                  25                  30

Lys Asp Ser Asp Glu Thr Lys Ser Thr Val Val Asn Thr His Leu Met
        35                  40                  45

Pro Lys Ser Ser Glu Val Glu Ala Leu Ile Ser Glu Ile Thr Asp Ser
    50                  55                  60

Ser Ser Ile Ala Glu Phe Glu Leu Lys Leu Gly Gly Phe Arg Leu Tyr
65                  70                  75                  80

Val Ala Arg Lys Leu Thr Asp Glu Ser Ser Pro Pro Gln Gln Ile
            85                  90                  95

Gln Pro Val Val Ala Ala Ser Ala Thr Pro Glu Gly Val His Thr Asn
            100                 105                 110

Gly Ser Ala Thr Ser Ser Ser Leu Ala Ile Thr Lys Thr Ser Ser Ser
            115                 120                 125

Ser Ala Asp Arg Pro Gln Thr Leu Ala Asn Lys Ala Ala Asp Gln Gly
    130                 135                 140

Leu Val Ile Leu Gln Ser Pro Thr Val Gly Tyr Phe Arg Arg Ser Lys
145                 150                 155                 160

Thr Ile Lys Gly Lys Arg Thr Pro Thr Ile Cys Lys Glu Lys Asp Ile
                165                 170                 175

Val Lys Glu Gly Gln Val Leu Cys Tyr Ile Glu Gln Leu Gly Gly Gln
            180                 185                 190

Ile Pro Val Glu Ser Asp Val Ser Gly Glu Ile Val Lys Ile Leu Arg
        195                 200                 205

Glu Asp Gly Glu Pro Val Gly Tyr Asn Asp Ala Leu Ile Thr Val Leu
    210                 215                 220
```

-continued

Pro Ser Phe Pro Gly Ile Lys Lys Leu Gln
225                 230

<210> SEQ ID NO 9
<211> LENGTH: 275
<212> TYPE: PRT
<213> ORGANISM: Arabidopsis thaliana

<400> SEQUENCE: 9

Met Ala Ser Cys Ser Leu Gly Val Pro Lys Ile Lys Ile Ser Ala Val
1               5                   10                  15

Asp Leu Ser Arg Val Arg Ser Gly Ser Leu Leu Ile Pro Tyr Asn Gln
            20                  25                  30

Arg Ser Leu Leu Arg Gln Arg Pro Val Lys Tyr Leu Ser Leu Lys Thr
        35                  40                  45

Thr Phe Gly Ser Val Lys Ala Val Gln Val Ser Thr Val Pro Thr Ala
    50                  55                  60

Glu Thr Ser Ala Thr Ile Glu Val Lys Asp Ser Lys Glu Ile Lys Ser
65                  70                  75                  80

Ser Arg Leu Asn Ala Gln Leu Val Pro Lys Pro Ser Glu Val Glu Ala
                85                  90                  95

Leu Val Thr Glu Ile Cys Asp Ser Ser Ile Ala Glu Phe Glu Leu
            100                 105                 110

Lys Leu Gly Gly Phe Arg Leu Tyr Val Ala Arg Asn Ile Ala Asp Asn
        115                 120                 125

Ser Ser Leu Gln Pro Pro Thr Pro Ala Val Thr Ala Ser Asn Ala
    130                 135                 140

Thr Thr Glu Ser Pro Glu Ser Asn Gly Ser Ala Ser Ser Thr Ser Leu
145                 150                 155                 160

Ala Ile Ser Lys Pro Ala Ser Ser Ala Ala Asp Gln Gly Leu Met Ile
                165                 170                 175

Leu Gln Ser Pro Lys Val Gly Phe Phe Arg Arg Ser Lys Thr Ile Lys
            180                 185                 190

Gly Lys Arg Leu Pro Ser Ser Cys Lys Glu Lys Asp Gln Val Lys Glu
        195                 200                 205

Gly Gln Ile Leu Cys Tyr Ile Glu Gln Leu Gly Gly Gln Phe Pro Ile
    210                 215                 220

Glu Ser Asp Val Thr Gly Glu Val Val Lys Ile Leu Arg Glu Asp Gly
225                 230                 235                 240

Gly Lys Ser Leu Val Phe Phe Asn Leu Ser Ser Phe Leu Lys Pro
                245                 250                 255

Arg Cys Asn Asp Phe Ser Tyr Arg Phe Leu Ile Arg Asn Arg Ala Cys
            260                 265                 270

Arg Ile Gln
        275

<210> SEQ ID NO 10
<211> LENGTH: 263
<212> TYPE: PRT
<213> ORGANISM: Arabidopsis thaliana

<400> SEQUENCE: 10

Met Ala Ser Cys Ser Leu Gly Val Pro Lys Ile Lys Ile Ser Ala Val
1               5                   10                  15

Asp Leu Ser Arg Val Arg Ser Gly Ser Leu Leu Ile Pro Tyr Asn Gln
            20                  25                  30

```
Arg Ser Leu Arg Gln Arg Pro Val Lys Tyr Leu Ser Leu Lys Thr
         35                  40                  45

Thr Phe Gly Ser Val Lys Ala Val Gln Val Ser Thr Val Pro Thr Ala
 50                  55                  60

Glu Thr Ser Ala Thr Ile Glu Val Lys Asp Ser Lys Glu Ile Lys Ser
 65                  70                  75                  80

Ser Arg Leu Asn Ala Gln Leu Val Pro Lys Pro Ser Glu Val Glu Ala
                 85                  90                  95

Leu Val Thr Glu Ile Cys Asp Ser Ser Ile Ala Glu Phe Glu Leu
            100                 105                 110

Lys Leu Gly Gly Phe Arg Leu Tyr Val Ala Arg Asn Ile Ala Asp Asn
        115                 120                 125

Ser Ser Leu Gln Pro Pro Thr Pro Ala Val Thr Ala Ser Asn Ala
130                 135                 140

Thr Thr Glu Ser Pro Glu Ser Asn Gly Ser Ala Ser Ser Thr Ser Leu
145                 150                 155                 160

Ala Ile Ser Lys Pro Ala Ser Ser Ala Ala Asp Gln Gly Leu Met Ile
                165                 170                 175

Leu Gln Ser Pro Lys Val Gly Phe Phe Arg Arg Ser Lys Thr Ile Lys
            180                 185                 190

Gly Lys Arg Leu Pro Ser Ser Cys Lys Glu Lys Asp Gln Val Lys Glu
        195                 200                 205

Gly Gln Ile Leu Cys Tyr Ile Glu Gln Leu Gly Gln Phe Pro Ile
    210                 215                 220

Glu Ser Asp Val Thr Gly Glu Val Val Lys Ile Leu Arg Glu Asp Gly
225                 230                 235                 240

Glu Pro Val Gly Tyr Asn Asp Ala Leu Ile Ser Ile Leu Pro Ser Phe
                245                 250                 255

Pro Gly Ile Lys Lys Leu Gln
            260

<210> SEQ ID NO 11
<211> LENGTH: 274
<212> TYPE: PRT
<213> ORGANISM: Arabidopsis thaliana

<400> SEQUENCE: 11

Met Asn Ser Cys Ser Leu Gly Ala Pro Lys Val Arg Ile Phe Ala Thr
 1               5                  10                  15

Asn Phe Ser Arg Leu Arg Cys Gly Asn Leu Leu Ile Pro Asn Asn Gln
                 20                  25                  30

Arg Leu Phe Val Asp Gln Ser Pro Met Lys Tyr Leu Ser Leu Arg Thr
            35                  40                  45

Thr Leu Arg Ser Val Lys Ala Ile Gln Leu Ser Thr Val Pro Pro Ala
 50                  55                  60

Glu Thr Glu Ala Ile Ala Asp Val Lys Asp Ser Asp Glu Thr Lys Ser
 65                  70                  75                  80

Thr Val Val Asn Thr His Leu Met Pro Lys Ser Ser Glu Val Glu Ala
                 85                  90                  95

Leu Ile Ser Glu Ile Thr Asp Ser Ser Ile Ala Glu Phe Glu Leu
            100                 105                 110

Lys Leu Gly Gly Phe Arg Leu Tyr Val Ala Arg Lys Leu Thr Asp Glu
        115                 120                 125

Ser Ser Pro Pro Gln Gln Ile Gln Pro Val Val Ala Ala Ser Ala
130                 135                 140
```

```
Thr Pro Glu Gly Val His Thr Asn Gly Ser Ala Thr Ser Ser Ser Leu
145                 150                 155                 160

Ala Ile Thr Lys Thr Ser Ser Ser Ala Asp Arg Pro Gln Thr Leu
                165                 170                 175

Ala Asn Lys Ala Ala Asp Gln Gly Leu Val Ile Leu Gln Ser Pro Thr
            180                 185                 190

Val Gly Tyr Phe Arg Arg Ser Lys Thr Ile Lys Gly Lys Arg Thr Pro
                195                 200                 205

Thr Ile Cys Lys Glu Lys Asp Ile Val Lys Glu Gly Gln Val Leu Cys
210                 215                 220

Tyr Ile Glu Gln Leu Gly Gly Gln Ile Pro Val Glu Ser Asp Val Ser
225                 230                 235                 240

Gly Glu Ile Val Lys Ile Leu Arg Glu Asp Gly Glu Pro Val Gly Tyr
                245                 250                 255

Asn Asp Ala Leu Ile Thr Val Leu Pro Ser Phe Pro Gly Ile Lys Lys
            260                 265                 270

Leu Gln

<210> SEQ ID NO 12
<211> LENGTH: 281
<212> TYPE: PRT
<213> ORGANISM: Arabidopsis thaliana

<400> SEQUENCE: 12

Met Ala Ser Ser Ala Ala Leu Gly Ser Leu His Gln Thr Leu Gly Ser
1               5                   10                  15

Ala Ile Asn Ser Gln Ser Glu Val His Ser Leu Ser Gly Asn Trp Ser
                20                  25                  30

Ala Ser Gly Asn Ser Cys Val Pro Arg Trp Arg Leu Ser Asn Arg Asn
            35                  40                  45

Ser Asn Tyr Arg Leu Val Leu Arg Ala Lys Ala Lys Ser Ser Ser Thr
        50                  55                  60

Thr Thr Ile Ser Asp Gly Ser Ser Asp Ala Ser Val Ser Asp Gly Lys
65                  70                  75                  80

Lys Thr Val Arg Arg Ile Thr Phe Pro Lys Glu Val Glu Ala Leu Val
                85                  90                  95

His Glu Met Cys Asp Glu Thr Glu Val Ala Val Leu Gln Leu Lys Val
            100                 105                 110

Gly Asp Phe Glu Met Asn Leu Lys Arg Lys Ile Gly Ala Ala Thr Asn
        115                 120                 125

Pro Ile Pro Val Ala Asp Ile Ser Pro Thr Val Ala Pro Pro Ile Pro
130                 135                 140

Ser Glu Pro Met Asn Lys Ser Ala Ser Ser Ala Pro Ser Pro Ser Gln
145                 150                 155                 160

Ala Lys Pro Ser Ser Glu Lys Val Ser Pro Phe Lys Asn Thr Ser Tyr
                165                 170                 175

Gly Lys Pro Ala Lys Leu Ala Ala Leu Glu Ala Ser Gly Ser Thr Asn
            180                 185                 190

Tyr Val Leu Val Thr Ser Pro Ala Val Gly Lys Phe Gln Arg Ser Arg
        195                 200                 205

Thr Val Lys Gly Lys Lys Gln Ser Pro Ser Cys Lys Glu Gly Asp Ala
    210                 215                 220

Ile Lys Glu Gly Gln Val Ile Gly Tyr Leu His Gln Leu Gly Thr Glu
225                 230                 235                 240
```

Leu Pro Val Thr Ser Asp Val Ala Gly Glu Val Leu Lys Leu Leu Ser
              245                 250                 255

Asp Asp Gly Asp Ser Val Gly Tyr Gly Asp Pro Leu Val Ala Val Leu
              260                 265                 270

Pro Ser Phe His Asp Ile Asn Ile Gln
              275                 280

<210> SEQ ID NO 13
<211> LENGTH: 80
<212> TYPE: PRT
<213> ORGANISM: Polytomella parva

<400> SEQUENCE: 13

Gly Lys Arg Val Gly Lys Asn Asn Cys Val Asn Lys Gly Asp Arg Leu
1               5                   10                  15

Lys Lys Gly Gln Thr Leu Gly Phe Ile Glu Gln Leu Gly Thr His Val
              20                  25                  30

Pro Val Glu Cys Pro Val Ala Gly Glu Leu Ile Lys Phe Asn Val Glu
          35                  40                  45

Asp Gly Lys Pro Val Glu Tyr Ser Gln Ala Ile Cys Glu Ile Thr Pro
      50                  55                  60

Phe Phe Gly Gly Tyr Thr Gly Ser Asp Arg Ala Thr Lys Val Val Ala
65                  70                  75                  80

<210> SEQ ID NO 14
<211> LENGTH: 299
<212> TYPE: PRT
<213> ORGANISM: Picea sitchensis

<400> SEQUENCE: 14

Met Ala Ala Ser Cys Pro Tyr Ser Pro Phe His Cys Ser Leu Gly Thr
1               5                   10                  15

Ser Thr Gln Ala Gln Gly Leu Leu Glu Lys Gly Val Val Arg Asn Leu
              20                  25                  30

His Tyr Gly Phe Ser Tyr Arg Ser Leu Pro Arg Met Asp Ser Gly Asp
          35                  40                  45

Ser Phe Arg Asn Lys Arg Gly Thr Leu Ser Asn Ala Gly Arg Ser Lys
      50                  55                  60

Val Trp Leu Ser Ser Asn Val Lys Ala Ser His Ala Thr Phe Ala Met
65                  70                  75                  80

Ala Ser Asp Lys Asp Ala Leu Glu Ser Gly Ser Leu Gly Glu Leu Glu
              85                  90                  95

Lys Gly Asn Gln Asn Gly Ala Leu Phe Pro Asp Gly Ile Glu Ser Phe
              100                 105                 110

Ile Thr Glu Val Cys Asp Glu Thr Asp Ile Ala Glu Ile Lys Leu Lys
          115                 120                 125

Ala Gly Ser Phe Ala Met His Ile Arg Arg Asn Ile Glu Lys Ser Lys
      130                 135                 140

Arg Pro Ser Ser Val Ala Ser Pro Leu Thr Ala Pro Val Pro Ser
145                 150                 155                 160

Glu Pro Met Val Asp Phe Asp His Thr Val Thr Pro Pro Ser Ser
              165                 170                 175

Pro Ala Pro Lys Ala Pro Pro Thr Arg Ser Phe Asn Pro Phe Thr Thr
              180                 185                 190

Lys Leu Ser Leu Ser Lys Thr Ser Lys Phe Gly Leu Leu Glu Ala Ala
          195                 200                 205

Gly Asp Glu Gly Leu Cys Phe Val Thr Ala Pro Lys Val Gly Leu Phe
        210                 215                 220

Lys Arg Ser Arg Val Val Lys Gly Arg Asn Gly Arg Pro Leu Cys Glu
225                 230                 235                 240

Glu Gly Gln Ser Ile Lys Glu Gly Gln Val Val Cys Phe Leu Asp Gln
            245                 250                 255

Leu Gly Gly Gln Thr Pro Val Thr Ser Glu Val Ser Gly Glu Ile Val
        260                 265                 270

Lys Ile Leu Trp Ser Asp Gly Glu Pro Val Gly Tyr Gly Asp Pro Leu
    275                 280                 285

Ile Ala Val Leu Pro Ser Phe Arg Gly Ile Lys
        290                 295

<210> SEQ ID NO 15
<211> LENGTH: 282
<212> TYPE: PRT
<213> ORGANISM: Medicago truncatula

<400> SEQUENCE: 15

Met Val Ile Trp Val Ile Lys His Ile Thr Gly Ser Leu Gly Thr Gln
1               5                   10                  15

Asn Val Lys Val Leu Asn Leu His Phe Gly Gln Glu Arg Ala Glu Phe
            20                  25                  30

Ser Gln His Phe Gly Thr Arg Ser Trp Ile Ser Arg Lys Ser Leu Gln
        35                  40                  45

Tyr Ala Arg Leu Val Ala Ser Lys Gln Thr Val Arg Ser Leu Thr Pro
    50                  55                  60

Ser Asn Asp Gln Ser Ala Glu Ile Gln Ser Val Ser Arg Ser Glu Asp
65                  70                  75                  80

Gly Ser Glu Glu Ser Lys Ser Ser Gly Leu Thr Asn Gln Leu Phe Pro
                85                  90                  95

Asn Phe Asn Asp Val Glu Phe Leu Leu Thr Asn Leu Cys Asp Thr Ala
            100                 105                 110

Ser Ile Gly Glu Leu Glu Leu Lys Leu Asp Gly Phe His Leu Arg Val
        115                 120                 125

Val Arg Asp Leu Thr Glu Lys Ser Lys Thr Leu Pro Pro Ser Ile Pro
    130                 135                 140

Ala Pro Val Ser Ile Asn Thr Pro Ala Glu Ala Pro Lys Pro Asn Gly
145                 150                 155                 160

Ser Val Ser Thr Leu Thr Thr Leu Ala Ile Ser Lys Pro Ala Pro Ser
                165                 170                 175

Ser Leu Ser Ile Glu Gly Phe Leu Glu Lys Ala Ala Asp Glu Gly Leu
            180                 185                 190

Val Ile Ile His Ser Pro Thr Val Gly Ile Phe Arg Arg Ser Arg Thr
        195                 200                 205

Ile Lys Gly Lys Arg Ala Pro Pro Ser Cys Gln Glu Met Gln Asn Val
    210                 215                 220

Glu Glu Gly Lys Val Ile Cys Tyr Ile Glu Gln Leu Gly Gly Gln Leu
225                 230                 235                 240

Pro Val Glu Ser Asp Val Ser Gly Glu Val Ile Lys Ile Leu Arg Glu
                245                 250                 255

Asp Gly Asp Pro Val Gly Tyr Gly Asp Thr Leu Ile Ala Ile Leu Pro
            260                 265                 270

Ser Phe Pro Gly Ile Lys Lys Leu Gln Tyr
        275                 280

-continued

```
                275                 280

<210> SEQ ID NO 16
<211> LENGTH: 252
<212> TYPE: PRT
<213> ORGANISM: Vitis vinifera

<400> SEQUENCE: 16

Met Ala Asn Asn Lys Asp His Lys Leu Pro Ala Thr Pro Ala Met Gly
1               5                   10                  15

Lys Asn Met Val Ile Pro Phe Leu Leu Trp Phe Ala Lys Thr Met Ala
            20                  25                  30

Ile Asn Lys Arg Ser Val Pro Thr Pro Glu Leu Val Gly Ser Ala Val
        35                  40                  45

Asn Leu Glu Asp Gly Ser Glu Glu Thr Lys Ser Ser Gly Leu Thr Ser
    50                  55                  60

Gln Leu Thr Pro Asn Ala Tyr Glu Val Glu Ser Leu Leu Ser Glu Ile
65                  70                  75                  80

Cys Asp Thr Thr Ser Ile Ala Glu Phe Glu Leu Lys Leu Gly Gly Phe
                85                  90                  95

Arg Leu Tyr Met Met Arg Asp Leu Ala Gly Lys Ile Glu Pro Thr Pro
            100                 105                 110

Pro Pro Ser Ser Thr Pro Val Thr Val Ser Leu Asn Asp Glu Ala Pro
        115                 120                 125

Lys Leu Asn Gly Ser Ala Ser Met Ser Ser Leu Pro Ile Ser Lys Ser
    130                 135                 140

Ala Leu Leu Leu Gly Gln Ser Gln Thr Leu Leu Asp Arg Ala Ala Asp
145                 150                 155                 160

Glu Gly Leu Met Ile Leu Gln Ser Pro Lys Val Gly Phe Phe Arg Arg
                165                 170                 175

Ser Arg Thr Ile Lys Gly Lys Arg Ala Pro Pro Ser Cys Lys Glu Lys
            180                 185                 190

Gln Ile Val Lys Glu Gly Gln Val Leu Cys Tyr Ile Glu Gln Leu Gly
        195                 200                 205

Gly Glu Ile Pro Ile Glu Ser Asp Val Ser Gly Glu Val Ile Lys Ile
    210                 215                 220

Leu Arg Glu Asp Gly Glu Pro Val Gly Tyr Gly Asp Ala Leu Ile Ala
225                 230                 235                 240

Ile Leu Pro Ser Phe Pro Gly Ile Lys Lys Leu Gln
                245                 250

<210> SEQ ID NO 17
<211> LENGTH: 209
<212> TYPE: PRT
<213> ORGANISM: Elaeis guineensis
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (135)..(135)
<223> OTHER INFORMATION: Xaa can be any naturally occurring amino acid

<400> SEQUENCE: 17

Met Gly Thr Cys Ser Leu Gly Ser Thr Ser Lys Ile Lys Leu Leu Ser
1               5                   10                  15

Phe His Pro Glu Phe Lys Lys Leu Arg Cys Thr Ala Arg Leu Thr His
            20                  25                  30
```

-continued

```
His Asn Leu Lys Cys Gly Arg Leu Glu Thr Pro Asn Gly Ser Xaa Gly
        35                  40                  45

Thr Gln Ile Trp Lys Glu Leu Val Arg Ala Ala Gly Phe Asp Lys Gln
    50                  55                  60

Ala Arg Arg Phe Ser Asn Ser Leu Gly Ala Arg Cys Ser Ile Ser Ser
65                  70                  75                  80

Gly Thr Glu Asn Asn Ser Asn Ile Leu Glu Leu Glu Glu Asn Arg Ser
                85                  90                  95

Asn Gly Asn Gln Ile Ile Pro Ile Ser Leu Glu Val Glu Pro Leu Leu
            100                 105                 110

Thr Ala Val Cys Asp Ala Thr Ser Val Ala Glu Phe Lys Leu Asp Val
        115                 120                 125

Gly Phe Phe Arg Arg Ser Xaa Thr Ile Lys Gly Lys Gln Ala Pro Arg
    130                 135                 140

Ser Cys Lys Val Gly Gln Asp Gly Lys Gly Gln Val Leu Cys Tyr
145                 150                 155                 160

Ile Glu Gln Ile Gly Gly Ile Pro Val Glu Ser Asp Val Ser Gly
                165                 170                 175

Glu Val Ile Lys Ile Leu Arg Glu Gly Glu Ala Val Gly Tyr Gly
            180                 185                 190

Asp Ala Leu Ile Ala Ile Leu Pro Ser Phe Pro Gly Ile Lys Lys Leu
        195                 200                 205

Gln

<210> SEQ ID NO 18
<211> LENGTH: 232
<212> TYPE: PRT
<213> ORGANISM: Chlamydomonas reinhardtii

<400> SEQUENCE: 18

Met Leu Cys Arg Thr Val Ala Pro Thr Arg Pro Ala Gly Val Ala Arg
1               5                   10                  15

Ser Val Arg Ser Val Arg Pro Ser Pro Ile Ala Arg Val Pro Pro Met
            20                  25                  30

Lys Ala Thr Ala Ser Thr Ala Glu Lys Lys Ala Glu Ala Ala Glu Val
        35                  40                  45

Glu Glu Glu Phe Asp Gly Pro Glu Val Asn Pro Ser Thr Gln Glu Val
    50                  55                  60

Ala Ala Phe Ile Asn Thr Leu Cys Asn Asp Thr Glu Ile Ala Glu Met
65                  70                  75                  80

His Leu Lys Met Gly Ser Phe Glu Leu Lys Val Lys Arg Ser Val Ser
                85                  90                  95

Gly Gly Ala Pro Val Tyr Ala His Ala Pro Val Ala Ala Pro Ala Ala
            100                 105                 110

Pro Ala Pro Ala Ala Thr Val Ser Val Asp Val Pro Ala Pro Thr Val
        115                 120                 125

Glu Asp Thr Val Asp Glu Ser Leu Val Tyr Val Asn Ala Pro Lys Val
    130                 135                 140

Gly Val Phe Arg Arg Gly Lys Tyr Ala Gly Lys Arg Val Gly Lys
145                 150                 155                 160

Gly Asn Leu Ile Glu Val Gly Ala Gln Val Lys Lys Gly Gln Cys Ile
                165                 170                 175

Gly Tyr Val Glu Gln Leu Gly Thr Phe Val Glu Val Lys Cys Pro Ile
            180                 185                 190
```

```
Ala Gly Glu Leu Val Lys Val His Val Glu Asp Gly Lys Pro Val Glu
        195                 200                 205

Tyr Gln Gln Leu Val Ala Glu Val Ala Pro Phe Phe Gly Gly His Ile
210                 215                 220

Ile Gly Asp Ser Lys Tyr Ala Phe
225                 230
```

<210> SEQ ID NO 19
<211> LENGTH: 294
<212> TYPE: PRT
<213> ORGANISM: Physcomitrella patens

<400> SEQUENCE: 19

```
Met Ala Leu Ala Ala Val Gly Arg Phe Ala Val Thr Gly Ser Ser Leu
1               5                   10                  15

Gln Ser Val Ile Gly Ser Glu Lys Gln Cys Val Val Ala Ala Pro Ala
                20                  25                  30

Glu Arg Ile Ser Ile Ser Ser Arg Ser Ser Ile Ala Ala Pro Leu
        35                  40                  45

Arg Glu Cys Ile Ile Thr Gly Leu Ala Pro Val Thr Arg Thr Phe Gln
50                  55                  60

Pro Arg Ala Val Thr Ala Asp Tyr Leu Gly Glu Ser Glu Val Leu
65                  70                  75                  80

Asp Ala Glu Asn Glu Val Glu Glu Ala Asp Asn Pro Leu Val Pro
                85                  90                  95

Ser Ala Phe Glu Val Gln Asn Leu Leu Met Gln Val Cys Asp Glu Thr
            100                 105                 110

Ser Asn Ile Ala Glu Val Gln Leu Lys Val Gly Ser Phe Ser Leu Arg
        115                 120                 125

Val Lys Arg Lys Ile Gly Lys Ala Ala Pro Ala Pro Lys Pro Val Ala
    130                 135                 140

Ala Gly Pro Pro Val Leu Gly Lys Pro Met Val Glu Ser Ile Pro Ala
145                 150                 155                 160

Asp Ser Val Pro Thr Ala Pro Ala Pro Lys Ser Thr Lys Leu Thr Lys
                165                 170                 175

Asn Thr Ala Leu Ser Ala Ala Ser Leu Lys Pro Val Ser Asn Phe Gly
            180                 185                 190

Leu Met Glu Ala Ala Ala Asp Ala Gly Ile Val Phe Val Thr Ser Pro
        195                 200                 205

Lys Val Gly Leu Phe Arg Lys Gly Arg Thr Val Lys Gly Arg Ser Gly
    210                 215                 220

Pro Pro Leu Cys Glu Glu Gly Gln Val Ile Lys Lys Gly Gln Val Val
225                 230                 235                 240

Cys Tyr Leu Glu Gln Leu Gly Thr Gln Gln Pro Val Glu Ala Glu Val
                245                 250                 255

Thr Gly Glu Val Glu Lys Val Leu Trp Glu Asp Gly Ala Pro Val Gly
            260                 265                 270

Tyr Gly Asp Pro Leu Ile Ala Ile Arg Pro Ser Phe Pro Gly Ile Lys
        275                 280                 285

Val Lys Gly Gln Ile Gln
    290
```

<210> SEQ ID NO 20
<211> LENGTH: 260
<212> TYPE: PRT

<213> ORGANISM: Populus trichocarpa

<400> SEQUENCE: 20

```
Met Glu Ser Ser Val Leu Leu Arg Ser Phe Gln Cys Asn Leu Leu Ala
1               5                   10                  15

Gln Gly Gln Gly Leu Thr Val Gly Arg Lys Leu Ile Ser Tyr Pro Ser
            20                  25                  30

Lys Arg Asn Leu Arg Leu Val Ser Cys Val Lys Thr Ser Glu Ala Pro
        35                  40                  45

Ala Ile Ala Lys Ser Asp Asp Gly Asn Lys Gln Gly Ser Leu Glu Lys
    50                  55                  60

Asn Ser Leu Arg Asn Ala Thr Phe Pro Asn Gly Phe Glu Ala Leu Val
65                  70                  75                  80

Leu Glu Val Cys Asp Glu Thr Glu Ile Ala Glu Leu Lys Leu Lys Val
                85                  90                  95

Gly Asp Phe Glu Met His Leu Lys Arg Asn Val Gly Ala Ala Lys Ala
            100                 105                 110

Pro Leu Ile Ser Ser Thr Pro Leu Pro Pro Ile Pro Thr Pro Pro Met
        115                 120                 125

Glu Val Ser Ala Ala Val Ser Pro Ser Pro Ser Pro Ser Lys Ser Ser
    130                 135                 140

Val Glu Lys Thr Thr Pro Phe Thr Asn Val Ser Phe Gly Lys Ser Ser
145                 150                 155                 160

Lys Leu Ala Ala Leu Glu Ala Ser Gly Ala Ser Gly Tyr Val Leu Val
                165                 170                 175

Ala Ser Pro Thr Val Gly Ser Phe Arg Arg Asn Arg Thr Val Lys Gly
            180                 185                 190

Lys Lys Gln Pro Pro Ile Cys Lys Glu Gly Asp Val Ile Lys Glu Gly
        195                 200                 205

Gln Val Ile Gly Tyr Leu Asp Gln Phe Gly Thr Glu Leu Pro Val Lys
    210                 215                 220

Ser Asp Val Ala Gly Glu Val Leu Lys Leu Leu Phe Asn Asp Gly Asp
225                 230                 235                 240

Ala Val Gly Tyr Gly Asp Pro Leu Ile Ala Val Leu Pro Ser Phe His
                245                 250                 255

Gly Ile Asn Thr
            260
```

<210> SEQ ID NO 21
<211> LENGTH: 274
<212> TYPE: PRT
<213> ORGANISM: Vitis vinifera

<400> SEQUENCE: 21

```
Met Ala Ser Cys Gly Leu Gly Ala Pro Ser Ile Lys Ile Ser Asn Leu
1               5                   10                  15

Asp Leu Val Arg Thr Arg Leu Gly Val Leu Gln Ser Arg Phe Ser Ile
            20                  25                  30

Arg Thr Ser Thr Ala Trp Thr Pro Leu Asn Asn Ser Gly Leu Val Ile
        35                  40                  45

Ser Gln Arg Ser Gln Lys Ala Ile Ile Leu Cys Arg Gly Ser Ser Ser
    50                  55                  60

Glu Ala Glu Ser Ala Val Asn Leu Glu Asp Gly Ser Glu Glu Thr Lys
65                  70                  75                  80

Ser Ser Gly Leu Thr Ser Gln Leu Thr Pro Asn Ala Tyr Glu Val Glu
```

```
            85                  90                  95
Ser Leu Leu Ser Glu Ile Cys Asp Thr Thr Ser Ile Ala Glu Phe Glu
            100                 105                 110

Leu Lys Leu Gly Gly Phe Arg Leu Tyr Met Met Arg Asp Leu Ala Gly
            115                 120                 125

Lys Ile Glu Pro Thr Pro Pro Ser Ser Thr Pro Val Thr Val Ser
        130                 135                 140

Leu Asn Asp Glu Ala Pro Lys Leu Asn Gly Ser Ala Ser Met Ser Ser
145                 150                 155                 160

Leu Pro Ile Ser Lys Ser Ala Leu Leu Gly Gln Ser Gln Thr Leu
            165                 170                 175

Leu Asp Arg Ala Ala Asp Glu Gly Leu Met Ile Leu Gln Ser Pro Lys
            180                 185                 190

Val Gly Phe Phe Arg Arg Ser Arg Thr Ile Lys Gly Lys Arg Ala Pro
            195                 200                 205

Pro Ser Cys Lys Glu Lys Gln Ile Val Lys Glu Gly Gln Val Leu Cys
        210                 215                 220

Tyr Ile Glu Gln Leu Gly Gly Glu Ile Pro Ile Glu Ser Asp Val Ser
225                 230                 235                 240

Gly Glu Val Ile Lys Ile Leu Arg Glu Asp Gly Pro Val Gly Tyr
            245                 250                 255

Gly Asp Ala Leu Ile Ala Ile Leu Pro Ser Phe Pro Gly Ile Lys Lys
            260                 265                 270

Leu Gln

<210> SEQ ID NO 22
<211> LENGTH: 225
<212> TYPE: PRT
<213> ORGANISM: Ricinus communis
<220> FEATURE:
<221> NAME/KEY: misc_feature
<222> LOCATION: (29)..(30)
<223> OTHER INFORMATION: Xaa can be any naturally occurring amino acid

<400> SEQUENCE: 22

Met Asp Glu Lys Glu Thr Lys Ser Ser Gly Leu Thr Ser Gln Leu Leu
1               5                   10                  15

Pro Asn Ser Ala Glu Met Ser Val Trp Cys Ile Met Xaa Xaa Glu Ser
            20                  25                  30

Leu Ile Thr Glu Ile Cys Asn Ser Thr Ser Ile Ala Glu Phe Glu Leu
            35                  40                  45

Lys Leu Asp Gly Phe Arg Leu Tyr Val Thr Arg Asp Leu Thr Glu Lys
        50                  55                  60

Ser Lys Leu Gln Pro Leu Ser Ala Ser Ala Pro Ala Leu Ser
65                  70                  75                  80

Pro Pro Pro Ala Pro Ala Ala Leu Ala Ser Val Ser Thr Asp Thr
            85                  90                  95

Thr Thr Ala Ala Pro Asp Leu Asn Gly Ser Val Ser Ser Thr Ser Arg
            100                 105                 110

Ala Ile Ser Lys Ser Gly Ser Phe Ser Gly Val Gln Ser Ile Leu
            115                 120                 125

Asp Arg Ala Ala Asp Glu Gly Leu Met Ile Leu Gln Ser Pro Arg Val
        130                 135                 140

Gly Phe Phe Arg Arg Ser Arg Thr Ile Lys Gly Lys Arg Ala Pro Pro
145                 150                 155                 160
```

```
Ser Cys Lys Glu Lys Gln Ile Val Lys Glu Gly Gln Val Leu Cys Tyr
            165                 170                 175

Ile Glu Gln Leu Gly Gly Glu Leu Pro Ile Glu Ser Asp Val Ser Gly
        180                 185                 190

Glu Val Ile Lys Ile Leu Arg Glu Asp Gly Glu Pro Val Gly Tyr Gly
            195                 200                 205

Asp Ala Leu Ile Ala Ile Leu Pro Ser Phe Pro Gly Ile Lys Lys Leu
        210                 215                 220

Gln
225

<210> SEQ ID NO 23
<211> LENGTH: 258
<212> TYPE: PRT
<213> ORGANISM: Ricinus communis

<400> SEQUENCE: 23

Met Glu Ser Ser Ile Ala Leu Gln Cys Lys Met Tyr Gly Gln Arg
  1               5                  10                  15

Leu Thr Val Gly Arg Lys Leu Met Ser Ser Tyr Pro Lys Met Arg
            20                  25                  30

Arg Asn Val Met Ser Val Ser Cys Val Lys Ala Pro Glu Val Gly Ala
            35                  40                  45

Thr Ala Lys Ser Asp Ala Ala Asp Gly Ala Val Glu Lys Thr Arg Pro
        50                  55                  60

Arg Thr Ala Thr Phe Pro Ser Gly Phe Glu Ala Leu Met Leu Glu Val
 65                  70                  75                  80

Cys Asp Glu Thr Glu Val Ala Glu Leu Lys Leu Lys Val Gly Asp Phe
                85                  90                  95

Glu Met His Leu Arg Arg Asn Val Gly Ala Thr Lys Ala Pro Leu Ser
            100                 105                 110

His Ile Ser Pro Ile Glu Pro Pro Ile Pro Thr Lys Pro Met Asp
        115                 120                 125

Val Pro Ala Thr Val Ala Ala Pro Ala Ser Pro Lys Pro Ser Ser
        130                 135                 140

Glu Lys Ala Thr Pro Phe Thr Asn Val Ser Phe Gly Lys Ser Ala Lys
145                 150                 155                 160

Leu Ala Ala Leu Glu Ala Ser Gly Ala Thr Gly Tyr Val Leu Val Ala
                165                 170                 175

Ser Pro Thr Val Gly Ser Phe Arg Arg Asn Arg Ser Val Lys Gly Lys
            180                 185                 190

Arg Gln Pro Pro Ile Phe Lys Glu Gly Asp Leu Ile Lys Glu Gly Gln
        195                 200                 205

Val Ile Gly Tyr Leu Asp Gln Phe Gly Thr Glu Leu Pro Val Lys Ser
        210                 215                 220

Asp Val Ala Gly Glu Val Leu Lys Leu Leu Phe Asp Asp Gly Asp Ala
225                 230                 235                 240

Val Gly Tyr Gly Asp Pro Leu Val Ala Val Leu Pro Ser Phe His Gly
                245                 250                 255

Ile Gln

<210> SEQ ID NO 24
<211> LENGTH: 291
<212> TYPE: PRT
<213> ORGANISM: Glycine max
```

<400> SEQUENCE: 24

Met Glu Ser Ser Ala Ile Arg Ser Phe His Tyr Pro Ile Gly Thr
1               5                   10                  15

Met Ser His Val Arg Ala Ser Leu Glu Lys Gln Ala Val Val Pro Ile
            20                  25                  30

His Asn Ala Gly Trp Asn Ser Lys Ser Arg Leu Phe Ile Gln His Leu
        35                  40                  45

Ala Tyr Gly Gln Lys His Ile Asn Ser His Thr Lys Gly Lys Asn Thr
    50                  55                  60

Leu Ile Ser Cys Gly Lys Thr Ala Glu Ala Ile Asn Ala Ser Lys Ser
65                  70                  75                  80

Asp Ala Ser Ser Asp Asn Thr Pro Gln Gly Ser Leu Glu Lys Lys Pro
                85                  90                  95

Leu Gln Thr Ala Thr Phe Pro Asn Gly Phe Glu Ala Leu Val Leu Glu
            100                 105                 110

Val Cys Asp Glu Thr Glu Ile Ala Glu Leu Lys Val Lys Val Gly Asp
        115                 120                 125

Phe Glu Met His Ile Lys Arg Asn Ile Gly Ala Thr Lys Val Pro Leu
    130                 135                 140

Ser Asn Ile Ser Pro Thr Thr Pro Pro Ile Pro Ser Lys Pro Met
145                 150                 155                 160

Asp Glu Ser Ala Pro Gly Ser Leu Pro Ser Pro Lys Ser Ser
                165                 170                 175

Pro Glu Lys Asn Asn Pro Phe Ala Asn Val Ser Lys Glu Lys Ser Pro
                180                 185                 190

Arg Leu Ala Ala Leu Glu Ala Ser Gly Thr Asn Thr Tyr Val Leu Val
            195                 200                 205

Ser Ser Pro Thr Val Gly Leu Phe Arg Arg Gly Arg Thr Val Lys Gly
    210                 215                 220

Lys Lys Gln Pro Pro Ile Cys Lys Glu Gly Asp Val Ile Lys Glu Gly
225                 230                 235                 240

Gln Val Ile Gly Tyr Leu Asp Gln Phe Gly Thr Gly Leu Pro Ile Lys
                245                 250                 255

Ser Asp Val Ala Gly Glu Val Leu Lys Leu Leu Val Glu Asp Gly Glu
            260                 265                 270

Pro Val Gly Tyr Gly Asp Pro Leu Ile Ala Val Leu Ser Ser Phe His
        275                 280                 285

Asp Ile Lys
        290

<210> SEQ ID NO 25
<211> LENGTH: 281
<212> TYPE: PRT
<213> ORGANISM: Arabidopsis lyrata subsp. lyrata

<400> SEQUENCE: 25

Met Ala Ser Ser Ala Ala Leu Gly Ser Leu His Gln Thr Leu Val Cys
1               5                   10                  15

Ala Ile Asn Ser Gln Ser Glu Val His Ser Leu Ser Gly Asn Trp Ser
            20                  25                  30

Ala Ser Gly Asn Ser Cys Val Pro Arg Trp Arg Leu Ser Asn Arg Asn
        35                  40                  45

Ser Lys Tyr Thr Leu Val Leu Arg Ala Lys Ala Lys Ser Ser Thr
    50                  55                  60

```
Ala Thr Lys Ser Asp Asp Ser Ser Glu Ala Ser Val Ser Asn Gly Lys
 65                  70                  75                  80

Lys Thr Val Arg Arg Ile Thr Phe Pro Lys Glu Val Glu Ala Leu Val
                 85                  90                  95

His Glu Met Cys Asp Glu Thr Glu Val Ala Val Leu Gln Leu Lys Val
            100                 105                 110

Gly Asp Phe Glu Met Asn Leu Lys Arg Lys Ile Gly Ala Ala Thr Asn
        115                 120                 125

Pro Ile Pro Met Val Asp Ile Ser Pro Thr Ile Ala Pro Pro Ile Pro
    130                 135                 140

Ser Glu Pro Met Asn Lys Ser Val Ser Ser Ala Pro Ser Pro Ser Lys
145                 150                 155                 160

Ala Lys Pro Ser Ser Glu Lys Val Ser Pro Phe Lys Asn Thr Ser Tyr
                165                 170                 175

Gly Lys Pro Ala Lys Leu Ala Ala Leu Glu Ala Ser Gly Ser Asn Asn
            180                 185                 190

Tyr Val Leu Val Thr Ser Pro Ala Val Gly Lys Phe Gln Arg Ser Arg
        195                 200                 205

Thr Val Lys Gly Lys Lys Gln Ser Pro Ser Cys Lys Glu Gly Asp Ala
    210                 215                 220

Ile Lys Glu Gly Gln Val Ile Gly Tyr Leu His Gln Leu Gly Thr Glu
225                 230                 235                 240

Leu Pro Val Thr Ser Asp Val Ala Gly Glu Val Leu Lys Leu Leu Ser
                245                 250                 255

Asp Asp Gly Asp Ser Val Gly Tyr Gly Asp Pro Leu Val Ala Ile Leu
            260                 265                 270

Pro Ser Phe His Asp Ile Asn Ile Gln
        275                 280

<210> SEQ ID NO 26
<211> LENGTH: 263
<212> TYPE: PRT
<213> ORGANISM: Arabidopsis lyrata subsp. lyrata

<400> SEQUENCE: 26

Met Ala Ser Cys Ser Leu Gly Val Pro Lys Ile Lys Ile Ser Ala Val
 1               5                  10                  15

Asp Leu Ser Arg Val Arg Ser Ala Ser Phe Leu Ile Pro Tyr Asn Gln
             20                  25                  30

Lys Ser Leu Leu Gly Gln Arg Pro Val Lys Tyr Leu Ser Leu Arg Thr
         35                  40                  45

Thr Phe Gly Ser Val Lys Ala Val Gln Leu Ser Thr Val Pro Ala Ala
     50                  55                  60

Glu Thr Ser Ala Thr Ile Glu Val Lys Asp Ser Glu Thr Lys Ser
 65                  70                  75                  80

Ser Arg Leu Asn Ala Gln Leu Val Pro Lys Pro Ser Glu Val Glu Ala
                 85                  90                  95

Leu Val Thr Glu Ile Cys Asp Ser Ser Ile Ala Glu Phe Glu Leu
            100                 105                 110

Lys Leu Gly Gly Phe Arg Leu Tyr Val Ala Arg Asn Ile Ala Asp Asn
        115                 120                 125

Ser Ser Pro Gln Pro Pro Thr Pro Ala Val Ala Ala Ser Asn Ala
    130                 135                 140

Thr Thr Glu Ser Pro Asp Leu Asn Gly Ser Ala Ser Ser Thr Ser Leu
145                 150                 155                 160
```

Ala Ile Ser Lys Pro Ala Ser Ala Ala Asp Gln Gly Leu Met Ile
            165                 170                 175

Leu Gln Ser Pro Lys Val Gly Phe Phe Arg Arg Ser Lys Thr Ile Lys
        180                 185                 190

Gly Lys Arg Leu Pro Ser Ser Cys Lys Glu Lys Asp Leu Val Lys Glu
        195                 200                 205

Gly Gln Ile Leu Cys Tyr Ile Glu Gln Leu Gly Gly Gln Phe Pro Ile
        210                 215                 220

Glu Ala Asp Val Thr Gly Glu Val Val Lys Ile Leu Arg Glu Asp Gly
225                 230                 235                 240

Glu Pro Val Gly Tyr Asn Asp Ala Leu Ile Ser Ile Leu Pro Ser Phe
                245                 250                 255

Pro Gly Ile Lys Lys Leu Gln
            260

<210> SEQ ID NO 27
<211> LENGTH: 275
<212> TYPE: PRT
<213> ORGANISM: Arabidopsis lyrata subsp. lyrata

<400> SEQUENCE: 27

Met Asn Ser Cys Ser Leu Gly Ala Pro Arg Val Arg Ile Ser Ala Thr
1               5                   10                  15

Ser Phe Ser Arg Leu Arg Cys Gly Asn Phe Leu Ile Pro Asn Asn Gln
            20                  25                  30

Thr Leu Phe Ile Asp Gln Ser Pro Ile Lys Asn Leu Ser Gln Arg Thr
        35                  40                  45

Thr Thr Leu Arg Ser Val Lys Ala Ile Gln Leu Ser Thr Val Pro Pro
    50                  55                  60

Ala Glu Thr Gln Ala Ile Ala Asp Val Glu Asp Ser Glu Thr Lys
65                  70                  75                  80

Ser Thr Val Val Asn Ser Gln Leu Ile Pro Asn Ser Ser Glu Val Glu
                85                  90                  95

Ala Leu Ile Ser Glu Ile Thr Asp Ser Thr Ser Ile Ala Glu Phe Glu
            100                 105                 110

Leu Lys Leu Gly Gly Phe Arg Leu Tyr Val Ala Arg Lys Leu Ala Asp
        115                 120                 125

Gln Ser Ser Pro Leu Pro Gln Gln Ile Pro Pro Val Val Ala Ala Ser
    130                 135                 140

Ala Thr Pro Glu Gly Val His Thr Asn Gly Ser Ala Thr Ser Ser Ser
145                 150                 155                 160

Leu Ala Ile Thr Lys Thr Ser Thr Ser Ser Ala Asp Arg Pro Gln Thr
                165                 170                 175

Leu Ala Asn Lys Ala Ala Asp Gln Gly Leu Val Ile Leu Gln Ser Pro
            180                 185                 190

Thr Val Gly Tyr Phe Arg Arg Ser Lys Thr Ile Lys Gly Lys Arg Thr
        195                 200                 205

Pro Thr Ile Cys Lys Glu Lys Asp Ile Val Lys Glu Gly Gln Val Leu
    210                 215                 220

Cys Tyr Ile Glu Gln Leu Gly Gly Gln Ile Pro Val Glu Ser Asp Val
225                 230                 235                 240

Ser Gly Glu Ile Val Lys Ile Leu Arg Glu Asp Gly Glu Pro Val Gly
                245                 250                 255

Tyr Asn Asp Ala Leu Ile Thr Val Leu Pro Ser Phe Pro Gly Ile Lys

Lys Leu Gln
        275

<210> SEQ ID NO 28
<211> LENGTH: 245
<212> TYPE: PRT
<213> ORGANISM: Selaginella moellendorffii

<400> SEQUENCE: 28

Met Ala Ala Ser Ser Leu Leu Gln Ala Gln Phe Ser Pro Ala Ser Ser
1               5                   10                  15

Ser Leu Asp Ala Cys His Val Ser Tyr Gly Ser Ser Ala Ile Ile Ser
            20                  25                  30

Val Ser Arg Val Ser Val Arg Gln Cys Trp Ala Arg Arg Ser Gln Arg
        35                  40                  45

Val Phe Cys Val Ala Thr Lys Ile Glu Glu Leu Glu Pro Val Ile Pro
    50                  55                  60

Thr Ser Ala Glu Ile His Thr Leu Leu Arg Glu Val Cys Asp Glu Thr
65                  70                  75                  80

Lys Ile Ala Glu Leu Asn Val Lys Val Gly Ala Phe Asn Leu His Met
                85                  90                  95

Arg Arg Ser Val Pro Ala Pro Lys Pro Pro Ala Ala Ser Val Ala
            100                 105                 110

Ala Pro Pro Val Ala Ala Pro Ala Ala Pro Val Ser Ser Lys Pro
        115                 120                 125

Ala Ala Pro Ser Lys Pro Ala Ala Lys Thr Ser Lys Val Ser Pro Met
    130                 135                 140

Met Ser Lys Ala Val Ala Tyr Asp Glu Leu Gln Lys Ala Ala Ala Glu
145                 150                 155                 160

Thr Gly Val Val Phe Val Asn Ala Pro Lys Val Gly Leu Phe Arg Arg
                165                 170                 175

Ser Arg Leu Val Lys Gly Lys Phe Gly Ala Pro Leu Cys Gln Glu Gly
            180                 185                 190

Gln Thr Val Lys Glu Gly Gln Val Val Cys Tyr Leu Glu Gln Phe Gly
        195                 200                 205

Thr Gln Thr Ala Val Glu Ser Glu Thr Ser Gly Asp Val Ile Lys Val
    210                 215                 220

Leu Trp Glu Asp Gly Val Pro Val Gly Tyr Gly Asp Pro Leu Ile Ala
225                 230                 235                 240

Leu Lys Pro Lys Lys
            245

<210> SEQ ID NO 29
<211> LENGTH: 239
<212> TYPE: PRT
<213> ORGANISM: Volvox carteri f. nagariensis

<400> SEQUENCE: 29

Met Leu Thr Arg Ser Ser Ala Pro Gln Arg Pro Ala Gly Val Ala Ala
1               5                   10                  15

Ser Arg Ser Val Arg Ala Val Arg Thr Thr Ile Thr Thr Arg Leu Pro
            20                  25                  30

Ile Leu Lys Ala Ala Ala Thr Glu Ala Lys Lys Glu Val Asp Val Ser
        35                  40                  45

Val Glu Asp Glu Tyr Asn Gly Pro Asp Ile Ala Pro Ser Thr Gln Gln

```
            50                  55                  60
Val Ala Ser Phe Leu Asn Thr Leu Cys Asn Glu Thr Glu Ile Ala Glu
 65                  70                  75                  80

Met His Leu Lys Met Gly Asn Phe Glu Leu Lys Val Lys Arg Ser Val
                 85                  90                  95

Ala Gly Ser Ala Ala Ala Pro Leu Tyr Ala Ser Thr Val Ala Pro
                100                 105                 110

Ala Thr Pro Ala Glu Pro Val Val Ala Ser Ser Pro Leu Gln Ser Val
            115                 120                 125

Glu Ala Pro Pro Ala Ser Val Glu Asp Thr Val Asp Glu Ser Leu
        130                 135                 140

Val Tyr Val Thr Ser Pro Lys Val Gly Thr Phe Arg Arg Gly Lys Tyr
145                 150                 155                 160

Ala Gly Gly Lys Arg Val Gly Lys Gly Asn Cys Ala Asp Val Asn Ala
                165                 170                 175

Pro Val Lys Lys Gly Gln Thr Leu Gly Tyr Val Glu Gln Leu Gly Thr
            180                 185                 190

Phe Val Glu Val Lys Ala Pro Ile Ala Gly Glu Leu Val Lys Val His
        195                 200                 205

Leu Glu Asp Gly Ala Pro Val Glu Tyr Gln Gln Leu Ile Phe Glu Val
    210                 215                 220

Ala Pro Phe Phe Gly Gly His Ile Ile Gly Asp Ser Lys Tyr Ala
225                 230                 235

<210> SEQ ID NO 30
<211> LENGTH: 298
<212> TYPE: PRT
<213> ORGANISM: Glycine max

<400> SEQUENCE: 30

Met Leu Phe Thr Phe Phe Thr Ser Leu Pro Phe Thr Leu Leu Cys Asp
 1               5                  10                  15

Thr His Ser Phe Cys Phe Thr Phe Ser Met Ala Ser Cys Ser Ile Gly
                20                  25                  30

Thr Pro Asn Ile Lys Val Leu Asn Leu His Phe Gly Gly Lys Lys Val
            35                  40                  45

Gly Leu Ser Arg Gln Phe Gly Thr Arg Ser Trp Ile Ser Arg Leu Gln
 50                  55                  60

Tyr Thr Ser Leu Val Met Ser Arg Gln Thr Val Arg Phe Leu Ala Ser
 65                  70                  75                  80

Ser Asn Gly Pro Ser Thr Glu Ile Gln Phe Ala Ala Arg Ser Glu Gly
                85                  90                  95

Ser Glu Glu Ile Arg Ser Ser Gly Leu Thr Ser Glu Leu Ile Pro Asn
            100                 105                 110

Ile Asn Glu Val Glu Phe Leu Leu Thr Lys Leu Cys Asp Thr Ser Ser
        115                 120                 125

Ile Gly Glu Leu Asp Leu Lys Leu Ala Gly Phe His Leu His Val Val
    130                 135                 140

Arg Asp Leu Thr Glu Lys Thr Lys Thr Leu Pro Pro Leu Ile Pro Ala
145                 150                 155                 160

Ser Val Ser Ile Ile Asn Val Thr Glu Thr Pro Lys Thr Asn Gly Ser
                165                 170                 175

Val Pro Thr Thr Ser Leu Ala Val Ser Lys Pro Val Asp Pro Val Pro
            180                 185                 190
```

```
Ser Ser Gly Ser Ile Gln Arg Phe Leu Asp Lys Ala Ala Asp Glu Gly
            195                 200                 205

Leu Val Ile Ile Gln Ser Pro Lys Val Gly Phe Phe Arg Arg Ser Arg
        210                 215                 220

Thr Ile Lys Gly Lys Arg Ala Pro Pro Ser Cys Lys Glu Lys Gln Asn
225                 230                 235                 240

Val Glu Glu Gly Gln Val Ile Cys Tyr Ile Glu Gln Leu Gly Gly Glu
                245                 250                 255

Leu Pro Ile Glu Ser Asp Val Ser Gly Val Ile Lys Ile Leu Arg
                260                 265                 270

Gln Asp Gly Asp Pro Val Gly Tyr Gly Asp Ala Leu Val Ala Ile Leu
            275                 280                 285

Pro Ser Phe Pro Gly Ile Lys Lys Leu Gln
            290                 295

<210> SEQ ID NO 31
<211> LENGTH: 269
<212> TYPE: PRT
<213> ORGANISM: Glycine max

<400> SEQUENCE: 31

Met Ala Ser Cys Ser Ile Gly Thr Pro Asn Ile Lys Ala Leu Asn Leu
1               5                   10                  15

His Phe Gly Gly Lys Lys Val Gly Leu Ser Gln Gln Phe Gly Thr Arg
            20                  25                  30

Ser Trp Ile Ser Lys Gln Ser Leu Gln Tyr Thr Ser Leu Val Met Ser
        35                  40                  45

Arg Gln Lys Val Arg Phe Ser Pro Thr Glu Ile Gln Phe Val Thr Arg
    50                  55                  60

Ser Glu Gly Ser Glu Glu Val Lys Ser Ser Gly Leu Thr Ser Glu Leu
65                  70                  75                  80

Ile Pro Asn Leu Ile Glu Val Glu Phe Leu Leu Thr Lys Leu Cys Asp
                85                  90                  95

Thr Ser Ser Ile Gly Glu Leu Asp Leu Lys Leu Ala Gly Phe His Leu
            100                 105                 110

His Val Val Arg Asp Leu Thr Glu Lys Thr Lys Thr Leu Pro Pro Pro
        115                 120                 125

Ile Pro Ala Ser Glu Ser Ile Ile Asn Val Thr Glu Thr Pro Lys Thr
    130                 135                 140

Asn Gly Ser Val Ser Thr Thr Ser Leu Ala Val Ser Lys Pro Val Asp
145                 150                 155                 160

Pro Ile Pro Ser Ser Gly Ser Ile Gln Arg Phe Leu Asn Lys Ala Ala
                165                 170                 175

Asp Glu Gly Leu Val Ile Ile Gln Ser Pro Lys Val Gly Phe Phe Arg
            180                 185                 190

Arg Ser Arg Thr Ile Lys Gly Arg Arg Ala Pro Pro Ser Cys Lys Glu
        195                 200                 205

Lys Gln Asn Val Glu Glu Gly Gln Val Ile Cys Tyr Ile Glu Gln Leu
    210                 215                 220

Gly Gly Glu Leu Pro Ile Glu Ser Asp Val Ser Gly Val Ile Lys
225                 230                 235                 240

Ile Leu Gln Lys Asp Gly Asp Pro Val Gly Tyr Gly Asp Ala Leu Val
                245                 250                 255

Ala Ile Leu Pro Ser Phe Pro Gly Ile Lys Lys Leu Gln
            260                 265
```

<210> SEQ ID NO 32
<211> LENGTH: 278
<212> TYPE: PRT
<213> ORGANISM: Glycine max

<400> SEQUENCE: 32

```
Met Gly Thr Met Ser His Val Arg Ala Cys Leu Glu Lys Gln Ala Val
1               5                   10                  15

Leu Pro Ile His Asn Ala Arg Trp Asn Ser Lys Arg Arg Leu Phe Ile
            20                  25                  30

Gln His Leu Ala Tyr Gly Gln Lys His Ile Asn Ser His Met Lys Gly
        35                  40                  45

Lys Ser Thr Leu Val Ser Ser Ala Lys Thr Ala Glu Ala Ile Asn Thr
 50                  55                  60

Ser Asn Ser Asp Ala Ser Ser Asp Asn Thr Pro Gln Gly Ser Leu Glu
65                  70                  75                  80

Lys Lys Pro Leu Gln Thr Ala Thr Phe Pro Asn Gly Phe Glu Ala Leu
                85                  90                  95

Val Leu Glu Val Cys Asp Glu Thr Glu Ile Ala Glu Leu Lys Val Lys
            100                 105                 110

Val Gly Asp Phe Glu Met His Ile Lys Arg Asn Ile Gly Ala Thr Lys
        115                 120                 125

Val Pro Leu Ser Asn Ile Ser Pro Thr Thr Pro Pro Ile Pro Ser
130                 135                 140

Lys Pro Met Asp Glu Ser Ala Pro Asn Ser Leu Pro Pro Ser Pro Pro
145                 150                 155                 160

Lys Ser Ser Pro Glu Lys Asn Asn Pro Phe Ala Asn Val Ser Lys Glu
                165                 170                 175

Lys Ser Pro Lys Leu Ala Ala Leu Glu Ala Ser Gly Thr Asn Thr Tyr
            180                 185                 190

Val Leu Val Thr Ser Pro Thr Val Gly Leu Phe Arg Arg Gly Arg Thr
        195                 200                 205

Val Lys Gly Lys Lys Gln Pro Pro Ile Cys Lys Glu Gly Asp Val Ile
210                 215                 220

Lys Glu Gly Gln Val Ile Gly Tyr Leu Asp Gln Phe Gly Thr Gly Leu
225                 230                 235                 240

Pro Ile Arg Ser Asp Val Ala Gly Glu Val Leu Lys Leu Leu Val Glu
                245                 250                 255

Asp Gly Glu Pro Val Gly Tyr Gly Asp Arg Leu Ile Ala Val Leu Pro
            260                 265                 270

Ser Phe His Asp Ile Lys
        275
```

<210> SEQ ID NO 33
<211> LENGTH: 284
<212> TYPE: PRT
<213> ORGANISM: Medicago truncatula

<400> SEQUENCE: 33

```
Met Val Ile Trp Val Ile Lys His Ile Thr Gly Ser Leu Gly Thr Gln
1               5                   10                  15

Asn Val Lys Val Leu Asn Leu His Phe Gly Gln Glu Arg Ala Glu Phe
            20                  25                  30

Ser Gln His Phe Gly Thr Arg Ser Trp Ile Ser Arg Lys Ser Leu Gln
        35                  40                  45
```

Tyr Ala Arg Leu Val Ala Ser Lys Gln Thr Val Arg Ser Leu Thr Pro
        50                  55                  60

Ser Asn Asp Gln Ser Ala Glu Ile Gln Ser Val Ser Arg Ser Glu Asp
65                  70                  75                  80

Gly Ser Glu Glu Ser Lys Ser Ser Gly Leu Thr Asn Gln Leu Phe Pro
                85                  90                  95

Asn Phe Asn Asp Val Ser Val Glu Phe Leu Leu Thr Asn Leu Cys Asp
                100                 105                 110

Thr Ala Ser Ile Gly Glu Leu Glu Leu Lys Leu Asp Gly Phe His Leu
            115                 120                 125

Arg Val Val Arg Asp Leu Thr Glu Lys Ser Lys Thr Leu Pro Pro Ser
130                 135                 140

Ile Pro Ala Pro Val Ser Ile Asn Thr Pro Ala Glu Ala Pro Lys Pro
145                 150                 155                 160

Asn Gly Ser Val Ser Thr Leu Thr Thr Leu Ala Ile Ser Lys Pro Ala
                165                 170                 175

Pro Ser Ser Leu Ser Ile Glu Gly Phe Leu Glu Lys Ala Ala Asp Glu
                180                 185                 190

Gly Leu Val Ile Ile His Ser Pro Thr Val Gly Ile Phe Arg Arg Ser
            195                 200                 205

Arg Thr Ile Lys Gly Lys Arg Ala Pro Pro Ser Cys Gln Glu Met Gln
        210                 215                 220

Asn Val Glu Glu Gly Lys Val Ile Cys Tyr Ile Gln Leu Gly Gly
225                 230                 235                 240

Gln Leu Pro Val Glu Ser Asp Val Ser Gly Glu Val Ile Lys Ile Leu
                245                 250                 255

Arg Glu Asp Gly Asp Pro Val Gly Tyr Gly Asp Thr Leu Ile Ala Ile
            260                 265                 270

Leu Pro Ser Phe Pro Gly Ile Lys Lys Leu Gln Tyr
            275                 280

<210> SEQ ID NO 34
<211> LENGTH: 274
<212> TYPE: PRT
<213> ORGANISM: Medicago truncatula

<400> SEQUENCE: 34

Met Asp Ser Ser Ala Ala Ile Arg Ser Phe His Tyr Pro Ile Gly Thr
1               5                   10                  15

Ile Ser His Val Arg Ser Ile Glu Arg Ala Ala Val Val Pro Cys
            20                  25                  30

His Lys Ile Arg Trp Asn Ser Asn Arg Gly Lys Lys Ala Leu Val Ser
        35                  40                  45

Cys Ala Lys Ala Val Glu Ala Ile Asn Thr Thr Lys Ser Asp Ala Ser
    50                  55                  60

Leu Asp Ser Thr Gln Gln Asp Lys Leu Gly Lys Lys Pro Leu Gln Thr
65                  70                  75                  80

Ala Thr Phe Pro Asp Gly Phe Glu Ala Leu Ile Leu Asp Val Cys Asp
                85                  90                  95

Glu Thr Glu Ile Ala Glu Leu Lys Leu Lys Val Gly Glu Phe Glu Met
                100                 105                 110

His Leu Lys Arg Asn Ile Gly Ala Thr Lys Ala Pro Leu Ser Asn Ile
            115                 120                 125

Ser Pro Thr Thr Pro Pro Pro Ile Pro Ser Lys Pro Met Asp Glu Ser

Ala Pro Thr Thr Ala Gln Pro Leu Pro Pro Thr Ser Ser Ser Glu Lys
145                 150                 155                 160

Thr Asn Pro Phe Ala Asn Val Ser Ser Gln Lys Ser Lys Leu Ile
        165                 170                 175

Ala Leu Glu Ala Ser Gly Thr Ser Thr Tyr Ala Leu Val Ser Ser Pro
            180                 185                 190

Thr Val Gly Ser Phe Arg Arg Gly Arg Thr Val Lys Gly Gln Lys His
                195                 200                 205

Pro Pro Ile Cys Lys Glu Gly Asp Val Ile Arg Glu Gly Gln Val Ile
            210                 215                 220

Gly Tyr Leu Asp Gln Phe Gly Val Gly Ala Gly Ile Pro Ile Lys Ser
225                 230                 235                 240

Asp Val Ala Gly Glu Val Leu Lys Leu Leu Glu Glu Gly Asp Pro
                245                 250                 255

Val Gly Phe Gly Asp Pro Ile Leu Ala Val Leu Pro Ser Phe His Asp
            260                 265                 270

Ile Lys

<210> SEQ ID NO 35
<211> LENGTH: 288
<212> TYPE: PRT
<213> ORGANISM: Vitis vinifera

<400> SEQUENCE: 35

Met Glu Ser Val Ala Val Leu Arg Ser Val His Tyr Ser Val Gly Ala
1               5                   10                  15

Ile Ser Asn Val Arg Ser Phe Ile Glu Arg Pro Thr Met Val Pro Met
            20                  25                  30

Tyr Asn Ala Thr Trp Pro Thr Ser Asn Thr Leu His Val Gln Gly Leu
        35                  40                  45

Thr Val Gly Gly Lys Leu Ile Ser Ser Pro Ile Lys Gln Lys Gly Thr
    50                  55                  60

Leu Ile Ser Cys Val Lys Thr Pro Glu Thr Ala Gly Thr Ala Lys Cys
65                  70                  75                  80

Asp Asp Gly Asn Pro Gln Gly Leu Leu Gln Lys Asp Thr Leu Pro Ser
                85                  90                  95

Ala Thr Phe Pro Asn Gly Phe Glu Ala Leu Ile Leu Glu Val Cys Asp
            100                 105                 110

Glu Thr Asp Val Ala Glu Leu Lys Leu Lys Val Gly Asp Phe Glu Met
        115                 120                 125

His Leu Arg Arg Asn Val Gly Val Thr Asn Pro Pro Met Pro Val Ile
    130                 135                 140

Ala Pro Thr Ala Pro Thr Val Ser Ala Lys Pro Pro Val Glu Ser
145                 150                 155                 160

Ala Pro Ala Ala Pro Ser Leu Pro Lys Pro Ser Gln Glu Lys
                165                 170                 175

Ile Ser Pro Phe Thr Lys Ser Leu Leu Glu Lys Pro Ser Lys Leu Arg
            180                 185                 190

Ala Leu Glu Ala Ser Gly Ala Asn Ala Tyr Val Leu Val Ser Ser Pro
        195                 200                 205

Thr Val Gly Ser Phe Arg Thr Gly Arg Thr Leu Lys Gly Lys Arg Gln
    210                 215                 220

Pro Pro Val Cys Lys Glu Gly Asp Val Ile Lys Glu Gly Gln Val Ile

```
                225                 230                 235                 240

Gly Tyr Leu Asp Gln Phe Gly Ser Glu Leu Pro Val Lys Ser Asp Thr
                        245                 250                 255

Ala Gly Glu Val Leu Lys Val Ile Phe Asn Asp Gly Glu Ala Val Gly
                        260                 265                 270

Tyr Gly Asp Pro Leu Val Ala Val Leu Pro Ser Phe His Gly Ile Glu
                        275                 280                 285

<210> SEQ ID NO 36
<211> LENGTH: 291
<212> TYPE: PRT
<213> ORGANISM: Glycine max

<400> SEQUENCE: 36

Met Glu Ser Ser Pro Ala Ile Arg Ser Phe His Tyr Pro Met Gly Thr
        1               5                   10                  15

Met Ser His Val Arg Ala Cys Leu Glu Lys Gln Ala Val Leu Pro Ile
                        20                  25                  30

His Asn Ala Arg Trp Asn Ser Lys Arg Arg Leu Phe Ile Gln His Leu
                        35                  40                  45

Ala Tyr Gly Gln Lys His Ile Asn Ser His Met Lys Gly Lys Ser Thr
            50                  55                  60

Leu Val Ser Ser Ala Lys Thr Ala Glu Ala Ile Asn Thr Ser Asn Ser
        65                  70                  75                  80

Asp Ala Ser Ser Asp Asn Thr Pro Gln Gly Ser Leu Glu Lys Lys Pro
                        85                  90                  95

Leu Gln Thr Ala Thr Phe Pro Asn Gly Phe Glu Ala Leu Val Leu Glu
                        100                 105                 110

Val Cys Asp Glu Thr Glu Ile Ala Glu Leu Lys Val Lys Val Gly Asp
                        115                 120                 125

Phe Glu Met His Ile Lys Arg Asn Ile Gly Ala Thr Lys Val Pro Leu
        130                 135                 140

Ser Asn Ile Ser Pro Thr Thr Pro Pro Ile Pro Ser Lys Pro Met
        145                 150                 155                 160

Asp Glu Ser Ala Pro Asn Ser Leu Pro Pro Ser Pro Lys Ser Ser
                        165                 170                 175

Pro Glu Lys Asn Asn Pro Phe Ala Asn Val Ser Lys Glu Lys Ser Pro
                        180                 185                 190

Lys Leu Ala Ala Leu Glu Ala Ser Gly Thr Asn Thr Tyr Val Leu Val
                        195                 200                 205

Thr Ser Pro Thr Val Gly Leu Phe Arg Arg Gly Arg Thr Val Lys Gly
        210                 215                 220

Lys Lys Gln Pro Pro Ile Cys Lys Glu Gly Asp Val Ile Lys Glu Gly
        225                 230                 235                 240

Gln Val Ile Gly Tyr Leu Asp Gln Phe Gly Thr Gly Leu Pro Ile Arg
                        245                 250                 255

Ser Asp Val Ala Gly Glu Val Leu Lys Leu Val Glu Asp Gly Glu
                        260                 265                 270

Pro Val Gly Tyr Gly Asp Arg Leu Ile Ala Val Leu Pro Ser Phe His
                        275                 280                 285

Asp Ile Lys
            290

<210> SEQ ID NO 37
<211> LENGTH: 279
```

<212> TYPE: PRT
<213> ORGANISM: Medicago truncatula

<400> SEQUENCE: 37

Met Asp Ser Ser Ala Ala Ile Arg Ser Ser His Cys Phe Met Ser His
1               5                   10                  15

Met Gln Ser Ser Leu Gln Lys Pro Gly Leu Ile His Val Gln Asn Val
            20                  25                  30

Gly Cys Asn Phe Gln Ser Arg Ser Phe Val Gln Asn Leu Ala Ile Ser
        35                  40                  45

Asp Lys His Ile Val Ser His Asn Lys Trp Asn Arg Val Leu Val Ser
    50                  55                  60

Cys Thr Lys Thr Ala Lys Glu Ile Asp Ala Ala Lys Ser Glu Thr Ser
65                  70                  75                  80

Leu Glu Ser Ile Ala Lys Glu Ser Leu Val Lys Pro Leu Gln Thr
                85                  90                  95

Phe Pro Asn Gly Phe Glu Ala Leu Ile Ser Glu Val Cys Asp Glu Thr
            100                 105                 110

Glu Ile Ala Glu Leu Lys Leu Lys Val Gly Glu Phe Glu Met His Met
        115                 120                 125

Lys Arg Asn Ile Gly Leu Ser Ala Ala Pro Val Ser Asn Ile Ser Pro
    130                 135                 140

Thr Lys Pro Met Val Asp Ser Ala Ser Ser Thr Pro Thr Pro Ser Pro
145                 150                 155                 160

Ser Lys Ser Ser Pro Ala Lys Thr Asn Pro Phe Val Asn Asp Ser Asn
                165                 170                 175

Asp Lys Ser Pro Lys Leu Ala Ala Leu Glu Ala Ser Gly Asn Lys Asn
            180                 185                 190

Tyr Val Leu Val Ala Ser Thr Thr Val Gly Ser Phe Gln Arg Gly Arg
        195                 200                 205

Thr Val Lys Gly Asn Lys Leu Pro Pro Val Cys Lys Glu Gly Asp Met
    210                 215                 220

Ile Lys Asp Gly Gln Val Ile Gly Tyr Val Asp Asn Phe Gly Thr Ser
225                 230                 235                 240

Leu Pro Val Lys Ser Asp Val Asp Gly Glu Val Leu Lys Leu Leu Phe
                245                 250                 255

Gln Asp Gly Glu Ala Val Gly Tyr Gly Asp Ala Leu Ile Ala Val Leu
            260                 265                 270

Pro Ser Phe His Asp Ile Lys
        275

<210> SEQ ID NO 38
<211> LENGTH: 288
<212> TYPE: PRT
<213> ORGANISM: Lotus japonicus

<400> SEQUENCE: 38

Met Glu Ser Ser Ala Ala Ile Arg Ser Phe His Cys Thr Val Pro His
1               5                   10                  15

Val Arg Ser Ser Phe Glu Lys Val Ala Val Val Pro Cys His Asn Ala
            20                  25                  30

Arg Trp Asn Ser Lys Ser Gly Leu Phe Ile Gln Arg Leu Ala Asn Asp
        35                  40                  45

Arg Met Leu Ile Asn Ser Gln Ala Lys Gly Arg Lys Thr Leu Val Ser
    50                  55                  60

```
Cys Ala Lys Ala Val Glu Ala Ile Asn Thr Ala Lys Ser Asp Ala Ser
 65                  70                  75                  80

Leu Asp Ser Thr Ser Gln Asp Ser Val Glu Lys Lys Ala Leu Gln Ser
                 85                  90                  95

Ala Thr Phe Pro Asn Gly Leu Glu Ala Leu Val Leu Glu Val Cys Asp
            100                 105                 110

Glu Thr Glu Ile Ala Glu Leu Lys Val Lys Val Gly Glu Phe Glu Met
        115                 120                 125

His Leu Lys Arg Asn Ile Gly Ala Thr Lys Ala Pro Leu Ser Asn Ile
    130                 135                 140

Ser Pro Thr Thr Pro Pro Ile Pro Ser Lys Pro Met Asp Glu Ser
145                 150                 155                 160

Ala Pro Ser Thr Pro Gln Ser Leu Pro Pro Lys Ser Ser Pro Glu Lys
                165                 170                 175

Thr Asn Pro Phe Val Asn Ala Ser Val Gln Lys Ser Ser Lys Leu Ala
            180                 185                 190

Gln Leu Glu Ala Ser Gly Thr Asn Asn Tyr Val Ile Ile Ser Ser Pro
        195                 200                 205

Thr Val Gly Leu Phe Arg Arg Gly Arg Thr Val Lys Gly Lys Arg Gln
    210                 215                 220

Pro Pro Thr Tyr Lys Glu Gly Asp Leu Ile Lys Glu Gly Gln Val Ile
225                 230                 235                 240

Gly Tyr Leu Asp Gln Phe Gly Thr Gly Leu Pro Val Lys Ser Asp Val
                245                 250                 255

Ala Gly Glu Val Leu Lys Leu Val Glu Asp Gly Pro Val Gly
            260                 265                 270

Tyr Gly Asp Asn Leu Ile Ala Val Leu Pro Ser Phe His Asp Ile Lys
        275                 280                 285

<210> SEQ ID NO 39
<211> LENGTH: 267
<212> TYPE: PRT
<213> ORGANISM: Lotus japonicus

<400> SEQUENCE: 39

Met Ala Ser Cys Asn Val Lys Ala Leu Asn Leu Cys Phe Gly Gly Lys
1               5                   10                  15

Arg Val Ser Leu Ser Gln Gln Phe Gly Thr Arg Asn Trp Ile Ile Arg
            20                  25                  30

Lys Ser Val Gln Tyr Thr Ser Leu Asp Met Ser Gln His Arg Val Gly
        35                  40                  45

Phe Leu Lys Ser Ser Asn Gly Pro Leu Ser Gln Ile Gln Pro Val Thr
    50                  55                  60

Ser Ser Glu Asn Gly Ser Lys Glu Ile Glu Ser Gly Leu Thr Ser
 65                  70                  75                  80

Thr Leu Ile Pro Lys Leu Asn Glu Val Glu Phe Leu Leu Thr Lys Leu
                85                  90                  95

Cys Glu Thr Ser Ile Gly Glu Leu Glu Leu Lys Leu Ala Gly Phe His
            100                 105                 110

Leu His Val Leu Arg Asp Ser Thr Glu Lys Val Lys Thr Leu Pro Arg
        115                 120                 125

Gln Thr Pro Ala Ser Val Asn Ile Asn Val Val Pro Glu Ala Pro Lys
    130                 135                 140

Ser Asn Gly Pro Val Ala Ser Ser Ser Leu Ala Ile Leu Lys Pro Glu
145                 150                 155                 160
```

Pro Ser Ser Gly Ser Val Gln Arg Phe Leu Asp Lys Ala Ala Asp Glu
                165                 170                 175

Gly Phe Val Ile Ile Tyr Ser Pro Lys Val Gly Phe Phe Arg Arg Ser
            180                 185                 190

Arg Thr Ile Lys Gly Lys Arg Ala Pro Pro Ser Cys Lys Glu Thr Gln
        195                 200                 205

Lys Val Gln Glu Gly Gln Val Ile Cys Tyr Ile Glu Gln Leu Gly Gly
210                 215                 220

Gln Leu Pro Ile Glu Ser Asp Val Ser Gly Glu Val Ile Arg Ile Leu
225                 230                 235                 240

Arg Glu Asp Gly Asp Pro Val Gly Tyr Gly Asp Ala Leu Ile Ala Ile
                245                 250                 255

Leu Pro Ser Phe Pro Gly Ile Lys Lys Leu Gln
                260                 265

<210> SEQ ID NO 40
<211> LENGTH: 277
<212> TYPE: PRT
<213> ORGANISM: Medicago truncatula

<400> SEQUENCE: 40

Met Ala Ser Ser His Cys Ser Leu Gly Thr Gln Asn Val Lys Val Leu
1               5                   10                  15

Asn Leu His Phe Gly Gln Glu Arg Ala Glu Phe Ser Gln His Phe Gly
            20                  25                  30

Thr Arg Ser Trp Ile Ser Arg Lys Ser Leu Gln Tyr Ala Arg Leu Val
        35                  40                  45

Ala Ser Lys Gln Thr Val Arg Ser Leu Thr Pro Ser Asn Asp Gln Ser
    50                  55                  60

Ala Glu Ile Gln Ser Val Ser Arg Ser Glu Asp Gly Ser Glu Glu Ser
65                  70                  75                  80

Lys Ser Ser Gly Leu Thr Asn Gln Leu Phe Pro Asn Phe Asn Asp Val
                85                  90                  95

Glu Phe Leu Leu Thr Asn Leu Cys Asp Thr Ala Ser Ile Gly Glu Leu
            100                 105                 110

Glu Leu Lys Leu Asp Gly Phe His Leu Arg Val Val Arg Asp Leu Thr
        115                 120                 125

Glu Lys Ser Lys Thr Leu Pro Pro Ser Ile Ser Ala Pro Val Ser Ile
130                 135                 140

Asn Thr Pro Ala Glu Ala Pro Lys Pro Asn Gly Ser Val Ser Thr Leu
145                 150                 155                 160

Thr Thr Leu Ala Ile Ser Lys Pro Ala Pro Ser Ser Leu Ser Phe Glu
                165                 170                 175

Gly Phe Leu Glu Lys Ala Ala Asp Glu Gly Leu Val Ile Ile His Ser
            180                 185                 190

Pro Thr Val Gly Ile Phe Arg Arg Ser Arg Thr Ile Lys Gly Lys Arg
        195                 200                 205

Ala Pro Pro Ser Cys Gln Glu Met Gln Asn Val Glu Glu Gly Lys Val
    210                 215                 220

Ile Cys Tyr Ile Glu Gln Leu Gly Gln Leu Pro Val Glu Ser Asp
225                 230                 235                 240

Val Ser Gly Glu Val Ile Lys Ile Leu Arg Glu Asp Gly Asp Pro Val
                245                 250                 255

Gly Tyr Gly Asp Thr Leu Ile Ala Ile Leu Pro Ser Phe Pro Gly Ile

Lys Lys Leu Gln Tyr
        275

<210> SEQ ID NO 41
<211> LENGTH: 277
<212> TYPE: PRT
<213> ORGANISM: Cucumis sativus

<400> SEQUENCE: 41

Met Ala Phe Cys Ser Leu Arg Ala Ala Asp Ile Lys Phe Ser Lys Leu
1               5                   10                  15

Asp Ile Arg Arg Gly Arg Val Ser Thr Leu Gln Pro Cys Ser Leu Arg
            20                  25                  30

Asn Trp Ile Gly Arg Thr Pro His Gln Tyr Ser Ser Leu Val Ile Ser
        35                  40                  45

His Ser Ser Gln Lys Ala Leu His Ala Cys Ser Gly Ala Ser Pro Lys
    50                  55                  60

Ala Gln Thr Val Ile Lys Ser Glu Thr Gly Ser Glu Glu Ile Lys Pro
65                  70                  75                  80

Ser Ser Leu Gly Ser Gln Leu Ile Pro Asn Phe His Glu Val Glu Thr
                85                  90                  95

Leu Leu Thr Asn Val Cys Asp Thr Ser Ser Ile Ala Glu Phe Glu Leu
            100                 105                 110

Lys Leu Ser Gly Phe Asn Leu Arg Met Val Arg Ser Leu Lys Ser Lys
        115                 120                 125

Asn Leu Pro Leu Pro Pro Val Pro Ala Pro Ala Pro Asp Ile Gln Asn
    130                 135                 140

Thr Ser Ile Pro Ser Asp Ser Asn Gly Leu Val Lys Thr Thr Ser
145                 150                 155                 160

Leu Ala Leu Val Lys Pro Glu Pro Val Ser Ser Pro Arg Gly Ile
                165                 170                 175

Ser Arg Tyr Val Glu Lys Ala Arg Asp Gly Val Thr Ile Leu Ser
            180                 185                 190

Ser Pro Asn Val Gly Val Phe Arg Arg Ser Arg Thr Ile Lys Gly Lys
        195                 200                 205

Arg Ala Pro Pro Ser Cys Ala Glu Asp Gln Val Val Arg Glu Gly Gln
    210                 215                 220

Val Leu Cys Tyr Ile Glu Gln Leu Gly Gly Gln Ile Pro Val Lys Ser
225                 230                 235                 240

Asp Thr Pro Gly Glu Ile Leu Lys Ile Leu Arg Lys Asp Gly Glu Pro
                245                 250                 255

Val Gly Tyr Gly Asp Ala Leu Ile Ala Val Leu Pro Ser Phe Pro Gly
            260                 265                 270

Ile Lys Lys Leu Arg
        275

<210> SEQ ID NO 42
<211> LENGTH: 271
<212> TYPE: PRT
<213> ORGANISM: Cucumis sativus

<400> SEQUENCE: 42

Met Glu Ser Ser Ala Ser Leu Arg Ser Phe His Tyr Phe Ala Gly Gly
1               5                   10                  15

Ser Arg Leu Gln Leu Ile Glu Lys Pro Ser Arg Ile Tyr Val Ser Ser

```
                    20                  25                  30
Thr Asn Lys Thr Ser Ile Gln Arg Leu Ser Ile Phe Gly Lys Pro Ile
                35                  40                  45
His Asn Pro Thr Ser Gln Lys Lys Ile Ala Val Ser Cys Thr Lys Thr
            50                  55                  60
Pro Glu Val Thr Glu Thr Gly Lys Asp Ser Ala Lys Gly Ser Leu Gln
65                  70                  75                  80
Lys Lys Pro Ala Ser Asn Val Thr Phe Pro Asn Gly Phe Glu Glu Leu
                85                  90                  95
Leu Leu Glu Val Cys Asp Asp Thr Glu Ile Ala Glu Leu Lys Leu Lys
                100                 105                 110
Val Gly Glu Phe Glu Met His Val Lys Arg Asn Ile Gly Val Val Ser
            115                 120                 125
Ala Pro Leu Ser Ala Ile Ser Pro Thr Val Pro Pro Ile Pro Ser
            130                 135                 140
Lys Pro Met Val Glu Ser Ala Leu Ala Ala Pro Ala Pro Pro Ile Pro
145                 150                 155                 160
Ser Pro Glu Lys Ala Asn Ala Phe Thr Asp Val Pro Phe Lys Lys Ser
                165                 170                 175
Ser Lys Leu Ala Ala Leu Glu Ala Ser Gly Ala Lys Gly Tyr Val Leu
                180                 185                 190
Val Gly Ser Phe Arg Ser Gly Arg Thr Val Lys Gly Arg Arg Met Pro
            195                 200                 205
Pro Ile Cys Lys Glu Asn Asp Leu Ile Arg Glu Gly Gln Val Val Ala
            210                 215                 220
Tyr Val Asp Gln Phe Gly Ser Gln Leu Pro Val Lys Ser Asp Val Ala
225                 230                 235                 240
Gly Glu Val Leu Arg Ile Leu Phe Lys Glu Asp Glu Pro Val Gly Phe
                245                 250                 255
Gly Asp Pro Leu Ile Ala Val Leu Pro Ile Phe His Gly Ile Arg
                260                 265                 270

<210> SEQ ID NO 43
<211> LENGTH: 276
<212> TYPE: PRT
<213> ORGANISM: Cucumis sativus

<400> SEQUENCE: 43

Met Glu Ser Ser Ala Ser Leu Arg Ser Phe His Tyr Phe Ala Gly Gly
1               5                   10                  15
Ser Arg Leu Gln Leu Asn Glu Lys Pro Ser Arg Ile Tyr Val Ser Ser
                20                  25                  30
Thr Asn Lys Thr Ser Ile Gln Arg Leu Ser Ile Phe Gly Lys Pro Ile
                35                  40                  45
His Asn Pro Thr Ser Gln Lys Lys Ile Val Val Ser Cys Thr Lys Thr
            50                  55                  60
Pro Glu Val Thr Glu Thr Ala Lys Asp Ser Ala Lys Gly Ser Leu Gln
65                  70                  75                  80
Lys Lys Pro Ala Ser Asn Val Thr Phe Pro Asn Gly Phe Glu Glu Leu
                85                  90                  95
Leu Leu Glu Val Cys Asp Asp Thr Glu Ile Ala Glu Leu Lys Leu Lys
                100                 105                 110
Val Gly Glu Phe Glu Met His Val Lys Arg Asn Ile Gly Val Val Ser
            115                 120                 125
```

```
Ala Pro Leu Ser Ala Ile Ser Pro Thr Val Pro Pro Ile Pro Ser
    130                 135                 140

Lys Pro Met Val Glu Ser Ala Leu Ala Ala Pro Ala Pro Pro Ile Pro
145                 150                 155                 160

Ser Pro Glu Lys Ala Asn Ala Phe Thr Asp Val Pro Phe Lys Lys Ser
                165                 170                 175

Ser Lys Leu Ala Ala Leu Glu Ala Ser Gly Ala Lys Gly Tyr Val Leu
            180                 185                 190

Val Thr Ser Pro Thr Val Gly Ser Phe Arg Ser Gly Arg Thr Val Lys
        195                 200                 205

Gly Arg Arg Met Pro Pro Ile Cys Lys Glu Asn Asp Leu Ile Arg Glu
210                 215                 220

Gly Gln Val Val Ala Tyr Val Asp Gln Phe Gly Ser Gln Leu Pro Val
225                 230                 235                 240

Lys Ser Asp Val Ala Gly Glu Val Leu Arg Ile Leu Phe Lys Glu Asp
                245                 250                 255

Glu Pro Val Gly Phe Gly Asp Pro Leu Ile Ala Val Leu Pro Ile Phe
                260                 265                 270

His Gly Ile Arg
        275

<210> SEQ ID NO 44
<211> LENGTH: 290
<212> TYPE: PRT
<213> ORGANISM: Solanum lycopersicum

<400> SEQUENCE: 44

Met Glu Ser Ala Ala Val Leu Arg Ser Phe His His Ser Val Gly Thr
1               5                   10                  15

Thr Ser His Val Arg Ser Val Ile Glu Met Pro Gly Val Ile Pro Thr
            20                  25                  30

Asn Asn Ile Ala Phe Ser Lys Pro Thr Lys Phe Ser Leu Lys Gly Ser
        35                  40                  45

Ser Asn Gly Ala Arg Arg Ile Ser Ser Pro Asn Lys His Gly Arg Leu
    50                  55                  60

Ile Leu Ser Cys Ala Lys Thr Ser Glu Thr Thr Val Thr Ala Lys Ser
65                  70                  75                  80

Gly Asp Gly Asn His Lys Val Pro Thr Glu Ser Ser Pro Leu Pro Thr
                85                  90                  95

Ala Thr Phe Pro Lys Gly Phe Glu Ala Leu Ile Thr Glu Val Cys Asp
            100                 105                 110

Asp Thr Glu Val Ala Glu Leu Lys Leu Lys Val Gly Asp Phe Glu Leu
        115                 120                 125

His Leu Lys Arg Asn Ile Glu Ala Pro Val Val Pro Ala Pro Val Val
    130                 135                 140

Ser Ala Pro Pro Pro Pro Pro Pro Ser Ala Ser Lys Pro Ser
145                 150                 155                 160

Ile Ser Ser Thr Ala Ala Pro Ala Ala Ser Pro Gly Lys Ser Thr Ser
                165                 170                 175

Gly Lys Ile Ser Pro Phe Thr Asn Val Ala Ala Glu Lys Ser Ala Lys
            180                 185                 190

Leu Ala Ala Leu Glu Ser Thr Gly Ala Ser Gly Tyr Val Leu Val Ser
        195                 200                 205

Cys Pro Thr Val Gly Ser Phe Arg Arg Ala Arg Thr Leu Lys Gly Lys
    210                 215                 220
```

Lys Gln Pro Pro Ala Cys Lys Glu Gly Asp Ile Ile Lys Glu Gly Gln
225                 230                 235                 240

Ile Ile Gly Phe Leu Asp Gln Phe Gly Thr Glu Leu Pro Val Arg Ser
            245                 250                 255

Asp Ala Ala Gly Glu Val Leu Lys Ile Leu Phe Asn Asp Gly Glu Ala
            260                 265                 270

Val Gly Tyr Gly Asp Pro Leu Ile Ala Val Leu Pro Ser Phe His Gly
        275                 280                 285

Ile Asn
    290

<210> SEQ ID NO 45
<211> LENGTH: 288
<212> TYPE: PRT
<213> ORGANISM: Solanum lycopersicum

<400> SEQUENCE: 45

Met Glu Ser Ala Ala Val Leu Arg Ser Phe His His Ser Val Gly Thr
1               5                   10                  15

Thr Ser His Val Arg Ser Val Ile Glu Met Pro Gly Val Ile Pro Thr
            20                  25                  30

Asn Asn Ile Ala Phe Ser Lys Pro Thr Lys Phe Ser Leu Lys Gly Ser
        35                  40                  45

Ser Asn Gly Ala Arg Arg Ile Ser Ser Pro Asn Lys His Gly Arg Leu
    50                  55                  60

Ile Leu Ser Cys Ala Lys Thr Ser Glu Thr Thr Val Thr Ala Lys Ser
65                  70                  75                  80

Gly Asp Gly Asn His Lys Val Pro Thr Glu Ser Ser Pro Leu Pro Thr
            85                  90                  95

Ala Thr Phe Pro Lys Gly Phe Glu Ala Leu Ile Thr Glu Val Cys Asp
            100                 105                 110

Asp Thr Glu Val Ala Glu Leu Lys Leu Lys Val Gly Asp Phe Glu Leu
        115                 120                 125

His Leu Lys Arg Asn Ile Glu Ala Pro Val Val Pro Ala Pro Val Val
    130                 135                 140

Ser Ala Pro Pro Pro Pro Pro Pro Ser Ala Ser Lys Pro Ser
145                 150                 155                 160

Ile Ser Ser Thr Ala Ala Pro Ala Ala Ser Pro Gly Lys Ser Thr Ser
            165                 170                 175

Gly Lys Ile Ser Pro Phe Thr Asn Val Ala Ala Glu Lys Ser Ala Lys
        180                 185                 190

Leu Ala Ala Leu Glu Ser Thr Gly Ala Ser Gly Tyr Val Leu Val Ser
    195                 200                 205

Cys Pro Thr Val Gly Ser Phe Arg Arg Ala Arg Thr Leu Lys Gly Lys
210                 215                 220

Lys Gln Pro Pro Ala Cys Lys Glu Gly Asp Ile Ile Lys Glu Gly Gln
225                 230                 235                 240

Ile Ile Gly Phe Leu Asp Gln Phe Gly Thr Glu Leu Pro Val Arg Ser
            245                 250                 255

Asp Ala Ala Gly Glu Val Leu Lys Ile Leu Phe Asn Asp Gly Glu Ala
            260                 265                 270

Val Gly Tyr Gly Asp Pro Leu Ile Ala Val Leu Pro Ser Phe His Gly
        275                 280                 285

-continued

<210> SEQ ID NO 46
<211> LENGTH: 274
<212> TYPE: PRT
<213> ORGANISM: Solanum lycopersicum

<400> SEQUENCE: 46

Met Ala Ala Cys Gly Phe Gly Ala Ser Gly Leu Lys Leu Thr Ser Leu
1               5                   10                  15

Asn Leu Gly Ser Thr Lys Pro Lys Leu Ser Val Val His Asn Leu Arg
            20                  25                  30

Thr Lys Lys Phe Val Gln Ser Asp Gly Leu Leu Thr Thr Lys Ser
        35                  40                  45

Arg Lys Thr Phe Asp Cys Arg Cys Ser Thr Val Glu Ala Glu Ser Val
    50                  55                  60

Ala Ala Thr Ala Ile Pro Asn Ser Asp Asp Ser Ser Ser Lys Ile Val
65                  70                  75                  80

Ser Ser Glu Thr Ala Ser Pro Leu Thr Pro Asn Ser Tyr Glu Val Glu
                85                  90                  95

Ser Leu Leu Thr Glu Ile Cys Asp Thr Thr Ser Ile Ala Glu Val Asp
            100                 105                 110

Leu Lys Leu Gly Gly Phe Arg Leu Tyr Val Lys Arg Asp Leu Thr Gly
        115                 120                 125

Gln Ser Thr Thr Ser Leu Pro Pro Ile Ser Ser Pro Val Ser Val Ser
    130                 135                 140

Ser Ser Val Glu Val Ala Asp Ser Asn Gly Ser Ala Ser Ser Thr Ser
145                 150                 155                 160

Leu Ala Ile Thr Lys Ser Ser Pro Pro Ser Asp Gly Ile Gln Thr Met
                165                 170                 175

Ile Glu Lys Ala Ala Asp Glu Gly Leu Val Ile Ile Gln Ser Pro Arg
            180                 185                 190

Val Gly Phe Phe Arg Arg Ser Arg Thr Ile Lys Gly Lys Arg Ala Pro
        195                 200                 205

Pro Ala Cys Lys Glu Lys Gln Gln Val Lys Glu Gly Gln Val Val Phe
    210                 215                 220

Tyr Ile Glu Gln Leu Gly Gly Glu Leu Pro Val Glu Ser Asp Val Ser
225                 230                 235                 240

Gly Glu Val Ile Arg Ile Leu Arg Lys Asp Gly Asp Pro Val Gly Tyr
                245                 250                 255

Gly Asp Pro Leu Ile Ser Ile Leu Pro Ser Phe Pro Gly Ile Lys Lys
            260                 265                 270

Leu Gln

<210> SEQ ID NO 47
<211> LENGTH: 272
<212> TYPE: PRT
<213> ORGANISM: Fragaria vesca subsp. vesca

<400> SEQUENCE: 47

Met Ala Ser Cys Ser Leu Gly Thr Ser Tyr Pro Lys Ile Thr Asn Leu
1               5                   10                  15

Asn Leu Gly Arg Thr Arg Val Gly Ile Ser Gln Ser Tyr Gly Val Arg
            20                  25                  30

Thr Trp Thr Leu Gln Arg Pro Gln Leu Tyr Ser Gly Leu Ser Ile Ser
        35                  40                  45

Arg Arg Ser Glu Lys Val Ser His Val His Ser Ala Pro Ser Leu Glu
    50                  55                  60

Ile Ile Ser Ala Thr Ser Ser Asp Asp Gly Ser Lys Glu Ser Asp Ser
65                  70                  75                  80

Gly Ser Ala Ser Pro Arg Ile Pro Asn Phe Asp Glu Ile Gln Ser Leu
            85                  90                  95

Leu Thr Thr Ile Cys Asp Thr Thr Ser Val Ala Glu Val Gln Leu Lys
                100                 105                 110

Leu Gly Gly Phe Arg Leu His Val Val Arg Glu Leu Thr Glu Asn Val
                115                 120                 125

Ser Thr Pro Pro Ser Ile Pro Ala Pro Val Ser Val Ser Thr Pro
            130                 135                 140

Ala Glu Val Pro Glu Ser Asn Gly Ser Val Pro Thr Gln Ser Leu Ala
145                 150                 155                 160

Ile Thr Arg Ala Glu Ser Ser Arg Asp Ile Gln Thr Leu Leu Asp
                165                 170                 175

Lys Ala Ala Asp Glu Gly Leu Val Leu Ile Gln Ser Pro Arg Val Gly
                180                 185                 190

Ser Phe Arg Arg Ser Arg Thr Ile Lys Gly Lys Arg Ala Pro Pro Ser
                195                 200                 205

Cys Lys Glu Lys Gln Ile Val Lys Glu Gly Gln Val Ile Cys Tyr Ile
210                 215                 220

Glu Gln Leu Gly Gly Glu Leu Pro Ile Glu Ser Asp Val Ala Gly Glu
225                 230                 235                 240

Val Ile Lys Ile Leu Arg Glu Asp Gly Glu Pro Val Gly Tyr Gly Asp
                245                 250                 255

Ala Leu Val Ala Val Leu Pro Ser Phe Pro Gly Ile Lys Lys Leu Gln
                260                 265                 270

<210> SEQ ID NO 48
<211> LENGTH: 291
<212> TYPE: PRT
<213> ORGANISM: Fragaria vesca subsp. vesca

<400> SEQUENCE: 48

Met Glu Ser Ser Ala Val Leu Arg Ser Leu Asn Cys Ser Val Gly Thr
1               5                   10                  15

Val Ser Gln Ile Arg Ser Phe Ile Asp Lys Pro Gly Val Leu Pro Val
                20                  25                  30

Tyr Asn Ala Arg Arg Pro Thr Tyr Ser Arg Ser Tyr Phe Gln Gly Met
                35                  40                  45

Met Val Ser Glu Lys Phe Ile Tyr Ser Pro Gln Lys Arg Lys Gly Val
50                  55                  60

Leu Ile Ser Cys Val Lys Thr Thr Glu Ala Ala Lys Thr Glu Asn Ser
65                  70                  75                  80

Ser Val Leu Leu Asp Thr Lys Ser Glu Ser Thr Ser Glu Gly Ser Pro
                85                  90                  95

Gln Ser Thr Val Phe Pro Ser Gly Tyr Glu Ala Leu Met Leu Glu Val
                100                 105                 110

Cys Asp Glu Thr Glu Ile Ala Glu Leu Lys Leu Lys Ile Gly Asp Phe
                115                 120                 125

Gln Met His Ile Lys Arg Asn Ile Gly Ala Thr Ser Ala Pro Val Ser
                130                 135                 140

Asn Ile Ser Pro Thr Val Ala Pro Ile Pro Ser Pro Pro Met Ala
145                 150                 155                 160

Ala Ser Ala Pro Ala Pro Pro Ala Ala Pro Lys Ser Ser Pro Ala

```
              165                 170                 175
Lys Ala Thr Pro Phe Asn Asn Gly Ser Val Ala Lys Ser Ser Lys Leu
            180                 185                 190

Ala Ala Leu Glu Ala Ser Gly Ser Asn Gly Tyr Val Leu Val Thr Ser
            195                 200                 205

Pro Thr Val Gly Ser Phe Arg Arg Gly Arg Thr Val Lys Gly Lys Lys
        210                 215                 220

Gln Pro Pro Ile Phe Asn Glu Gly Asp Leu Ile Lys Glu Gly Gln Val
225                 230                 235                 240

Ile Gly Tyr Val Asp Gln Phe Gly Thr Glu Leu Pro Val Lys Thr Asp
                245                 250                 255

Val Gly Gly Glu Val Leu Lys Leu Leu Phe Asn Asp Gly Asp Ala Val
            260                 265                 270

Gly Tyr Gly Asp Ala Leu Ile Ala Val Leu Pro Ser Phe Arg Gly Ile
        275                 280                 285

Gly Val Leu
    290

<210> SEQ ID NO 49
<211> LENGTH: 276
<212> TYPE: PRT
<213> ORGANISM: Cicer arietinum

<400> SEQUENCE: 49

Met Ala Ser Ser Ser Cys Asn Leu Gly Thr Gln Asn Val Glu Val Leu
1               5                   10                  15

Asn Leu His Phe Gly Gln Lys Arg Ile Gly Leu Ser Gln Gln Phe Gly
            20                  25                  30

Thr Lys Asn Trp Ile Ser Arg Lys Ser Leu Gln Tyr Thr Ser Leu Val
        35                  40                  45

Thr Ser Gln Gln Arg Val Arg Ser Leu Thr Ser Thr Asn Gly Gln Leu
    50                  55                  60

Ala Glu Ile Gln Ser Val Ser Ser Ser Glu Glu Asp Ser Glu Glu Ile
65                  70                  75                  80

Lys Ser Ser Gly Leu Ala Ser Glu Leu Ile Pro Asn Phe Asn Glu Val
                85                  90                  95

Glu Phe Leu Leu Thr Asn Leu Cys Asp Thr Thr Ser Ile Ala Glu Leu
            100                 105                 110

Glu Leu Lys Leu Asp Gly Phe His Leu His Val Val Arg Asp Leu Thr
        115                 120                 125

Glu Lys Thr Thr Thr Leu Pro Pro Ile Pro Thr Pro Ala Ser Thr
    130                 135                 140

Ser Ile Ala Ala Glu Ala Pro Lys Pro Asn Gly Leu Val Ser Thr Leu
145                 150                 155                 160

Ser Ser Leu Ala Ile Ser Lys Ser Gly Pro Ser Ser Val Ser Met Gln
                165                 170                 175

Gly Phe Leu Asp Lys Ala Ala Asp Glu Gly Leu Val Ile Ile Gln Ser
            180                 185                 190

Pro Lys Val Gly Phe Phe Arg Arg Ser Arg Thr Ile Lys Gly Lys Arg
        195                 200                 205

Ala Arg Pro Ser Cys Lys Glu Met Gln Lys Val Glu Glu Gly Gln Val
    210                 215                 220

Ile Cys Tyr Ile Glu Gln Leu Gly Gly Glu Leu Pro Ile Glu Cys Asp
225                 230                 235                 240
```

```
Val Ser Gly Glu Val Ile Lys Ile Leu Arg Lys Asp Gly Asp Pro Val
            245                 250                 255

Gly Tyr Gly Asp Ala Leu Val Ala Val Leu Pro Ser Phe Pro Gly Ile
            260                 265                 270

Lys Lys Leu Gln
        275

<210> SEQ ID NO 50
<211> LENGTH: 292
<212> TYPE: PRT
<213> ORGANISM: Cicer arietinum

<400> SEQUENCE: 50

Met Asp Ser Ser Leu Ala Ile Arg Ser Phe Gln Tyr Pro Ile Gly Thr
1               5                   10                  15

Met Pro Gln Val Arg Ser Pro Ile Glu Arg Ala Thr Val Ile Pro Cys
            20                  25                  30

His Lys Val Arg Trp Asn Ser Asn Ser Gly Ile Phe Gln His Leu Thr
        35                  40                  45

His Ser Glu Asn His Ile Tyr Phe His Thr Arg Gly Lys Lys Thr Leu
    50                  55                  60

Val Ser Cys Ala Lys Thr Val Glu Ala Ile Asn Thr Thr Lys Ser Asp
65                  70                  75                  80

Ala Ser Ser Asp Ser Thr Leu Gln Asn Ser Leu Glu Lys Glu Gln Leu
                85                  90                  95

Gln Ile Ala Ala Phe Pro Asn Gly Phe Glu Ala Leu Val Leu Glu Val
            100                 105                 110

Cys Asp Glu Thr Glu Ile Ala Glu Leu Lys Leu Lys Val Gly Glu Phe
        115                 120                 125

Glu Met His Leu Lys Arg Asn Ile Gly Ala Thr Lys Ala Pro Leu Ser
    130                 135                 140

Asn Ile Ser Pro Thr Ile Pro Pro Ile Pro Ser Lys Pro Met Asp
145                 150                 155                 160

Glu Ser Ala Pro Ala Thr Pro Gln Pro Leu Leu Pro Lys Ser Ser Ser
                165                 170                 175

Glu Lys Thr Asn Pro Phe Ala Asn Val Ser Ser Gln Lys Ser Ser Lys
            180                 185                 190

Leu Thr Ala Leu Glu Ala Ser Gly Ser Asn Thr Tyr Val Leu Val Ser
        195                 200                 205

Ser Pro Thr Val Gly Leu Phe Arg Arg Gly Arg Thr Val Lys Gly Lys
    210                 215                 220

Lys His Pro Pro Leu Cys Lys Glu Gly Asp Val Ile Lys Glu Gly Gln
225                 230                 235                 240

Val Ile Gly Tyr Leu Asp Gln Phe Ser Thr Ser Leu Pro Val Lys Ser
                245                 250                 255

Asp Val Ala Gly Glu Val Leu Lys Leu Leu Leu Glu Asp Gly Glu Pro
            260                 265                 270

Val Gly Tyr Gly Asp Pro Leu Leu Ala Val Leu Pro Ser Phe His Asp
        275                 280                 285

Ile Asn Ile Met
    290

<210> SEQ ID NO 51
<211> LENGTH: 252
<212> TYPE: PRT
<213> ORGANISM: Genlisea aurea
```

<400> SEQUENCE: 51

```
Leu Glu Met Ala Ala Cys Gly Phe Gly Ala Ser Gly Leu Lys His Val
1               5                   10                  15

His Leu Asn Ser Ser Ile Ile Gly Pro Lys Leu Ser Ile Leu Ala Pro
            20                  25                  30

Phe His Gly Leu Lys Thr Pro Lys Thr Ile Arg Phe Gly Gly Met Val
        35                  40                  45

Leu Leu Arg Arg Glu Asn Asn Gly Thr Thr Asn Cys Arg Ser Leu Lys
    50                  55                  60

Ser Glu Asn Asp Ser Ser Ala Gln Leu Glu Asp Asp Ser Lys Gly Thr
65                  70                  75                  80

Val Ser Ser Asp Ala Val Arg Thr Leu Leu Pro Asn Ser Leu Glu Val
                85                  90                  95

Glu Ser Leu Leu Lys Thr Val Cys Asp Thr Thr Ser Ile Ala Glu Leu
            100                 105                 110

Glu Leu Lys Leu Gly Gly Phe Arg Leu His Val Arg Arg Ser Leu Thr
        115                 120                 125

Glu Gln Gly Leu Pro Leu Gln Leu Pro Ser Pro Ala Pro Val Val Ala
    130                 135                 140

His Ser Val Val Ala Ala Thr Pro Ala Asn Gly Ser Ala Ser Ser Thr
145                 150                 155                 160

Ser Leu Ala Ile Ala Asn Ala Gly Pro Ser Ser Asp Gly Ala Arg Ser
                165                 170                 175

Phe Leu Asp Lys Ala Ser Asp Glu Gly Leu Thr Ile Leu Gln Ser Pro
            180                 185                 190

Arg Val Gly Phe Phe Arg Arg Ser Arg Thr Ile Lys Gly Lys Arg Ala
        195                 200                 205

Pro Pro Ser Cys Lys Glu Lys Asp Thr Val Lys Glu Gly Gln Val Leu
    210                 215                 220

Cys Phe Ile Glu Gln Leu Gly Gly Glu Ile Pro Val Glu Ser Asp Thr
225                 230                 235                 240

Ser Gly Glu Val Val Lys Ile Leu Lys Asp Glu Gly
                245                 250
```

<210> SEQ ID NO 52
<211> LENGTH: 283
<212> TYPE: PRT
<213> ORGANISM: Coccomyxa subellipsoidea

<400> SEQUENCE: 52

```
Met Ala Ser Gln Cys Leu Thr Met Gln Ser Asn Ile Val Arg Pro Gln
1               5                   10                  15

Lys Leu Asn Ser Cys Gln Lys Arg Thr Gln Phe Ala Arg Ala Asn Val
            20                  25                  30

Ser Gln Val Phe Arg Ile Lys Gly Gly Ser Phe Gly Arg Arg Ala Gly
        35                  40                  45

Arg Cys Leu Gly Thr Thr Lys Thr Arg Ala Val Asn Phe Lys Glu Glu
    50                  55                  60

Thr Ala Val Gly Thr Ser Asp Glu Val Trp Glu Val Asp Glu Glu Glu
65                  70                  75                  80

Glu Phe Asp Asp Gly Pro Asp Asp Gly Gln Gly Leu Ser Thr Gln Gln
                85                  90                  95

Val Gln Ser Leu Leu His Val Leu Cys Asp Glu Thr Glu Val Ala Glu
            100                 105                 110
```

```
Leu Glu Leu Lys Met Gly Ser Phe Glu Leu Val Arg Arg Ser Thr
            115                 120                 125
Lys Gly Asp Ile Ser Ser Ser Leu Asn Gly Ala Ala Ser Asn Gly
    130                 135                 140
Ala Met Val Ala Pro Pro Ala Ser Ala Phe Ala Ser Thr Gln Ser
145                 150                 155                 160
Met Asp Ile Pro Ala Gly Asp Phe Pro Ala Ala Gln Ser Val Ser Val
                165                 170                 175
Ser Ser Ile Asp Glu Asp Ile Asp Asp Glu Ser Thr Ile Phe Leu Thr
                180                 185                 190
Ala Pro Lys Val Gly Ile Ile Arg Leu Gly Arg Tyr Val Lys Gly Lys
            195                 200                 205
Lys Val Gly Lys Gly Asn Ile Ile Asn Val Gly Asp Glu Val Lys Lys
    210                 215                 220
Gly Gln Thr Leu Gly Phe Ile Glu Gln Leu Gly Thr Tyr Val Pro Met
225                 230                 235                 240
Glu Ala Pro Gln Ala Gly Glu Ile Val Asp Phe Leu Val Asp Glu Gly
                245                 250                 255
Thr Ala Val Glu Tyr Asn Gln Pro Val Val Glu Leu Met Pro Phe Phe
                260                 265                 270
Gly Gly His Ile Ile Gly Asp Arg Lys His Ala
            275                 280

<210> SEQ ID NO 53
<211> LENGTH: 275
<212> TYPE: PRT
<213> ORGANISM: Chlorella variabilis

<400> SEQUENCE: 53

Met Ala Ala Ala Gln Leu Ser Ala Ala Arg Cys Ser Arg Val Ile Gly
1               5                   10                  15
Ser Arg Gln Val Thr Ala Pro Arg Arg Leu Pro Ala Ala Ser Asn Val
                20                  25                  30
Arg Lys Leu Val Leu Ser Arg Val Ala Gln Val Glu Ala Asn Ser Ser
            35                  40                  45
Val Lys His Thr Glu Lys Ala Glu Lys Lys His Lys Glu Glu Glu
    50                  55                  60
Glu Glu Glu Leu Glu Gly Ser Glu Asp Asp Gly Leu Asn Pro Gln Gln
65                  70                  75                  80
Ala Arg Pro Gln Ser Pro Ala Pro Val Pro Leu Arg Arg Val Val Pro
                85                  90                  95
Trp Ala Thr Val Glu Ser Phe Leu Ser Val Leu Cys Glu Glu Thr Asp
                100                 105                 110
Ile Ala Glu Val Glu Leu Lys Met Gly Ser Phe Lys Met Arg Val Arg
            115                 120                 125
Arg Ser Leu Asn Gly Ala Ala Ala Pro Ala Ala Ala Ala Pro
    130                 135                 140
Ala Ala Ala Ala Pro Ala Pro Ala Ala Pro Pro Ala Tyr Val Pro
145                 150                 155                 160
Glu Ala Pro Ala Ala Arg Pro Ala Ala Ala Val Glu Thr Val Asp Glu
                165                 170                 175
Asp Glu Ser Leu Leu Asp Val Thr Ala Asn Lys Val Gly Ile Leu Arg
                180                 185                 190
Arg Gly Arg Tyr Met Lys Gly Lys Gln Val Gly Lys Gly Thr Met Val
```

```
            195                 200                 205
Gln Pro Gly Asp Gln Val Lys Lys Gly Gln Thr Leu Ala Phe Ile Glu
    210                 215                 220

Gln Leu Gly Thr His Trp Pro Leu Glu Ala Pro Gln Ala Gly Glu Val
225                 230                 235                 240

Val Glu Phe Leu Val Asp Glu Gly Ser Pro Val Glu Tyr Lys Gln Pro
                245                 250                 255

Val Leu Val Ile Ala Pro Phe Phe Gly Gly His Ile Ile Gly Asp Arg
            260                 265                 270

Lys His Ala
        275

<210> SEQ ID NO 54
<211> LENGTH: 289
<212> TYPE: PRT
<213> ORGANISM: Solanum tuberosum

<400> SEQUENCE: 54

Met Glu Ser Ala Ala Val Leu Arg Ser Phe His His Ser Val Gly Thr
1               5                   10                  15

Thr Ser His Val Arg Ser Val Ile Glu Met Pro Gly Val Ile Pro Thr
            20                  25                  30

Asn Ser Ile Ala Phe Ser Lys Pro Thr Lys Leu Ser Leu Lys Gly Ser
        35                  40                  45

Ser Asn Gly Ala Arg Leu Met Ser Ser Pro Asn Lys His Gly Arg Leu
    50                  55                  60

Thr Leu Ser Cys Ala Lys Thr Ser Glu Thr Thr Val Thr Ala Lys Ser
65                  70                  75                  80

Gly Asp Ser Asn Gln Lys Val Pro Thr Glu Ser Ser Pro Leu Pro Thr
                85                  90                  95

Ala Thr Phe Pro Lys Gly Phe Glu Ala Leu Ile Ile Glu Val Cys Asp
            100                 105                 110

Asp Thr Glu Val Ala Glu Leu Lys Leu Lys Val Gly Asp Phe Glu Leu
        115                 120                 125

His Leu Lys Arg Asn Ile Glu Ala Pro Val Val Pro Ala Pro Val Val
    130                 135                 140

Ser Ala Pro Pro Pro Pro Pro Ser Ala Ser Lys Thr Ser Ile Ser
145                 150                 155                 160

Ser Thr Ala Ala Ala Pro Ala Ala Ser Pro Gly Lys Ser Ser Ser Gly
                165                 170                 175

Lys Ile Ser Pro Phe Thr Asn Val Ala Ala Glu Lys Ser Ala Lys Leu
            180                 185                 190

Ala Ala Leu Glu Ser Thr Gly Ala Ser Gly Tyr Val Leu Val Ser Cys
        195                 200                 205

Pro Thr Val Gly Ser Phe Arg Arg Ala Arg Thr Leu Lys Gly Lys Lys
    210                 215                 220

Gln Pro Pro Ala Cys Lys Glu Gly Asp Ile Ile Lys Glu Gly Gln Ile
225                 230                 235                 240

Ile Gly Phe Leu Asp Gln Phe Gly Thr Glu Leu Pro Val Arg Ser Asp
                245                 250                 255

Ala Ala Gly Glu Val Leu Lys Ile Leu Phe Asn Asp Gly Glu Ala Val
            260                 265                 270

Gly Tyr Gly Asp Pro Leu Ile Ala Val Leu Pro Ser Phe Arg Gly Ile
        275                 280                 285
```

Asn

<210> SEQ ID NO 55
<211> LENGTH: 274
<212> TYPE: PRT
<213> ORGANISM: Solanum tuberosum

<400> SEQUENCE: 55

Met Ala Ala Cys Gly Phe Gly Ala Ser Gly Leu Lys Leu Thr Ser Leu
1               5                   10                  15

Asn Leu Gly Ser Thr Lys Pro Lys Leu Ser Val Val His Asn Leu Arg
            20                  25                  30

Thr Lys Lys Phe Val Gln Asn Asp Gly Leu Leu Leu Thr Thr Lys Ser
        35                  40                  45

Arg Lys Thr Phe Asp Cys Arg Cys Ser Thr Val Glu Ala Lys Pro Ala
50                  55                  60

Ala Ala Thr Ala Ile Pro Lys Ser Asp Asp Ser Ser Lys Ile Val
65                  70                  75                  80

Ser Ser Glu Thr Ala Ser Pro Leu Ile Pro Asn Ser Tyr Glu Val Glu
                85                  90                  95

Ser Leu Leu Ala Glu Ile Cys Asp Thr Thr Ser Ile Ala Glu Val Asp
            100                 105                 110

Leu Lys Leu Gly Gly Phe Arg Leu Tyr Val Lys Arg Asp Leu Thr Gly
        115                 120                 125

Gln Ser Thr Thr Ser Leu Pro Pro Ile Thr Ser Pro Val Ser Ile Pro
130                 135                 140

Ser Ser Val Glu Val Ala Asp Ser Asn Gly Ser Ala Ser Ser Thr Ser
145                 150                 155                 160

Leu Ala Ile Thr Lys Ser Ser Pro Pro Ser Asp Gly Ile Gln Thr Met
                165                 170                 175

Ile Glu Lys Ala Ala Asp Glu Gly Leu Val Ile Ile Gln Ser Pro Arg
            180                 185                 190

Val Gly Phe Phe Arg Arg Ser Arg Thr Ile Lys Gly Lys Arg Ala Pro
        195                 200                 205

Pro Ala Cys Lys Glu Lys Gln Gln Val Lys Gly Gly Val Val Phe
    210                 215                 220

Tyr Ile Glu Gln Leu Gly Gly Glu Leu Pro Val Glu Ser Asp Val Ser
225                 230                 235                 240

Gly Glu Val Ile Lys Ile Leu Arg Lys Asp Gly Asp Pro Val Gly Tyr
                245                 250                 255

Gly Asp Pro Leu Ile Ser Ile Leu Pro Ser Phe Pro Gly Ile Lys Lys
            260                 265                 270

Leu Gln

<210> SEQ ID NO 56
<211> LENGTH: 323
<212> TYPE: PRT
<213> ORGANISM: Capsella rubella

<400> SEQUENCE: 56

Ser Glu Pro Asn Gln Gln Arg Ala Leu Thr Ser Ile Phe Cys Phe Leu
1               5                   10                  15

Phe Tyr Phe Asp Leu Ile Ile Ser Thr Leu Val Lys Ser Cys Val Leu
            20                  25                  30

Val Gly Ile Val Ile Val Ser Ala His Thr Ile Ser Phe Leu Phe Leu
        35                  40                  45

```
Ser Phe Phe Cys Phe Ser Asn Pro Leu Ser Pro Ser Met Ala Ser Cys
    50                  55                  60

Ser Leu Gly Val Pro Lys Ile Lys Ile Ser Ala Val Asp Leu Ser Arg
 65                  70                  75                  80

Val Arg Ser Gly Ser Leu Leu Ile Pro Phe Asn Gln Arg Ser Leu Leu
                 85                  90                  95

Gly Gln Lys Pro Val Lys Tyr Leu Ser Leu Arg Thr Thr Phe Gly Thr
            100                 105                 110

Val Lys Ala Val Gln Val Ser Thr Val Pro Ala Pro Glu Thr Ser Ala
            115                 120                 125

Thr Ile Glu Val Glu Asp Ser Asp Glu Thr Lys Ser Ser Lys Leu Asn
130                 135                 140

Ala Gln Leu Val Pro Lys Pro Ser Glu Val Glu Ala Leu Val Thr Glu
145                 150                 155                 160

Ile Cys Asp Thr Ser Ser Ile Ala Glu Phe Glu Leu Lys Leu Gly Gly
                165                 170                 175

Phe Arg Leu Tyr Val Ala Arg Asp Leu Ala Asp Lys Ser Ser Pro Gln
                180                 185                 190

Pro His Ala Thr Pro Ala Val Ala Ala Thr Ser Glu Thr Thr Asn Ser
                195                 200                 205

Thr Asp Ser Asn Gly Ser Ala Pro Ser Thr Ser Leu Ala Ile Thr Arg
210                 215                 220

Pro Ala Ser Ser Ala Ala Asp Lys Gly Leu Met Ile Leu Gln Ser Pro
225                 230                 235                 240

Lys Val Gly Phe Phe Arg Arg Ser Lys Thr Ile Lys Gly Lys Arg Met
                245                 250                 255

Pro Ser Ser Cys Lys Glu Lys Asp Gln Val Lys Glu Gly Gln Ile Leu
                260                 265                 270

Cys Tyr Ile Glu Gln Leu Gly Gly Gln Phe Pro Ile Glu Ser Asp Val
                275                 280                 285

Thr Gly Glu Val Val Lys Ile Leu Arg Glu Asp Gly Glu Pro Val Gly
            290                 295                 300

Tyr Asn Asp Ala Leu Ile Ser Ile Leu Pro Ser Phe Pro Gly Ile Lys
305                 310                 315                 320

Lys Leu Gln

<210> SEQ ID NO 57
<211> LENGTH: 272
<212> TYPE: PRT
<213> ORGANISM: Capsella rubella

<400> SEQUENCE: 57

Met Asn Ser Cys Ser Leu Gly Ala Pro Lys Leu Arg Ile Ser Leu Ala
  1               5                  10                  15

Asn Phe Ser Arg Leu Arg Cys Gly Asn Leu Leu Ile Pro Asn Asn Gln
             20                  25                  30

Arg Leu Phe Ile Asp Gln Gly Gln Ser Pro Ile Lys Phe Pro Ser Leu
         35                  40                  45

Arg Thr Thr Leu Arg Ala Val Lys Ala Val Gln Leu Ser Thr Val Pro
     50                  55                  60

Pro Ala Glu Thr Ser Asp Val Glu Asp Ser Glu Glu Thr Glu Pro Thr
 65                  70                  75                  80

Ile Val Asn Thr Gln Leu Ile Pro Asn Ser Ser Glu Val Glu Ala Leu
                 85                  90                  95
```

Ile Ser Glu Ile Thr Asp Ser Ser Ile Ala Glu Phe Glu Leu Lys
              100                 105                 110

Leu Gly Gly Phe Arg Leu Tyr Val Ala Arg Lys Leu Ala Asp Gln Ser
            115                 120                 125

Ser Pro Pro Gln Gln Ile Pro Asn Val Val Ala Ser Ala Ala
    130                 135                 140

Pro Glu Gly Val His Thr Asn Gly Ser Ala Thr Ser Ser Ser Leu Ala
145                 150                 155                 160

Ile Thr Lys Ser Ser Ser Ser Asp Arg Pro Gln Thr Leu Ser Asn
                165                 170                 175

Lys Ala Ala Asp Gln Gly Leu Val Ile Leu Gln Ser Pro Thr Val Gly
            180                 185                 190

Tyr Phe Arg Arg Ser Lys Thr Ile Lys Gly Lys Arg Thr Pro Thr Ile
            195                 200                 205

Cys Lys Glu Lys Asp Ile Val Lys Glu Gly Gln Val Leu Cys Tyr Ile
            210                 215                 220

Glu Gln Leu Gly Gly Gln Ile Pro Val Glu Ser Asp Val Ser Gly Glu
225                 230                 235                 240

Ile Val Lys Ile Leu Arg Glu Asp Gly Glu Pro Val Gly Tyr Asn Asp
                245                 250                 255

Ala Leu Ile Thr Val Leu Pro Ser Phe Pro Gly Ile Lys Lys Leu Gln
            260                 265                 270

<210> SEQ ID NO 58
<211> LENGTH: 271
<212> TYPE: PRT
<213> ORGANISM: Populus trichocarpa

<400> SEQUENCE: 58

Met Ala Ser Cys Ser Leu Gly Ala Ser Asn Met Lys Leu Ser Lys Leu
1               5                   10                  15

Asp Phe Gly Arg Ala Thr Val Val Asn Leu Gln Lys Gln Ser Gly Leu
            20                  25                  30

Ile Ala Trp Arg Gly Arg Gly Arg Leu Gln His Ala Gly Val Ala Ile
        35                  40                  45

Ser His Lys Ser Arg Glu Ala Phe Arg Cys Arg Gly Ser Ala Ser Glu
    50                  55                  60

Thr Glu Leu Thr Thr Lys Glu Thr Lys Ser Ser Gly Leu Thr Ser Gln
65                  70                  75                  80

Leu Ile Pro Asn Ser Ser Glu Ile Glu Ser Leu Val Thr Glu Ile Cys
                85                  90                  95

Asn Thr Thr Ser Val Ala Glu Leu Glu Leu Lys Leu Gly Gly Phe Arg
            100                 105                 110

Leu Tyr Val Arg Arg Asp Leu Thr Glu Lys Asn Lys Asp Thr His Gln
        115                 120                 125

Pro Leu Pro Ala Pro Pro Ala Ser Leu Ala Val Thr Val Lys Thr Thr
    130                 135                 140

Thr Asp Ala Ser Asp Leu Asn Gly Ser Val Ser Thr Ser Leu Ala Ile
145                 150                 155                 160

Ser Lys Gln Glu Pro Ser Ser Gly Gly Ile Ile Ser Phe Leu Asp Arg
                165                 170                 175

Ala Ala Asp Glu Gly Leu Met Ile Leu Gln Ser Pro Arg Val Gly Phe
            180                 185                 190

Phe Arg Arg Ser Arg Thr Ile Lys Gly Lys Arg Ala Pro Pro Ser Cys

-continued

```
                195                 200                 205
Lys Glu Lys Gln Ile Val Lys Glu Gly Gln Val Leu Cys Phe Ile Glu
        210                 215                 220
Gln Leu Gly Gly Glu Leu Pro Ile Glu Thr Asp Ile Ser Gly Glu Val
225                 230                 235                 240
Ile Arg Ile Leu Arg Glu Asp Gly Glu Pro Val Gly Tyr Gly Asp Ala
                245                 250                 255
Leu Ile Ala Ile Leu Pro Ser Phe Pro Gly Ile Lys Lys Leu Gln
        260                 265                 270

<210> SEQ ID NO 59
<211> LENGTH: 210
<212> TYPE: PRT
<213> ORGANISM: Populus trichocarpa

<400> SEQUENCE: 59

Met Pro Ser Cys Gln Thr Thr Arg Met Asp Ser Leu Gly Ala Leu Asn
1               5                   10                  15
Val Lys Leu Ser Lys Leu Asp Phe Gly Gly Lys Phe Gly Asn Leu
                20                  25                  30
Gln Gln Arg Ser Gly Val Arg Val Trp Met Gly Arg Val Gln Leu Gln
        35                  40                  45
Tyr Ala Gly Thr Thr Lys Glu Thr Thr Ser Leu Gly Leu Thr Ser Gln
    50                  55                  60
Leu Ile Pro Asn Ser Ser Glu Ile Glu Ser Leu Val Thr Glu Ile Cys
65                  70                  75                  80
Asn Thr Thr Ser Ile Ala Glu Phe Glu Leu Lys Leu Ala Ser Thr Ser
                85                  90                  95
Leu Ala Ile Ser Lys Gln Glu Pro Ser Phe Gly Gly Ile Lys Ser Phe
            100                 105                 110
Leu Asp Arg Thr Ala Asp Glu Gly Leu Met Ile Leu Pro Ser Pro Arg
        115                 120                 125
Val Gly Phe Phe Arg Arg Ser Arg Thr Ile Lys Gly Lys Arg Ala Pro
    130                 135                 140
Pro Ser Cys Lys Glu Lys Gln Ile Ile Lys Glu Gly Gln Val Leu Cys
145                 150                 155                 160
Tyr Ile Glu Gln Leu Gly Gly Glu Leu Pro Ile Glu Ser Asp Ile Ser
                165                 170                 175
Gly Glu Val Ile Lys Ile Leu Arg Glu Asp Gly Glu Pro Val Gly Tyr
            180                 185                 190
Gly Asp Ala Leu Ile Ala Ile Leu Pro Ser Phe Pro Gly Ile Lys Lys
        195                 200                 205
Leu Gln
    210

<210> SEQ ID NO 60
<211> LENGTH: 270
<212> TYPE: PRT
<213> ORGANISM: Eutrema salsugineum

<400> SEQUENCE: 60

Met Ser Ser Cys Ser Leu Gly Ala Pro Lys Ile Lys Ile Tyr Ala Ser
1               5                   10                  15
Asn Leu Ile Arg Cys Asp Lys Phe Leu Leu Ile Pro Asn Asn Gln Arg
                20                  25                  30
Leu Cys Ile Gly Gln Ile Pro Met Lys Tyr Pro Ser Leu Arg Thr Thr
```

```
            35                  40                  45
Leu Gln Ser Val Lys Ala Ser Gln Leu Ser Val Val Pro Thr Ala Glu
 50                  55                  60
Thr Ala Asp Val Glu Asp Ser Glu Glu Thr Lys Ser Ser Val Val Asn
65                  70                  75                  80
Ala Gln Leu Ile Pro Lys Ser Ser Glu Val Ala Leu Ile Ser Glu
                85                  90                  95
Ile Ala Glu Ser Pro Ser Ile Ala Glu Phe Glu Leu Lys Leu Gly Gly
                100                 105                 110
Phe Arg Leu Tyr Val Ala Lys Lys Leu Ala Asp Gln Ser Ser Pro Pro
                115                 120                 125
Pro His Gln Thr Pro His Val Val Ala Ser Val Thr Pro Glu Gly
            130                 135                 140
Ile Asn Thr Asn Gly Ser Ala Thr Ser Ser Leu Ser Ile Thr Lys
145                 150                 155                 160
Thr Ser Ser Ser Gly Asp Arg Pro Gln Thr Leu Ala Asn Lys Ala
                165                 170                 175
Ala Asn Asn Glu Gly Leu Val Ile Leu Gln Ser Pro Thr Val Gly Tyr
                180                 185                 190
Phe Arg Arg Ser Lys Thr Val Lys Gly Lys Arg Leu Pro Thr Ile Cys
                195                 200                 205
Lys Glu Lys Asp Ile Val Lys Glu Gly Gln Val Leu Cys Tyr Ile Glu
                210                 215                 220
Gln Leu Gly Gly Gln Ile Pro Val Glu Ser Asp Val Ser Gly Glu Ile
225                 230                 235                 240
Val Lys Ile Leu Arg Glu Asp Gly Glu Pro Val Gly Tyr Asp Asp Ala
                245                 250                 255
Leu Ile Thr Val Leu Pro Ser Phe Pro Gly Ile Lys Lys Leu
                260                 265                 270

<210> SEQ ID NO 61
<211> LENGTH: 281
<212> TYPE: PRT
<213> ORGANISM: Eutrema salsugineum

<400> SEQUENCE: 61

Met Glu Ser Ser Ala Ala Leu Gly Ser Leu His Gln Thr Leu Gly Ser
1               5                   10                  15
Ala Ile Lys Ser Glu Ser Lys Val His Ser Leu Ser Gly Asn Trp Ser
                20                  25                  30
Ser Ser Gly Asn Ser Cys Val Pro Arg Trp Arg Leu Phe Asn Arg Asn
                35                  40                  45
Ser Asn Phe Thr Leu Val Leu Arg Ala Glu Ala Ser Lys Ser Ser Thr
            50                  55                  60
Thr Thr Lys Ser Asp Asp Ser Ser Asp Ala Cys Val Ser Asn Gly Lys
65                  70                  75                  80
Asn Thr Val Arg Arg Thr Thr Phe Pro Lys Glu Val Glu Ala Leu Val
                85                  90                  95
His Glu Met Cys Asp Glu Thr Glu Val Ala Val Leu Lys Leu Lys Val
                100                 105                 110
Gly Asp Phe Glu Met Asn Leu Lys Arg Lys Ile Gly Glu Thr Ala Asn
                115                 120                 125
Pro Ile Pro Val Ala Asp Ile Ser Pro Thr Ile Ala Pro Pro Ile Pro
                130                 135                 140
```

```
Ser Glu Pro Met Asn Lys Ser Val Ser Ala Ala Pro Ser Pro Ser Lys
145                 150                 155                 160

Ala Lys Pro Ala Ser Glu Lys Val Ser Pro Phe Met Asn Val Ser Tyr
            165                 170                 175

Arg Lys Ser Ser Lys Leu Ser Ala Leu Glu Ala Ser Gly Thr Asn Asn
        180                 185                 190

Tyr Val Leu Val Thr Ser Pro Ser Val Gly Lys Phe Gln Arg Ser Arg
            195                 200                 205

Thr Val Lys Gly Lys Lys Gln Pro Pro Ser Cys Lys Glu Gly Asp Ala
        210                 215                 220

Ile Lys Glu Gly Gln Val Ile Gly Tyr Leu His Gln Leu Gly Thr Glu
225                 230                 235                 240

Leu Pro Val Lys Ser Asp Val Ala Gly Glu Val Leu Lys Leu Leu Ser
            245                 250                 255

Asp Asp Gly Asp Thr Val Gly Tyr Gly Glu Pro Leu Val Ala Val Leu
        260                 265                 270

Pro Ser Phe His Asp Ile Asn Ile His
        275                 280

<210> SEQ ID NO 62
<211> LENGTH: 261
<212> TYPE: PRT
<213> ORGANISM: Eutrema salsugineum

<400> SEQUENCE: 62

Met Ala Ser Cys Ser Leu Gly Val Pro Lys Ile Lys Ile Ser Ala Val
1               5                   10                  15

Glu Leu Ser Arg Val Arg Ser Gly Ser Leu Gln Ile Val Pro Cys Asn
            20                  25                  30

Gln Arg Ser Leu Ile Cys Gln Arg Pro Val Lys Tyr Leu Ser Leu Arg
        35                  40                  45

Ala Thr Leu Gly Ser Val Lys Ala Val Gln Ala Ser Thr Val Thr Ala
    50                  55                  60

Ala Glu Thr Ala Glu Val Glu Asp Ser Glu Glu Thr Lys Ser Tyr Pro
65                  70                  75                  80

Leu Asn Ala Gln Leu Ile Pro Lys Pro Ser Glu Val Glu Ala Leu Val
            85                  90                  95

Thr Glu Ile Cys Asp Ser Ser Ile Ala Glu Phe Glu Leu Lys Leu
        100                 105                 110

Gly Gly Phe Arg Leu Tyr Val Ala Arg Asn Leu Ala Glu Lys Ser Ser
        115                 120                 125

Pro Gln Pro Gln Pro Ile Pro Ala Val Val Ala Ala Asn Ala Thr Thr
130                 135                 140

Glu Asn Leu Asp Ser Asn Gly Ser Ala Ser Ser Thr Ser Leu Ala Ile
145                 150                 155                 160

Thr Lys Pro Ala Ser Ser Ala Ala Asp Gln Gly Leu Val Ile Leu Gln
            165                 170                 175

Ser Pro Lys Val Gly Phe Phe Arg Arg Ser Lys Thr Ile Lys Gly Lys
        180                 185                 190

Arg Thr Pro Ser Ser Cys Lys Glu Lys Asp Gln Val Lys Glu Gly Gln
        195                 200                 205

Val Leu Cys Tyr Ile Glu Gln Leu Gly Gly Gln Phe Pro Ile Glu Ser
    210                 215                 220

Asp Val Thr Gly Glu Val Val Lys Ile Leu Arg Glu Asp Gly Glu Pro
225                 230                 235                 240
```

```
Val Gly Tyr Asn Asp Ala Leu Ile Ser Ile Leu Pro Ser Phe Pro Gly
                245                 250                 255

Ile Lys Lys Leu Gln
            260

<210> SEQ ID NO 63
<211> LENGTH: 270
<212> TYPE: PRT
<213> ORGANISM: Citrus clementina

<400> SEQUENCE: 63

Met Ala Ser Tyr Ser Leu Gly Ala Ser Asn Ile Lys Ile Pro Lys Gly
1               5                   10                  15

Asn Leu Gly Arg Ala Arg Val Gly Asp Leu Gln Pro Arg Ser Asp Val
            20                  25                  30

Arg Lys Trp Met Gly Arg Lys Pro Phe Gln Tyr Ala Gly Leu Ala Met
        35                  40                  45

Ser Gln Pro Leu Glu Lys Ala Phe Thr Val Phe Cys Gly Gln Ser Ser
    50                  55                  60

Glu Ala Glu Ser Thr Arg Asn Ala Arg Asp Gly His Glu Asp Met Lys
65                  70                  75                  80

Ser Thr Gln Leu Ile Pro Asp Ser Ser Glu Val Glu Ser Leu Val Thr
                85                  90                  95

Asp Ile Cys Asn Thr Thr Ser Val Ala Glu Phe Glu Leu Lys Leu Asp
            100                 105                 110

Gly Phe Arg Leu Tyr Val Thr Arg Asp Ile Ala Gly Ala Ser Ser Pro
        115                 120                 125

Leu Leu Pro Ser Ser Pro Ala Pro Val Thr Val Asn Lys Pro Ala Asp
    130                 135                 140

Arg Pro Asp Ser Asn Gly Ser Val Pro Thr Pro Ser Leu Ala Ile Thr
145                 150                 155                 160

Lys Pro Val Ser Ser Ser Gly Gly Ile Gln Thr Leu Leu Asp Lys Ala
                165                 170                 175

Ala Asp Glu Gly Leu Val Ile Leu Glu Ser Pro Lys Val Gly Tyr Phe
            180                 185                 190

Arg Arg Ser Arg Thr Ile Lys Gly Lys Arg Ala Pro Pro Ser Cys Lys
        195                 200                 205

Glu Lys Gln Thr Val Arg Glu Gly Gln Val Leu Cys Tyr Ile Glu Gln
    210                 215                 220

Leu Gly Gly Glu Ile Pro Ile Glu Ser Asp Ile Ala Gly Glu Val Ile
225                 230                 235                 240

Lys Ile Leu Arg Lys Asp Gly Asp Pro Ile Gly Tyr Gly Asp Pro Leu
                245                 250                 255

Ile Val Ile Leu Pro Ser Phe Pro Gly Ile Lys Leu Leu Gln
            260                 265                 270

<210> SEQ ID NO 64
<211> LENGTH: 287
<212> TYPE: PRT
<213> ORGANISM: Citrus clementina

<400> SEQUENCE: 64

Met Ala Ser Ser Ala Ala Leu Arg Ser Phe His Tyr Ser Val Gly Ala
1               5                   10                  15

Val Ala Lys Ser Gly Ser Ser Phe Glu Arg Pro Gly Ile Val Leu Pro
            20                  25                  30
```

Val Arg Asn Ser Ser Trp Pro Ser Ala Ala Ser Lys Ser Phe Asn Leu
 35                  40                  45

Val Thr Pro Pro Val Trp Arg Gly Val Thr Val Val Ser Ser Ala
 50                  55                  60

Lys Thr Ser Glu Asn Thr Ser Thr Ala Lys Thr Asp Glu Ser Thr Glu
 65                  70                  75                  80

Glu Ser Ser Ser Glu Lys Ser Thr Leu Arg Ser Pro Ile Phe Pro Ser
                 85                  90                  95

Gly Phe Glu Ala Leu Met Leu Glu Val Cys Asp Thr Glu Ile Ala
                100                 105                 110

Glu Leu Lys Leu Lys Val Gly Asp Phe Glu Met His Leu Lys Arg Asn
                115                 120                 125

Val Gly Ala Pro Lys Ala Pro Ala Pro Leu Ser Asn Ile Ser Pro Thr
130                 135                 140

Thr Pro Pro Pro Ile Pro Thr Glu Pro Met Glu Val Ser Asp Pro Val
145                 150                 155                 160

Ser Pro Pro Pro Pro Ser Pro Pro Lys Pro Tyr Ser Glu Lys Ala
                165                 170                 175

Ala Pro Phe Ile Asn His Ser Phe Gly Lys Ser Ser Lys Leu Ala Ala
                180                 185                 190

Leu Glu Ala Ser Gly Ser Asn Gly Tyr Val Leu Val Phe Ser Pro Thr
                195                 200                 205

Val Gly Ser Phe Arg Arg Asn Arg Thr Val Lys Gly Lys Lys Gln Ser
210                 215                 220

Pro Ile Cys Lys Glu Gly Asp Val Ile Lys Glu Gly Gln Ile Ile Gly
225                 230                 235                 240

Tyr Leu Asp Gln Phe Gly Thr Glu Leu Pro Val Lys Ser Asp Val Ala
                245                 250                 255

Gly Glu Val Leu Lys Leu Leu Phe Asp Asp Gly Asp Ala Val Gly Phe
                260                 265                 270

Gly Asp Pro Leu Ile Ala Val Leu Pro Ser Phe His Asp Ile Lys
                275                 280                 285

<210> SEQ ID NO 65
<211> LENGTH: 271
<212> TYPE: PRT
<213> ORGANISM: Citrus sinensis

<400> SEQUENCE: 65

Met Ala Ser Tyr Ser Leu Gly Ala Ser Asn Ile Lys Ile Pro Lys Gly
1                   5                  10                  15

Asn Leu Gly Arg Ala Arg Val Gly Asp Leu Gln Pro Arg Ser Asp Val
                20                  25                  30

Arg Lys Trp Met Gly Arg Lys Pro Phe Gln Tyr Ala Gly Leu Ala Met
                 35                  40                  45

Ser Gln Pro Leu Glu Lys Ala Phe Thr Val Phe Cys Gly Gln Ser Ser
                 50                  55                  60

Glu Ala Glu Ser Thr Arg Asn Ala Arg Asp Gly His Glu Asp Met Lys
65                  70                  75                  80

Ser Pro Gln Leu Ile Pro Asp Ser Ser Glu Val Glu Ser Leu Val Thr
                 85                  90                  95

Asp Ile Cys Asn Thr Thr Ser Val Ala Glu Phe Glu Leu Lys Leu Asp
                100                 105                 110

Gly Phe Arg Leu Tyr Val Thr Arg Asp Ile Ala Gly Asp Ser Ile Pro

```
            115                 120                 125
Pro Leu Pro Pro Ser Ser Pro Ala Pro Val Thr Val Asn Lys Pro Ala
        130                 135                 140

Asp Arg Pro Asp Ser Asn Gly Ser Val Pro Thr Ser Ser Leu Ala Ile
145                 150                 155                 160

Thr Lys Pro Val Ser Ser Gly Gly Ile Gln Thr Leu Leu Asp Lys
                165                 170                 175

Ala Ala Asp Glu Gly Leu Val Ile Leu Glu Ser Pro Lys Val Gly Tyr
            180                 185                 190

Phe Arg Arg Ser Arg Thr Ile Lys Gly Lys Arg Ala Pro Pro Ser Cys
        195                 200                 205

Lys Glu Lys Gln Thr Val Arg Glu Gly Gln Val Leu Cys Tyr Ile Glu
    210                 215                 220

Gln Leu Gly Gly Glu Ile Pro Ile Glu Ser Asp Ile Ala Gly Glu Val
225                 230                 235                 240

Ile Lys Ile Leu Arg Lys Asp Gly Asp Pro Ile Gly Tyr Gly Asp Pro
                245                 250                 255

Leu Ile Val Ile Leu Pro Ser Phe Pro Gly Ile Lys Leu Leu Gln
            260                 265                 270

<210> SEQ ID NO 66
<211> LENGTH: 297
<212> TYPE: PRT
<213> ORGANISM: Glycine max

<400> SEQUENCE: 66

Met Phe Leu Gln Ile Tyr Asn Gln Arg Met Leu Cys Asn His Pro Arg
1               5                   10                  15

Ala Tyr Pro Ile Gly Thr Met Ser His Val Arg Ala Ser Leu Glu Lys
            20                  25                  30

Gln Ala Val Val Pro Ile His Asn Ala Gly Trp Asn Ser Lys Ser Arg
        35                  40                  45

Leu Phe Ile Gln His Leu Ala Tyr Gly Gln Lys His Ile Asn Ser His
    50                  55                  60

Thr Lys Gly Lys Asn Thr Leu Ile Ser Cys Gly Lys Thr Ala Glu Ala
65                  70                  75                  80

Ile Asn Ala Ser Lys Ser Asp Ala Ser Ser Asp Asn Thr Pro Gln Gly
                85                  90                  95

Ser Leu Glu Lys Lys Pro Leu Gln Thr Ala Thr Phe Pro Asn Gly Phe
            100                 105                 110

Glu Ala Leu Val Leu Glu Val Cys Asp Glu Thr Glu Ile Ala Glu Leu
        115                 120                 125

Lys Val Lys Val Gly Asp Phe Glu Met His Ile Lys Arg Asn Ile Gly
    130                 135                 140

Ala Thr Lys Val Pro Leu Ser Asn Ile Ser Pro Thr Thr Pro Pro Pro
145                 150                 155                 160

Ile Pro Ser Lys Pro Met Asp Glu Ser Ala Pro Gly Ser Leu Pro Pro
                165                 170                 175

Ser Pro Pro Lys Ser Ser Pro Glu Lys Asn Asn Pro Phe Ala Asn Val
            180                 185                 190

Ser Lys Glu Lys Ser Pro Arg Leu Ala Ala Leu Glu Ala Ser Gly Thr
        195                 200                 205

Asn Thr Tyr Val Leu Val Ser Ser Pro Thr Val Gly Leu Phe Arg Arg
    210                 215                 220
```

```
Gly Arg Thr Val Lys Gly Lys Gln Pro Pro Ile Cys Lys Glu Gly
225                 230                 235                 240

Asp Val Ile Lys Glu Gly Gln Val Ile Gly Tyr Leu Asp Gln Phe Gly
                245                 250                 255

Thr Gly Leu Pro Ile Lys Ser Asp Val Ala Gly Glu Val Leu Lys Leu
            260                 265                 270

Leu Val Glu Asp Gly Glu Pro Val Gly Tyr Gly Asp Pro Leu Ile Ala
        275                 280                 285

Val Leu Pro Ser Phe His Asp Ile Lys
        290                 295
```

<210> SEQ ID NO 67
<211> LENGTH: 234
<212> TYPE: PRT
<213> ORGANISM: Amborella trichopoda

<400> SEQUENCE: 67

```
Met Thr His Gln Ser Asn Gly Lys Glu Val Ser Leu Ile Phe Ala Asp
1               5                   10                  15

Glu Asp Pro Thr Arg Gly Ala Val Thr Ser Glu Ser Ser Asp Gly
            20                  25                  30

Lys Leu Glu Lys Lys Ser Leu His Lys Thr Thr Phe Pro Asp Gly Phe
        35                  40                  45

Glu Ala Trp Val Ser Asp Ile Cys Asp Glu Thr Glu Val Ala Glu Leu
    50                  55                  60

Lys Leu Lys Val Gly Asp Phe Glu Met His Leu Arg Arg Asn Ile Gly
65                  70                  75                  80

Asn Thr Lys Ala Pro Ala Pro Ser Pro Ile Val Ser Pro Ser Thr Pro
                85                  90                  95

Pro Pro Val Pro Thr Lys Pro Met Val Glu Ser Ala Pro Ala Thr Ala
            100                 105                 110

Pro Ser Val Thr Gln Lys Ala Pro Pro Val Ala Ser Ser Pro Phe Ser
        115                 120                 125

Asn Val Ser Ala Lys Ala Ser Lys Leu Ala Ser Leu Asp Ser Asp Gly
    130                 135                 140

Ala Asn Ala Tyr Val Ile Val Ala Ser Pro Thr Val Gly Lys Phe Arg
145                 150                 155                 160

Thr Gly Arg Thr Val Lys Gly Lys Arg Gln Pro Pro Val Ala Lys Glu
                165                 170                 175

Gly Asp Val Ile Lys Glu Asp Gln Ile Ile Gly Tyr Leu Asp Gln Phe
            180                 185                 190

Gly Ser Glu Leu Pro Val Lys Ser Asp Val Ala Gly Glu Val Leu Lys
        195                 200                 205

Ile Leu Phe Arg Asp Gly Glu Ala Val Gly Tyr Gly Asp Pro Leu Ile
    210                 215                 220

Ala Val Leu Pro Ser Phe His Gly Ile Lys
225                 230
```

<210> SEQ ID NO 68
<211> LENGTH: 297
<212> TYPE: PRT
<213> ORGANISM: Amborella trichopoda

<400> SEQUENCE: 68

```
Met Ile Arg Ser Tyr Leu Lys Ile Pro Phe Val Thr Glu Pro Ile Pro
1               5                   10                  15
```

```
Glu Ile Ala Arg Leu Ser Cys Ser Phe Gly Pro Leu Ala Lys Val Glu
             20                  25                  30

Leu Ser Thr Leu Asn Leu Pro Asn His Ser Thr Cys Lys Tyr Ile Gly
         35                  40                  45

Pro Pro Asp Leu Arg Met Met Arg Arg Cys Thr Gly Pro Gln Ser
 50                  55                  60

Leu His Tyr Glu Gly Phe Arg Met Gln Ser Arg Asn Leu Val Lys Pro
 65                  70                  75                  80

Val Ser Leu Leu Ser Gly Pro Ser Ala Glu Ala Met Ser Thr Ser Asp
                 85                  90                  95

Asp Gly Ser Lys Glu Asp Pro Lys Gly Lys Ser Ser Pro Ile Val Pro
             100                 105                 110

Asn Ser Leu Glu Val Gln Ser Leu Val Lys Glu Ile Cys Glu Thr Thr
         115                 120                 125

Ser Ile Ala Glu Phe Glu Leu Lys Leu Asp Gly Phe Arg Leu Tyr Val
 130                 135                 140

Ala Arg Asp Ile Asn Gly Lys Asp Met Pro Pro Thr Ser Pro Ser
145                 150                 155                 160

Ser Pro Ile His Thr Thr Thr Asn Val Ala Glu Glu Thr Leu Asp Ser
             165                 170                 175

Asn Gly Ser Ala Ser Pro Pro Thr Ile Ser Lys Pro Glu Pro Pro
         180                 185                 190

Leu Thr Arg Ile Gln Arg Leu Leu Glu Ala Ala Ala Asp Glu Gly Leu
                 195                 200                 205

Val Ile Ile Asn Ser Pro Lys Val Gly Tyr Phe Arg Arg Ala Arg Thr
210                 215                 220

Val Lys Gly Lys Arg Gly Pro Ala Ala Cys Lys Glu Lys Gln Ile Val
225                 230                 235                 240

Lys Glu Gly Gln Val Ile Cys Tyr Val Glu Gln Leu Gly Gly Glu Val
                 245                 250                 255

Pro Val Glu Ser Asp Val Ala Gly Glu Val Ile Lys Ile Leu Arg Glu
             260                 265                 270

Asp Gly Glu Pro Val Gly Tyr Gly Asp Pro Leu Ile Ala Ile Leu Pro
         275                 280                 285

Ser Phe Pro Gly Ile Lys Lys Leu Gln
 290                 295

<210> SEQ ID NO 69
<211> LENGTH: 290
<212> TYPE: PRT
<213> ORGANISM: Theobroma cacao

<400> SEQUENCE: 69

Met Glu Ser Ser Ala Ala Leu Arg Ser Phe His Tyr Ser Val Gly Ala
 1               5                  10                  15

Val Ser Gln Ala His Cys Ser Leu Glu Arg Pro Ser Thr Val His Met
             20                  25                  30

Tyr Ser Cys Gly Leu Ala Thr Ser Arg Lys Ser Cys Val Pro Gly Leu
         35                  40                  45

Met Phe Gly Gly Lys Asn Asn Ser Ala Thr Lys Arg Asn Val Thr Leu
     50                  55                  60

Ile Ser Cys Met Lys Thr Pro Glu Ala Ser Val Thr Ala Lys Ser Asn
 65                  70                  75                  80

Val Pro Leu Asp Ser Thr Ala Gln Gly Ser Met Glu Lys Lys Thr Ser
                 85                  90                  95
```

-continued

Arg Asn Ala Thr Phe Pro Asn Gly Phe Glu Ala Leu Val Leu Glu Val
                100                 105                 110

Cys Asp Glu Thr Glu Val Ala Glu Leu Lys Met Lys Ile Gly Asp Phe
            115                 120                 125

Glu Met His Leu Lys Arg Asn Val Gly Ala Thr Lys Ala Pro Leu Ser
    130                 135                 140

Asn Ile Ser Pro Thr Thr Ala Pro Pro Ile Pro Thr Lys Pro Met Asn
145                 150                 155                 160

Glu Ser Ala Ala Val Ala Pro Pro Ser Pro Pro Lys Pro Ser Pro
                165                 170                 175

Glu Lys Pro Thr Pro Phe Lys Asn Ala Ala Phe Gly Lys Ser Ser Lys
                180                 185                 190

Leu Ala Ala Leu Glu Ala Ser Gly Ser Ser Asn Tyr Val Leu Val Pro
            195                 200                 205

Ser Pro Ile Val Gly Thr Phe Arg Arg Gly Arg Thr Val Lys Gly Lys
        210                 215                 220

Lys Gln Pro Pro Ile Cys Lys Glu Gly Asp Leu Ile Lys Glu Gly Gln
225                 230                 235                 240

Val Ile Gly Phe Leu Asp Gln Phe Gly Thr Glu Leu Pro Val Lys Ser
                245                 250                 255

Asp Val Ala Gly Glu Val Leu Lys Leu Leu Phe Asp Asp Gly Asp Ala
            260                 265                 270

Val Gly Tyr Gly Asp Pro Leu Ile Ala Val Leu Pro Ser Phe His Gly
        275                 280                 285

Ile Glu
    290

<210> SEQ ID NO 70
<211> LENGTH: 274
<212> TYPE: PRT
<213> ORGANISM: Theobroma cacao

<400> SEQUENCE: 70

Met Ala Ser Cys Gly Ile Gly Ala Pro Asn Ile Lys Val Pro Lys Leu
1               5                   10                  15

Ser Phe Gly Lys Ala Arg Val Asp Lys Leu Lys Leu Asn Asn Val Arg
                20                  25                  30

Ile Trp Thr Arg Gln Arg Thr Met Gln Tyr Ala Gly Leu Val Arg His
            35                  40                  45

Ser Glu Lys Thr Phe Asn Ile Gly Cys Gly Pro Thr Leu Gln Thr Leu
    50                  55                  60

Ala Thr Thr Asn Leu Ala Asp Asp Phe Glu Glu Thr Lys Met Ser Gly
65                  70                  75                  80

Leu Thr Ser Gln Leu Ile Pro Asn Ser Ser Gly Val Glu Ser Leu Val
                85                  90                  95

Arg Asp Ile Cys Asp Thr Thr Ser Val Ala Glu Phe Glu Leu Lys Leu
                100                 105                 110

Gly Gly Phe Arg Leu Tyr Ile Met Arg Asp Leu Ala Gly Lys Ser Glu
            115                 120                 125

Pro Pro Pro Ala Ile Pro Ser Pro Pro Val Ser Val Ser Thr Ser
        130                 135                 140

Lys Thr Val Glu Ala Pro Asp Ser Asn Gly Ser Val Ser Thr Pro Thr
145                 150                 155                 160

Leu Ala Ile Thr Lys Pro Leu Ser Ser Ser Gly Arg Ile Gln Leu Leu

```
                    165                 170                 175
Leu Asp Lys Ala Ala Asp Glu Gly Leu Val Ile Leu Gln Ser Pro Lys
                180                 185                 190

Val Gly Phe Phe Arg Arg Ser Arg Thr Ile Lys Gly Lys Arg Ala Pro
            195                 200                 205

Pro Ser Cys Lys Glu Lys Gln Thr Val Lys Glu Gly Gln Val Leu Cys
        210                 215                 220

Tyr Ile Glu Gln Leu Gly Gly Glu Ile Pro Ile Glu Ser Asp Val Ser
225                 230                 235                 240

Gly Glu Val Ile Lys Ile Leu Arg Asp Asp Gly Asp Pro Val Gly Tyr
                245                 250                 255

Gly Asp Ala Leu Ile Ala Leu Leu Pro Ser Phe Pro Gly Ile Lys Lys
            260                 265                 270

Leu Gln

<210> SEQ ID NO 71
<211> LENGTH: 277
<212> TYPE: PRT
<213> ORGANISM: Phaseolus vulgaris

<400> SEQUENCE: 71

Met Ala Ser Cys Cys Leu Gly Thr Pro Lys Ile Lys Val Leu Asn Leu
1               5                   10                  15

Arg Phe Ser Gly Lys Asn Val Gly Leu Ser Gln Gln Val Gly Thr Arg
                20                  25                  30

Ser Trp Arg Arg Gln Ser Leu Gln Tyr Thr Ser Leu Val Met Ser Arg
            35                  40                  45

Gln Thr Asp Arg Phe Leu Ala Ser Ala Asn Ala Pro Ser Ser Glu Thr
        50                  55                  60

Gln Ile Ile Thr Arg Ser Glu Glu Gly Ser Glu Gly Thr Lys Ser Ser
65                  70                  75                  80

Val Leu Thr Ser Gln Leu Ile Pro Asn Phe Asn Glu Val Glu Phe Leu
                85                  90                  95

Val Thr Lys Leu Cys Asp Ser Ser Ser Ile Gly Glu Ile Asp Leu Lys
            100                 105                 110

Leu Ala Gly Phe His Leu His Ile Val Arg Asp Leu Thr Glu Gln Asn
        115                 120                 125

Glu Thr Leu Pro Pro Pro Thr Pro Ile Pro Ala Ser Val Ser Val Asn
    130                 135                 140

Asp Val Val Glu Thr Pro Lys Thr Asn Gly Ser Val Ser Thr Thr Ser
145                 150                 155                 160

Leu Ala Ile Ser Asn Pro Leu Gly Gln Val Tyr Phe Pro Gly Ser Ile
                165                 170                 175

Gln Arg Phe Leu Asp Lys Ala Lys Asp Glu Gly Leu Val Ile Ile Pro
            180                 185                 190

Cys Pro Lys Val Gly Tyr Phe Arg Arg Ser Arg Thr Ile Lys Gly Lys
        195                 200                 205

Arg Ala Pro Pro Ser Cys Lys Glu Lys Gln Ile Val Glu Glu Gly Gln
    210                 215                 220

Val Ile Cys Tyr Ile Glu Met Leu Gly Val Glu Val Ala Ile Glu Ala
225                 230                 235                 240

Asp Val Ser Gly Glu Ile Ile Lys Ile Leu Arg Lys Asp Gly Glu Pro
                245                 250                 255

Val Ala Tyr Gly Asp Ala Leu Ile Ala Ile Leu Pro Ser Phe Pro Gly
```

260                 265                 270
Ile Lys Lys Leu Gln
            275

<210> SEQ ID NO 72
<211> LENGTH: 289
<212> TYPE: PRT
<213> ORGANISM: Phaseolus vulgaris

<400> SEQUENCE: 72

Met Glu Ser Ser Ala Ala Ile Arg Ser Phe His Tyr Pro Met Gly Thr
1               5                   10                  15

Met Ser His Met Arg Pro Ser Tyr Asp Lys Gln Val Val Val Pro Ile
            20                  25                  30

His Asn Val Arg Trp Asn Ser Lys Ser Arg Leu Phe Ile Gln His Leu
        35                  40                  45

Ala Tyr Asp Arg Lys His Ile Asn Ser His Met Lys Gly Ser Thr Thr
    50                  55                  60

Leu Val Ser Cys Ala Lys Thr Ala Glu Pro Ile Asn Thr Ser Asn Ser
65                  70                  75                  80

Asp Asp Ala Ser Pro Gly Ser Thr Pro Gln Gly Ser Leu Glu Lys Lys
                85                  90                  95

Pro Leu Gln Ala Ala Thr Phe Pro Asn Gly Phe Glu Asp Leu Val Leu
            100                 105                 110

Glu Val Cys Asp Glu Thr Glu Ile Ala Glu Leu Lys Val Lys Val Gly
        115                 120                 125

Asp Phe Glu Met His Ile Lys Arg Asn Ile Gly Ala Thr Thr Val Pro
    130                 135                 140

Leu Ser Asn Ile Ser Pro Thr Thr Pro Pro Ile Pro Ser Lys Pro
145                 150                 155                 160

Met Asp Ser Ala Pro Gly Thr Leu Pro Pro Ser Pro Pro Lys Ser Ser
                165                 170                 175

Pro Glu Lys Lys Asn Pro Ile Ile Asp Ala Ser Arg Lys Lys Ser Pro
            180                 185                 190

Ile Leu Thr Ala Leu Glu Ala Ser Glu Ser Gly Thr Tyr Val Leu Ile
        195                 200                 205

Pro Ser Pro Thr Val Gly Phe Phe Arg Arg Gly Arg Thr Val Lys Gly
    210                 215                 220

Lys Arg Gln Pro Pro Ile Cys Lys Glu Gly Asp Phe Val Gln Glu Gly
225                 230                 235                 240

Gln Val Ile Gly Tyr Leu Asp Gln Leu Gly Ser Gly Asn Pro Val Lys
                245                 250                 255

Thr Asp Val Thr Gly Gln Val Leu Lys Leu Leu Val Glu Asp Gly Glu
            260                 265                 270

Pro Val Gly Tyr Gly Asp Pro Leu Ile Ala Val Phe Pro Leu Asp Leu
        275                 280                 285

Lys

<210> SEQ ID NO 73
<211> LENGTH: 275
<212> TYPE: PRT
<213> ORGANISM: Prunus persica

<400> SEQUENCE: 73

Met Ile Trp Val Ala Gly Ser Leu Gly Thr Leu Asn Ala Lys Ile Thr
1               5                   10                  15

```
Asn Leu Asn Phe Gly Arg Thr Arg Val Gly Ile Leu Gln Ser Ser Gly
             20                  25                  30

Leu Lys Pro Trp Thr Gly Gln Lys Pro Gln Leu Tyr Ser Cys Leu Ser
         35                  40                  45

Ile Ser Arg Arg Pro Asp Asn Val Leu Arg Ala His Ser Gly Pro Ser
 50                  55                  60

Leu Glu Thr Leu Pro Thr Thr Ser Leu Glu Asp Gly Pro Ala Glu Ser
 65                  70                  75                  80

Arg Asp Ser Gly Ser Thr Asn Gln Leu Ile Pro Asn Phe Asp Glu Val
                 85                  90                  95

Glu Ser Leu Val Thr Thr Ile Cys Asp Thr Thr Ser Val Ala Glu Phe
            100                 105                 110

Glu Leu Lys Ile Gly Gly Phe Arg Leu His Val Leu Arg Glu Leu Thr
        115                 120                 125

Glu Lys Ile Ser Thr Leu Pro Pro Ser Pro Ala Pro Val Ser Val
130                 135                 140

Asn Ala Thr Ser Glu Ala Pro Ala Ser Asn Gly Ser Val Pro Thr Gln
145                 150                 155                 160

Ser Leu Ala Val Ile Arg Gln Glu His Ser Ser Arg Asn Ile Gln Thr
                165                 170                 175

Leu Leu Asp Arg Ala Ala Asp Asp Gly Leu Val Leu Ile His Ser Pro
            180                 185                 190

Arg Val Gly Leu Phe Arg Arg Ser Arg Thr Ile Lys Gly Lys Arg Ala
        195                 200                 205

Pro Pro Ser Cys Lys Glu Lys Gln Ile Val Lys Glu Gly Gln Val Ile
    210                 215                 220

Cys Tyr Ile Glu Gln Leu Gly Glu Leu Pro Ile Glu Ser Asp Val
225                 230                 235                 240

Ser Gly Glu Val Ile Lys Ile Leu Arg Glu Asp Gly Asp Pro Val Gly
                245                 250                 255

Tyr Gly Asp Ala Leu Ile Ala Val Leu Pro Ser Phe Pro Gly Ile Lys
            260                 265                 270

Lys Leu Gln
        275

<210> SEQ ID NO 74
<211> LENGTH: 291
<212> TYPE: PRT
<213> ORGANISM: Prunus persica

<400> SEQUENCE: 74

Met Glu Ser Ser Ala Val Phe Arg Ser Phe Asn Cys Ser Val Gly Thr
 1               5                  10                  15

Val Ser His Val Arg Ser Ser Leu Asp Lys Pro Gly Met Leu Pro Ala
            20                  25                  30

Tyr Asn Thr Ala Arg Pro Thr Val Ser Arg Ser Tyr Phe Gln Gly Leu
        35                  40                  45

Met Val Ser Glu Lys Phe Ile Tyr Ser Pro Gln Lys Arg Arg Gly Val
 50                  55                  60

Gln Val Ser Cys Val Lys Thr Ser Glu Ala Ala Lys Ser Glu Lys Ser
65                  70                  75                  80

Ser Asp Ser Lys Pro Gln Val Ser Ser Glu Arg Thr Thr Gln Pro Ala
                 85                  90                  95

Thr Phe Pro Asn Gly Phe Glu Ala Leu Met Leu Glu Val Cys Asp Glu
```

```
            100                 105                 110
Thr Glu Val Ala Glu Leu Lys Leu Lys Val Gly Asp Phe Glu Met His
            115                 120                 125
Leu Lys Arg Asn Ile Gly Ala Thr Ser Ala Pro Val Ser Ser Ile Ser
            130                 135                 140
Pro Ala Ala Pro Pro Ile Pro Ser Lys Pro Met Val Glu Ser Ala
145                 150                 155                 160
Pro Ala Pro Pro Ala Pro Ala Pro Lys Ser Ser Ser Glu
                165                 170                 175
Lys Ala Thr Pro Phe Thr Asn Thr Ser Val Asp Lys Ser Ser Arg Leu
            180                 185                 190
Ala Ala Leu Glu Ala Ser Gly Ala Asn Gly Tyr Val Leu Val Ser Ser
            195                 200                 205
Pro Thr Val Gly Ser Phe Arg Arg Gly Arg Thr Val Lys Gly Lys Lys
        210                 215                 220
Gln Pro Pro Ile Cys Lys Glu Gly Asp Leu Ile Lys Gly Gln Val
225                 230                 235                 240
Ile Gly Tyr Val Asp Gln Phe Gly Thr Glu Leu Pro Val Lys Ser Asp
                245                 250                 255
Val Gly Gly Glu Val Leu Lys Leu Leu Phe Asn Asp Gly Glu Ala Val
            260                 265                 270
Gly Tyr Gly Asp Pro Leu Ile Ala Val Leu Pro Ser Phe His Gly Ile
        275                 280                 285
Asn Ile Asn
    290

<210> SEQ ID NO 75
<211> LENGTH: 292
<212> TYPE: PRT
<213> ORGANISM: Erythranthe guttata

<400> SEQUENCE: 75

Met Glu Ser Ala Ala Val Leu Arg Ser Phe Gln Tyr Ala Val Gly Ser
1               5                   10                  15
Ser Ser His Leu Lys Ser Gly Val Glu Arg Pro Ala Met Ile Thr Met
            20                  25                  30
Asn Asn Ala Ala Phe Tyr Asn Leu Ser Arg Leu Pro Val Phe Gly Gly
            35                  40                  45
Asn Thr Val Ser Ser Thr Asn Arg His Gly Ala Leu Leu Val Ser Cys
    50                  55                  60
Val Lys Thr Ser Glu Ala Thr Val Thr Ala Lys Ser Lys Gly Asp Pro
65                  70                  75                  80
Asn Gly Ala Val Leu Ala Asp Ser Pro Gln Asn Gly Ser Pro Glu Lys
                85                  90                  95
Lys Ser Pro Ile Asn Ala Thr Phe Pro Asn Gly Phe Glu Asn Leu Leu
            100                 105                 110
Ser Glu Val Cys Asp Glu Thr Lys Ile Ala Glu Leu Lys Val Lys Ile
            115                 120                 125
Gly Gly Phe Glu Leu His Met Lys Arg Asn Ile Asp Gly Pro Ala Ile
        130                 135                 140
Ser Ala Pro Val Val Ser Gln Thr Thr Val Pro Ser Leu Pro Ser Lys
145                 150                 155                 160
Pro Ala Asn Glu Leu Ser Pro Ser Ala Pro Pro Pro Ser Lys Ser
                165                 170                 175
```

```
Ser Ala Glu Lys Val Asn Pro Phe Ala Asn Val Ser Val Glu Lys Ala
            180                 185                 190

Ala Lys Leu Ala Ala Leu Asp Ala Ser Gly Ser Ser Gly Tyr Val Ile
        195                 200                 205

Val Ser Ser Pro Thr Val Gly Ser Phe Arg Arg Ala Arg Thr Leu Lys
    210                 215                 220

Gly Lys Lys Gln Pro Pro Ala Cys Lys Glu Gly Asp Leu Ile Lys Glu
225                 230                 235                 240

Gly Gln Val Ile Gly Tyr Leu Asp Gln Phe Gly Thr Glu Leu Pro Val
                245                 250                 255

Asn Ser Asp Val Ala Gly Glu Val Leu Lys Leu Leu Tyr Asn Asp Gly
            260                 265                 270

Glu Ala Val Gly Tyr Gly Asp Pro Leu Ile Ala Val Leu Pro Ser Phe
        275                 280                 285

His Gly Ile Arg
        290

<210> SEQ ID NO 76
<211> LENGTH: 273
<212> TYPE: PRT
<213> ORGANISM: Erythranthe guttata

<400> SEQUENCE: 76

Met Ala Ala Cys Gly Phe Gly Ala Ser Gly Ile Lys Ile Lys Ser Leu
1               5                   10                  15

Asp Phe Gly Ser Val Arg Pro Lys Leu Arg Thr Leu Gln Pro Leu His
            20                  25                  30

Gly Leu Lys Thr Pro Ser Ile Val Arg Phe Asp Gly Leu Val Leu Ser
        35                  40                  45

Asn Arg Ser Lys Lys Met Leu Ile Gly Cys Arg Ser Ser Ser Leu Glu
    50                  55                  60

Ser Asp Ser Asn Ala Ser Ile Glu Asp Ile Ser Lys Glu Thr Glu Ser
65                  70                  75                  80

Pro Glu Ala Val Ser Thr Leu Ile Pro Asn Ala Phe Glu Val Glu Ser
                85                  90                  95

Leu Leu Thr Val Leu Cys Asp Thr Thr Ser Ile Ala Glu Ile Glu Leu
            100                 105                 110

Lys Leu Gly Gly Phe Arg Leu Tyr Val Ser Arg Asp Leu Ala Glu Gln
        115                 120                 125

Asn Ala Pro Pro Gln Pro Pro Ala Pro Ala His Val Ile Ala His Ser
    130                 135                 140

Val Val Glu Thr Pro Ser Ser Asn Gly Ser Ala Ser Ser Pro Ser Leu
145                 150                 155                 160

Ala Leu Ser Lys Pro Thr Ser Ser Ser Ala Gly Ile Gln Thr Met Leu
                165                 170                 175

Asp Lys Ala Ala Asp Glu Gly Leu Val Ile Leu Gln Ser Pro Arg Val
            180                 185                 190

Gly Tyr Phe Lys Arg Cys Arg Thr Ile Lys Gly Lys Lys Ala Pro Pro
        195                 200                 205

Ser Cys Lys Glu Lys Asp Thr Val Lys Glu Gly Gln Val Leu Cys Phe
    210                 215                 220

Ile Glu Gln Leu Gly Gly Glu Ile Pro Ile Gly Ser Asp Ile Ser Gly
225                 230                 235                 240

Glu Val Val Lys Ile Leu Arg Glu Asp Gly Ala Pro Val Gly Tyr Gly
                245                 250                 255
```

Asp Ala Leu Ile Ala Ile Leu Pro Ser Phe Pro Gly Ile Lys Lys Leu
            260                 265                 270

Gln

<210> SEQ ID NO 77
<211> LENGTH: 287
<212> TYPE: PRT
<213> ORGANISM: Eucalyptus grandis

<400> SEQUENCE: 77

Met Glu Ser Ser Val Ser Ala Leu Arg Ser Leu His Ser Asn Ile
1               5                   10                  15

Ala Gly Ala Leu Pro Arg Val Glu Pro Leu Pro His Lys Pro Gly Val
            20                  25                  30

Val Pro Val Gln Ser Tyr Ser Pro Ser Lys Lys Leu Tyr Val His
            35                  40                  45

Gly Phe Ala Ala Arg Gly Ile Ala Pro Ser Arg Thr Arg Asn Ala Ala
50                  55                  60

Val Val Ser Cys Leu Lys Thr Ser Glu Ala Thr Gly Val Ala Lys Ser
65                  70                  75                  80

Ser Gly Asn Thr Arg Asp Ser Lys Asp Lys Thr Thr Leu Pro Arg Ala
            85                  90                  95

Thr Phe Pro Ser Ala Phe Glu Glu Leu Leu Glu Val Cys Asp Glu
            100                 105                 110

Thr Gln Ile Ala Glu Leu Lys Leu Lys Ile Gly Asp Ile Glu Met Gln
            115                 120                 125

Val Lys Arg Asn Leu Gly Ala Thr Lys Glu Ala Phe Ala Ser Ile Pro
130                 135                 140

Ser Pro Thr Thr Pro Pro Ile Pro Thr Glu Pro Met Glu Asn Ser
145                 150                 155                 160

Gly Ala Val Val Pro Pro Lys Pro Ser Pro Glu Lys Thr Ser Pro
            165                 170                 175

Phe Thr Asn Phe Ser Phe Gly Lys Ser Ser Lys Leu Ala Ala Leu Glu
            180                 185                 190

Ala Pro Gly Ser Ser Gly Tyr Val Leu Val Ser Ser Pro Thr Val Gly
            195                 200                 205

Ser Phe Arg Arg Gly Arg Thr Leu Lys Gly Lys Gln Pro Pro Ser
210                 215                 220

Cys Lys Glu Gly Asp Val Ile Lys Glu Gly Gln Val Ile Gly Trp Leu
225                 230                 235                 240

Asp Gln Phe Gly Thr Glu Leu Pro Val Lys Ser Asp Val Ser Gly Glu
            245                 250                 255

Val Leu Lys Leu Leu Val Asn Asp Gly Glu Pro Val Gly Tyr Gly Asp
            260                 265                 270

Pro Leu Ile Ala Val Leu Pro Ala Phe His Ser Ile Asn Ile Met
            275                 280                 285

<210> SEQ ID NO 78
<211> LENGTH: 142
<212> TYPE: PRT
<213> ORGANISM: Eucalyptus grandis

<400> SEQUENCE: 78

Met Cys Ser Tyr Phe Ala Lys Pro Val Asn Lys Ser Ser Gly Val
1               5                   10                  15

```
Ser Pro Pro Ser Ala Leu Lys Pro Ser Ser Glu Lys Ala Ala Pro Phe
            20                  25                  30

Met Asn Val Thr Phe Gly Lys Ser Ala Lys Val Lys Ala Leu Glu Ala
            35                  40                  45

Ser Gly Ser Ser Gly Tyr Ala Leu Val Ser Ser Pro Thr Val Gly Ser
        50                  55                  60

Phe Gln Lys Gly Arg Thr Val Lys Gly Lys Lys Gln Gly Pro Ser Cys
65                  70                  75                  80

Lys Glu Gly Asp Leu Ile Lys Glu Gly Gln Val Ile Gly Trp Leu Asp
                85                  90                  95

Gln Phe Gly Thr Glu Leu Pro Val Lys Ser Asp Val Ser Gly Glu Val
            100                 105                 110

Leu Lys Leu Leu Ile Asp Asp Gly Glu Ala Val Gly Tyr Gly Asp Pro
        115                 120                 125

Leu Leu Ala Val Leu Pro Ser Phe Pro Gly Val Gly Val Gln
    130                 135                 140
```

<210> SEQ ID NO 79
<211> LENGTH: 304
<212> TYPE: PRT
<213> ORGANISM: Helicosporidium sp.

<400> SEQUENCE: 79

```
Met Ser Ala Leu Ser Ser Ala Ala Leu Pro Ser Ile Gly Pro Cys Ile
1               5                   10                  15

Gly Gln Ala Leu Ser Ala Arg Asn Ala Val Val Ser Arg Val Val Ala
            20                  25                  30

Lys Arg Arg Glu Pro Ile Arg Ser Arg Glu His Leu Ser Lys Arg Ala
        35                  40                  45

Gly Ala Asn Cys Ala Ala Leu Ala Val Thr Glu Glu Glu Glu Glu Glu
    50                  55                  60

Ser Asp Asn Asn Trp Ser Met Pro Thr Pro Glu Glu Asp Asp Pro Ala
65                  70                  75                  80

Glu Leu Ser Pro Lys Gln Val Glu Ala Leu Leu Ser Thr Leu Cys Asn
                85                  90                  95

Glu Thr Glu Ile Ala Glu Leu Lys Leu Asp Leu Gly Ser Asn Phe His
            100                 105                 110

Leu Lys Val Thr Arg Ala Phe Gln Asn Thr Thr Ala Val Ala Pro Pro
        115                 120                 125

Thr Thr Pro Ala Pro Ala Leu Pro Ser Ala Gln Ser Val Pro Phe Ala
    130                 135                 140

Asn Ser Gly Ala Ile Ser Ser Asp Asp Glu Ala Glu Glu Val Arg Leu
145                 150                 155                 160

Val Val Arg Ala Ser Lys Val Gly Lys Ile Arg Tyr Gly Lys Phe Val
                165                 170                 175

Lys Gly Lys Arg Val Ser Pro Glu Pro Thr Val Lys Val Gly Asp Gln
            180                 185                 190

Val Lys Lys Gly Gln Val Ile Cys Tyr Thr Glu Gln Leu Gly Thr Val
        195                 200                 205

Trp Pro Leu Glu Ala Pro Gln Ala Gly Glu Leu Arg Glu Phe Leu Val
    210                 215                 220

Lys Glu Gly Glu Ala Leu Glu Arg Ser Arg Ala Gln Leu Asn Ala Leu
225                 230                 235                 240

Lys Leu Lys Asp Gly Arg Ser Met Ser Ala Thr Glu Ile Arg Lys Ala
                245                 250                 255
```

```
Phe Ala Lys Arg Glu Thr Ser Ile Ala Gln Asn Leu Glu Ser Met Thr
            260                 265                 270

Leu Lys Ser Val Arg Gln Gln Leu Ala Asp Asp Met Gly Val Asp Pro
        275                 280                 285

Asp Ser Leu Lys Ala His Lys Asp Leu Ile Ala Ser Leu Val Asp Lys
        290                 295                 300

<210> SEQ ID NO 80
<211> LENGTH: 170
<212> TYPE: PRT
<213> ORGANISM: Citrus sinensis

<400> SEQUENCE: 80

Val Gly Asp Phe Glu Met His Leu Lys Arg Asn Val Gly Ala Pro Lys
1               5                   10                  15

Ala Pro Ala Pro Leu Ser Asn Ile Ser Pro Thr Thr Pro Pro Pro Ile
            20                  25                  30

Pro Thr Glu Pro Met Glu Val Ser Asp Pro Val Ser Pro Pro Pro Pro
        35                  40                  45

Pro Ser Pro Pro Lys Pro Tyr Ser Glu Lys Ala Ala Pro Phe Ile Asn
50                  55                  60

His Ser Phe Gly Lys Ser Ser Lys Leu Ala Ala Leu Glu Ala Ser Gly
65                  70                  75                  80

Ser Asn Gly Tyr Val Leu Val Phe Ser Pro Thr Val Gly Ser Phe Arg
                85                  90                  95

Arg Asn Arg Thr Val Lys Gly Lys Lys Gln Ser Pro Ile Cys Lys Glu
            100                 105                 110

Gly Asp Val Ile Lys Glu Gly Gln Thr Ile Gly Tyr Leu Asp Gln Phe
        115                 120                 125

Gly Thr Glu Leu Pro Val Lys Ser Asp Val Ala Gly Glu Val Leu Lys
    130                 135                 140

Leu Leu Phe Asp Asp Gly Asp Ala Val Gly Phe Gly Asp Pro Leu Ile
145                 150                 155                 160

Ala Val Leu Pro Ser Phe His Asp Ile Lys
                165                 170

<210> SEQ ID NO 81
<211> LENGTH: 271
<212> TYPE: PRT
<213> ORGANISM: Citrus sinensis

<400> SEQUENCE: 81

Met Ala Ser Tyr Ser Leu Gly Ala Ser Asn Ile Lys Ile Pro Lys Gly
1               5                   10                  15

Asn Leu Gly Arg Ala Arg Val Gly Asp Leu Gln Pro Arg Ser Asp Val
            20                  25                  30

Arg Lys Trp Met Gly Arg Lys Pro Phe Gln Tyr Ala Gly Leu Ala Met
        35                  40                  45

Ser Gln Pro Leu Glu Lys Ala Phe Thr Val Phe Cys Gly Gln Ser Ser
50                  55                  60

Glu Ala Glu Ser Thr Arg Asn Ala Arg Asp Gly His Glu Asp Met Lys
65                  70                  75                  80

Ser Thr Gln Leu Ile Pro Asp Ser Ser Glu Val Glu Ser Leu Val Thr
                85                  90                  95

Asp Ile Cys Asn Thr Thr Ser Val Ala Glu Phe Glu Leu Lys Leu Asp
            100                 105                 110
```

```
Gly Phe Arg Leu Tyr Val Thr Arg Asp Ile Ala Gly Asp Ser Ile Pro
            115                 120                 125

Pro Leu Pro Pro Ser Ser Pro Ala Pro Val Thr Val Asn Lys Pro Ala
        130                 135                 140

Asp Arg Pro Asp Ser Asn Gly Ser Val Pro Thr Ser Ser Leu Ala Ile
145                 150                 155                 160

Thr Lys Pro Val Ser Ser Ser Gly Gly Ile Gln Thr Leu Leu Asp Lys
                165                 170                 175

Ala Ala Asp Glu Gly Leu Val Ile Leu Glu Ser Pro Lys Val Gly Tyr
            180                 185                 190

Phe Arg Arg Ser Arg Thr Ile Lys Gly Lys Arg Ala Pro Pro Ser Cys
        195                 200                 205

Lys Glu Lys Gln Thr Val Arg Glu Gly Gln Val Leu Cys Tyr Ile Glu
    210                 215                 220

Gln Leu Gly Gly Glu Ile Pro Ile Glu Ser Asp Ile Ala Gly Glu Val
225                 230                 235                 240

Ile Lys Ile Leu Arg Lys Asp Gly Asp Pro Ile Gly Tyr Gly Asp Pro
                245                 250                 255

Leu Ile Val Ile Leu Pro Ser Phe Pro Gly Ile Lys Leu Leu Gln
            260                 265                 270

<210> SEQ ID NO 82
<211> LENGTH: 285
<212> TYPE: PRT
<213> ORGANISM: Jatropha curcas

<400> SEQUENCE: 82

Met Ala Ser Cys Ser Leu Gly Ala Ser Asn Ile Lys Leu Ser Lys Leu
1               5                   10                  15

Asn Phe Gly Arg Glu Arg Ala Gly Asn Ile Gln Gln Trp Ser Gly Met
            20                  25                  30

Arg Thr Ser Ile Gly Trp Arg Gln Leu Gln Tyr Thr Gly Leu Thr Val
        35                  40                  45

Ile Tyr Lys Pro Lys Glu Thr Phe Ser Val Arg Cys Cys Pro Thr Leu
    50                  55                  60

Glu Lys Glu Thr Ser Thr Asn Arg Val Asp Ser Ile Lys Gln Thr Lys
65                  70                  75                  80

Ser Ser Gly Leu Thr Ser Gln Leu Ile Pro Asn Ser Ser Glu Ile Glu
                85                  90                  95

Phe Leu Val Thr Glu Val Cys Asn Ala Thr Ser Ile Ala Glu Phe Glu
            100                 105                 110

Leu Lys Val Gly Gly Phe Trp Leu Tyr Leu Thr Arg Asn Leu Thr Gln
        115                 120                 125

Lys Ser Lys Pro Ser Pro Val Pro Thr Leu Ala Pro Leu Pro Pro Asp
    130                 135                 140

Pro Ala Pro Ala Pro Asp Pro Leu Thr Ala Asp Lys Thr Ile Lys Ala
145                 150                 155                 160

Pro Glu Leu Asn Gly Ser Val Ser Ser Thr Ser Phe Ala Ile Ser Lys
                165                 170                 175

Pro Ala Pro Phe Ser Gly Gly Ile Gln Ser Phe Leu Asp Lys Ala Val
            180                 185                 190

Asp Glu Gly Leu Met Ile Leu Gln Ser Pro Arg Val Gly Phe Phe Arg
        195                 200                 205

Arg Ser Arg Thr Ile Lys Gly Lys Arg Ala Pro Pro Ser Cys Lys Glu
```

Lys Gln Ile Val Lys Glu Gly Gln Val Leu Cys Tyr Ile Glu Gln Leu
225                 230                 235                 240

Gly Gly Glu Leu Pro Ile Glu Ser Asp Val Ser Gly Glu Val Ile Lys
            245                 250                 255

Ile Leu Arg Glu Asp Gly Asp Pro Val Gly Tyr Gly Asp Ala Leu Ile
            260                 265                 270

Ala Ile Leu Pro Ser Phe Pro Gly Ile Lys Lys Leu Gln
            275                 280                 285

<210> SEQ ID NO 83
<211> LENGTH: 236
<212> TYPE: PRT
<213> ORGANISM: Jatropha curcas

<400> SEQUENCE: 83

Met Val Ser Ser Pro Val Lys Arg Asn Val Ala Leu Val Ser Cys Val
1               5                   10                  15

Lys Ala Pro Glu Ala Ala Glu Thr Val Lys Ser Asp Ala Gly Gly Ala
            20                  25                  30

Lys Gly Ser Leu Glu Asn Ser Asn Leu Arg Ser Ala Thr Phe Pro Asn
        35                  40                  45

Gly Phe Glu Ala Leu Val Leu Glu Val Cys Asp Glu Thr Glu Ile Ala
    50                  55                  60

Glu Leu Lys Leu Lys Val Gly Asp Phe Glu Met His Leu Arg Arg Asn
65                  70                  75                  80

Val Gly Ala Ile Thr Ala Pro Leu Ser His Ile Ser Pro Thr Glu Pro
                85                  90                  95

Pro Pro Ile Pro Thr Glu Pro Met Asn Val Ser Ala Pro Val Thr Pro
            100                 105                 110

Pro Pro Ala Pro Pro Lys Pro Ser Thr Glu Lys Ser Thr Pro Phe Lys
        115                 120                 125

Asn Val Ser Phe Gly Lys Ser Ser Lys Leu Ala Ala Leu Glu Ala Ser
    130                 135                 140

Gly Ala Thr Gly Tyr Val Leu Val Thr Ser Pro Thr Val Gly Ser Phe
145                 150                 155                 160

Arg Arg Asn Arg Thr Val Lys Gly Lys Arg Gln Pro Pro Ile Phe Lys
                165                 170                 175

Glu Gly Asp Leu Ile Lys Glu Gly Gln Val Ile Gly Tyr Leu Asp Gln
            180                 185                 190

Phe Gly Thr Glu Leu Pro Val Lys Ser Asp Val Ala Gly Glu Val Leu
        195                 200                 205

Lys Leu Leu Phe Asp Asp Gly Asp Ala Val Gly Tyr Gly Asp Pro Leu
    210                 215                 220

Ile Ala Val Leu Pro Ser Phe His Asp Ile Asn Lys
225                 230                 235

<210> SEQ ID NO 84
<211> LENGTH: 273
<212> TYPE: PRT
<213> ORGANISM: Prunus mume

<400> SEQUENCE: 84

Met Ala Ser Cys Ser Leu Gly Thr Leu Asn Ala Lys Ile Thr Asn Leu
1               5                   10                  15

Asn Phe Gly Arg Thr Arg Val Gly Ile Leu Gln Ser Ser Gly Leu Lys

```
            20                  25                  30
Thr Trp Thr Gly Gln Lys Pro Gln Leu Tyr Ser Cys Leu Ser Met Ser
        35                  40                  45

Arg Arg Pro Asp Lys Val Leu Arg Ala His Ser Gly Pro Ser Leu Glu
    50                  55                  60

Thr Leu Pro Thr Thr Ser Leu Glu Asp Gly Pro Ala Glu Ser Arg Asp
65                  70                  75                  80

Ser Gly Ser Thr Asn Gln Leu Ile Pro Asn Phe Asp Glu Val Glu Ser
                85                  90                  95

Leu Val Thr Thr Ile Cys Asp Thr Thr Ser Val Ala Glu Phe Glu Leu
            100                 105                 110

Lys Ile Gly Gly Phe Arg Leu His Val Leu Arg Glu Leu Thr Glu Lys
        115                 120                 125

Ile Ser Thr Leu Pro Pro Ser Pro Ala Pro Val Ser Val Asn Ala
        130                 135                 140

Thr Ala Glu Ala Pro Ala Ser Asn Gly Thr Val Pro Thr Gln Ser Leu
145                 150                 155                 160

Ala Ile Ile Arg Gln Glu His Ser Ser Arg Asn Ile Gln Thr Leu Leu
                165                 170                 175

Asp Arg Ala Ala Asp Asp Gly Leu Val Leu Ile His Ser Pro Arg Val
                180                 185                 190

Gly Leu Phe Arg Arg Ser Arg Thr Ile Lys Gly Lys Arg Ala Pro Pro
        195                 200                 205

Ser Cys Lys Glu Lys Gln Ile Val Lys Glu Gly Gln Val Ile Cys Tyr
    210                 215                 220

Ile Glu Gln Leu Gly Gly Glu Leu Pro Ile Glu Ser Asp Val Ser Gly
225                 230                 235                 240

Glu Val Ile Lys Ile Leu Arg Glu Asp Gly Asp Pro Val Gly Tyr Gly
                245                 250                 255

Asp Ala Leu Ile Ala Val Leu Pro Ser Phe Pro Gly Ile Lys Lys Leu
                260                 265                 270

Gln

<210> SEQ ID NO 85
<211> LENGTH: 289
<212> TYPE: PRT
<213> ORGANISM: Prunus mume

<400> SEQUENCE: 85

Met Glu Ser Ser Ala Val Phe Arg Ser Phe Asn Cys Ser Val Gly Thr
1               5                   10                  15

Val Ser His Val Arg Ser Ser Leu Asp Lys Pro Gly Met Leu Ala Ala
            20                  25                  30

Tyr Asn Thr Ala Arg Pro Thr Val Ser Arg Ser Tyr Phe Gln Gly Leu
        35                  40                  45

Met Val Ser Glu Lys Phe Ile Tyr Ser Pro Gln Lys Arg Arg Gly Val
    50                  55                  60

Pro Val Ser Cys Val Lys Thr Ser Glu Ala Ala Lys Ser Glu Lys Ser
65                  70                  75                  80

Ser Asp Ser Lys Pro Gln Val Ser Ser Glu Arg Thr Thr Gln Pro Ala
                85                  90                  95

Thr Phe Pro Ser Gly Phe Glu Ala Leu Met Leu Glu Val Cys Asp Glu
            100                 105                 110

Thr Glu Val Ala Glu Leu Lys Leu Lys Val Gly Asp Phe Glu Met His
```

```
            115                 120                 125
Leu Lys Arg Asn Ile Gly Ala Thr Ser Ala Pro Val Ser Ser Ile Ser
        130                 135                 140

Pro Ala Val Ala Pro Ile Pro Ser Lys Pro Met Val Glu Ser Ala
145                 150                 155                 160

Ser Ala Pro Pro Ala Pro Ala Pro Lys Ser Ser Ser Glu Lys Ala
                165                 170                 175

Thr Pro Phe Thr Asn Thr Ser Val Asp Lys Ser Ser Arg Leu Ala Ala
            180                 185                 190

Leu Glu Ala Ser Gly Ala Asn Gly Tyr Val Leu Val Ser Ser Pro Thr
        195                 200                 205

Val Gly Ser Phe Arg Arg Gly Arg Thr Val Lys Gly Lys Lys Gln Pro
    210                 215                 220

Pro Ile Cys Lys Glu Gly Asp Leu Ile Lys Gly Gly Gln Val Val Gly
225                 230                 235                 240

Tyr Val Asp Gln Phe Gly Thr Glu Leu Pro Val Lys Ser Asp Val Gly
                245                 250                 255

Gly Glu Val Leu Lys Leu Leu Phe Asn Asp Gly Glu Ala Val Gly Tyr
            260                 265                 270

Gly Asp Pro Leu Ile Ala Val Leu Pro Ser Phe His Gly Ile Asn Ile
        275                 280                 285

Lys

<210> SEQ ID NO 86
<211> LENGTH: 277
<212> TYPE: PRT
<213> ORGANISM: Medicago truncatula

<400> SEQUENCE: 86

Met Ala Ser Ser His Cys Ser Leu Gly Thr Gln Asn Val Lys Val Leu
1               5                   10                  15

Asn Leu His Phe Gly Gln Glu Arg Ala Glu Phe Ser Gln His Phe Gly
            20                  25                  30

Thr Arg Ser Trp Ile Ser Arg Lys Ser Leu Gln Tyr Ala Arg Leu Val
        35                  40                  45

Ala Ser Lys Gln Thr Val Arg Ser Leu Thr Pro Ser Asn Asp Gln Ser
    50                  55                  60

Ala Glu Ile Gln Ser Val Ser Arg Ser Glu Asp Gly Ser Glu Glu Ser
65                  70                  75                  80

Lys Ser Ser Gly Leu Thr Asn Gln Leu Phe Pro Asn Phe Asn Asp Val
                85                  90                  95

Glu Phe Leu Leu Thr Asn Leu Cys Asp Thr Ala Ser Ile Gly Glu Leu
            100                 105                 110

Glu Leu Lys Leu Asp Gly Phe His Leu Arg Val Val Arg Asp Leu Thr
        115                 120                 125

Glu Lys Ser Lys Thr Leu Pro Pro Ser Ile Pro Ala Pro Val Ser Ile
    130                 135                 140

Asn Thr Pro Ala Glu Ala Pro Lys Pro Asn Gly Ser Val Ser Thr Leu
145                 150                 155                 160

Thr Thr Leu Ala Ile Ser Lys Pro Ala Pro Ser Ser Leu Ser Ile Glu
                165                 170                 175

Gly Phe Leu Glu Lys Ala Ala Asp Glu Gly Leu Val Ile Ile His Ser
            180                 185                 190

Pro Thr Val Gly Ile Phe Arg Arg Ser Arg Thr Ile Lys Gly Lys Arg
```

```
            195                 200                 205
Ala Pro Pro Ser Cys Gln Glu Met Gln Asn Val Glu Glu Gly Lys Val
    210                 215                 220

Ile Cys Tyr Ile Glu Gln Leu Gly Gly Gln Leu Pro Val Glu Ser Asp
225                 230                 235                 240

Val Ser Gly Glu Val Ile Lys Ile Leu Arg Glu Asp Gly Asp Pro Val
                245                 250                 255

Gly Tyr Gly Asp Thr Leu Ile Ala Ile Leu Pro Ser Phe Pro Gly Ile
            260                 265                 270

Lys Lys Leu Gln Tyr
        275

<210> SEQ ID NO 87
<211> LENGTH: 278
<212> TYPE: PRT
<213> ORGANISM: Cucumis melo

<400> SEQUENCE: 87

Met Glu Ser Ser Ala Ser Leu Arg Ser Phe His Tyr Phe Ala Gly Gly
1               5                   10                  15

Ser Arg Leu Gln Leu Val Asp Lys Pro Ser Lys Ile Tyr Val Ala Ser
            20                  25                  30

Thr Asn Lys Ser Ser Ile Gln Arg Leu Ser Ile Phe Gly Lys Pro Ile
        35                  40                  45

His Ser Pro Thr Ser Gln Lys Lys Ile Val Val Ser Cys Ile Lys Thr
    50                  55                  60

Pro Glu Val Ser Glu Ala Lys Pro Lys Asp Ser Ala Gln Gly Ser
65                  70                  75                  80

Leu Gln Lys Lys Pro Ala Ser Asn Ala Thr Phe Pro Asn Gly Phe Glu
                85                  90                  95

Ala Leu Val Leu Glu Val Cys Asp Glu Thr Glu Ile Ala Glu Leu Lys
            100                 105                 110

Leu Lys Val Gly Glu Phe Glu Met His Leu Lys Arg Asn Ile Gly Val
        115                 120                 125

Val Arg Ala Pro Leu Ser Ser Ile Ser Pro Thr Val Pro Pro Pro Ile
    130                 135                 140

Pro Ser Lys Pro Met Val Glu Ser Ala Pro Thr Ala Pro Ala Pro Pro
145                 150                 155                 160

Lys Pro Ser Pro Glu Lys Ala Ala Ala Phe Thr Asn Ile Pro Leu Gln
                165                 170                 175

Lys Ser Ser Lys Leu Ala Ala Leu Glu Ser Ser Gly Ala Lys Gly Tyr
            180                 185                 190

Val Leu Val Pro Ser Pro Thr Val Gly Ser Phe Arg Ser Gly Arg Thr
        195                 200                 205

Ile Lys Gly Lys Lys Gln Pro Pro Ile Cys Lys Glu Asn Asp Leu Ile
    210                 215                 220

Lys Glu Gly Gln Val Ile Gly Tyr Val Asp Gln Phe Gly Thr Glu Leu
225                 230                 235                 240

Pro Val Lys Ser Asp Val Ala Gly Glu Val Leu Arg Val Leu Phe Lys
                245                 250                 255

Asp Gly Glu Ala Val Gly Tyr Gly Asp Pro Leu Ile Ala Val Leu Pro
            260                 265                 270

Glu Phe His Gly Ile Arg
        275
```

<210> SEQ ID NO 88
<211> LENGTH: 403
<212> TYPE: PRT
<213> ORGANISM: Cucumis melo

<400> SEQUENCE: 88

```
Met Ile Phe Phe Gln Asn Ser Phe Gly Lys Lys Leu Val Lys Leu Glu
1               5                   10                  15

Arg Asn Lys Ser Leu Thr Arg Leu Leu Gly Pro Thr Val His Leu Asn
            20                  25                  30

Gln Lys Arg Phe Glu Phe Leu Trp Gly Phe Ile Phe Pro Val Phe
        35                  40                  45

Val Asn Glu Leu Lys Arg Val Ser Val Arg Leu Leu Phe Gln Ser Pro
    50                  55                  60

Phe Cys Leu Gln Asn Leu Leu Phe Leu Ser Trp Asn Phe Ala His His
65                  70                  75                  80

Gln Asn Ser Ser Pro Phe Ser Ser Cys Leu Arg Arg Asn Gln Arg Gly
                85                  90                  95

Phe Leu Phe Leu Ile Leu Tyr Phe Cys Ser Val Gly Pro Tyr Ser Glu
            100                 105                 110

Leu Leu Cys Pro Ser His Ser Ala Arg Ser Phe Phe Phe Ser Thr Met
        115                 120                 125

Ala Ser Cys Ser Leu Arg Ala Val Asp Ile Lys Val Ser Lys Leu Asp
    130                 135                 140

Ile Arg Arg Gly Arg Val Ser Thr Leu Gln Pro Cys Ser Leu Arg Asn
145                 150                 155                 160

Trp Ile Gly Arg Thr Pro His Gln Tyr Ser Thr Leu Val Ile Ser His
                165                 170                 175

Ser Ser Gln Lys Ala Leu His Ala Cys Ser Ser Ala Ser Pro Glu Thr
            180                 185                 190

Gln Thr Val Ile Lys Ser Glu Thr Gly Ser Glu Glu Ile Lys Pro Ser
        195                 200                 205

Asn Leu Val Ser Gln Leu Ile Pro Asn Leu His Glu Val Glu Thr Leu
    210                 215                 220

Leu Thr Asn Ile Cys Asp Thr Ser Ser Ile Ala Glu Phe Glu Leu Lys
225                 230                 235                 240

Leu Ser Gly Phe Asn Leu Arg Met Val Arg Ser Leu Lys Ser Glu Asn
                245                 250                 255

Leu Pro Leu Pro Pro Ala Pro Ala Pro Ala Pro Asp Ile Gln Asn Thr
            260                 265                 270

Ser Ser Ile Pro Ser Asp Ser Asn Gly Leu Val Lys Thr Ser Leu Ala
        275                 280                 285

Leu Val Lys Pro Glu Pro Val Ser Ser Pro Glu Gly Ile Ser Arg
    290                 295                 300

Tyr Val Glu Lys Ala Thr Asp Gly Gly Leu Ser Ile Leu Val Ser Pro
305                 310                 315                 320

Lys Val Gly Val Phe Arg Arg Ser Arg Thr Ile Lys Gly Lys Arg Ala
                325                 330                 335

Pro Pro Ser Cys Glu Glu Asn Gln Val Val Lys Glu Gly Lys Val Leu
            340                 345                 350

Cys Tyr Ile Asp Gln Leu Gly Ala Glu Ile Pro Ile Glu Ser Asp Ile
        355                 360                 365

Ser Gly Glu Ile Val Lys Ile Leu Arg Lys Asp Gly Glu Pro Val Gly
    370                 375                 380
```

```
Tyr Gly Asp Pro Leu Ile Ala Val Leu Pro Ser Phe Pro Gly Ile Lys
385                 390                 395                 400

Lys Leu Leu

<210> SEQ ID NO 89
<211> LENGTH: 282
<212> TYPE: PRT
<213> ORGANISM: Coffea canephora

<400> SEQUENCE: 89

Met Glu Ser Ala Ala Val Leu Arg Ser Phe His Cys Ile Thr Ser Pro
1               5                   10                  15

Leu Lys Ser Ile Ile Asp Lys Pro Gly Ala Val Pro Met Thr Thr Val
            20                  25                  30

Gly Phe Ser Gly Leu Ala Lys Cys His Ile Gln Gly Leu Ala Tyr Asn
        35                  40                  45

Gly Lys Leu Ile Ser Ser Thr Ser Lys Met Gly Gly Val Ile Val Ser
    50                  55                  60

Cys Val Lys Thr Ser Glu Val Pro Val Thr Ala Lys Ser Asp Asp Ser
65                  70                  75                  80

Ser Gln Lys Glu Ser Gly Pro Lys Asn Ser Ile Arg Arg Ala Thr Phe
                85                  90                  95

Pro Asn Gly Phe Lys Ala Leu Leu Thr Glu Val Cys Asp Asp Thr Glu
            100                 105                 110

Ile Ala Glu Leu Arg Val Lys Val Gly Asp Phe Glu Met His Leu Lys
        115                 120                 125

Arg Asn Ile Gln Pro Pro Ile Ala Pro Ala Pro Val Glu Ser Pro Thr
    130                 135                 140

Val Ala Pro Pro Ile Pro Ser Glu Pro Met Asn Gln Ser Val Pro Pro
145                 150                 155                 160

Pro Ala Pro Pro Lys Pro Ala Thr Glu Lys Met Ser Pro Phe Thr Asn
                165                 170                 175

Val Pro Ala Glu Lys Ser Ala Lys Leu Ala Ala Leu Glu Ala Ser Gly
            180                 185                 190

Ala Ser Gly Tyr Val Leu Ala Ala Ser Pro Thr Val Gly Ser Phe Arg
        195                 200                 205

Arg Gly Arg Thr Leu Lys Gly Lys Arg Gln Pro Pro Ile Leu Lys Glu
    210                 215                 220

Gly Asp Leu Ile Lys Glu Gly Gln Thr Ile Gly Tyr Leu Asp Gln Phe
225                 230                 235                 240

Gly Thr Glu Leu Pro Val Lys Ser Asp Val Ala Gly Glu Val Leu Lys
                245                 250                 255

Ile Leu Tyr Asn Asp Gly Glu Ala Val Gly Tyr Gly Asp Pro Leu Ile
            260                 265                 270

Ala Val Leu Pro Ser Phe His Gly Ile Lys
        275                 280

<210> SEQ ID NO 90
<211> LENGTH: 272
<212> TYPE: PRT
<213> ORGANISM: Coffea canephora

<400> SEQUENCE: 90

Met Ala Ala Cys Gly Phe Gly Ala Ser Gly Leu Glu Ile Ser Ser Leu
1               5                   10                  15
```

-continued

```
Asn Leu Gly Ser Ala Arg Pro Lys Phe Ser Ala Leu Gln Pro Leu Asn
             20                  25                  30

Gly Phe Pro Val Gly Ile Leu Lys Phe Asn Gln Phe Asp Gly Leu Glu
         35                  40                  45

Ile Val Ser Ala Arg Ser Arg Arg Ala Val Ala Gly Cys Lys Phe Ser
     50                  55                  60

Ala Ser Glu Ala Ile Leu Thr Ile Thr Ala Lys Thr Asp Asp Ser Pro
 65                  70                  75                  80

Glu Gly Ile Arg Ser Ser Asn Gly Ala Ser Lys Leu Ile Leu Asn Ser
                 85                  90                  95

Phe Glu Val Glu Ser Leu Ile Lys Glu Val Cys Asp Thr Thr Ser Ile
            100                 105                 110

Ala Glu Leu Glu Leu Lys Leu Gly Gly Phe Arg Leu Tyr Val Met Arg
        115                 120                 125

Asn Leu Ala Val Pro Thr Pro Ala Ser Ala Pro Ile Ser Val Asn Thr
    130                 135                 140

Ala Ile Asp Val Pro Asn Glu Asn Gly Ser Ser Ser Thr Ser Leu
145                 150                 155                 160

Ala Ile Ser Lys Ser Glu Pro Ser Pro Ser Asp Ile Gln Thr Ser Leu
                165                 170                 175

Val Lys Ala Ala Asp Glu Gly Leu Val Met Leu Gln Ser Pro Arg Val
            180                 185                 190

Gly Phe Phe Arg Arg Ser Arg Thr Ile Lys Gly Lys Arg Ala Pro Pro
        195                 200                 205

Ser Cys Lys Lys Gln Gln Val Lys Glu Gly Gln Val Leu Cys Phe
    210                 215                 220

Ile Glu Gln Leu Gly Gly Glu Ile Pro Ile Glu Ser Asp Val Ser Gly
225                 230                 235                 240

Glu Val Val Lys Ile Leu Arg Glu Asp Gly Glu Pro Val Gly Tyr Gly
                245                 250                 255

Asp Ala Leu Ile Ala Ile Leu Pro Ser Phe Pro Gly Ile Lys Asn Leu
            260                 265                 270

<210> SEQ ID NO 91
<211> LENGTH: 290
<212> TYPE: PRT
<213> ORGANISM: Phoenix dactylifera

<400> SEQUENCE: 91

Met Ala Thr Cys Gly Leu Gly Ser Thr Ser Asn Val Lys Leu Leu Ser
 1               5                  10                  15

Phe Tyr Pro Asp Phe Lys Lys Leu Arg Ser Thr Ala Leu Leu Thr Pro
             20                  25                  30

His Asn Leu Lys Cys Gly Gly Leu Glu Thr Leu Asn Gly Ser Lys Gly
         35                  40                  45

Thr Gln Ile Trp Lys Glu Pro Val His Ala Ala Gly Phe Asp Lys Gln
     50                  55                  60

Ala Gln Arg Phe Ser Asn Ser Leu Val Ala Arg Cys Cys Ile Ser Pro
 65                  70                  75                  80

Gly Thr Glu Asn Asp Ser Lys Val Ile Glu Leu Glu Glu Asn Lys Ser
                 85                  90                  95

Asn Gly Asp Gln Ile Ile Pro Val Ser Leu Glu Val Glu Pro Leu Leu
            100                 105                 110

Thr Ala Val Cys Asp Thr Thr Ser Ile Ala Glu Phe Lys Leu Asp Phe
        115                 120                 125
```

```
Ala Gly Phe Arg Leu Tyr Val Lys Arg Asp Leu Val Glu Lys Asn Val
            130                 135                 140

Pro Pro Pro Ile Pro Thr Leu Pro Pro Thr Gln Thr Asn Thr Thr Asn
145                 150                 155                 160

Gln Thr Thr Asp Ser Asn Gly Ser Ala Ala Thr Ala Ser Leu Ala Ile
                165                 170                 175

Ser Lys Pro Lys Pro Ser Thr Gly Gly Ile Gln Arg Thr Ala Ser Asp
            180                 185                 190

Glu Gly Leu Met Met Leu Pro Ser Pro Lys Val Gly Phe Phe Arg Arg
            195                 200                 205

Ser Arg Thr Ile Lys Gly Lys Gln Ala Pro Pro Ser Cys Lys Glu Gly
210                 215                 220

Gln Asp Val Arg Glu Asp Gln Val Leu Cys Tyr Ile Glu Gln Leu Gly
225                 230                 235                 240

Gly Glu Val Pro Val Glu Ser Asp Val Ser Gly Val Ile Lys Ile
                245                 250                 255

Leu Arg Glu Asp Gly Glu Pro Val Gly Tyr Gly Asp Ala Ile Ile Ala
            260                 265                 270

Ile Leu Pro Ser Phe Pro Gly Ile Lys Lys Leu Gln Gln Ala Gly Ser
            275                 280                 285

Phe Pro
    290

<210> SEQ ID NO 92
<211> LENGTH: 268
<212> TYPE: PRT
<213> ORGANISM: Phoenix dactylifera

<400> SEQUENCE: 92

Met Ala Thr Cys Gly Leu Gly Ser Thr Ser Asn Val Lys Leu Leu Ser
1               5                   10                  15

Phe Tyr Pro Asp Phe Lys Lys Leu Arg Ser Thr Ala Leu Leu Thr Pro
            20                  25                  30

His Asn Leu Lys Cys Gly Gly Leu Glu Thr Leu Asn Gly Ser Lys Gly
        35                  40                  45

Thr Gln Ile Trp Lys Glu Pro Val His Ala Ala Gly Phe Asp Lys Gln
    50                  55                  60

Ala Gln Arg Phe Ser Asn Ser Leu Val Ala Arg Cys Cys Ile Ser Pro
65                  70                  75                  80

Gly Thr Glu Asn Asp Ser Lys Val Ile Glu Leu Glu Glu Asn Lys Ser
                85                  90                  95

Asn Gly Asp Gln Ile Ile Pro Val Ser Leu Glu Val Glu Pro Leu Leu
            100                 105                 110

Thr Ala Val Cys Asp Thr Thr Ser Ile Ala Glu Phe Lys Leu Asp Phe
        115                 120                 125

Ala Gly Phe Arg Leu Tyr Val Lys Arg Asp Leu Val Glu Lys Asn Val
    130                 135                 140

Pro Pro Pro Ile Pro Thr Leu Pro Pro Thr Gln Thr Asn Thr Thr Asn
145                 150                 155                 160

Gln Thr Thr Asp Ser Asn Gly Ser Ala Ala Thr Ala Ser Leu Ala Ile
                165                 170                 175

Ser Lys Pro Lys Pro Ser Thr Gly Gly Ile Gln Arg Thr Ala Ser Asp
            180                 185                 190

Glu Gly Leu Met Met Leu Pro Ser Pro Lys Val Gly Phe Phe Arg Arg
```

```
                195                 200                 205
Ser Arg Thr Ile Lys Gly Lys Gln Ala Pro Ser Cys Lys Glu Gly
    210                 215                 220

Gln Asp Val Arg Glu Asp Gln Val Leu Cys Tyr Ile Glu Gln Leu Gly
225                 230                 235                 240

Gly Glu Val Pro Val Glu Ser Asp Val Ser Gly Glu Val Ile Lys Ile
                245                 250                 255

Leu Arg Glu Asp Gly Gly Lys Asp Ala Arg Asn Gln
    260                 265

<210> SEQ ID NO 93
<211> LENGTH: 284
<212> TYPE: PRT
<213> ORGANISM: Phoenix dactylifera

<400> SEQUENCE: 93

Met Glu Ala Ala Ala Val Leu Arg Ser Phe Arg Gly Gly Val Arg Thr
1               5                   10                  15

Lys Gln Pro Ser Glu Ser Phe Leu Glu Lys Pro Ala Val Ala His Val
                20                  25                  30

Ser Asn Val Ser Asn Val Ala Leu Lys Thr Pro Phe Ser Gly Gly Phe
            35                  40                  45

Met Val Ala Gln Gly Trp Asn Arg Thr Phe Leu Pro Tyr Leu Lys Ala
    50                  55                  60

Ser Lys Thr Asn Ser Val Leu Thr Ser Glu Asp Arg Ser Ser Gln Glu
65              70                  75                  80

Pro Leu Glu Lys Ile Ser Val Gln Asn Ser Thr Phe Pro Ile Gly Phe
                85                  90                  95

Glu Ala Leu Ile Leu Glu Val Cys Asp Glu Thr Asn Ile Ala Glu Phe
            100                 105                 110

Lys Ile Lys Ile Gly Asp Phe Glu Met His Leu Lys Arg Asp Ile Glu
        115                 120                 125

Ser Pro Arg Ala Pro Ser Pro Gly Thr His Ile Val Ser Pro Thr Thr
    130                 135                 140

Ala Pro Pro Ile Pro Ser Gln Pro Met Asn Glu Ser Gly Ala Ala Ala
145                 150                 155                 160

Gln Pro Val Val Ser Gln Lys Ser Pro Thr Ala Ala Thr Ser Pro Phe
                165                 170                 175

Ala Asn Ile Ser Ser Ala Lys Ala Ser Lys Leu Val Ala Leu Glu Ala
            180                 185                 190

Ser Ala Ser Asn Ala Tyr Val Leu Val Ser Ser Pro Thr Val Gly Thr
        195                 200                 205

Phe Gln Arg Gly Arg Thr Leu Lys Gly Lys Gln Pro Pro Ser Cys
    210                 215                 220

Lys Glu Gly Asp Val Ile Lys Glu Gly Gln Ile Ile Gly Phe Leu Asp
225                 230                 235                 240

Gln Phe Gly Asn Glu Leu Pro Val Lys Ser Asp Val Ala Gly Glu Val
                245                 250                 255

Val Lys Val Leu Cys Gln Asp Gly Glu Ala Val Gly Tyr Gly Asp Pro
            260                 265                 270

Leu Val Ala Val Leu Pro Ser Phe His Gly Ile Glu
        275                 280

<210> SEQ ID NO 94
<211> LENGTH: 296
```

```
<212> TYPE: PRT
<213> ORGANISM: Phoenix dactylifera

<400> SEQUENCE: 94

Met Glu Ser Ala Val Val Leu Arg Ser Phe Gln Gly Ser Leu Gln Pro
1               5                   10                  15

Thr Pro Tyr Ala His Ser Phe Leu Arg Lys Pro Ala Ala Val His Ile
            20                  25                  30

Cys Arg Ala Ala Ser Lys Lys Ser Ser Phe Trp Arg Leu His Val Glu
        35                  40                  45

Gly Trp Arg Asn Phe Ser Thr Met Ala Lys Lys Arg Pro Ser Leu Leu
    50                  55                  60

Ser Val Lys Ala Ser Glu Thr Thr Ser Ala Met Thr Ala Asp Ala Met
65                  70                  75                  80

Ser Leu Asp Ala Ala Asp Glu Ser Leu Gln Gly Ala Ile Gln Lys Ile
                85                  90                  95

Asn Ala Gln Asn Ser Thr Phe Pro Asn Gly Phe Glu Thr Phe Val Leu
            100                 105                 110

Glu Val Cys Asp Glu Thr Asn Val Ala Glu Leu Lys Leu Lys Val Gly
        115                 120                 125

Asp Phe Glu Met His Leu Lys Arg Gly Ile Glu Thr Pro Lys Val Pro
    130                 135                 140

Thr Ser Ile Ala Pro Pro Ile Glu Ser Pro Thr Thr Ala Pro Pro Ile
145                 150                 155                 160

Pro Ser Lys Pro Met Val Glu Ser Ala Pro Ala Pro Pro Pro Ala Val
                165                 170                 175

Ser Gln Lys Ser Asp Pro Thr Ala Ile Ser Pro Phe Thr Asn Val Ser
            180                 185                 190

Thr Ala Ala Lys Ser Lys Leu Ala Leu Glu Ala Ser Gly Ser Asn
        195                 200                 205

Ala Tyr Val Leu Val Ser Ser Pro Thr Val Gly Ser Phe Arg Ser Gly
    210                 215                 220

Arg Thr Leu Lys Gly Lys Lys Gln Pro Pro Ser Cys Lys Glu Gly Asp
225                 230                 235                 240

Ile Ile Lys Asp Gly Gln Ile Ile Gly Phe Leu Asp Gln Phe Gly Asn
                245                 250                 255

Glu Leu Pro Val Arg Ser Asp Val Glu Gly Glu Val Lys Val Leu
            260                 265                 270

Leu Lys Asp Gly Glu Val Val Gly Tyr Gly Asp Pro Leu Val Ala Val
        275                 280                 285

Leu Pro Ser Phe His Gly Ile Lys
    290                 295

<210> SEQ ID NO 95
<211> LENGTH: 285
<212> TYPE: PRT
<213> ORGANISM: Phoenix dactylifera

<400> SEQUENCE: 95

Met Ala Thr Cys Ser Gln Gly Ser Thr Ser Asn Ile Thr Leu Phe Asn
1               5                   10                  15

Phe His Pro Glu Phe Gln Lys Leu Arg Cys Thr Ala Leu Phe Thr Pro
            20                  25                  30

Arg Arg Thr Lys Ser Gly Arg Leu Glu Ala Leu Asn Gly Ser Lys Gly
        35                  40                  45
```

```
Thr Gln Ile Trp Gln Glu Pro Val His Ala Ala Gly Phe Asp Lys Gln
 50                  55                  60

Ala Gln Arg Leu Thr Asn Ser Leu Ala Ala Arg Cys Cys Leu Ser Ser
 65                  70                  75                  80

Gly Ile Ala Glu Asn Asp Ser Asp Ala Ile Met Leu Glu Glu Asn Lys
                 85                  90                  95

Ser Lys Val Asp Gln Ile Ile Pro Val Ser Leu Glu Val Glu Pro Leu
            100                 105                 110

Leu Thr Ala Ile Cys Asp Thr Ser Ile Ser Glu Phe Lys Leu Asp
            115                 120                 125

Leu Ala Gly Phe His Leu Tyr Val Lys Arg Asp Leu Val Glu Asn
130                 135                 140

Val Pro Pro Val Pro Ile Leu Pro Pro Ala Gln Thr Asn Thr Thr
145                 150                 155                 160

Asn Gln Thr Ala Asp Ser Asn Gly Ser Ala Ala Thr Ala Ser Leu Ala
                165                 170                 175

Ile Ser Lys Pro Lys Pro Ser Ala Gly Gly Ile Gln Arg Thr Ala Ser
            180                 185                 190

Asp Glu Gly Leu Val Met Leu Pro Ser Pro Asn Val Gly Phe Phe Arg
            195                 200                 205

Thr Ser Arg Thr Ile Lys Gly Lys Arg Ala Pro Pro Leu Cys Lys Glu
            210                 215                 220

Lys Gln Glu Val Lys Glu Gly Gln Ile Leu Cys Cys Ile Glu Gln Leu
225                 230                 235                 240

Gly Gly Glu Ile Pro Val Glu Ser Asp Val Ser Gly Glu Ile Val Lys
                245                 250                 255

Ile Leu Arg Lys Asp Gly Glu Pro Val Gly Tyr Gly Asp Ala Leu Ile
            260                 265                 270

Ala Ile Leu Pro Ser Phe Pro Gly Ile Lys Lys Leu Gln
            275                 280                 285

<210> SEQ ID NO 96
<211> LENGTH: 277
<212> TYPE: PRT
<213> ORGANISM: Arabis alpina

<400> SEQUENCE: 96

Met Ala Ser Ser Ala Thr Leu Gly Ser Leu His Gln Thr Leu Gly Ser
 1                5                  10                  15

Val Ser Lys Val His Ser Ile Ser Gly Asn Trp Ser Ala Ser Gly Asn
            20                  25                  30

Ser Cys Leu Pro Arg Trp Arg Leu Cys Asn Lys Asn Arg Asn Ser Met
            35                  40                  45

Phe Val Leu Ser Thr Lys Ala Ser Lys Ser Ser Thr Thr Thr Lys Ser
 50                  55                  60

Asp Asp Ser Ser Asp Thr Ser Val Ser Asn Gly Lys Asn Ala Val Arg
 65                  70                  75                  80

Arg Ile Thr Phe Pro Lys Glu Val Glu Ala Leu Val His Glu Met Cys
                 85                  90                  95

Asp Glu Thr Glu Val Ala Val Leu Gln Leu Lys Val Gly Asp Phe Glu
            100                 105                 110

Met Asn Leu Lys Arg Lys Ile Gly Gln Ala Ala Asn His Ile Pro Val
            115                 120                 125

Asp Asp Ile Ser Pro Thr Ile Ala Pro Pro Ile Pro Ser Glu Pro Met
130                 135                 140
```

Asn Lys Ser Val Ser Ala Ala Pro Thr Pro Ser Gln Thr Lys Ala Ser
145                 150                 155                 160

Ser Glu Arg Val Ser Pro Phe Ile Asn Thr Ser Tyr Arg Lys Ser Ser
                165                 170                 175

Thr Leu Ala Ala Leu Glu Ala Ser Gly Ile Asn Asn Tyr Val Leu Val
            180                 185                 190

Thr Ser Pro Ser Val Gly Lys Phe Glu Arg Ser Arg Thr Val Lys Gly
        195                 200                 205

Lys Lys Gln Pro Pro Ser Cys Lys Glu Gly Asp Ala Ile Lys Glu Gly
    210                 215                 220

Gln Val Ile Gly Tyr Leu His Gln Leu Gly Thr Glu Leu Pro Val Thr
225                 230                 235                 240

Ser Asp Val Ala Gly Glu Val Leu Lys Leu Leu Ser Asn Asp Gly Asp
                245                 250                 255

Ser Val Gly Tyr Gly Glu Pro Leu Val Ala Val Leu Pro Ser Phe His
            260                 265                 270

Asp Ile Asn Ile Gln
        275

<210> SEQ ID NO 97
<211> LENGTH: 263
<212> TYPE: PRT
<213> ORGANISM: Arabis alpina

<400> SEQUENCE: 97

Met Ala Ser Cys Ser Leu Gly Val Pro Lys Ile Lys Ile Ser Ala Val
1               5                   10                  15

Asp Leu Ser Ile Val Arg Ser Val Ser Leu Gln Ile Pro Cys Ser Gln
            20                  25                  30

Arg Ser Leu Val Lys Gln Arg Pro Val Lys Tyr Leu Ser Leu Arg Thr
        35                  40                  45

Ser Leu Gly Ser Val Arg Ala Val Gln Val Ser Thr Val Pro Ala Ala
    50                  55                  60

Glu Ala Ser Ala Thr Val Glu Ile Glu Asp Ser Glu Glu Thr Lys Ser
65                  70                  75                  80

Tyr Pro Leu Asn Ala Gln Leu Val Pro Lys Pro Ser Glu Val Glu Ala
                85                  90                  95

Leu Val Thr Glu Ile Cys Asp Ser Ser Ile Ala Glu Phe Glu Leu
            100                 105                 110

Lys Leu Gly Gly Phe Arg Leu Tyr Val Ala Arg Asp Leu Ala Asp Lys
        115                 120                 125

Ser Ser Pro Gln Pro Gln Pro Ile Ser Ala Ala Val Thr Val Asn Ala
    130                 135                 140

Thr Thr Glu Ser Ser Asp Ser Asn Gly Ser Ala Ser Ser Thr Ser Leu
145                 150                 155                 160

Ala Ile Ile Lys Pro Ala Ser Ser Ala Ala Asp Gln Gly Leu Met Ile
                165                 170                 175

Leu Gln Ser Pro Lys Val Gly Phe Phe Arg Arg Ser Lys Thr Ile Lys
            180                 185                 190

Gly Lys Arg Thr Pro Ser Ser Cys Lys Glu Lys Asp Gln Val Lys Glu
        195                 200                 205

Gly Gln Val Leu Cys Tyr Ile Glu Gln Leu Gly Gly Gln Phe Pro Ile
    210                 215                 220

Glu Ser Asp Val Thr Gly Glu Val Val Lys Ile Leu Arg Glu Asp Gly

-continued

```
                225                 230                 235                 240
Glu Pro Val Gly Tyr Asn Asp Ala Leu Ile Ser Ile Leu Pro Ser Phe
                    245                 250                 255
Pro Gly Ile Lys Lys Leu Gln
            260
```

<210> SEQ ID NO 98
<211> LENGTH: 254
<212> TYPE: PRT
<213> ORGANISM: Brassica napus

<400> SEQUENCE: 98

```
Met Ala Ser Cys Ser Leu Gly Val Pro Lys Ile Lys Ile Ser Ala Val
1               5                   10                  15

Asp Leu Ser Arg Val Arg Ser Gly Ser Leu Gln Ile Pro Cys Asn Gln
                20                  25                  30

Arg Val Leu Ile Gly Gln Arg Pro Val Lys Tyr Leu Ser Leu Arg Ala
            35                  40                  45

Thr Leu Gly Ser Val Lys Ala Pro Gln Ala Ser Thr Val Thr Ala Ala
        50                  55                  60

Glu Ser Ala Ala Thr Val Glu Val Glu Asp Ala Glu Met Thr Lys Pro
65                  70                  75                  80

Ser Pro Leu Asn Ala Gln Leu Val Pro Lys Pro Ser Glu Val Glu Ala
                85                  90                  95

Leu Val Thr Glu Ile Cys Asp Ser Ser Ile Ala Glu Phe Glu Leu
                100                 105                 110

Lys Leu Gly Gly Phe Arg Leu Tyr Val Ala Thr Asn Leu Ala Asp Asn
            115                 120                 125

Asn Ser Ser Pro Pro Gln Pro Gln Pro Ile Pro Ala Ala Val Ala Ala
        130                 135                 140

Ser Ala Thr Thr Glu Gly Val Asp Ser Asn Gly Ser Ala Ser Ser Thr
145                 150                 155                 160

Ser Leu Ala Ile Thr Lys Pro Thr Ser Ser Ala Ala Asp Gln Gly Leu
                165                 170                 175

Val Ile Leu Gln Ser Pro Lys Val Gly Phe Phe Arg Arg Ser Lys Thr
            180                 185                 190

Ile Lys Gly Lys Arg Thr Pro Ser Ser Cys Lys Glu Lys Asp Gln Val
        195                 200                 205

Lys Glu Gly Gln Val Leu Cys Tyr Ile Glu Gln Leu Gly Gly Gln Phe
    210                 215                 220

Pro Ile Glu Ser Asp Val Thr Gly Glu Val Val Lys Ile Leu Arg Glu
225                 230                 235                 240

Asp Gly Gly Lys Ser Phe Phe Leu Leu Phe Phe Asn Leu Ser
                245                 250
```

<210> SEQ ID NO 99
<211> LENGTH: 270
<212> TYPE: PRT
<213> ORGANISM: Brassica napus

<400> SEQUENCE: 99

```
Met Glu Ser Ser Ala Ala Leu Gly Ser Leu Arg Gln Ser Leu Gly Ser
1               5                   10                  15

Ala Val Asn Val His Ser Leu Ser Gly Asn Trp Ser Pro Ser Gly Asn
                20                  25                  30

Ser Cys Ala Pro Arg Trp Ser Leu Phe Asn Arg Asn Met Leu Val Leu
```

```
                35                  40                  45
Arg Ala Asp Ser Ser Lys Ser Ser Thr Thr Thr Thr Lys Thr Asp Glu
 50                  55                  60

Ser Ser Asp Ala Ser Asn Gly Thr Lys Thr Lys Thr Val Arg Arg Thr
 65                  70                  75                  80

Thr Phe Pro Lys Glu Val Glu Ala Leu Val His Glu Met Cys Asp Glu
                 85                  90                  95

Thr Glu Val Gly Asp Phe Glu Met Asn Leu Lys Arg Lys Ile Gly Leu
                100                 105                 110

Ala Glu Thr Pro Ile Pro Val Pro Asp Ile Ser Pro Ser Val Ala Pro
                115                 120                 125

Pro Ile Pro Ser Glu Pro Met Asn Lys Ser Val Ser Ala Ser Ala Asp
130                 135                 140

Ala Ser Pro Ser Lys Ala Lys Pro Ala Ser Glu Lys Val Ser Pro Phe
145                 150                 155                 160

Ile Asn Ala Ala Tyr Arg Lys Ser Ser Lys Leu Ala Ala Leu Glu Ala
                165                 170                 175

Ala Gly Ser Asn Asn Tyr Val Leu Val Thr Ser Pro Ser Val Gly Lys
                180                 185                 190

Phe Gln Arg Ser Arg Thr Val Lys Gly Lys Lys Gln Gly Pro Thr Cys
                195                 200                 205

Lys Glu Gly Asp Ala Ile Lys Glu Gly Gln Val Ile Gly Tyr Leu His
210                 215                 220

Gln Leu Gly Lys Glu Leu Pro Val Thr Ser Asp Val Ala Gly Glu Val
225                 230                 235                 240

Leu Lys Leu Leu Ser Asp Asp Gly Asp Ser Val Gly Tyr Gly Glu Pro
                245                 250                 255

Leu Val Ala Val Leu Pro Ser Phe His Asp Ile Asn Ile Gln
                260                 265                 270

<210> SEQ ID NO 100
<211> LENGTH: 254
<212> TYPE: PRT
<213> ORGANISM: Brassica napus

<400> SEQUENCE: 100

Met Ala Ser Cys Ser Leu Gly Val Pro Lys Ile Lys Ile Ser Ala Val
 1               5                  10                  15

Asp Val Ser Arg Val Arg Ser Gly Gly Leu Gln Ile Pro Tyr Ser Gln
                20                  25                  30

Arg Ser Leu Phe Val Gln Arg Gln Val Lys Tyr Leu Ser Leu Arg Thr
                35                  40                  45

Ser Val Gly Ser Leu Lys Ala Leu Gln Val Ser Thr Val Thr Ala Ala
 50                  55                  60

Glu Thr Ala Ala Ser Ala Glu Val Glu Asp Ala Glu Glu Thr Lys Ser
 65                  70                  75                  80

Ser Pro Leu Asn Ala Gln Leu Val Pro Lys Pro Ser Glu Val Glu Ala
                 85                  90                  95

Leu Val Thr Glu Ile Cys Asp Ser Ser Ser Ile Ala Glu Phe Glu Leu
                100                 105                 110

Lys Leu Gly Gly Phe Arg Leu Tyr Val Ala Arg Asn Leu Ala Asp Asn
                115                 120                 125

Asn Ile Ser Pro Pro Gln Pro Gln Pro Ile Pro Ala Ala Phe Ser Ala
                130                 135                 140
```

```
Ala Asn Glu Ser Ala Gly Ser Asn Gly Ser Ala Ser Ser Thr Ser Leu
145                 150                 155                 160

Ala Ile Thr Lys Pro Ala Ser Ser Ala Ala Asp Gln Gly Leu Ile Ile
                165                 170                 175

Leu Gln Ser Pro Lys Val Gly Phe Phe Arg Arg Ser Lys Thr Ile Lys
            180                 185                 190

Gly Lys Arg Thr Pro Ser Ser Cys Lys Glu Lys Asp Gln Val Lys Glu
        195                 200                 205

Gly Gln Val Leu Cys Tyr Ile Glu Gln Leu Gly Gly Gln Phe Pro Ile
    210                 215                 220

Glu Ser Asp Val Thr Gly Glu Val Val Lys Ile Leu Arg Glu Asp Gly
225                 230                 235                 240

Gly Lys Ser Phe Phe Phe Asn Leu Phe Met Phe Phe Ser
                245                 250

<210> SEQ ID NO 101
<211> LENGTH: 249
<212> TYPE: PRT
<213> ORGANISM: Brassica napus

<400> SEQUENCE: 101

Met Ala Ser Cys Ser Leu Gly Val Pro Lys Ile Lys Ile Ser Ala Val
1               5                   10                  15

Asp Val Ser Arg Val Arg Ser Gly Arg Leu Gln Ile Pro Tyr Ser Gln
                20                  25                  30

Arg Ser Leu Phe Ala Gln Arg Gln Val Lys Tyr Leu Ser Leu Arg Thr
            35                  40                  45

Ser Val Gly Ser Leu Lys Ala Leu Gln Val Ser Thr Val Thr Ala Val
        50                  55                  60

Glu Thr Ser Ala Thr Val Glu Val Glu Asp Ala Glu Lys Thr Lys Ser
65                  70                  75                  80

Ser Pro Leu Asn Ala Gln Leu Val Pro Lys Pro Ser Glu Val Glu Ala
                85                  90                  95

Leu Val Thr Glu Ile Cys Asp Ser Ser Ile Ala Glu Phe Glu Leu
                100                 105                 110

Lys Leu Gly Gly Phe Arg Leu Tyr Val Ala Arg Asn Leu Ala Asp Asn
            115                 120                 125

Asn Ile Ser Pro Pro Gln Pro Gln Pro Thr Pro Ala Ala Leu Ser Ala
        130                 135                 140

Asn Ala Val Thr Glu Ser Ala Asp Ser Asn Gly Ser Ala Ser Ser Thr
145                 150                 155                 160

Ser Leu Ala Ile Thr Lys Pro Ala Ser Ser Ala Ala Asp Gln Gly Leu
                165                 170                 175

Ile Ile Leu Gln Ser Pro Lys Val Gly Phe Phe Arg Arg Ser Lys Thr
            180                 185                 190

Ile Lys Gly Lys Arg Thr Pro Ser Ser Cys Lys Glu Lys Asp Gln Val
        195                 200                 205

Lys Glu Gly Gln Val Leu Cys Tyr Ile Glu Gln Leu Gly Gly Gln Phe
    210                 215                 220

Pro Ile Glu Ser Asp Val Thr Gly Glu Val Val Lys Ile Leu Arg Glu
225                 230                 235                 240

Asp Gly Gly Lys Ser Tyr Leu Leu Leu
                245

<210> SEQ ID NO 102
```

```
<211> LENGTH: 253
<212> TYPE: PRT
<213> ORGANISM: Brassica napus

<400> SEQUENCE: 102

Met Ala Ser Cys Ser Leu Ala Val Pro Lys Ile Lys Ile Ser Ala Ala
1               5                   10                  15

Val Asp Leu Ser Leu Val Arg Ser Gly Arg Phe Gln Ile Pro Cys Asn
            20                  25                  30

Gln Arg Val Leu Leu Ile Gly Gln Arg Pro Val Lys Tyr Leu Ser Leu
        35                  40                  45

Arg Ala Thr Leu Gly Ser Val Gln Ala Ser Thr Val Thr Ala Ala Glu
    50                  55                  60

Ser Ala Ala Thr Val Glu Val Glu Asp Thr Glu Thr Thr Lys Pro Ser
65                  70                  75                  80

Pro Leu Asn Ala Gln Leu Val Pro Lys Pro Ser Glu Val Glu Ala Leu
                85                  90                  95

Val Thr Glu Ile Cys Asp Ser Ser Ile Ala Glu Phe Glu Leu Lys
            100                 105                 110

Leu Gly Gly Phe Arg Leu Tyr Val Ala Arg Asn Leu Ala Asp Asn Asn
        115                 120                 125

Ser Ser Pro Pro Gln Pro Gln Pro Ile Pro Ala Ala Val Ala Ala Ser
    130                 135                 140

Ala Thr Thr Glu Ser Val Asp Ser Asn Gly Ser Ala Ser Ser Thr Ser
145                 150                 155                 160

Leu Ala Ile Thr Lys Pro Thr Ser Ser Ala Ala Asp Gln Gly Leu Val
                165                 170                 175

Ile Leu Gln Ser Pro Lys Val Gly Phe Phe Arg Arg Ser Lys Thr Ile
            180                 185                 190

Lys Gly Lys Arg Thr Pro Ser Ser Cys Lys Glu Lys Asp Gln Val Lys
        195                 200                 205

Glu Gly Gln Val Leu Cys Tyr Ile Glu Gln Leu Gly Gly Gln Phe Pro
    210                 215                 220

Ile Glu Ser Asp Val Thr Gly Glu Val Val Lys Ile Leu Arg Glu Asp
225                 230                 235                 240

Gly Gly Lys Ser Phe Phe Leu Leu Phe Phe Asn Leu Ser
                245                 250

<210> SEQ ID NO 103
<211> LENGTH: 258
<212> TYPE: PRT
<213> ORGANISM: Brassica napus

<400> SEQUENCE: 103

Met Glu Ser Leu Gly Ser Leu His Gln Ser Leu Gly Ser Ala Val Asn
1               5                   10                  15

Val His Ser Leu Ser Gly Lys Ser Cys Ala Pro Pro Arg Trp Ser Leu
            20                  25                  30

Phe Asn Arg Asn Thr Leu Val Leu Arg Ala Glu Ser Ser Lys Ser Ser
        35                  40                  45

Thr Thr Thr Lys Thr Asp Glu Ser Ser Asp Ala Ser Asn Gly Thr Lys
    50                  55                  60

Thr Val Arg Arg Thr Thr Phe Pro Lys Glu Val Glu Ala Leu Val His
65                  70                  75                  80

Glu Met Cys Asp Glu Thr Glu Val Gly Asp Phe Glu Met Asn Leu Lys
                85                  90                  95
```

```
Arg Lys Ile Gly Leu Ala Glu Thr Pro Ile Pro Val Pro Asp Ile Ser
            100                 105                 110

Pro Ser Val Ala Pro Ile Pro Ser Glu Pro Met Asn Lys Ser Val
        115                 120                 125

Ser Ser Ser Ala Ala Ala Thr Ser Pro Ser Lys Ala Lys Pro Ala
    130                 135                 140

Val Ser Pro Phe Ile Asn Ala Ala Tyr Arg Lys Ser Ser Lys Leu Ala
145                 150                 155                 160

Ala Leu Asp Ala Ser Gly Ser Asn Asn Tyr Val Leu Val Thr Ser Pro
                165                 170                 175

Ser Val Gly Lys Phe Gln Arg Ser Arg Thr Val Lys Gly Lys Lys Gln
                180                 185                 190

Gly Pro Thr Cys Lys Glu Gly Asp Ala Ile Lys Glu Gly Gln Val Ile
                195                 200                 205

Gly Tyr Leu His Gln Leu Gly Lys Glu Leu Pro Val Thr Ser Asp Val
            210                 215                 220

Ala Gly Glu Val Leu Lys Leu Leu Ser Asp Asp Gly Asp Ser Val Gly
225                 230                 235                 240

Tyr Gly Glu Pro Leu Val Ala Val Leu Pro Ser Phe His Asp Ile Asn
                245                 250                 255

Ile Gln

<210> SEQ ID NO 104
<211> LENGTH: 237
<212> TYPE: PRT
<213> ORGANISM: Auxenochlorella protothecoides

<400> SEQUENCE: 104

Met Ala Phe Arg Ala Ser Ala Met Arg Ala Ala Arg Pro Gln Gly Leu
1               5                   10                  15

Arg Leu His Ala Thr Arg Met Ala Glu Ile Ser Pro Pro Ser Ser Ser
            20                  25                  30

Gly Lys Gly Gly Ala Lys Pro Lys Ser Lys Lys Glu Glu Glu Ser Asp
        35                  40                  45

Ser Glu Ser Glu Asp Glu Phe Phe Asp Glu Asp Gly Glu Gly Leu Asp
    50                  55                  60

Pro Gln Gln Val Glu Ser Leu Leu Ala Thr Leu Cys Glu Gly Thr Asp
65                  70                  75                  80

Leu Ala His Leu Glu Leu Lys Leu Pro Gly Phe Gln Leu Arg Val Arg
                85                  90                  95

Arg Ser Leu Ser Lys Ala Ala Ser Pro Ala Ala Ala Ala Ala Ala Pro
                100                 105                 110

Val Ala Ala Pro Ala Pro Val Pro Ala Pro Ala Pro Ala Pro Ala Thr
            115                 120                 125

Pro Pro Pro Val Ala Ser Ala Asp Glu Ala Asp Glu Ser Arg Leu Ala
        130                 135                 140

Val Val Ala Thr Lys Val Gly Val Phe Arg Arg Gly Arg Tyr Val Lys
145                 150                 155                 160

Gly Lys Arg Val Gly Lys Gly Pro Leu Ala Ala Ala Gly Asp Ser Val
                165                 170                 175

Lys Lys Gly Gln Val Leu Ala Phe Val Glu Gln Leu Gly Thr His Trp
            180                 185                 190

Pro Val Glu Ala Pro Gln Ser Gly Glu Leu Glu Gly Phe Leu Leu Glu
                195                 200                 205
```

Asp Gly Asp Pro Val Glu Tyr Asn Gln Thr Val Leu Glu Leu Thr Pro
        210                 215                 220

Phe Phe Gly Gly His Ile Ile Gly Asp Lys Lys Tyr Arg
225                 230                 235

<210> SEQ ID NO 105
<211> LENGTH: 265
<212> TYPE: PRT
<213> ORGANISM: Brassica rapa

<400> SEQUENCE: 105

Met Ala Ser Cys Ser Leu Gly Val Pro Lys Ile Lys Ile Ser Ala Val
1               5                   10                  15

Asp Val Ser Arg Val Arg Ser Gly Arg Leu Gln Ile Pro Tyr Ser Gln
            20                  25                  30

Arg Ser Leu Phe Ala Gln Arg Gln Val Lys Tyr Leu Ser Leu Arg Thr
        35                  40                  45

Ser Val Gly Ser Leu Lys Ala Leu Gln Val Ser Thr Val Thr Ala Val
    50                  55                  60

Glu Thr Ser Ala Thr Val Glu Val Glu Asp Ala Glu Lys Thr Lys Ser
65                  70                  75                  80

Ser Pro Leu Asn Ala Gln Leu Val Pro Lys Pro Ser Glu Val Glu Ala
                85                  90                  95

Leu Val Thr Glu Ile Cys Asp Ser Ser Ile Ala Glu Phe Glu Leu
            100                 105                 110

Lys Leu Gly Gly Phe Arg Leu Tyr Val Ala Arg Asn Leu Ala Asp Asn
        115                 120                 125

Asn Ile Ser Pro Pro Gln Pro Gln Pro Thr Pro Ala Ala Leu Ser Ala
    130                 135                 140

Asn Ala Val Thr Glu Ser Ala Asp Ser Asn Gly Ser Ala Ser Ser Thr
145                 150                 155                 160

Ser Leu Ala Ile Thr Lys Pro Ala Ser Ser Ala Ala Asp Gln Gly Leu
                165                 170                 175

Ile Ile Leu Gln Ser Pro Lys Val Gly Phe Phe Arg Arg Ser Lys Thr
            180                 185                 190

Ile Lys Gly Lys Arg Thr Pro Ser Ser Cys Lys Glu Lys Asp Gln Val
        195                 200                 205

Lys Glu Gly Gln Val Leu Cys Tyr Ile Glu Gln Leu Gly Gly Gln Phe
    210                 215                 220

Pro Ile Glu Ser Asp Val Thr Gly Glu Val Lys Ile Leu Arg Glu
225                 230                 235                 240

Asp Gly Glu Pro Val Gly Tyr Asn Asp Ala Leu Ile Ser Ile Leu Pro
                245                 250                 255

Ser Phe Pro Gly Ile Lys Lys Leu Gln
            260                 265

<210> SEQ ID NO 106
<211> LENGTH: 264
<212> TYPE: PRT
<213> ORGANISM: Brassica rapa

<400> SEQUENCE: 106

Met Ala Ser Cys Ser Leu Gly Val Pro Lys Ile Lys Ile Ser Ala Ala
1               5                   10                  15

Val Asp Leu Ser Leu Val Arg Ser Gly Arg Phe Gln Ile Pro Cys Asn
            20                  25                  30

```
Gln Arg Val Leu Leu Ile Gly Gln Arg Pro Val Lys Tyr Leu Ser Leu
             35                  40                  45

Arg Ala Thr Leu Gly Ser Val Gln Ala Ser Thr Val Thr Ala Ala Glu
 50                  55                  60

Ser Ala Ala Thr Val Glu Val Glu Asp Thr Glu Thr Thr Lys Pro Ser
 65                  70                  75                  80

Pro Leu Asn Ala Gln Leu Val Pro Lys Pro Ser Glu Val Glu Ala Leu
                 85                  90                  95

Val Thr Glu Ile Cys Asp Ser Ser Ile Ala Glu Phe Glu Leu Lys
                100                 105                 110

Leu Gly Gly Phe Arg Leu Tyr Val Ala Arg Asn Leu Ala Asp Asn Asn
                115                 120                 125

Ser Ser Pro Pro Gln Pro Gln Pro Ile Pro Ala Val Ala Ala Ser
        130                 135                 140

Ala Thr Thr Glu Ser Val Asp Ser Asn Gly Ser Ala Ser Ser Thr Ser
145                 150                 155                 160

Leu Ala Ile Thr Lys Pro Thr Ser Ser Ala Ala Asp Gln Gly Leu Val
                165                 170                 175

Ile Leu Gln Ser Pro Lys Val Gly Phe Phe Arg Arg Ser Lys Thr Ile
                180                 185                 190

Lys Gly Lys Arg Thr Pro Ser Ser Cys Lys Glu Lys Asp Gln Val Lys
                195                 200                 205

Glu Gly Gln Val Leu Cys Tyr Ile Glu Gln Leu Gly Gly Gln Phe Pro
210                 215                 220

Ile Glu Ser Asp Val Thr Gly Glu Val Val Lys Ile Leu Arg Glu Asp
225                 230                 235                 240

Gly Glu Pro Val Gly Tyr Asn Asp Ala Leu Ile Ser Ile Leu Pro Ser
                245                 250                 255

Phe Pro Gly Ile Lys Lys Leu Gln
                260

<210> SEQ ID NO 107
<211> LENGTH: 277
<212> TYPE: PRT
<213> ORGANISM: Brassica rapa

<400> SEQUENCE: 107

Met Glu Ser Ser Ala Ala Leu Gly Ser Leu Arg Gln Ser Leu Gly Ser
1               5                   10                  15

Ala Val Asn Val His Ser Leu Ser Gly Asn Trp Ser Pro Ser Gly Asn
                20                  25                  30

Ser Cys Val Pro Arg Trp Ser Leu Phe Asn Arg Asn Met Leu Val Leu
            35                  40                  45

Arg Ala Asp Ser Ser Lys Ser Ser Thr Thr Thr Lys Thr Asp Glu
 50                  55                  60

Ser Ser Asp Ala Ser Asn Gly Thr Lys Thr Lys Thr Val Arg Arg Thr
 65                  70                  75                  80

Thr Phe Pro Lys Glu Val Glu Ala Leu Val His Glu Met Cys Asp Glu
                85                  90                  95

Thr Glu Val Ala Val Leu Lys Leu Lys Val Gly Asp Phe Glu Met Asn
                100                 105                 110

Leu Lys Arg Lys Ile Gly Leu Ala Glu Thr Pro Ile Pro Val Pro Asp
                115                 120                 125

Ile Ser Pro Ser Val Ala Pro Pro Ile Pro Ser Glu Pro Met Asn Lys
```

```
                130                 135                 140
Ser Val Ser Ala Ser Ala Asp Ala Ser Pro Ser Lys Ala Lys Pro Ala
145                 150                 155                 160

Ser Glu Lys Val Ser Pro Phe Ile Asn Ala Ala Tyr Arg Lys Ser Ser
                165                 170                 175

Lys Leu Ala Ala Leu Glu Ala Ala Gly Ser Asn Asn Tyr Val Leu Val
                180                 185                 190

Thr Ser Pro Ser Val Gly Lys Phe Gln Arg Ser Arg Thr Val Lys Gly
                195                 200                 205

Lys Lys Gln Gly Pro Thr Cys Lys Glu Gly Asp Ala Ile Lys Glu Gly
                210                 215                 220

Gln Val Ile Gly Tyr Leu His Gln Leu Gly Lys Glu Leu Pro Val Thr
225                 230                 235                 240

Ser Asp Val Ala Gly Glu Val Leu Lys Leu Ser Asp Asp Gly Asp
                245                 250                 255

Ser Val Gly Tyr Gly Glu Pro Leu Val Ala Val Leu Pro Ser Phe His
                260                 265                 270

Asp Ile Asn Ile Gln
        275

<210> SEQ ID NO 108
<211> LENGTH: 288
<212> TYPE: PRT
<213> ORGANISM: Pyrus x bretschneideri

<400> SEQUENCE: 108

Met Glu Ser Ser Ala Ala Leu Arg Ser Phe Asn Cys Ser Val Gly Thr
1               5                   10                  15

Val Ser His Val Gly Ser Leu Leu Asp Lys Arg Gly Met Leu Pro Val
                20                  25                  30

Tyr Asn Thr Arg Arg Pro Thr Pro Ser Arg Ser Tyr Phe Gln Gly Leu
            35                  40                  45

Met Val Ser Glu Lys Phe Ile Tyr Ser Ser Gln Lys Arg Lys Gly Val
        50                  55                  60

Leu Val Ser Cys Val Asn Thr Ser Glu Ala Ala Lys Thr Glu Asn Ser
65                  70                  75                  80

Ser Val Ser Ala Asp Ser Lys Pro Gln Cys Ser Ser Glu Lys Ala Ala
                85                  90                  95

His Pro Thr Ile Phe Pro Ser Gly Phe Glu Ala Leu Met Leu Glu Val
                100                 105                 110

Cys Asp Glu Thr Glu Val Ala Glu Leu Lys Leu Lys Val Gly Asp Phe
                115                 120                 125

Glu Met Tyr Leu Lys Arg Asn Ile Ala Val Thr Ser Ala Pro Val Pro
            130                 135                 140

Ser Ile Ser Pro Ala Thr Pro Pro Val Pro Ser Lys Pro Met Asp
145                 150                 155                 160

Ser Thr Pro Ala Pro Pro Ala Ser Pro Lys Thr Ser Glu Lys
                165                 170                 175

Thr Thr Pro Phe Thr Asn Val Ser Val Asp Lys Leu Ser Arg Leu Ala
                180                 185                 190

Ala Leu Glu Ala Ser Gly Ala Lys Gly Tyr Asp Leu Val Ser Ser Pro
                195                 200                 205

Thr Val Gly Ser Phe Arg Arg Gly Arg Thr Val Lys Gly Lys Lys Gln
                210                 215                 220
```

```
Pro Pro Ile Phe Lys Glu Gly Asp Leu Ile Lys Lys Gly Gln Val Ile
225                 230                 235                 240

Gly Tyr Val Asp Gln Phe Gly Thr Glu Leu Pro Val Lys Thr Asp Val
                245                 250                 255

Gly Gly Glu Val Leu Lys Leu Leu Phe Asn Asp Gly Glu Ala Val Gly
            260                 265                 270

Phe Gly Asp Pro Leu Ile Ala Val Leu Pro Ser Phe Ala Gly Ile Gln
        275                 280                 285

<210> SEQ ID NO 109
<211> LENGTH: 441
<212> TYPE: PRT
<213> ORGANISM: Pyrus x bretschneideri

<400> SEQUENCE: 109

Met Lys Val Leu Phe Gln Gln Pro Val Thr Phe Gly Ala Trp Asp Met
1               5                   10                  15

Gly Gly Ser Phe His Lys Arg Leu Glu Ser Phe Leu Ser Gln Glu Glu
                20                  25                  30

Ser His Trp Arg Gln His Ser Lys Leu Ser Trp Leu Arg Asp Gly Asp
            35                  40                  45

Lys Asn Thr Arg Tyr Phe His Glu Lys Ala Ser Asn His Gln Arg Lys
        50                  55                  60

Asn Cys Ile Lys Val Ile Phe Asp Gly Asn Gly Ile Leu Lys Ser Asp
65                  70                  75                  80

Ala Glu Ser Leu Glu Lys Val Val Asn Asp Tyr Phe Thr Asp Met Phe
                85                  90                  95

Ala Thr Asn Gly Asn Val Ser Phe Ser Glu Val Leu Asp Cys Ala Pro
                100                 105                 110

Arg Gln Val Asn Phe Glu Met Asn Gln Ser Leu Val Ala Asn Tyr Ser
            115                 120                 125

Asn Lys Glu Ile Arg Glu Thr Leu Phe Gln Met Asp Pro His Thr Ala
        130                 135                 140

Ser Gly Phe Met Asp Ser Ile Ile Ser Asp Gln Gln Gly Ala Ser Val
145                 150                 155                 160

Pro Gly His Leu Ile Ser Asp Asn Phe Ile Val Val Leu Lys Gly Tyr
                165                 170                 175

Leu Glu Glu Leu Asn Ala Asp Ala Leu Glu Asn Val Ile Thr Arg Ser
            180                 185                 190

Met Glu Leu Lys Thr Lys Gly Gly Glu Leu Leu Leu Thr His Gly Thr
        195                 200                 205

His Ala Leu Ser Leu Ala Val Pro Pro Ser Glu Glu Phe Ile Glu Leu
    210                 215                 220

Val Ala Ala Leu Glu Ser Leu Pro Lys His Asp Gly Trp Phe Ser Ile
225                 230                 235                 240

Asp Leu Asp Gly Ile Val Lys Tyr Arg Asp Ile Phe Thr Lys Ser Val
                245                 250                 255

Tyr Phe Leu Phe Pro Val Gln Ser Leu Leu Thr Ala Ile Cys Asp Thr
            260                 265                 270

Pro Thr Val Ala Glu Val Lys Val Lys Ile Gly Gly Phe Arg Leu Asn
        275                 280                 285

Val Val Arg Gln Pro Thr Glu Lys Phe Ser Thr Pro Pro Pro Pro Ser
    290                 295                 300

Pro Thr Pro Val Ser Ala Ser Glu Asn Thr Lys Ala Leu Asp Ser Asn
305                 310                 315                 320
```

```
Gly Ala Val Pro Thr Gln Ser Val Ala Ile Thr Arg Gln Val Ser Ser
                325                 330                 335

Ser Arg Ser Ile Gln Thr Leu Val Asp Arg Ala Thr Asp Asp Gly Leu
            340                 345                 350

Val Leu Ile Arg Ser Pro Arg Val Gly Leu Phe Arg Arg Ser Arg Thr
        355                 360                 365

Ile Lys Gly Lys Arg Ala Pro Pro Ser Cys Lys Glu Lys Gln Thr Val
    370                 375                 380

Lys Glu Gly Gln Val Ile Cys Tyr Ile Glu Gln Leu Gly Gly Glu Leu
385                 390                 395                 400

Pro Ile Glu Ser Asp Val Ala Gly Glu Val Ser Arg Ile Leu Arg Glu
                405                 410                 415

Asp Gly Asp Pro Val Gly Tyr Gly Asp Ala Leu Val Ala Val Leu Pro
            420                 425                 430

Ser Phe Pro Gly Ile Met Lys Leu Gln
        435                 440

<210> SEQ ID NO 110
<211> LENGTH: 273
<212> TYPE: PRT
<213> ORGANISM: Pyrus x bretschneideri

<400> SEQUENCE: 110

Met Ala Ser Ser Leu Gly Thr Leu Asn Ala Lys Ile Thr Asn Leu
1               5                   10                  15

Asn Phe Gly Lys Ala Arg Val Gly Val Leu Lys Ser Tyr Gly Val Arg
            20                  25                  30

Ser Trp Thr Gly Arg Lys Pro Gln Leu Tyr Ser Cys Leu Ser Ile Ser
        35                  40                  45

Arg Gln Pro Glu Lys Ala Leu His Val Arg Ser Ile Pro Ser Leu Glu
    50                  55                  60

Thr Leu Ser Ala Thr Ser Leu Glu Glu Val Pro Glu Ser Gly Asp
65                  70                  75                  80

Ser Gly Pro Thr Asn Gln Leu Ile Gln Asn Phe Asp Glu Val Gln Ser
                85                  90                  95

Leu Leu Thr Ala Ile Cys Asp Thr Pro Thr Val Ala Glu Val Lys Val
            100                 105                 110

Lys Ile Gly Gly Phe Arg Leu Asn Val Val Arg Gln Pro Thr Glu Lys
        115                 120                 125

Phe Ser Thr Pro Pro Pro Ser Pro Thr Val Ser Ala Ser Glu
    130                 135                 140

Asn Thr Lys Ala Leu Asp Ser Asn Gly Ala Val Pro Thr Gln Ser Val
145                 150                 155                 160

Ala Ile Thr Arg Gln Val Ser Ser Arg Ser Ile Gln Thr Leu Val
                165                 170                 175

Asp Arg Ala Thr Asp Asp Gly Leu Val Leu Ile Arg Ser Pro Arg Val
            180                 185                 190

Gly Leu Phe Arg Arg Ser Arg Thr Ile Lys Gly Lys Arg Ala Pro Pro
        195                 200                 205

Ser Cys Lys Glu Lys Gln Thr Val Lys Glu Gly Gln Val Ile Cys Tyr
    210                 215                 220

Ile Glu Gln Leu Gly Gly Glu Leu Pro Ile Glu Ser Asp Val Ala Gly
225                 230                 235                 240

Glu Val Ser Arg Ile Leu Arg Glu Asp Gly Asp Pro Val Gly Tyr Gly
```

-continued

```
                       245                 250                 255

Asp Ala Leu Val Ala Val Leu Pro Ser Phe Pro Gly Ile Met Lys Leu
                260                 265                 270

Gln
```

<210> SEQ ID NO 111
<211> LENGTH: 273
<212> TYPE: PRT
<213> ORGANISM: Pyrus x bretschneideri

<400> SEQUENCE: 111

```
Met Ala Ser Ser Leu Gly Thr Leu Asn Ala Lys Ile Thr Asn Leu
1               5                   10                  15

Asn Phe Ser Arg Ala Arg Val Gly Val Leu Arg Ser Tyr Gly Ile Ile
                20                  25                  30

Thr Trp Thr Gly Arg Lys Pro Gln Leu Tyr Ser Cys Leu Ser Ile Ser
            35                  40                  45

Arg Gln Ser Glu Lys Val Leu His Ala Arg Ser Val Pro Ser Leu Glu
        50                  55                  60

Ile Leu Ser Ala Lys Ser Leu Glu Glu Val Ser Glu Glu Ser Gly Asp
65                  70                  75                  80

Ser Gly Pro Thr Asn Gln Leu Ile Gln Asn Phe Asp Glu Val Gln Ser
                85                  90                  95

Leu Leu Thr Ala Ile Cys Asp Thr Thr Val Ala Glu Val Lys Leu
                100                 105                 110

Lys Ile Gly Gly Phe Gln Leu Asn Val Val Arg Lys Leu Thr Glu Lys
            115                 120                 125

Ile Ser Thr Pro Pro Pro Ser Pro Ala Pro Val Ser Ala Ser Glu
130                 135                 140

Asn Ala Lys Ala Leu Asp Leu Asn Gly Ala Val Pro Thr Gln Ser Val
145                 150                 155                 160

Ala Ile Thr Arg Gln Glu Ser Ser Arg Ser Ile Gln Thr Leu Leu
                165                 170                 175

Asp Arg Ala Ala Asp Asp Gly Leu Val Leu Ile His Ser Pro Arg Val
            180                 185                 190

Gly Leu Phe Arg Arg Ser Arg Thr Ile Lys Gly Lys Arg Ala Pro Pro
        195                 200                 205

Ser Cys Lys Glu Lys Gln Ile Val Lys Glu Gly Gln Val Ile Cys Tyr
    210                 215                 220

Ile Glu Gln Leu Gly Gly Glu Leu Pro Ile Glu Ser Asp Val Ala Gly
225                 230                 235                 240

Glu Val Ile Arg Ile Leu Arg Glu Asp Gly Asp Pro Val Gly Tyr Gly
                245                 250                 255

Asp Ala Leu Val Ala Val Leu Pro Ser Phe Pro Gly Ile Glu Lys Leu
            260                 265                 270

Pro
```

<210> SEQ ID NO 112
<211> LENGTH: 276
<212> TYPE: PRT
<213> ORGANISM: Musa acuminata subsp. malaccensis

<400> SEQUENCE: 112

```
Met Ala Leu Arg Leu Phe Pro Gly Ala Ser Lys Thr Ile Leu Gln Val
1               5                   10                  15
```

```
Asp Ser Ser Leu Asn Ser Lys Ser Leu Leu Trp Arg Val Pro Glu Glu
            20                  25                  30

Pro Gln Arg Leu Ile Ser Ser Gly Ala Phe Gln Lys Gln Phe Leu His
        35                  40                  45

Val Lys Ala Ser Gln Asn Thr Ser Ser Leu Thr Thr Asn Ala Asp Ile
 50                  55                  60

Asn Lys Lys Asn Ala Thr Ala Thr Leu Gln Lys Lys Asn Val Tyr Lys
65                  70                  75                  80

Ser Thr Phe Pro Ser Gly Phe Gln Thr Leu Val Glu Val Cys Asp
                85                  90                  95

Gln Thr Asp Val Ala Glu Leu Lys Leu Lys Val Gly Asp Phe Glu Met
            100                 105                 110

Leu Leu Lys Arg Asp Thr Gly Asn Ser Lys Ala Pro Ile Ser Val Ser
        115                 120                 125

Ala Pro Ile Glu Ser Pro Thr Thr Ala Pro Pro Ile Pro Ser Lys Pro
130                 135                 140

Met Val Glu Thr Ile Ser Ser Pro Ser Pro Val Ala Glu Gln Glu Ser
145                 150                 155                 160

Ala Ala Ala Thr Phe Gly Ser Phe Thr Asn Thr Ser Ala Ala Lys Thr
                165                 170                 175

Ser Lys Leu Ala Ala Leu Asp Ala Ser Gly Gln Asn Ala Tyr Val Leu
            180                 185                 190

Val Ser Ser Thr Val Gly Leu Phe Gln Arg Gly Arg Thr Leu Lys
        195                 200                 205

Glu Lys Arg Gln Pro Pro Ser Cys Lys Glu Gly Asp Ile Ile Lys Glu
210                 215                 220

Gly Gln Ile Ile Gly Phe Leu Asp Gln Phe Gly Asn Glu Leu Pro Val
225                 230                 235                 240

Arg Ser Asp Val Ala Gly Glu Val Leu Lys Ile Ile Tyr Glu Asp Gly
                245                 250                 255

Glu Ala Val Gly Tyr Gly Asp Pro Leu Val Ala Val Leu Pro Ser Phe
            260                 265                 270

His Gly Ile Lys
        275

<210> SEQ ID NO 113
<211> LENGTH: 278
<212> TYPE: PRT
<213> ORGANISM: Musa acuminata subsp. malaccensis

<400> SEQUENCE: 113

Met Ala Leu Pro Ser Phe Leu Gly Ala Pro Arg Thr Ile Phe His Gly
1               5                   10                  15

His Ser Ser Val Glu Lys Pro Val Pro Ile Leu Val Ser Thr Val
            20                  25                  30

Ser Lys Tyr Leu Leu Gln Arg Val Pro Glu Glu Cys Gln Arg Ser Ile
        35                  40                  45

Ser Ser Met Val Leu Pro Lys His Ser Leu His Val Lys Ala Ser Gln
 50                  55                  60

Asn Thr Ser Ala Leu Thr Thr Asn Ala Asp Thr Asp Gln Lys Asn Ser
65                  70                  75                  80

Ile Thr Ser Thr Phe Pro Asn Gly Cys Gln Thr Leu Ile Glu Glu Val
                85                  90                  95

Cys Asp Leu Thr Asp Ile Ala Glu Leu Lys Met Lys Val Gly Asp Phe
            100                 105                 110
```

```
Glu Met Phe Leu Lys Arg Asp Val Gly Ile Ser Asn Ala Pro Asn Ser
        115                 120                 125
Val Ser Ala Pro Ile Glu Ser Pro Ile Thr Ala Pro Pro Ile Pro Ser
    130                 135                 140
Lys Pro Met Val Glu Ala Val Pro Ser Ser Pro Pro Val Leu Glu Gln
145                 150                 155                 160
Lys Ser Pro Ala Thr Ala Ser Ser Pro Phe Thr Tyr Val Ser Ala Ala
                165                 170                 175
Lys Thr Ser Lys Leu Ala Ala Leu Glu Ala Ser Gly Leu Asn Ala Tyr
            180                 185                 190
Ala Leu Val Ser Ser Thr Val Gly Ser Phe Gln Ser Gly Arg Ser
        195                 200                 205
Leu Lys Gly Glu Arg Gln Pro Pro Ile Cys Lys Glu Gly Asp Ile Ile
        210                 215                 220
Lys Glu Gly Gln Ile Ile Gly Phe Leu Asp Gln Phe Gly Asn Glu Leu
225                 230                 235                 240
Pro Ile Arg Ser Asp Val Ala Gly Glu Val Ile Lys Ile Leu Cys Glu
                245                 250                 255
Asn Gly Glu Ala Val Gly Tyr Gly Asp Pro Leu Val Ala Val Leu Pro
            260                 265                 270
Ser Phe His Gly Val Lys
            275

<210> SEQ ID NO 114
<211> LENGTH: 285
<212> TYPE: PRT
<213> ORGANISM: Musa acuminata subsp. malaccensis

<400> SEQUENCE: 114

Met Glu Ile Ala Ala Phe Gly Ser His Gly Ser Val Gln Ile Leu Trp
1               5                   10                  15
Asn Ser His Ser Ser Ile Asp Lys Pro Asn Trp Ile Arg His Ser Asn
            20                  25                  30
Ser Ala Trp Lys Arg Ile Ile Phe Pro Lys Ala Trp Val Ser Gln Ala
        35                  40                  45
Gln Lys Gly Ser Leu Leu Lys Arg Leu Lys Ala Ser Glu Arg Thr Ala
    50                  55                  60
Asp Leu Thr Ser Asn Val Ala Ala Ser Glu Asn Ser Ser Gln Gly Pro
65                  70                  75                  80
Leu Glu Lys Lys Ala Val Trp Lys Ser Thr Phe Pro Asn Gly Phe Glu
                85                  90                  95
Glu Leu Val Leu Thr Val Cys Asp Glu Thr Ser Ile Ala Glu Leu Ser
            100                 105                 110
Met Lys Val Gly Asn Phe Glu Met His Leu Lys Arg Asp Ile Gly Ile
        115                 120                 125
Ser Glu Ala Leu Thr Ser Thr Ile Ser Thr Ile Val Ser Pro Thr Thr
    130                 135                 140
Ala Pro Pro Ile Pro Ser Glu Pro Met Cys Val Ser Thr Ile Ala Pro
145                 150                 155                 160
Ala Gln Gln Asp Val Pro Lys Glu Pro Val Leu Pro Glu Thr Ser Pro
                165                 170                 175
Phe Ser Asp Ile Tyr Ser Ser Lys Ala Leu Lys Leu Ala Ala Leu Gly
            180                 185                 190
Ala Ser Ser Ser Asn Ala Tyr Val Leu Ile Ser Ser Pro Ser Val Gly
```

```
            195                 200                 205
Thr Phe Arg Ile Gly Thr Thr Leu Lys Gly Lys Lys Gln Pro Pro Cys
    210                 215                 220

Cys Glu Val Gly Asp Met Ile Lys Glu Gly Gln Ala Ile Gly Phe Leu
225                 230                 235                 240

Asp Gln Phe Gly Asn Glu Leu Pro Ile Arg Ser Asn Val Ala Gly Glu
                245                 250                 255

Val Leu Lys Ile Leu Cys Lys Asp Gly Glu Ala Val Gly Tyr Gly Asp
                260                 265                 270

Ala Leu Ile Ala Val Leu Pro Phe Phe Ala Gly Ile Glu
                275                 280                 285

<210> SEQ ID NO 115
<211> LENGTH: 295
<212> TYPE: PRT
<213> ORGANISM: Nicotiana tomentosiformis

<400> SEQUENCE: 115

Met Glu Ser Ala Ala Val Leu Arg Ser Phe His His Ser Val Gly Ala
1               5                   10                  15

Thr Ser His Met Arg Ser Val Ile Glu Met Pro Gly Val Phe Pro Met
            20                  25                  30

Asn Asn Val Ala Phe Ser Lys Pro Thr Lys Leu Pro Val Lys Gly Ser
        35                  40                  45

Ser Ser Gly Ala Lys Leu Val Ser Ser Thr Asn Lys His Asn Arg Leu
    50                  55                  60

Ile Leu Tyr Cys Ala Lys Thr Ser Glu Thr Thr Val Thr Ala Lys Ser
65                  70                  75                  80

Asp Gly Ala Val Leu Thr Asp Ser His Gln Lys Val Pro Thr Glu Lys
                85                  90                  95

Ser Pro Leu Pro Thr Ala Thr Phe Pro Lys Gly Phe Glu Ala Leu Ile
            100                 105                 110

Thr Glu Val Cys Asp Asp Thr Glu Val Ala Glu Leu Lys Leu Lys Ile
        115                 120                 125

Gly Asp Phe Glu Leu His Leu Lys Arg Asn Ile Glu Ala Pro Ile Val
    130                 135                 140

Pro Ala Pro Val Val Ser Thr Pro Pro Pro Pro Pro Pro Pro Pro Ser
145                 150                 155                 160

Ala Ser Lys Pro Ser Asn Ala Ser Thr Ala Ala Pro Ala Thr Ser
                165                 170                 175

Pro Gly Lys Ser Ser Glu Lys Ile Ser Pro Phe Thr Asn Val Ala
            180                 185                 190

Ala Glu Lys Ser Ala Lys Leu Ala Ala Leu Glu Thr Thr Gly Ala Ser
        195                 200                 205

Gly Tyr Val Leu Val Ser Cys Pro Thr Val Gly Ser Phe Arg Arg Ala
    210                 215                 220

Arg Thr Leu Lys Gly Lys Lys Gln Pro Pro Ala Cys Lys Glu Gly Asp
225                 230                 235                 240

Val Ile Lys Glu Gly Gln Ile Ile Gly Phe Leu Asp Gln Phe Gly Thr
                245                 250                 255

Glu Leu Pro Val Arg Ser Asp Ala Ala Gly Glu Val Leu Lys Ile Leu
            260                 265                 270

Phe Asn Asp Gly Glu Ala Val Gly Tyr Gly Asp Pro Leu Ile Ala Val
        275                 280                 285
```

```
Leu Pro Ser Phe Arg Gly Ile
    290             295
```

<210> SEQ ID NO 116
<211> LENGTH: 274
<212> TYPE: PRT
<213> ORGANISM: Nicotiana tomentosiformis

<400> SEQUENCE: 116

```
Met Ala Ala Cys Ser Phe Gly Ala Ala Gly Phe Lys Leu Thr Asn Leu
1               5                   10                  15

Asn Leu Gly Ser Thr Lys Pro Lys Phe Leu Leu His Asn Leu Arg Thr
            20                  25                  30

Lys Lys Leu Ile Gln Asn Asp Gly Leu Leu Leu Thr Lys Lys Ser Arg
        35                  40                  45

Lys Thr Leu Phe Gly Cys Arg Cys Ser Thr Val Glu Ala Glu Ser Ala
    50                  55                  60

Ala Ala Val Val Ser Asp Asn Ser Asp Asp Ser Leu Arg Lys Ile Ile
65                  70                  75                  80

Ser Ser Glu Ala Ala Ser Pro Leu Ile Pro Asn Ser Tyr Glu Val Glu
                85                  90                  95

Ser Leu Leu Thr Glu Ile Cys Asp Thr Thr Ser Ile Ala Glu Val Glu
            100                 105                 110

Leu Lys Leu Gly Gly Phe His Leu Tyr Val Lys Arg Asp Leu Thr Gly
        115                 120                 125

Pro Ser Thr Thr Ser Leu Pro Ala Ile Ser Asn Pro Val Asn Ile His
    130                 135                 140

Ser Ser Val Glu Val Ala Asp Ser Asn Gly Ser Ala Ser Ser Ser Ser
145                 150                 155                 160

Leu Ala Ile Thr Lys Ser Ser Pro Pro Ser Asp Gly Ile Gln Thr Met
                165                 170                 175

Ile Asp Lys Ala Ala Asp Glu Gly Leu Val Ile Ile Gln Ser Pro Arg
            180                 185                 190

Val Gly Tyr Phe Arg Arg Ser Arg Thr Ile Lys Gly Lys Arg Ala Pro
        195                 200                 205

Pro Ser Cys Lys Glu Lys Gln Gln Val Lys Glu Gly Gln Val Val Cys
    210                 215                 220

Phe Ile Glu Gln Leu Gly Gly Glu Leu Pro Val Glu Ser Asp Val Ser
225                 230                 235                 240

Gly Glu Val Ile Lys Ile Leu Gln Lys Asp Gly Glu Pro Val Gly Tyr
                245                 250                 255

Gly Asp Pro Leu Ile Ser Ile Leu Pro Ser Phe Pro Gly Ile Lys Lys
            260                 265                 270

Leu Gln
```

<210> SEQ ID NO 117
<211> LENGTH: 254
<212> TYPE: PRT
<213> ORGANISM: Nicotiana tomentosiformis

<400> SEQUENCE: 117

```
Met Ala Ala Cys Ser Phe Gly Ala Ala Gly Phe Lys Leu Thr Asn Leu
1               5                   10                  15

Asn Leu Gly Ser Thr Lys Pro Lys Phe Leu Leu His Asn Leu Arg Thr
            20                  25                  30

Lys Lys Leu Ile Gln Asn Asp Gly Leu Leu Leu Thr Lys Lys Ser Arg
```

```
              35                  40                  45
Lys Thr Leu Phe Gly Cys Arg Cys Ser Thr Val Glu Ala Glu Ser Ala
 50                  55                  60

Ala Ala Val Val Ser Asp Asn Ser Asp Ser Leu Arg Lys Ile Ile
 65                  70                  75                  80

Ser Ser Glu Ala Ala Ser Pro Leu Ile Pro Asn Ser Tyr Glu Leu Gly
                 85                  90                  95

Gly Phe His Leu Tyr Val Lys Arg Asp Leu Thr Gly Pro Ser Thr Thr
                100                 105                 110

Ser Leu Pro Ala Ile Ser Asn Pro Val Asn Ile His Ser Ser Val Glu
                115                 120                 125

Val Ala Asp Ser Asn Gly Ser Ala Ser Ser Ser Leu Ala Ile Thr
130                 135                 140

Lys Ser Ser Pro Pro Ser Asp Gly Ile Gln Thr Met Ile Asp Lys Ala
145                 150                 155                 160

Ala Asp Glu Gly Leu Val Ile Ile Gln Ser Pro Arg Val Gly Tyr Phe
                165                 170                 175

Arg Arg Ser Arg Thr Ile Lys Gly Lys Arg Ala Pro Pro Ser Cys Lys
                180                 185                 190

Glu Lys Gln Gln Val Lys Glu Gly Gln Val Val Cys Phe Ile Glu Gln
                195                 200                 205

Leu Gly Gly Glu Leu Pro Val Glu Ser Asp Val Ser Gly Glu Val Ile
                210                 215                 220

Lys Ile Leu Gln Lys Asp Gly Glu Pro Val Gly Tyr Gly Asp Pro Leu
225                 230                 235                 240

Ile Ser Ile Leu Pro Ser Phe Pro Gly Ile Lys Lys Leu Gln
                245                 250

<210> SEQ ID NO 118
<211> LENGTH: 290
<212> TYPE: PRT
<213> ORGANISM: Nicotiana sylvestris

<400> SEQUENCE: 118

Met Glu Ser Ala Ala Val Leu Arg Ser Phe His His Ser Val Gly Thr
 1               5                  10                  15

Thr Ser His Met Arg Ser Val Ile Glu Met Pro Gly Val Ile Pro Met
                20                  25                  30

Asn Asn Val Ala Phe Ser Lys Pro Thr Lys Leu Pro Leu Lys Gly Ser
                35                  40                  45

Ser Asn Gly Ala Lys Leu Val Ser Ser Thr Asn Lys His Ser Arg Leu
 50                  55                  60

Ile Leu Ser Cys Ala Lys Thr Ser Glu Thr Thr Val Thr Thr Lys Ser
 65                  70                  75                  80

Gly Ala Val Leu Thr Asp Ser His Gln Lys Val Ser Thr Glu Lys Ser
                85                  90                  95

Pro Leu Pro Thr Ala Thr Phe Pro Lys Gly Phe Glu Ala Leu Ile Thr
                100                 105                 110

Glu Val Cys Asp Asp Thr Glu Val Ala Glu Leu Lys Leu Lys Ile Gly
                115                 120                 125

Asp Phe Glu Leu His Leu Lys Arg Asn Ile Glu Ala Pro Ile Val Pro
                130                 135                 140

Ala Pro Val Val Ser Thr Pro Pro Pro Ser Ala Ser Lys Pro Ser
145                 150                 155                 160
```

```
Thr Ala Ser Thr Ala Ala Ala Pro Ala Thr Ser Pro Gly Lys Ser Ser
                165                 170                 175

Ser Glu Lys Ile Ser Pro Phe Thr Asn Val Ala Ala Glu Lys Ser Met
            180                 185                 190

Lys Leu Ala Glu Leu Gln Thr Thr Gly Ala Ser Gly Tyr Val Leu Val
        195                 200                 205

Ser Cys Pro Thr Val Gly Ser Phe Arg Arg Ala Arg Thr Leu Lys Gly
    210                 215                 220

Lys Lys Gln Pro Pro Ala Cys Lys Glu Gly Asp Val Ile Lys Glu Gly
225                 230                 235                 240

Gln Ile Ile Gly Phe Leu Asp Gln Phe Gly Thr Glu Leu Pro Val Arg
                245                 250                 255

Ser Asp Ala Ala Gly Glu Val Leu Lys Ile Leu Phe Asn Asp Gly Glu
            260                 265                 270

Ala Val Gly Tyr Gly Asp Pro Leu Ile Ala Val Leu Pro Ser Phe Arg
        275                 280                 285

Gly Ile
    290

<210> SEQ ID NO 119
<211> LENGTH: 360
<212> TYPE: PRT
<213> ORGANISM: Nicotiana sylvestris

<400> SEQUENCE: 119

Met Ser Leu Phe Leu Arg Val Phe Ser Arg Thr Val Arg Ala Arg Leu
1               5                   10                  15

Cys Trp Glu His Gly Ser Gly Phe Ala Ala Arg Leu Leu Leu Pro Val
            20                  25                  30

Glu Leu Ala Thr Phe Gln Arg Leu Leu Ala Ile Ile Arg Glu Thr Phe
        35                  40                  45

Ser Phe Leu Leu Ser Asn Phe Phe Val Cys Ile Asp Asn Glu Gln Ser
    50                  55                  60

Phe Lys Leu Tyr Gln Gln Leu Ser Ala Leu Leu Cys Ser Ser Arg Arg
65                  70                  75                  80

Val Leu Pro Leu Leu Met Ala Ala Cys Gly Phe Gly Ala Ser Gly Phe
                85                  90                  95

Lys Leu Thr Asn Leu Asn Leu Gly Ser Ser Lys Pro Lys Leu Thr Ala
            100                 105                 110

Leu His Asn Leu Arg Thr Lys Lys Leu Ser Gln Ser Asp Gly Leu Leu
        115                 120                 125

Leu Thr Thr Lys Ser Arg Lys Thr Leu Phe Gly Cys Trp Cys Ser Thr
    130                 135                 140

Ala Glu Val Glu Ser Ala Ala Ala Val Ser His Ser Ser Asp Asp
145                 150                 155                 160

Ser Ser Arg Lys Ile Ile Ser Ser Glu Thr Ala Ser Pro Leu Ile Pro
                165                 170                 175

Ser Ser Tyr Glu Val Glu Ser Leu Leu Thr Glu Ile Cys Asp Thr Thr
            180                 185                 190

Ser Ile Ala Glu Val Asp Leu Lys Leu Gly Gly Phe His Leu Tyr Val
        195                 200                 205

Lys Arg Asp Leu Thr Gly Pro Ser Thr Thr Ser Leu Pro Ala Ile Ser
    210                 215                 220

Asn Pro Val Asn Ile His Ser Ser Val Glu Val Ala Asp Ser Asn Gly
225                 230                 235                 240
```

```
Ser Ala Ser Ser Pro Ser Leu Ala Ile Thr Lys Ser Pro Pro Ser
            245                 250                 255

Asp Gly Ile Arg Thr Ile Ile Asp Lys Ala Ala Asp Glu Gly Leu Val
            260                 265                 270

Ile Ile Gln Ser Pro Arg Val Gly Tyr Phe Arg Arg Ser Arg Thr Ile
            275                 280                 285

Lys Gly Lys Arg Ala Pro Pro Ser Cys Lys Glu Lys Gln Gln Val Lys
            290                 295                 300

Glu Gly Gln Val Val Cys Phe Ile Glu Gln Leu Gly Gly Glu Leu Pro
305                 310                 315                 320

Val Glu Ser Asp Val Ser Gly Glu Val Ile Lys Ile Leu Gln Lys Asp
                325                 330                 335

Gly Asp Pro Val Gly Tyr Gly Asp Pro Leu Ile Ser Ile Leu Pro Ser
            340                 345                 350

Phe Pro Gly Ile Lys Lys Leu Gln
            355                 360

<210> SEQ ID NO 120
<211> LENGTH: 274
<212> TYPE: PRT
<213> ORGANISM: Cucumis sativus

<400> SEQUENCE: 120

Met Glu Ser Ser Ala Ser Leu Arg Ser Phe His Tyr Phe Ala Gly Gly
1               5                   10                  15

Ser Arg Leu Gln Leu Ile Glu Lys Pro Ser Arg Ile Tyr Val Ser Ser
            20                  25                  30

Thr Asn Lys Thr Ser Ile Gln Arg Leu Ser Ile Phe Gly Lys Pro Ile
            35                  40                  45

His Asn Pro Thr Ser Gln Lys Lys Ile Ala Val Ser Cys Thr Lys Thr
        50                  55                  60

Pro Glu Val Thr Glu Thr Asp Ser Ala Lys Gly Ser Leu Gln Lys Lys
65                  70                  75                  80

Pro Ala Ser Asn Val Thr Phe Pro Asn Gly Phe Glu Glu Leu Leu Leu
                85                  90                  95

Glu Val Cys Asp Asp Thr Glu Ile Ala Glu Leu Lys Leu Lys Val Gly
            100                 105                 110

Glu Phe Glu Met His Val Lys Arg Asn Ile Gly Val Val Ser Ala Pro
            115                 120                 125

Leu Ser Ala Ile Ser Pro Thr Val Pro Pro Ile Pro Ser Lys Pro
        130                 135                 140

Met Val Glu Ser Ala Leu Ala Ala Pro Ala Pro Pro Ile Pro Ser Pro
145                 150                 155                 160

Glu Lys Ala Asn Ala Phe Thr Asp Val Pro Phe Lys Lys Ser Ser Lys
                165                 170                 175

Leu Ala Ala Leu Glu Ala Ser Gly Ala Lys Gly Tyr Val Leu Val Thr
            180                 185                 190

Ser Pro Thr Val Gly Ser Phe Arg Ser Gly Arg Thr Val Lys Gly Arg
            195                 200                 205

Arg Met Pro Pro Ile Cys Lys Glu Asn Asp Leu Ile Arg Glu Gly Gln
            210                 215                 220

Val Val Ala Tyr Val Asp Gln Phe Gly Ser Gln Leu Pro Val Lys Ser
225                 230                 235                 240

Asp Val Ala Gly Glu Val Leu Arg Ile Leu Phe Lys Glu Asp Glu Pro
```

-continued

```
            245                 250                 255
Val Gly Phe Gly Asp Pro Leu Ile Ala Val Leu Pro Ile Phe His Gly
        260                 265                 270
Ile Arg

<210> SEQ ID NO 121
<211> LENGTH: 280
<212> TYPE: PRT
<213> ORGANISM: Eucalyptus grandis

<400> SEQUENCE: 121

Met Ala Ser Gly Asp Val Ser Val Ser Leu Ser Tyr Phe Phe Leu Ser
1               5                   10                  15
Gly Thr Leu Gly Thr Ser Arg Val Asn Ile Ser Asn Leu Asn Phe Asn
            20                  25                  30
Ile Ala Arg Val Gly Glu Ala His Gln Ser Asn Leu Arg Ile Thr Trp
        35                  40                  45
Ile Val His Asn Leu Gln Asn His Ala Gly Leu Arg Ile Ser Ser Thr
    50                  55                  60
Thr Asp Asp Gln Trp Arg Ile Tyr Cys Thr Ser Ser Gly Ser Gln
65                  70                  75                  80
His Gly Ser Asn Thr Ser Gly Phe Thr Arg Arg His Thr Pro Asp Leu
                85                  90                  95
Ser Glu Val Gly Ser Leu Ile Thr Gly Ile Cys Lys Ala Ser Ser Val
            100                 105                 110
Glu Glu Ile Glu Ile Lys Leu Ser Gly Phe Gln Leu Tyr Leu Ala Arg
        115                 120                 125
Asn Pro Thr Arg Lys Thr Thr Thr Leu Pro Pro Ser Pro Gln Leu His
    130                 135                 140
Ala Pro Pro Lys Ala Asp Ala Thr Pro Glu Glu Gln Val Ala Ser Ala
145                 150                 155                 160
Ser Leu Pro Lys Thr Ser Leu Ala Ile Thr Lys Ser Ile Phe Ser Ile
                165                 170                 175
Ser Arg Trp Gln Ile Thr Leu Lys Lys Ala Val Asn Glu Gly Leu Phe
            180                 185                 190
Val Leu Arg Ser Pro Arg Val Gly Phe Phe Lys Arg Ser Arg Thr Ile
        195                 200                 205
Lys Gly Lys Cys Ala Pro Pro Ala Cys Lys Glu Arg Gln Ile Val Lys
    210                 215                 220
Glu Gly Gln Val Val Cys Tyr Ile Asp Gln Leu Gly Gly Glu Met Pro
225                 230                 235                 240
Ile Lys Ala Asp Val Ser Gly Glu Val Ile Lys Ile Leu Leu Glu Asp
                245                 250                 255
Gly Asp Pro Val Gly Tyr Glu Asp Ala Leu Ile Thr Ile Leu Pro Tyr
            260                 265                 270
Ser Pro Glu Ile Lys Met Leu Gln
        275                 280

<210> SEQ ID NO 122
<211> LENGTH: 221
<212> TYPE: PRT
<213> ORGANISM: Eucalyptus grandis

<400> SEQUENCE: 122

Met Arg Thr Ser Asp Ser Ala Ile Ser Thr Asp Thr Asn Glu Cys Ile
1               5                   10                  15
```

```
Gly Arg Ser Val Glu Lys Gly Pro Leu Glu Asp Ala Thr Phe Pro Ser
             20                  25                  30

Gly Phe Gln Thr Leu Leu Glu Val Cys Asp Glu Thr Gln Ile Ala
         35                  40                  45

Glu Leu Lys Leu Lys Val Gly Asn Phe Glu Met His Val Lys Arg Asn
 50                  55                  60

Val Gly Ala Ala Glu Val Pro Thr Val Ile Ala Ser Pro Val Thr Pro
 65                  70                  75                  80

Pro Pro Ile Pro Ala Glu Pro Val Asn Lys Ser Ser Gly Val Ser
             85                  90                  95

Pro Pro Ser Ala Leu Lys Pro Ser Ser Glu Lys Ala Ala Pro Phe Met
            100                 105                 110

Asn Val Thr Phe Gly Lys Ser Ala Lys Val Lys Ala Leu Glu Ala Ser
            115                 120                 125

Gly Ser Ser Gly Tyr Ala Leu Val Ser Ser Pro Thr Val Gly Ser Phe
130                 135                 140

Gln Lys Gly Arg Thr Val Lys Gly Lys Gln Gly Pro Ser Cys Lys
145                 150                 155                 160

Glu Gly Asp Leu Ile Lys Glu Gly Gln Val Ile Gly Trp Leu Asp Gln
                165                 170                 175

Phe Gly Thr Glu Leu Pro Val Lys Ser Asp Val Ser Gly Glu Val Leu
            180                 185                 190

Lys Leu Leu Ile Asp Asp Gly Glu Ala Val Gly Tyr Gly Asp Pro Leu
                195                 200                 205

Leu Ala Val Leu Pro Ser Phe Pro Gly Val Gly Val Gln
210                 215                 220

<210> SEQ ID NO 123
<211> LENGTH: 288
<212> TYPE: PRT
<213> ORGANISM: Eucalyptus grandis

<400> SEQUENCE: 123

Met Glu Ser Ser Val Ser Ala Leu Arg Ser Ser Leu His Ser Asn Ile
 1               5                  10                  15

Ala Gly Ala Leu Pro Arg Val Glu Pro Leu Pro His Lys Pro Gly Val
             20                  25                  30

Val Pro Val Gln Ser Tyr Ser Pro Ser Lys Lys Leu Tyr Val His
         35                  40                  45

Gly Phe Ala Ala Arg Gly Ile Ala Pro Ser Arg Thr Arg Asn Ala Ala
 50                  55                  60

Val Val Ser Cys Leu Lys Thr Ser Glu Ala Thr Gly Val Ala Lys Ser
 65                  70                  75                  80

Ser Glu Gly Asn Thr Arg Asp Ser Lys Asp Lys Thr Leu Pro Arg
             85                  90                  95

Ala Thr Phe Pro Ser Ala Phe Glu Glu Leu Leu Leu Glu Val Cys Asp
            100                 105                 110

Glu Thr Gln Ile Ala Glu Leu Lys Leu Lys Ile Gly Asp Ile Glu Met
            115                 120                 125

Gln Val Lys Arg Asn Leu Gly Ala Thr Lys Glu Ala Phe Ala Ser Ile
130                 135                 140

Pro Ser Pro Thr Thr Pro Pro Ile Pro Thr Glu Pro Met Glu Asn
145                 150                 155                 160

Ser Gly Ala Val Val Pro Pro Lys Pro Ser Pro Glu Lys Thr Ser
```

```
                     165                 170                 175

Pro Phe Thr Asn Phe Ser Phe Gly Lys Ser Ser Lys Leu Ala Ala Leu
                180                 185                 190

Glu Ala Pro Gly Ser Ser Gly Tyr Val Leu Ser Ser Pro Thr Val
            195                 200                 205

Gly Ser Phe Arg Arg Gly Arg Thr Leu Lys Gly Lys Lys Gln Pro Pro
        210                 215                 220

Ser Cys Lys Glu Gly Asp Val Ile Lys Glu Gly Gln Val Ile Gly Trp
225                 230                 235                 240

Leu Asp Gln Phe Gly Thr Glu Leu Pro Val Lys Ser Asp Val Ser Gly
                245                 250                 255

Glu Val Leu Lys Leu Leu Val Asn Asp Gly Glu Pro Val Gly Tyr Gly
            260                 265                 270

Asp Pro Leu Ile Ala Val Leu Pro Ala Phe His Ser Ile Asn Ile Met
        275                 280                 285

<210> SEQ ID NO 124
<211> LENGTH: 276
<212> TYPE: PRT
<213> ORGANISM: Eucalyptus grandis

<400> SEQUENCE: 124

Met Leu Leu Ser Met Ala Ser Cys Ser Leu Gly Ala Ser Asn Val Lys
1               5                   10                  15

Ile Ala Asn Leu Asn Ser Gly Arg Pro Lys Ile Gly Glu Ser Arg Leu
                20                  25                  30

Ser Tyr Gly Arg Ser Trp Ile Val Leu Lys Thr Pro Lys Tyr Ala Gly
            35                  40                  45

Leu Thr Leu Phe Gln Gln Leu Asp Lys Ile Cys Pro Val Cys His
        50                  55                  60

Pro Ser Ser Gly Ser Pro Ser Thr Ser Ser Leu Leu Asp Asp Ser Glu
65                  70                  75                  80

Asp Ser Glu Pro Ser Ser Leu Thr Ser Gln Leu Ile Pro Asn Ser Ser
                85                  90                  95

Glu Val Glu Ser Leu Leu Thr Asp Ile Cys Glu Thr Ser Ile Ala Glu
            100                 105                 110

Phe Glu Leu Lys Leu Asn Gly Phe Arg Leu Tyr Val Ala Arg Asp Val
        115                 120                 125

Ser Gly Gly His Lys Pro Leu Pro Pro Phe Ser Pro Ala Pro Thr Pro
130                 135                 140

Val His Ser Asn Val Glu Ala Thr Asp Thr Asn Gly Ser Leu Ser Lys
145                 150                 155                 160

Pro Ser Leu Ala Ile Ser Lys Ala Leu Thr Ser Ser Asp Gly Gly Pro
                165                 170                 175

Thr Trp Leu Asp Lys Ala Ala Asp Ala Gly Leu Val Ile Leu Gln Ser
            180                 185                 190

Pro Arg Val Gly Phe Phe Arg Arg Ser Arg Thr Ile Lys Gly Lys Arg
        195                 200                 205

Ala Pro Pro Ala Cys Lys Glu Lys Gln Ile Val Lys Glu Gly Gln Val
    210                 215                 220

Val Cys Tyr Ile Glu Gln Leu Gly Gly Glu Leu Pro Ile Glu Ser Asp
225                 230                 235                 240

Val Ser Gly Glu Val Val Lys Ile Leu Arg Glu Asp Gly Asp Pro Val
                245                 250                 255
```

Gly Tyr Gly Asp Ala Leu Ile Ser Ile Leu Pro Ser Phe Pro Gly Ile
                260                 265                 270

Lys Lys Leu Gln
        275

<210> SEQ ID NO 125
<211> LENGTH: 285
<212> TYPE: PRT
<213> ORGANISM: Morus notabilis

<400> SEQUENCE: 125

Met Glu Ser Ser Ala Val Leu Arg Ser Phe Gln Leu Asp Thr Ile Ser
1               5                   10                  15

Arg Thr Lys Ser Phe Leu Glu Lys Pro Gly Met Val Pro Val Tyr Asn
            20                  25                  30

Ala Arg Gln Leu Asn Ala Asn Arg Ser Cys Ile Pro Ser Leu Thr Ala
        35                  40                  45

Ser Gly Arg Leu Ile Asn Ser Pro Arg Lys Gln Lys Gly Phe Arg Val
    50                  55                  60

Ser Cys Val Lys Thr Ser Glu Ala Lys Glu Thr Ala Lys Ser Asn Asp
65                  70                  75                  80

Cys Val Pro Gln Ser Ser Leu Glu Lys Thr Pro Arg Ser Ala Ile Phe
                85                  90                  95

Pro Asn Gly Phe Glu Ala Leu Met Leu Glu Val Cys Asp Glu Thr Glu
            100                 105                 110

Ile Ala Glu Leu Lys Leu Lys Val Gly Asp Phe Glu Met His Leu Lys
        115                 120                 125

Arg Asn Ile Gly Ala Thr Val Ala Pro Leu Ser His Ile Ser Pro Thr
    130                 135                 140

Ser Pro Pro Pro Ile Pro Ser Lys Pro Met Val Glu Ser Ala Pro Ala
145                 150                 155                 160

Ala Pro Pro Pro Ser Pro Pro Lys Thr Ser Ser Gln Thr Thr Ser Pro
                165                 170                 175

Phe Thr Asn Val Ser Met Val Lys Thr Ser Lys Leu Ala Ala Leu Glu
            180                 185                 190

Ala Ser Gly Ser Asn Ala Tyr Val Leu Val Ser Ser Pro Thr Val Gly
        195                 200                 205

Ser Phe Arg Arg Gly Arg Thr Val Lys Gly Lys Lys Gln Pro Pro Ile
    210                 215                 220

Cys Lys Glu Gly Asp Val Ile Lys Glu Gly Gln Val Ile Gly Tyr Val
225                 230                 235                 240

Asp Gln Phe Gly Thr Glu Leu Pro Val Lys Ser Asp Ile Gly Glu
                245                 250                 255

Val Leu Lys Val Leu Phe Thr Glu Gly Glu Ala Val Gly Tyr Gly Asp
            260                 265                 270

Pro Leu Ile Ala Val Leu Pro Ser Phe His Gly Ile Lys
        275                 280                 285

<210> SEQ ID NO 126
<211> LENGTH: 439
<212> TYPE: PRT
<213> ORGANISM: Morus notabilis

<400> SEQUENCE: 126

Met Val His Glu Phe His Asp Ser Val Ile Gly Gly Ser Gly Phe
1               5                   10                  15

-continued

Leu Arg Thr Tyr Lys Arg Leu Ser Ala Val Val Leu Trp Arg Gly Met
                 20              25                  30

Lys Arg Phe Ile Arg Asp Tyr Val Ala His Cys Glu Ile Cys Gln Gln
             35              40                  45

Asn Glu Ser Glu Asp Leu Ser Pro Val Gly Leu Leu Gln Pro Leu Pro
 50              55                  60

Ile Pro Asp Leu Val Trp Asp Val Ser Met Asn Phe Val Gly Gly
65              70              75                  80

Leu Pro Lys Ser Gly Gly Phe Asp Thr Ile Leu Val Val Asp Arg
                 85              90                  95

Leu Ser Lys Tyr Ala His Phe Cys Pro Leu Ala His Pro Tyr Ala Ala
                 100             105                 110

Lys Gln Val Ala Ala Leu Phe Val Ser His Ile Val Lys Leu His Gly
             115             120                 125

Val Pro Arg Ser Ile Val Ser Asp Arg Asp Ala Ile Phe Met Ser Gly
         130             135             140

Phe Trp Arg Glu Leu Phe Lys Leu Gln Gly Thr Lys Leu Tyr Thr Ser
145             150                 155                 160

Ser Ala Tyr His Pro Glu Ser Asp Gly Gln Thr Glu Val Val Asn Cys
                 165                 170                 175

Cys Leu Glu Ala Val Val Ser Ser Glu Asp Asp Gly Glu Gln Ser Lys
             180                 185                 190

Tyr Ser Gly Leu Thr Ser Gln Leu Val Pro Asn Phe Asp Glu Val Glu
             195                 200                 205

Ser Leu Leu Ser Thr Ile Cys Asp Thr Thr Ser Ile Ala Glu Phe Glu
210                 215                 220

Met Lys Leu Ser Gly Phe Arg Leu His Val Arg Arg Lys Leu Thr Glu
225                 230                 235                 240

Glu Val Asn Thr Ser Pro Pro Ser Ala Ala Pro Thr Ser Ala Tyr
                 245                 250                 255

Asn Val Ile Ala Glu Ser Ser Asp Leu Asn Gly Phe Val Ser Thr Pro
                 260                 265                 270

Ser Leu Ala Ile Thr Lys Ser Glu Thr Ser Ser Lys Asn Ile Gln Thr
             275                 280                 285

Leu Val Asp Arg Ala Ala Asp Ala Gly Leu Val Ile Ile Arg Ser Pro
             290                 295                 300

Arg Val Gly Phe Phe Arg Arg Ser Arg Thr Ile Lys Gly Lys Arg Ala
305                 310                 315                 320

Pro Pro Pro Cys Lys Glu Lys Gln Glu Val Lys Glu Gly Gln Val Val
                 325                 330                 335

Cys Tyr Ile Glu Gln Leu Gly Gly Glu Leu Pro Ile Glu Ser Asp Val
             340                 345                 350

Ser Gly Glu Val Ile Lys Ile Leu Arg Glu Asp Gly Asp Ser Ile Asn
             355                 360                 365

Tyr Arg Tyr Asn Glu Glu Ser Leu Phe Tyr Phe Ile Phe Ser Met Lys
             370                 375                 380

Pro Asn Lys Ile Leu Ile Arg Glu Ala Ala Gly Pro Ser Lys Asn Thr
385                 390                 395                 400

Gln Arg Glu Gly Lys Lys Glu Gly Gly Ala Ile Met Val Arg Gly Ser
                 405                 410                 415

Ala Gln Ala Arg His Arg Met Leu Ser Phe Gly Arg Gly Ser Cys His
             420                 425                 430

Leu Arg Arg Arg Asn Gly Cys

<210> SEQ ID NO 127
<211> LENGTH: 289
<212> TYPE: PRT
<213> ORGANISM: Nelumbo nucifera

<400> SEQUENCE: 127

Met Val Ser Val Thr Val Phe Arg Ser Phe His Gly Ala Ile Asp Ser
1               5                   10                  15

Ile Thr His Leu Gln Ser Leu Ser Glu Arg Pro Gly Ala Val Pro Ile
            20                  25                  30

Tyr Asn Ala Asn Ala Lys Lys Leu Ser Phe Ala Gln Gly Leu Ala Leu
        35                  40                  45

Gly Ser Arg Ile Thr Ser Ala Asn Glu Lys Arg Ala Phe Val Pro Cys
    50                  55                  60

Leu Lys Ala Ser Glu Ser Thr Thr Glu Ile Thr Ser Val Val Tyr Leu
65                  70                  75                  80

Asp Gly Lys Ser Gln Glu Pro Leu Glu Lys Arg Ser Leu Gln Ser Thr
                85                  90                  95

Thr Phe Pro Asn Gly Phe Glu Ala Leu Val Leu Glu Val Cys Asp Glu
            100                 105                 110

Thr Asn Val Ala Glu Leu Lys Leu Lys Val Gly Asp Phe Glu Met His
        115                 120                 125

Leu Lys Arg Asn Ile Asp Thr Thr Lys His Thr Thr Pro Ile Ile Ser
    130                 135                 140

Pro Thr Pro Pro His Leu Ser Ser Glu Pro Met Val Lys Ala Thr Pro
145                 150                 155                 160

Val Ala Pro Pro Ser Ser Pro Lys Ser Ser Ser Glu Thr Ala Ser
                165                 170                 175

Pro Phe Lys Asn Lys Ser Ser Thr Lys Ser Ser Lys Leu Ala Ala Leu
            180                 185                 190

Glu Ala Ser Gly Ala Asn Ser Tyr Val Leu Val Ser Ser Pro Lys Val
        195                 200                 205

Gly Ser Phe Arg Arg Gly Lys Thr Val Lys Gly Lys Gln Pro Pro
    210                 215                 220

Ile Cys Lys Glu Gly Asp Val Ile Lys Glu Gly Gln Thr Ile Gly Tyr
225                 230                 235                 240

Leu Asn Gln Phe Gly Ser Glu Leu Pro Val Met Gln Ser Asp Val Ala
                245                 250                 255

Gly Glu Val Leu Lys Phe Leu Tyr Asn Asp Gly Asp Ala Val Gly Tyr
            260                 265                 270

Gly Asp Pro Leu Val Ala Ile Leu Pro Ser Phe His Asp Ile Asn Ile
        275                 280                 285

Asn

<210> SEQ ID NO 128
<211> LENGTH: 279
<212> TYPE: PRT
<213> ORGANISM: Nelumbo nucifera

<400> SEQUENCE: 128

Met Ala Ala Phe Leu Ile Ser Gly Asn Leu Gly Cys Val Ser Asn Ala
1               5                   10                  15

Arg Leu Ser Ser Phe Tyr Met Asp Phe Gly Arg Thr Arg Ser Ala Ser
            20                  25                  30

```
Met Gln Thr Ser Tyr Ala Ile Arg Ser Trp Gly Arg Gln Lys Gln Pro
            35                  40                  45

Gln Tyr Ala Gly Phe Ile Ser Thr Lys Gln Lys Pro Leu Ser Val
    50                  55                  60

Ser Cys Ser Ser Ser Glu Val Glu Thr Ala Ala Asp Leu Asp Ser
65                  70                  75                  80

Leu Gln Glu Lys Lys Ser Asn Gly Ile Thr Arg Gln Ile Ile Pro Asn
                85                  90                  95

Ser Thr Glu Val Gln Ala Leu Leu Thr Glu Ile Cys Asp Thr Thr Tyr
                100                 105                 110

Ile Ala Glu Phe Glu Leu Lys Leu Ala Gly Phe Arg Leu Tyr Val Thr
            115                 120                 125

Arg Asp Val Ala Gly Lys Ser Ala Pro Pro Pro Pro Ser Ser Leu
130                 135                 140

Pro Ala Asn Val Ser Thr Thr Ser Asp Ala Pro Ala Leu Asn Gly Ser
145                 150                 155                 160

Val Ser Thr Pro Ser Leu Ala Ile Ala Lys Ala Val Pro Ser Ser Gly
                165                 170                 175

Glu Ile Gln Arg Met Leu Asn Lys Asp Thr Asp Glu Ser Leu Val Ile
            180                 185                 190

Leu Gln Ser Pro Lys Val Gly Tyr Phe Arg Arg Ser Arg Thr Ile Lys
            195                 200                 205

Gly Lys Arg Ala Pro Pro Ser Cys Gln Glu Lys Gln Val Val Lys Glu
210                 215                 220

Gly Gln Val Leu Cys Phe Ile Glu Gln Leu Gly Gln Ile Pro Ile
225                 230                 235                 240

Glu Ser Asp Val Ser Gly Glu Val Ile Lys Ile Leu Arg Asp Asp Gly
            245                 250                 255

Glu Pro Val Gly Tyr Gly Asp Ala Leu Ile Ala Ile Leu Pro Ser Phe
            260                 265                 270

Pro Gly Ile Lys Lys Leu Gln
        275

<210> SEQ ID NO 129
<211> LENGTH: 263
<212> TYPE: PRT
<213> ORGANISM: Camelina sativa

<400> SEQUENCE: 129

Met Ala Ser Cys Ser Leu Gly Val Pro Lys Ile Lys Ile Ser Ala Val
1               5                   10                  15

Asp Leu Ser Arg Val Ser Ser Gly Ser Leu Leu Ile Pro Phe Ser Gln
                20                  25                  30

Arg Ser Leu Leu Gly Gln Arg Pro Val Lys Tyr Leu Ser Leu Arg Thr
            35                  40                  45

Thr Phe Gly Ser Val Lys Ala Val Gln Val Ser Thr Val Pro Thr Ala
        50                  55                  60

Glu Thr Ser Ala Thr Ile Glu Val Glu Asp Ser Glu Thr Lys Ser
65                  70                  75                  80

Ser Pro Leu Asn Ala Gln Leu Val Pro Lys Pro Ser Glu Val Glu Ala
                85                  90                  95

Leu Val Thr Glu Ile Cys Asp Ser Ser Ser Ile Ala Glu Phe Glu Leu
                100                 105                 110

Lys Leu Gly Gly Phe Arg Leu Tyr Val Ala Arg Asp Leu Thr Asp Lys
```

```
              115                 120                 125
Ser Ser Pro Gln Pro His Pro Val Pro Ala Val Ala Ala Ala Ser Glu
130                 135                 140

Thr Thr Lys Ser Pro Asp Ser Asn Gly Ser Thr Pro Ser Thr Ser Leu
145                 150                 155                 160

Ala Ile Thr Arg Pro Ala Ser Ser Ala Ala Asp His Gly Leu Met Ile
                165                 170                 175

Leu Gln Ser Pro Lys Val Gly Phe Phe Arg Arg Ser Lys Thr Ile Lys
                180                 185                 190

Gly Lys Arg Met Pro Ser Ser Cys Lys Glu Lys Asp Gln Val Lys Glu
            195                 200                 205

Gly Gln Ile Leu Cys Tyr Ile Glu Gln Leu Gly Gly Gln Phe Pro Ile
        210                 215                 220

Glu Ser Asp Val Ser Gly Glu Val Val Lys Ile Leu Arg Glu Asp Gly
225                 230                 235                 240

Glu Pro Val Gly Tyr Asn Asp Ala Leu Ile Ser Ile Leu Pro Ser Phe
                245                 250                 255

Pro Gly Ile Lys Lys Leu Gln
            260

<210> SEQ ID NO 130
<211> LENGTH: 263
<212> TYPE: PRT
<213> ORGANISM: Camelina sativa

<400> SEQUENCE: 130

Met Ala Ser Cys Ser Leu Gly Val Pro Lys Ile Lys Ile Ser Ala Val
1               5                   10                  15

Asp Leu Ser Arg Val Ser Ser Gly Ser Leu Leu Ile Pro Phe Ser Gln
                20                  25                  30

Arg Ser Leu Leu Gly Gln Arg Pro Val Lys Tyr Leu Ser Leu Arg Thr
            35                  40                  45

Thr Phe Gly Ser Val Lys Ala Val Gln Val Ser Thr Val Pro Ala Ala
        50                  55                  60

Glu Thr Ser Ala Thr Val Gly Val Glu Asp Ser Glu Thr Lys Ser
65                  70                  75                  80

Ser Pro Leu Asn Ala Gln Leu Val Pro Lys Arg Ser Glu Val Glu Ala
                85                  90                  95

Leu Val Thr Glu Ile Cys Asp Ser Ser Ile Ala Glu Phe Glu Leu
                100                 105                 110

Lys Leu Gly Gly Phe Arg Leu Tyr Val Ala Arg Asp Leu Ala Asp Lys
            115                 120                 125

Ser Ser Pro Gln Pro His Pro Ile Pro Ala Val Ala Ala Ala Ser Glu
130                 135                 140

Thr Thr Lys Ser Pro Asp Ser Asn Gly Ser Thr Pro Ser Thr Ser Leu
145                 150                 155                 160

Ala Ile Thr Arg Pro Ala Ser Ser Ala Ala Asp Gln Gly Leu Met Ile
                165                 170                 175

Leu Gln Ser Pro Lys Val Gly Phe Phe Arg Arg Ser Lys Thr Ile Lys
                180                 185                 190

Gly Lys Arg Met Pro Ser Ser Cys Lys Glu Lys Asp Gln Val Lys Glu
            195                 200                 205

Gly Gln Ile Leu Cys Tyr Ile Glu Gln Leu Gly Gly Gln Phe Pro Ile
        210                 215                 220
```

```
Glu Ser Asp Val Ser Gly Glu Val Val Lys Ile Leu Arg Glu Asp Gly
225                 230                 235                 240

Glu Pro Val Gly Tyr Asn Asp Ala Leu Ile Ser Ile Leu Pro Ser Phe
                245                 250                 255

Pro Gly Ile Lys Lys Leu Gln
            260

<210> SEQ ID NO 131
<211> LENGTH: 231
<212> TYPE: PRT
<213> ORGANISM: Camelina sativa

<400> SEQUENCE: 131

Met Ala Ser Cys Ser Leu Gly Val Pro Lys Ile Lys Ile Ser Ala Val
1               5                   10                  15

Asp Leu Ser Arg Val Ser Ser Gly Ser Leu Leu Ile Pro Phe Ser Gln
                20                  25                  30

Arg Ser Leu Leu Gly Gln Arg Pro Val Lys Tyr Leu Ser Leu Arg Thr
            35                  40                  45

Thr Phe Gly Ser Val Lys Ala Val Gln Val Ser Thr Val Pro Thr Ala
        50                  55                  60

Glu Thr Ser Ala Thr Ile Glu Val Glu Asp Ser Glu Glu Thr Lys Ser
65                  70                  75                  80

Ser Pro Leu Asn Ala Gln Leu Val Pro Lys Pro Ser Glu Val Glu Ala
                85                  90                  95

Leu Val Thr Glu Ile Cys Asp Ser Ser Ser Ile Ala Glu Phe Glu Leu
            100                 105                 110

Lys Leu Gly Gly Phe Arg Leu Tyr Val Ala Arg Asp Leu Thr Asp Lys
        115                 120                 125

Ser Ser Pro Gln Pro His Pro Val Pro Ala Val Ala Ala Ala Ser Glu
130                 135                 140

Thr Thr Lys Ser Pro Asp Ser Asn Gly Ser Thr Pro Ser Thr Ser Leu
145                 150                 155                 160

Ala Ile Thr Arg Pro Ala Ser Ser Ala Ala Asp His Gly Leu Met Ile
                165                 170                 175

Leu Gln Ser Pro Lys Val Gly Phe Phe Arg Arg Ser Lys Thr Ile Lys
            180                 185                 190

Gly Lys Arg Met Pro Ser Ser Cys Lys Glu Lys Asp Gln Val Lys Glu
        195                 200                 205

Glu Pro Val Gly Tyr Asn Asp Ala Leu Ile Ser Ile Leu Pro Ser Phe
210                 215                 220

Pro Gly Ile Lys Lys Leu Gln
225                 230

<210> SEQ ID NO 132
<211> LENGTH: 269
<212> TYPE: PRT
<213> ORGANISM: Camelina sativa

<400> SEQUENCE: 132

Met Asn Ser Cys Ser Leu Gly Ala Pro Lys Val Arg Ile Ser Ala Ala
1               5                   10                  15

Tyr Phe Ser Arg Leu Arg Cys Gly Asn Leu Leu Ile Pro Asn Asn Gln
                20                  25                  30

Arg Leu Leu Ile Gly Gln Ser Pro Ile Lys Tyr Gln Ser Leu Arg Thr
            35                  40                  45
```

Thr Leu Arg Ala Val Gln Leu Ser Thr Val Pro Ala Glu Ile Ala
    50                  55                  60

Ala Val Ala Asp Val Glu Asp Ser Glu Thr Glu Ser Thr Val Val
65                  70                  75                  80

Asn Thr Gln Leu Ile Pro Lys Ser Ser Glu Val Glu Ala Leu Ile Lys
                85                  90                  95

Glu Ile Thr Asp Ser Ser Ser Ile Ala Glu Phe Glu Leu Lys Leu Gly
                100                 105                 110

Gly Phe Arg Leu Tyr Val Ala Arg Lys Leu Ala Asp Gln Ser Ser Pro
                115                 120                 125

Pro Pro Gln Gln Ile Pro Pro Val Val Ala Ala Ser Ser Ala Pro Glu
130                 135                 140

Gly Val His Thr Asn Gly Ser Ala Thr Ser Ser Leu Ala Ile Thr
145                 150                 155                 160

Lys Ser Ala Ser Pro Ser Asp Arg Pro Gln Thr Leu Ala Asn Lys Ala
                165                 170                 175

Ala Asp Gln Gly Leu Val Ile Leu Gln Ser Pro Thr Val Gly Tyr Phe
                180                 185                 190

Arg Arg Ser Lys Thr Ile Lys Gly Lys Arg Thr Pro Thr Ile Cys Lys
                195                 200                 205

Glu Lys Asp Thr Val Lys Glu Gly Gln Val Leu Cys Tyr Ile Glu Gln
210                 215                 220

Leu Gly Gly Gln Ile Pro Val Glu Ser Asp Val Ser Gly Glu Ile Val
225                 230                 235                 240

Lys Ile Leu Arg Glu Asp Gly Glu Pro Val Gly Tyr Asn Asp Ala Leu
                245                 250                 255

Ile Thr Val Leu Pro Ser Phe Pro Gly Ile Lys Lys Leu
                260                 265

<210> SEQ ID NO 133
<211> LENGTH: 276
<212> TYPE: PRT
<213> ORGANISM: Camelina sativa

<400> SEQUENCE: 133

Met Asn Ser Cys Ser Leu Gly Ala Pro Lys Val Arg Ile Ala Ala Ala
1               5                   10                  15

Asn Phe Ser Arg Leu Arg Cys Gly Asn Leu Leu Ile Pro Asn Asn Gln
                20                  25                  30

Arg Leu Phe Ile Asp Gln Ser Gln Ser Gln Ser Pro Ile Lys Tyr Pro
                35                  40                  45

Ser Leu Arg Thr Thr Leu Arg Ala Val Lys Ala Val Gln Leu Ser Thr
    50                  55                  60

Val Pro Pro Ala Asp Ile Ala Ala Val Ala Asp Val Glu Asp Ser Gln
65                  70                  75                  80

Glu Thr Glu Ser Thr Val Val Asn Thr Gln Leu Ile Pro Lys Ser Ser
                85                  90                  95

Glu Val Glu Ala Leu Ile Lys Glu Ile Thr Asp Ser Ser Ser Ile Ala
                100                 105                 110

Glu Phe Glu Leu Lys Leu Gly Gly Phe Arg Leu Tyr Val Ala Arg Lys
                115                 120                 125

Leu Ala Asp Gln Ser Ser Pro Pro Gln Gln Ile Pro Pro Val Val
130                 135                 140

Ala Ala Ser Ser Ala Pro Glu Gly Val His Thr Asn Gly Ser Ala Thr
145                 150                 155                 160

Ser Ser Ser Leu Ala Ile Thr Lys Ser Ala Ser Pro Ser Asp Arg Pro
            165                 170                 175

Gln Thr Leu Ala Asn Lys Ala Ala Asp Gln Gly Leu Val Ile Leu Gln
            180                 185                 190

Ser Pro Thr Val Gly Tyr Phe Arg Arg Ser Lys Thr Ile Lys Gly Lys
            195                 200                 205

Arg Thr Pro Thr Ile Cys Lys Glu Lys Asp Ile Val Lys Glu Gly Gln
            210                 215                 220

Val Leu Cys Tyr Ile Glu Gln Leu Gly Gly Gln Ile Pro Val Glu Ser
225                 230                 235                 240

Asp Val Ser Gly Glu Ile Val Lys Ile Leu Arg Glu Asp Gly Glu Pro
            245                 250                 255

Val Gly Tyr Asn Asp Ala Leu Ile Thr Val Leu Pro Ser Phe Pro Gly
            260                 265                 270

Ile Lys Lys Leu
            275

<210> SEQ ID NO 134
<211> LENGTH: 276
<212> TYPE: PRT
<213> ORGANISM: Camelina sativa

<400> SEQUENCE: 134

Met Ala Ser Ser Ala Leu Gly Ser Leu His Gln Thr Leu Gly Ser
1               5                   10                  15

Gln Ser Glu Leu His Leu Leu Ser Gly Asn Trp Ser Ala Ser Gly Thr
            20                  25                  30

Ser Cys Val Pro Arg Trp Arg Leu Ser Asn Arg Ser Ser Asn Tyr Thr
            35                  40                  45

Leu Val Leu Arg Ala Lys Ala Ser Lys Thr Ser Thr Thr Lys Ser
    50                  55                  60

Asp Asp Ser Ser Asp Ala Thr Val Ser Asn Gly Lys Lys Ser Val Arg
65                  70                  75                  80

Arg Thr Thr Phe Pro Lys Glu Val Glu Ala Leu Val His Glu Met Cys
            85                  90                  95

Asp Glu Thr Glu Val Ala Val Leu Lys Leu Lys Val Gly Asp Phe Glu
            100                 105                 110

Met Asn Leu Lys Arg Lys Ile Gly Ala Ala Thr Asn Pro Ile Pro Val
            115                 120                 125

Glu Asp Ile Ser Pro Thr Val Ala Pro Pro Ile Pro Ser Glu Pro Met
            130                 135                 140

Asp Lys Ser Val Ser Ser Ala Pro Ser Pro Ser Lys Ala Lys Pro Ser
145                 150                 155                 160

Glu Lys Val Ser Pro Phe Met Asn Thr Ser Tyr Gly Lys Pro Ala Lys
            165                 170                 175

Leu Val Ala Leu Glu Ala Ser Gly Ser Asn Asn Tyr Val Leu Val Lys
            180                 185                 190

Ser Pro Ser Val Gly Glu Phe His Arg Ser Arg Thr Val Lys Gly Lys
            195                 200                 205

Lys Leu Ser Pro Ser Cys Lys Glu Gly Asp Glu Ile Lys Glu Gly Gln
            210                 215                 220

Val Ile Gly Tyr Leu His Gln Leu Gly Thr Glu Leu Pro Val Thr Ser
225                 230                 235                 240

Asp Val Ala Gly Glu Val Leu Lys Leu Leu Ser Asp Asp Gly Asp Ser

```
                    245                 250                 255

Val Gly Tyr Gly Asp Pro Leu Val Ala Val Leu Pro Ser Phe His Asp
            260                 265                 270

Ile Asn Ile Gln
        275

<210> SEQ ID NO 135
<211> LENGTH: 44
<212> TYPE: PRT
<213> ORGANISM: Arabidopsis thaliana

<400> SEQUENCE: 135

Val Gly Lys Phe Gln Arg Ser Arg Thr Val Lys Gly Lys Lys Gln Ser
1               5                   10                  15

Pro Ser Cys Lys Glu Gly Asp Ala Ile Lys Glu Gly Gln Val Ile Gly
            20                  25                  30

Tyr Leu His Gln Leu Gly Thr Glu Leu Pro Val Thr
        35                  40

<210> SEQ ID NO 136
<211> LENGTH: 44
<212> TYPE: PRT
<213> ORGANISM: Artificial sequence
<220> FEATURE:
<223> OTHER INFORMATION: Polypeptide
<220> FEATURE:
<221> NAME/KEY: misc_feature
<222> LOCATION: (3)..(10)
<223> OTHER INFORMATION: Xaa can be any naturally occurring amino acid
<220> FEATURE:
<221> NAME/KEY: misc_feature
<222> LOCATION: (13)..(27)
<223> OTHER INFORMATION: Xaa can be any naturally occurring amino acid
<220> FEATURE:
<221> NAME/KEY: misc_feature
<222> LOCATION: (30)..(35)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (39)..(41)
<223> OTHER INFORMATION: Xaa can be any naturally occurring amino acid
<220> FEATURE:
<221> NAME/KEY: misc_feature
<222> LOCATION: (43)..(44)
<223> OTHER INFORMATION: Xaa can be any naturally occurring amino acid

<400> SEQUENCE: 136

Val Gly Xaa Xaa Xaa Xaa Xaa Xaa Xaa Xaa Lys Gly Xaa Xaa Xaa Xaa
1               5                   10                  15

Xaa Xaa Xaa Xaa Xaa Xaa Xaa Xaa Xaa Xaa Xaa Gly Gln Xaa Xaa Xaa
            20                  25                  30

Xaa Xaa Xaa Gln Xaa Gly Xaa Xaa Xaa Pro Xaa Xaa
        35                  40

<210> SEQ ID NO 137
<211> LENGTH: 44
<212> TYPE: PRT
<213> ORGANISM: Artificial sequence
<220> FEATURE:
<223> OTHER INFORMATION: Polypeptide
<220> FEATURE:
<221> NAME/KEY: MISC_FEATURE
<222> LOCATION: (3)..(3)
<223> OTHER INFORMATION: X = S or T or L or F or K or Y or I or V or L
```

-continued

```
<220> FEATURE:
<221> NAME/KEY: MISC_FEATURE
<222> LOCATION: (4)..(4)
<223> OTHER INFORMATION: X = F or I or L
<220> FEATURE:
<221> NAME/KEY: MISC_FEATURE
<222> LOCATION: (5)..(5)
<223> OTHER INFORMATION: X = R or Q or K
<220> FEATURE:
<221> NAME/KEY: MISC_FEATURE
<222> LOCATION: (6)..(6)
<223> OTHER INFORMATION: X = R or S or K or T or I or L or Y
<220> FEATURE:
<221> NAME/KEY: MISC_FEATURE
<222> LOCATION: (7)..(7)
<223> OTHER INFORMATION: X = N or G or A or S or C
<220> FEATURE:
<221> NAME/KEY: MISC_FEATURE
<222> LOCATION: (8)..(8)
<223> OTHER INFORMATION: X = R or I or K or T
<220> FEATURE:
<221> NAME/KEY: MISC_FEATURE
<222> LOCATION: (9)..(9)
<223> OTHER INFORMATION: X = T or K or S or V or Y or L or F
<220> FEATURE:
<221> NAME/KEY: MISC_FEATURE
<222> LOCATION: (10)..(10)
<223> OTHER INFORMATION: X = V or L or I or A or M
<220> FEATURE:
<221> NAME/KEY: MISC_FEATURE
<222> LOCATION: (13)..(13)
<223> OTHER INFORMATION: X = K or R or N or E
<220> FEATURE:
<221> NAME/KEY: MISC_FEATURE
<222> LOCATION: (14)..(14)
<223> OTHER INFORMATION: X = K or R or N or Q or C or S or F
<220> FEATURE:
<221> NAME/KEY: MISC_FEATURE
<222> LOCATION: (15)..(15)
<223> OTHER INFORMATION: X = Q or M or L or G or A or T
<220> FEATURE:
<221> NAME/KEY: MISC_FEATURE
<222> LOCATION: (16)..(16)
<223> OTHER INFORMATION: X = P or R or E or A or G or N or S
<220> FEATURE:
<221> NAME/KEY: MISC_FEATURE
<222> LOCATION: (17)..(17)
<223> OTHER INFORMATION: X = P or L or R or A or N or T or S
<220> FEATURE:
<221> NAME/KEY: MISC_FEATURE
<222> LOCATION: (18)..(18)
<223> OTHER INFORMATION: X = I or S or T or L or V or C
<220> FEATURE:
<221> NAME/KEY: MISC_FEATURE
<222> LOCATION: (19)..(19)
<223> OTHER INFORMATION: X = C or F or A or V or I
<220> FEATURE:
<221> NAME/KEY: MISC_FEATURE
<222> LOCATION: (20)..(20)
<223> OTHER INFORMATION: X = K or N or E or A or D or Q
<220> FEATURE:
<221> NAME/KEY: MISC_FEATURE
<222> LOCATION: (21)..(21)
<223> OTHER INFORMATION: X = E or V or K or D
<220> FEATURE:
<221> NAME/KEY: MISC_FEATURE
<222> LOCATION: (22)..(22)
<223> OTHER INFORMATION: X = G or N or K or R or D or M or T
<220> FEATURE:
<221> NAME/KEY: MISC_FEATURE
<222> LOCATION: (23)..(23)
<223> OTHER INFORMATION: X = D or Q or A
<220> FEATURE:
<221> NAME/KEY: MISC_FEATURE
<222> LOCATION: (24)..(24)
<223> OTHER INFORMATION: X = V or L or F or A or I or M or S or T or E
      or D or R or P or Q or K or N
<220> FEATURE:
<221> NAME/KEY: MISC_FEATURE
```

```
<222> LOCATION: (25)..(25)
<223> OTHER INFORMATION: X = I or V or G or L
<220> FEATURE:
<221> NAME/KEY: MISC_FEATURE
<222> LOCATION: (26)..(26)
<223> OTHER INFORMATION: X = K or R or Q or E
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: MISC_FEATURE
<222> LOCATION: (30)..(30)
<223> OTHER INFORMATION: X = T or V or I
<220> FEATURE:
<221> NAME/KEY: MISC_FEATURE
<222> LOCATION: (31)..(31)
<223> OTHER INFORMATION: X = I or V or L
<220> FEATURE:
<221> NAME/KEY: MISC_FEATURE
<222> LOCATION: (32)..(32)
<223> OTHER INFORMATION: X = G or A or C or F
<220> FEATURE:
<221> NAME/KEY: MISC_FEATURE
<222> LOCATION: (33)..(33)
<223> OTHER INFORMATION: X = Y or F or W or C
<220> FEATURE:
<221> NAME/KEY: MISC_FEATURE
<222> LOCATION: (34)..(34)
<223> OTHER INFORMATION: X = L or V or I
<220> FEATURE:
<221> NAME/KEY: MISC_FEATURE
<222> LOCATION: (35)..(35)
<223> OTHER INFORMATION: X = D or N or H or E
<220> FEATURE:
<221> NAME/KEY: MISC_FEATURE
<222> LOCATION: (37)..(37)
<223> OTHER INFORMATION: X = F or L or I
<220> FEATURE:
<221> NAME/KEY: MISC_FEATURE
<222> LOCATION: (39)..(39)
<223> OTHER INFORMATION: X = G or T or S or K or N or A or V
<220> FEATURE:
<221> NAME/KEY: MISC_FEATURE
<222> LOCATION: (40)..(40)
<223> OTHER INFORMATION: X = E or Q or G or S or H or Y or F or V
<220> FEATURE:
<221> NAME/KEY: MISC_FEATURE
<222> LOCATION: (41)..(41)
<223> OTHER INFORMATION: X = L or N or T or V or I or M or W or Q or F
<220> FEATURE:
<221> NAME/KEY: MISC_FEATURE
<222> LOCATION: (43)..(43)
<223> OTHER INFORMATION: X = V or I or M or L
<220> FEATURE:
<221> NAME/KEY: MISC_FEATURE
<222> LOCATION: (44)..(44)
<223> OTHER INFORMATION: X = E or K or R or M or T or N

<400> SEQUENCE: 137

Val Gly Xaa Xaa Xaa Xaa Xaa Xaa Xaa Lys Gly Xaa Xaa Xaa Xaa
1               5                   10                  15

Xaa Xaa Xaa Xaa Xaa Xaa Xaa Xaa Xaa Xaa Xaa Gly Gln Xaa Xaa Xaa
            20                  25                  30

Xaa Xaa Xaa Gln Xaa Gly Xaa Xaa Xaa Pro Xaa Xaa
        35                  40

<210> SEQ ID NO 138
<211> LENGTH: 1650
<212> TYPE: DNA
<213> ORGANISM: Artificial sequence
<220> FEATURE:
<223> OTHER INFORMATION: RNAi cassette

<400> SEQUENCE: 138
```

-continued

```
gcggccgcca aggctcattg gagaaaaagc ctttgcaaac tgctactttt cctaatggat      60
ttgaggcttt ggtattagag gtctgtgatg agactgaaat tgctgaactg aaagtaaagg     120
ttggagattt tgaaatgcat attaagcgaa acattggagc aacaaaggtt cctttgtcta     180
acatttcacc tgaggtggag ttcctgctca caaaattatg cgacacaagt tcaattgggg     240
agttagattt aaaacttgct ggcactgaat tgaattgttt aaggtttggt gagcctaaaa     300
gaatttgaac tggttttcaa ataaatgaat taagatgtta attaggagaa ttgaagttta     360
ttacaatttg gattggggat tagaatttga agctacattt aaaattcgaa aaaaaaagac     420
agtgaaactt aaaacgttca taaaaaggac caaaagttt taaaaaaatt gtcgctaaaa      480
ctcaaacata tatattacaa tgccatatgt gcttataagg acttaaggag cagtttcttg     540
ggtggctagg ggatatgaca ttttttttact gcacaataaa tatcctggcc gttgcacccg    600
gagatgcaca gagctttgag cagatcagat gaatgattaa attgttttga agagaatcta    660
ttccttcaca ctgaattctt gcacaaaacc ttgacactga atttaattgt gccaaatcaa    720
caattctttt agcccaggaa atataatcca ttttttaatt ttctgctact tattttcatc    780
ttcttaatac aaagatatac aagtattttg catattcaga tttttttttg ccaaaacaat    840
aaatctagct atatacattt tcctttgacc aactcggcta ctaaaattgg ttggattctg    900
attttactat ttgtgaattt caatcttagc tttgacctat acccaaaata aaccctcctg    960
atctgtttct ccagtggcga gagacatgat ttaacgagag ttgaacacaa gatctagact   1020
ctagaataaa aaaagacacg aatattagaa aatgatctaa tataaaataa ttataaggag   1080
tgagacttca aatctaggtc agctagccca ccatcttgtg gagctagttg gaaaaccccct  1140
gggtgtgttt ctctagactc tagaataaca ttgatcagcc taaccaaaca taacgaacga   1200
agatttaata tcaggacata tatatggatc ttggcaagtc aattaattaa ttaattaatt   1260
tccagcccaa caccttacag aaattagcat gtatgagact acttgtaagg aaaaacgagc   1320
aatgaaagat gcatgtgatc gatctgaata agaggggaaa caaagaatta taaacatata   1380
tgtataccct tccagcaagtt ttaaatctaa ctccccaatt gaacttgtgt cgcataattt   1440
tgtgagcagg aactccacct caggtgaaat gttagacaaa ggaaccttg ttgctccaat    1500
gtttcgctta atatgcatt caaaatctcc aacctttact ttcagttcag caatttcagt    1560
ctcatcacag acctctaata ccaaagcctc aaatccatta ggaaaagtag cagttttgcaa   1620
aggctttttc tccaatgagc cttgccgcgg                                    1650
```

<210> SEQ ID NO 139
<211> LENGTH: 48
<212> TYPE: PRT
<213> ORGANISM: Arabidopsis thaliana

<400> SEQUENCE: 139

```
Gln Lys Gly Gln Val Leu Cys Ile Val Glu Ala Met Lys Leu Met Asn
1               5                   10                  15
Glu Ile Glu Ser Asp His Thr Gly Thr Val Val Asp Ile Val Ala Glu
                20                  25                  30
Asp Gly Lys Pro Val Ser Leu Asp Thr Pro Leu Phe Val Val Gln Pro
            35                  40                  45
```

<210> SEQ ID NO 140
<211> LENGTH: 48
<212> TYPE: PRT
<213> ORGANISM: Arabidopsis thaliana

<400> SEQUENCE: 140

Gln Lys Gly Gln Ile Val Cys Ile Ile Glu Ala Met Lys Leu Met Asn
1               5                   10                  15

Glu Ile Glu Ala Glu Lys Ser Gly Thr Ile Met Glu Leu Leu Ala Glu
            20                  25                  30

Asp Gly Lys Pro Val Ser Val Asp Thr Pro Leu Phe Val Ile Ala Pro
        35                  40                  45

<210> SEQ ID NO 141
<211> LENGTH: 56
<212> TYPE: PRT
<213> ORGANISM: Arabidopsis thaliana

<400> SEQUENCE: 141

Lys Glu Gly Gln Val Ile Gly Tyr Leu His Gln Leu Gly Thr Glu Leu
1               5                   10                  15

Pro Val Thr Ser Asp Val Ala Gly Glu Val Leu Lys Leu Leu Ser Asp
            20                  25                  30

Asp Gly Asp Ser Val Gly Tyr Gly Asp Pro Leu Val Ala Val Leu Pro
        35                  40                  45

Ser Phe His Asp Ile Asn Ile Gln
    50                  55

<210> SEQ ID NO 142
<211> LENGTH: 57
<212> TYPE: PRT
<213> ORGANISM: Arabidopsis thaliana

<400> SEQUENCE: 142

Lys Glu Gly Gln Val Leu Cys Tyr Ile Glu Gln Leu Gly Gly Gln Ile
1               5                   10                  15

Pro Val Glu Ser Asp Val Ser Gly Glu Ile Val Lys Ile Leu Arg Glu
            20                  25                  30

Asp Gly Glu Pro Val Gly Tyr Asn Asp Ala Leu Ile Thr Val Leu Pro
        35                  40                  45

Ser Phe Pro Gly Ile Lys Lys Leu Gln
    50                  55

<210> SEQ ID NO 143
<211> LENGTH: 57
<212> TYPE: PRT
<213> ORGANISM: Arabidopsis thaliana

<400> SEQUENCE: 143

Lys Glu Gly Gln Ile Leu Cys Tyr Ile Glu Gln Leu Gly Gly Gln Phe
1               5                   10                  15

Pro Ile Glu Ser Asp Val Thr Gly Glu Val Val Lys Ile Leu Arg Glu
            20                  25                  30

Asp Gly Glu Pro Val Gly Tyr Asn Asp Ala Leu Ile Ser Ile Leu Pro
        35                  40                  45

Ser Phe Pro Gly Ile Lys Lys Leu Gln
    50                  55

<210> SEQ ID NO 144
<211> LENGTH: 36
<212> TYPE: DNA
<213> ORGANISM: Artificial sequence
<220> FEATURE:
<223> OTHER INFORMATION: Primer

```
<400> SEQUENCE: 144
catatgtcag ctgaaggaaa ggagaaaaac tcattg                              36

<210> SEQ ID NO 145
<211> LENGTH: 32
<212> TYPE: DNA
<213> ORGANISM: Artificial sequence
<220> FEATURE:
<223> OTHER INFORMATION: Primer

<400> SEQUENCE: 145
ggatccctac ggttgaacca caaacagagg ag                                  32

<210> SEQ ID NO 146
<211> LENGTH: 33
<212> TYPE: DNA
<213> ORGANISM: Artificial sequence
<220> FEATURE:
<223> OTHER INFORMATION: Primer

<400> SEQUENCE: 146
catatggaat ttatggctaa agtctctggt ctt                                 33

<210> SEQ ID NO 147
<211> LENGTH: 29
<212> TYPE: DNA
<213> ORGANISM: Artificial sequence
<220> FEATURE:
<223> OTHER INFORMATION: Primer

<400> SEQUENCE: 147
ggatcctcaa ggtgcgatga caaaaagag                                      29

<210> SEQ ID NO 148
<211> LENGTH: 29
<212> TYPE: DNA
<213> ORGANISM: Artificial sequence
<220> FEATURE:
<223> OTHER INFORMATION: Primer

<400> SEQUENCE: 148
gaattcgcta aggccgctaa atcttcgac                                      29

<210> SEQ ID NO 149
<211> LENGTH: 27
<212> TYPE: DNA
<213> ORGANISM: Artificial sequence
<220> FEATURE:
<223> OTHER INFORMATION: Primer

<400> SEQUENCE: 149
ctcgagtcac tggatgttga tgtcgtg                                        27

<210> SEQ ID NO 150
<211> LENGTH: 30
<212> TYPE: DNA
<213> ORGANISM: Artificial sequence
<220> FEATURE:
<223> OTHER INFORMATION: Primer

<400> SEQUENCE: 150
catatgacga ctctgcgatc tgtgaaagct                                     30

<210> SEQ ID NO 151
```

```
<211> LENGTH: 31
<212> TYPE: DNA
<213> ORGANISM: Artificial sequence
<220> FEATURE:
<223> OTHER INFORMATION: Primer

<400> SEQUENCE: 151
ggatccttac tgaagcttct tgatgccagg a                              31

<210> SEQ ID NO 152
<211> LENGTH: 29
<212> TYPE: DNA
<213> ORGANISM: Artificial sequence
<220> FEATURE:
<223> OTHER INFORMATION: Primer

<400> SEQUENCE: 152
catatggctg tccaagtgtc tactgtccc                                 29

<210> SEQ ID NO 153
<211> LENGTH: 31
<212> TYPE: DNA
<213> ORGANISM: Artificial sequence
<220> FEATURE:
<223> OTHER INFORMATION: Primer

<400> SEQUENCE: 153
ggatccttac tgaagcttct tgatcccagg g                              31

<210> SEQ ID NO 154
<211> LENGTH: 23
<212> TYPE: DNA
<213> ORGANISM: Artificial sequence
<220> FEATURE:
<223> OTHER INFORMATION: Primer

<400> SEQUENCE: 154
gtgttagtca catctcccgc agt                                       23

<210> SEQ ID NO 155
<211> LENGTH: 25
<212> TYPE: DNA
<213> ORGANISM: Artificial sequence
<220> FEATURE:
<223> OTHER INFORMATION: Primer

<400> SEQUENCE: 155
gatgttgatg tcgtggaaag atggc                                     25

<210> SEQ ID NO 156
<211> LENGTH: 20
<212> TYPE: DNA
<213> ORGANISM: Artificial sequence
<220> FEATURE:
<223> OTHER INFORMATION: Primer

<400> SEQUENCE: 156
gctcctagcc catctcaagc                                           20

<210> SEQ ID NO 157
<211> LENGTH: 20
<212> TYPE: DNA
<213> ORGANISM: Artificial sequence
<220> FEATURE:
<223> OTHER INFORMATION: Primer

<400> SEQUENCE: 157
```

```
<210> SEQ ID NO 158
<211> LENGTH: 21
<212> TYPE: DNA
<213> ORGANISM: Artificial sequence
<220> FEATURE:
<223> OTHER INFORMATION: Primer

<400> SEQUENCE: 158
ccagatcttc atcgtcgtgg t                                              21

<210> SEQ ID NO 159
<211> LENGTH: 22
<212> TYPE: DNA
<213> ORGANISM: Artificial sequence
<220> FEATURE:
<223> OTHER INFORMATION: Primer

<400> SEQUENCE: 159
atccagcctt aaccattcca gt                                             22

<210> SEQ ID NO 160
<211> LENGTH: 35
<212> TYPE: DNA
<213> ORGANISM: Artificial sequence
<220> FEATURE:
<223> OTHER INFORMATION: Primer

<400> SEQUENCE: 160
gcattgttga agccatgagg ttaatgaatg aaata                               35

<210> SEQ ID NO 161
<211> LENGTH: 35
<212> TYPE: DNA
<213> ORGANISM: Artificial sequence
<220> FEATURE:
<223> OTHER INFORMATION: Primer

<400> SEQUENCE: 161
tatttcattc attaacctca tggcttcaac aatgc                               35
```